(12) United States Patent
Giovannini et al.

(10) Patent No.: US 9,085,584 B2
(45) Date of Patent: Jul. 21, 2015

(54) SUBSTITUTED PYRIDO[3,2-E][1,2,4]-TRIAZOLO[4,3-A] PYRAZINES FOR THE TREATMENT OF CENTRAL NERVOUS SYSTEM DISORDERS

(71) Applicants: Riccardo Giovannini, Verona (IT); Barbara Bertani, Castiglione delle Stiviere (IT); Sara Frattini, Castelleone (IT); Giustino Di Antonio, Sant'Egidio alla Vibrata (IT); Hans-Joachim Lankau, Weinböhla (DE); Hans Stange, Riesa (DE); Christian Grunwald, Dresden (DE); Norbert Höfgen, Ottendorf-Okrilla (DE); Barbara Langen, Radebeul (DE); Ute Egerland, Radebeul (DE)

(72) Inventors: Riccardo Giovannini, Verona (IT); Barbara Bertani, Castiglione delle Stiviere (IT); Sara Frattini, Castelleone (IT); Giustino Di Antonio, Sant'Egidio alla Vibrata (IT); Hans-Joachim Lankau, Weinböhla (DE); Hans Stange, Riesa (DE); Christian Grunwald, Dresden (DE); Norbert Höfgen, Ottendorf-Okrilla (DE); Barbara Langen, Radebeul (DE); Ute Egerland, Radebeul (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/951,531

(22) Filed: Jul. 26, 2013

(65) Prior Publication Data
US 2014/0045857 A1 Feb. 13, 2014

(30) Foreign Application Priority Data
Jul. 31, 2012 (EP) .................................. 12178713

(51) Int. Cl.
*A61K 31/4985* (2006.01)
*C07D 487/14* (2006.01)
*C07D 471/14* (2006.01)

(52) U.S. Cl.
CPC ............ *C07D 487/14* (2013.01); *C07D 471/14* (2013.01)

(58) Field of Classification Search
CPC ......................... A61K 31/4985; C07D 487/14
USPC ........ 514/250; 544/346; 546/268.1; 549/356, 549/429, 510
See application file for complete search history.

(56) References Cited

U.S. PATENT DOCUMENTS

| | | |
|---|---|---|
| 6,998,402 B2 | 2/2006 | Niewohner et al. |
| 2004/0192698 A1 | 9/2004 | Benbow et al. |
| 2007/0135457 A1 | 6/2007 | Beyer et al. |
| 2007/0161628 A1 | 7/2007 | Bernard |
| 2010/0035882 A1 | 2/2010 | Ellinghaus et al. |
| 2012/0178748 A1 | 7/2012 | Campbell et al. |
| 2012/0302564 A1 | 11/2012 | Lankau et al. |

FOREIGN PATENT DOCUMENTS

| | | |
|---|---|---|
| WO | 02068423 A1 | 9/2002 |
| WO | 2005041957 A1 | 5/2005 |
| WO | 2005063723 A1 | 7/2005 |
| WO | 2005081497 A1 | 9/2005 |
| WO | 2005113517 A1 | 12/2005 |
| WO | 2006024640 A2 | 3/2006 |
| WO | 2006072612 A2 | 7/2006 |
| WO | 2006072615 A2 | 7/2006 |
| WO | 2006102728 A2 | 10/2006 |
| WO | 2007087250 A2 | 8/2007 |
| WO | 2007121319 A2 | 10/2007 |
| WO | 2007137819 A1 | 12/2007 |
| WO | 2007137820 A1 | 12/2007 |
| WO | 2008004117 A1 | 1/2008 |
| WO | 2008043461 A2 | 4/2008 |
| WO | 2009152825 A1 | 12/2009 |
| WO | 2010030785 A2 | 3/2010 |
| WO | 2010054253 A1 | 5/2010 |
| WO | 2013000924 A1 | 1/2013 |
| WO | 2013034758 A1 | 3/2013 |
| WO | 2013034761 A1 | 3/2013 |
| WO | 2014001314 A1 | 1/2014 |
| WO | WO 2014/019979 | * 2/2014 |

OTHER PUBLICATIONS

Jordan, V. C. Nature Reviews: Drug Discovery, 2, 2003, 205.*
Hackam, et al. JAMA, 296(14), 2006, 1731-1732.*
International Search Repot, Form PCT/ISA/210, and Written Opinion, Form PCT/ISA/237, for corresponding application PCT/EP2013/065894, date of mailing Sep. 25, 2013.
Kehler et al., Patented PDE10A inhibitors: novel compounds since 2007, Expert Opinion Ther Patents, 19 (12), 2009, pp. 1715-1725.

(Continued)

*Primary Examiner* — Douglas M Willis
(74) *Attorney, Agent, or Firm* — Michael P. Morris; Alan R. Stempel

(57) ABSTRACT

The compounds are of the class of pyrido[3,2-e][1,2,4]-tiazolo[4,3-a]pyrazines, useful in the treatment of central nervous system disorders. A species illustrative of members of the class is the following:

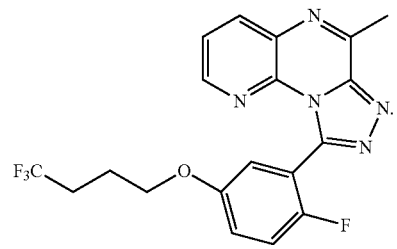

34 Claims, No Drawings

(56) References Cited

OTHER PUBLICATIONS

Andrés et al., Discoveryof a new series of [1,2,4]triazolo[4,3-a]quinoxalines as dual phosphodiesterase 2/phosphodiesterase 10 (PDE2/PDE10) inhibitors, Bioorganic & Medicinal Chemistry Letters, 2013, vol. 23, pp. 785-790.

Höfgen et al., Discovery of Imidazo[1,5-5]pyrido[3,2-e]pyrazines as a New Class of Phosphodiesterase 10A Inhibitors, Journal of Medicinal Chemistry, 2010, vol. 53, pp. 4399-4411.

Malamas et al., Highly potent selective and orally active phosphodiesterase 10A inhibitors, Journal of Medicinal Chemistry, 2011, vol. 54, pp. 7621-7638.

Soderling, elal. "Isolation and characterization of a dual-substrate phosphodiesterase gene family:PDE10A", Proc Natl. Acad. Sci. USA, vol. 96, (1999), pp. 7071-7076.

Soderling, elal. "Regulation of cAMP and cGMP s;gnaling: new phosphodiesterases and ne functions", Current Opinionin Cell Biology, 12, (2000), pp. 174-179.

Thompson, et at. "PositiVe, Negative, and Disorganisation Factors from the Schedule for Affective Disorders and Schizophrenia and the Present state Examination, A Three-Factor Solution", British J. of Psychiatry, 163, (1993), pp. 344-351.

Toman, et al. "The search for new drugs against epilepsy", Dept. of Pharmacol., Abbott Lab., lt; Meeting of Federation of American Societies for Experimental Biology; (1950), pp. 96-104.

Turner, et al. "Relative lack of cognitive effect & of methylphenidate in elderly male volunteers", Psychopharmacology, 166, (2003) pp. 455-464.

Valluzzi, et a.l "Effects offluoxetine on hippocampal-dependent and hippocampal-independent learning tasks", Behavioral Pharmacology, 18, Nos. 5 & 6, (2007), pp. 507-513.

Van Staveren, et at. "mRNA Expression Patterns of the cGMP-Hydrolyzing Phosphodiesterases Types 2.5. and 9 during Development of the Rat Brain". The Journal of Comparative Neurology, 467, (2003), pp. 566-580.

Vyas, et al. "Synthesis and Antimicrobial Actmty of 1-ARYI-4-METI-iY(I1,2,4) Triazolo (4,3,a) Quinoxalines", Indian Journal of Heterocyclic Chemistry, vol. 14, (2005), pp. 361-362.

Wagle, et at. "Synthesis of some new 4-styryttelrazolo[1,5-a]qulnoxaline and 1-substltuted-4-styryl[1,2,4]triazolo[4,3-a]quinoxaline derivatives as potent anticonvulsants", European Journal of Medicinal Chemistry, 44, (2009), pp. 1135-1143.

Winstanley, et al. Behavioral models of impulsivity in relation to ADHD: Translation between clinical and preclinical studies. Clinical Psychology Review. 26, (2006), pp. 379-395.

Xie, et al. cellular and sucellular localizaion of PDE10A, a striatum-enriched phsphodiesterase, Neuroscience, (2006), pp. 1-11.

Young, et al. "Using the MA TRICS to guide development of a preclinical cognitive test battery for research in sdlizophrenia", Pharmacology & Therapeutics,122,(2009), pp. 150-202.

Patani et al., Bioisosterism: A Rational Approach in Drup Design, Chem. Rev., 1996, 96, pp. 3147-3176.

Aggarwal, et al. Hypervalent Iodine-Mediated Synthesis of 1-Aryl-4-methyl-1,2,4-triaz.olo[4,3-a] quinoxallnes by Oxidative Cyclization of Arene Carbaldehyde-3-methylquinoxalin-2-yt Hydrazones', Synthetic Communications, 36, (2006), pp. 1873-1878.

Altamura, et al. "Mood stabilizers for patients with bipolar disorder: the state of the art", Expert Rev. Neumther. 11(1),(2011), pp. 85-99.

Baddeley, Alan "Working memory: looking back and looking forward", Nature Reviews 1 Neuroscience (2003), pp. 829-839.

Beck, Aaron T. "The Evolllition of the Cognitive Modelof Depression and Its Neurobiological Correlates", Am. J. Psychiatry (2008), 165, pp. 96 977.

Benke. et al., "Basal Ganglia Lesions and the Theory of Fronto-Subcortical loops: Neuropsychologycal Findings In Two Patients with Left Caudate Lesions", Neurocase, vol. 9 No. 1, (2003), pp. 70-85.

Blockland, et al. "Imrpoving Memory: A Role for Phosphodiesterases",Current Pharmaceutical Design, 12, (2006), pp. 2511-3523.

Boess, et al. "Inhibition of phosphodiesterase 2 increases neuronal cGMP.synaptic plasticity and memory performance",Neuropharmacology, 47 (2004). pp. 1081-1092.

Bolger. et al. "Differential CNS expression of alternative mRNA isoforms at the mammalian genes encoding cAMP-specific phosphodiesterases", Gene, 149, (1994), pp. 237-244.

Carosati, et al. "Ligand-based virtual screening and ADME-tox guided approach to identify triazolo-quinoxalines as folate cycle inhibitors", Bioorganic & MedicinalChemistry, 18, (2010), pp. 7773-7785.

Conti, et al."The Molecular Biology of Cyclic Nucleotide Phosphodiesterases", Progress in Nucleic Acid Research and Molecular Biology, 63, (2000), pp. 1-38.

Crawley, Jacqueline N. Exploratory Behavior Models of Anxiety in Mice~. Neuroscience & Blobehavioral Reviews 9, (1985), pp. 37-44.

Dunkin, et al. "Executive dysfunction predicts nonresponse to fluoxetine in major depression", J. Affective Disorders, 60 (2000), pp. 13-23.

Easton, et at Atomoxetine produces changes in cortioo-basal thalamic loop circt its: Assessed by phMRI BOLD contrasr. Neuropharmacology, 52 (2007). pp. 812-826.

Essayan.David M. "Cyclic nucleotide phosphodiesterases", J. Allergy and Clinicallmmunology, (2001), pp. 671-680.

Gajwani, Prashant "Treatment-refractory bipolar disorder. classification to aid in clinical management", Expert Opin. Phannacother., 10(12), (2009), pp. 1907-1915.

Gonzalez, et at., "Medial prefrontal transection enhances social interaction I: Behavioral Studies", Brain Research, 887,(2000), pp. 7-15.

Gorlyn, et al., "Neuropsychological characteristics as predictors of SSRI treatment response in depressed subjects", J. Neural Transm. 115, (2008), pp. 1213-1219.

Grauer,et al. "Phosphodiesterase 10A Inhibitor Activity in Preclinical Models of the Positive, Cognitive,and Negative Symptoms of Schizophrenia", J. of Pharmacal. and Experimental Therapeutics, vol. 331, No. 2 (2009), pp. 574-590.

Gualtieri,et al. "Neurocognition in Depression: Patients on and Off Medication Versus Healthy Comparison Subjects", J. Neuropsychiatry Clin. Neurosci. 18:2, (2006), pp. 217-225.

Gururaja, et al., "A Class of Small Molecules that Inhibit TNFa-Induced Survival and Death Pathways via Prevention of Interactions between TNFaRI, TRADD, and RIP1", Chemistry & Biology, 14. (2007}, pp. 1105-1118.

Jucaite, et al. "Reduced Midbrain Dopamine Transporter Binding in Male Adolescents with Attention-Deficit/Hyperactivity Disorder, Association Between Striatal Dopamine Markers and Motor Hyperactivity", Bioi. Psychiatry, 57, (2005), pp. 229-238.

Kehler,et al. "Patented PDE10A inhibitors:novel compounds since 2007", Expert Opin. Ther.Patents, 19(12), (2009), pp. 1715-1725.

Kotera,et al. "Characterizaion and Phosphorylation of PDE10A2,a Novel Alternative Splice Variant of Human Phosphodiesterase That Hydrolyzes cAMP and cGMP", Biochem. and Biophys. Research Communications, 261 (1999), pp. 551-557.

Kumar,et al. "Influence of antidepressant drugs on learning and memory paradigms in mice". Indian J. of Experimental Bioi., vol. 34,(1996), pp. 431-435.

Kumar. et al. "An expeditious synthesis of 1-aryl-4-methyl-1,2,4-triazolo[4,3-a}quinoxalines under solvent-free conditions using iodobenzene diacetate", Green Chern., 6, (2004), pp. 156-157.

Lakics, et al. "Analysis of phosphodiesterase expression using quantitative realtime PCR", BMC Pharmacology, 5, (2005), p. 29.

Lakics, et al. "Normalization of real-time PCR data in a panel of 24 human tissues and an application to pllosphodiesteras gene expression", Society of Neuroscience 35th Annual Meeting, Nov. 12-16, 2005, Washington, D.C.

Loescher, et al. "Which animalmodels should be used in the search for new antiepileptic drugs? A proposal based on experimental and clinicalconsiderations", Epilepsy Res., 2, (1988). pp. 145-181.

Mandelli, et al. "Improvement of cognitive functioning in mood disorder patients with depressive symptomatic recovery during treatment an exploratory analysis", Psychiatry and Clinical Neurosciences, 60,(2006). pp. 598-604.

(56) References Cited

OTHER PUBLICATIONS

Mandhane, et al. •Adenoslce A2 receptors modulate haloperidol-Induced catalepsy in rats, European J. of Pharmacology, 328, (1997), pp. 135-141.

Masood, et al. Anxiolytic Effects ofPhosphodiesterase-2Inhibltors Associated with Increased cGMP Signaling•, The Journal of Pharmacology and Experimental Therapeutics, vol. 331, No. 2, (2009), pp. 690-699.

Masood, et al. "Reversal of Oxidative Stress-Induced Anxiety by Inhibition of Phosphodeisterase-2 in Mice". The Journal of Pharmacology and Experimental Thentpeutics, vol. 326, No. 2, (2008), pp. 369-379.

Massoud, et al. "Update on the PharmacologicalTreatment of Alzheimer's Disease", Current Neuropharmacology, 8, (2010), pp. 69-80.

Menniti, et al. "Phosphodeisterases in the CNS: targets for drug development", Nature.com Reviews, vol. 5, (2006), pp. 660-670.

Menzaghi, et al. "Interactions between a Novel Cholinergic Ion Channel Agonist, SIB-1765F and I-DOPA in the 34 Reserpine Model of Parkinson's Disease in Rats", The Journal of Pharmacology and Experimental Therapeutics, vol. D 280, No. 1, (1997), pp. 393-401.

Modell, et al. "Basal Ganglia/Limbic Striatal and Thalamocortical Involvement in Craving and Loss of Control in Alcoholism", Journal of Neuropsychiatry, 2(2), (1990), pp. 123-144.

Nibuya, et al "Cronic Antidepressant Admllistration Increases the Expression of cAMP Response Element Binding Protein (CREB) in Rat Hippocampus". J. Neurosci., 16, (1996), pp. 2365-2372.

Paelecke-Habermann, et al. "Attention and executive functions in remitter major depression patients", J. Addictive Disorders, B9, (2005), pp. 125-135.

Pavuluri, et al. "Nuerocognitive Function in Pediatric Bipolar Disorder: 3-Year Follow-up Shows Cognitive Development Lagging Behind Healthy Youths", J. Am. Acad. Chid Adolesc. Psychiatry, 48:3, (2009). pp. 299-307.

Pliszka, Steven R. "The Neuropsychopharmacology of Attention-Dificit/Hiperactivity Disorder", Bioil Psychiatry, 57, (2005). pp. 1385-1390.

Post, et et al "Tolerance to the Prophylactic Effects of Carbamazepine and Pelated Mood Stabilizers in the Treatment of Bipolar Disorders",CNS Neuroscience & Therapeutics,17, (2011), pp. 649-660.

Priskaerts, et al. "cGMP. but not cAMP, in rat hippocampus is involved in early stage of object memory consolidation", European J. Of Pharmacology, 436, (2002), pp. 83-87.

Roberts, et al. Inhibitory Controland Affective Processing inthe PrefrontalCortex: NeuropsychologicalStudies in the CommonMarmoser. CerebralCortex, 10, (2000), pp. 252-262.

Rodefer.et al. PDE1OA inhibition reverses subchronic PCP-induced deficits in attentionalset-shifting in rats•, European J. of Neuroscience, 22, (2005), pp. 1070-1076.

Rutten, et al "Rolipram reverses scopolamine-induced and time-dependent memory deficits in object recognition by different mechanisms of action", Neurobiology of Learning and Memory, 85, (2006), pp. 132-138.

Rutten, et at "Time-dependent involvement of cAMP and cGMP in consolidation of object memory: Studies using selective phosphodiesterase type 2,3 and 5 inhibitors".European J. of Pharmacology, 558,(2007), pp. 107-112.

Sachs, et a.l "Cognitive Deficits in Bipolar Disorder", Neuropsychiatrie, 21(2), (2007), pp. 93-101 [English abstract only].

Schmidt, et al. "Prclinical Characterization of Selective Phosphodiesterase 10A Inhibitors: A New Therapeutic 46 Approach to the Treatment of Schizophrenia", The Journal of Pharmacology and Experimental Therapeutics, vol. 325, No. 2, (2008), pp. 681-690.

Seeger, et al. "Immunohistochemieal localization of PDE1OA in the rat brain", Brain Research, 985, (2003), pp. 113-126.

Siuciak, et al. "Genetic deletion of the stralatum-enriched phosphodiesterase PDE1OA: Evidence for altered striatal function", Neuropharmacology, 51, (2006). pp. 374-385.

\* cited by examiner

SUBSTITUTED PYRIDO[3,2-E][1,2,4]-TRIAZOLO[4,3-A] PYRAZINES FOR THE TREATMENT OF CENTRAL NERVOUS SYSTEM DISORDERS

FIELD OF THE INVENTION

The invention relates to 4-methyl-2,3,5,9,9b-pentaaza-cyclopenta[a]naphthalene derivatives of general formula (I) which are inhibitors of phosphodiesterase 2 and/or 10, useful in treating central nervous system diseases and other diseases. In addition, the invention relates to processes for preparing pharmaceutical compositions as well as processes for manufacture the compounds according to the invention.

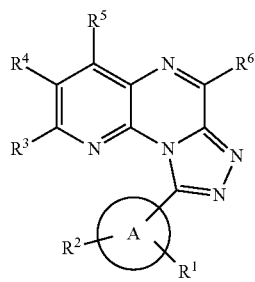

BACKGROUND OF THE INVENTION

Cognitive dysfunction plays a role in a number of central nervous system disorders, including neurological disorders, such as Alzheimer's disease (AD), Parkinson disease and dementia, but also psychiatric disorders, such as schizophrenia, depression and bipolar disorders. As world population grows older the number of patients with dementia and AD is growing. Therefore, most people are familiar with the cognitive deficits related to these neurological diseases (Massoud and Gauthier, 2010).

However, also in psychiatric disorders cognitive impairment adversely affect the progress and the treatment outcome of the disease. A most prominent example is schizophrenia. Schizophrenia has a heterogeneous symptomatic picture (American Psychiatric Association, 1994) that may be divided into three distinct disease domains: positive symptoms (psychotic episodes of hallucinations, delusions and agitation), negative symptoms (social withdrawal, anhedonia, flattened affect) and cognitive deficits (deficits in executive function, verbal learning and memory, verbal fluency) (Thompson and Meltzer, 1993).

Whereas positive symptoms are essentially alleviated by dopamine D2 receptor antagonist and second generation antipsychotics negative symptoms and cognitive deficits are still hardly affected by current treatments. Therefore, research on cognitive deficits in schizophrenia has been intensified over the past years. A worldwide network initiative, called MATRICS, has been founded to characterise the cognitive deficits more deeply and to find novel therapies (Young et al., 2009).

However, cognitive impairment is also seen in patients with depression, bipolar disorders (Sachs et al., 2007; Pavuluri et al., 2009) and in many patients with disorders usually first diagnosed in infancy, childhood and adolescence, such as attention deficit/hyperactivity disorder (ADHD) (Jucaite et al., 2005; Turner et al., 2003).

Depression is a severe mental disorder which extremely impairs daily life. Its prevalence is about 10% of the world population with an incidence of 2% according to WHO. Women are more affected than men and elder people more than younger people. The disorder mostly implies a life-long treatment due to the progression of the disease and permanent total disability.

The most prominent symptoms of the disease are anhedonia, feeling of hopelessness, decreased self esteem, loss of appetite and sleep disturbances. Suicide ideation is also a common symptom of depression and about 10% of depressed patients (Holma et al., 2010) attempt suicide. Depression is often combined with anxiety disorders. Interestingly, it is less known that depression is also regularly associated with various cognitive impairments (Gualtieri et al., 2006; Mandelli et al., 2006). Here, deficits of attentional and executive functions are mostly reported (Paelecke-Habermann et al., 2005). Cognitive deficits are even discussed to be involved in the development of the disease (Beck depression model, Beck, 2008). More recent studies indicate that the severity of the cognitive deficits may predict non-response to certain antidepressant treatment (Dunkin et al., 2000; Gorlyn et al., 2008).

Up to now, current antidepressant therapy seems not to be sufficient regarding cognitive deficits. Elder antidepressants are reported to impair memory in animal models of learning and memory probably due to their anticholinergic component (Kumar and Kulkarni, 1996). In contrast, SSRIs, in particular fluoxetine, are described to impair hippocampal-independent but not hippocampal dependent learning in different rodent models (Valluzi and Chan, 2007). At least, in clinic current therapy it is not possible to fully reverse cognitive deficits. Thus, in depressive patients who had been successfully treated cognitive performance could be improved but not normalised (Gualtieri et al., 2006). Therefore, an antidepressant with higher efficacy on cognitive impairment may improve disease outcome.

Bipolar disorders are characterized by complex symptomatology, including severe symptoms of mood disorders but also manic episodes and cognitive deficits. The Diagnostic and Statistical Manual, 4th edition and International Classification of Mental Disorder recommend subgroups of bipolar disorder based on whether depressive or manic [psychotic] symptoms and episodes are dominating and on the frequency of the episodes (Gaiwani, 2009). Pharmacological agents commonly used in the management of bipolar disorder include lithium; anticonvulsants, such as valproate, carbamazepine and lamotrigine; and recent years have witnessed increasing use of atypical antipsychotics (Altamura et al., 2011). As a problem of current therapy the development of tolerance against anticonvulsant treatment and 30% of treatment refractory cases are described (Post and Weiss, 2010; Gaiwani, 2009).

Attention deficit hyperactivity disorder (ADHD) is a central nervous system disorder that is mainly defined by its clinical signs. ADHD shows a heterogeneous symptom pattern in humans. The most important indicators are attention deficits, impulsivity and a hyperactivity that is primarily seen in boys. The disease starts at an early age and symptoms are most intense during childhood. After puberty the signs of the disease are more masked and focus on cognitive dysfunction (Jucaite et al. 2005; Turner et al. 2003). Although modern research broadened the understanding of the pathomechanism the exact etiology of the disease remains unclear.

Interestingly, the symptoms seen in ADHD are not due to a hyperactivity but a hypoactivity of the so called executive loop of the striatum (Winstanley et al., 2006; Plizska, 2005). The executive loop is responsible for the regulation of cognitive processes such as planning, working memory and attention (Benke et al., 2003; Easton et al., 2007). A dysfunction of the prefrontal cortex or other pathways within the loop induces impulsivity and a loss of the ability to filter stimuli that come from the outside. The latter causes the symptoms of sustained attention and hyperactivity (Roberts and Wallis, 2000; Gonzales et al., 2000). The dopaminergic neurotransmitter system plays a central role in regulating the activity of the executive loop (Jucaite et al., 2005). This conclusion is also supported by the current treatment for ADHD that aims for an activation of the dopaminergic neurotransmitter system (Jucaite et al., 2005).

Phosphodiesterases (PDE) are expressed in nearly all mammalian cells. To date eleven families of phosphodiesterases have been identified in mammals (Essayan, 2001). It is well established that PDEs are critically involved in cell signalling. Specifically, PDEs are known to inactivate the cyclic nucleotides cAMP and/or cGMP (Soderling and Beavo, 2000). The cyclic nucleotides cAMP and cGMP are synthesised by the adenylyl and guanylyl cyclases and are second messengers that control many key cellular functions. The synthesis of cAMP and cGMP is regulated by different G-protein-coupled receptor types including dopamine D1 and D2 receptors (Mutschler, 2001).

The phosphodiesterases of the different families vary in their substrate selectivity. Thus, some families only hydrolyse cAMP others only cGMP. Some phosphodiesterases, such as phosphodiesterase 2 and 10, inactivate both cAMP and cGMP (Menniti et al., 2006).

Furthermore, there is a difference in the distribution of the different phosphodiesterases within the organism and additionally, within any particular tissue or organ. For instance, the distribution pattern of the phosphodiesterases within the brain is quite specific (Menniti et al., 2006).

Finally, phosphodiesterase families have different regulatory properties and intracellular location; some are bound to cell membranes and some are dissociated in the cytoplasm, additionally, a division into various intracellular compartments has been reported (Conti and Jin, 1999).

These differences in the function and location of the different PDE enzyme families suggest that the individual phosphodiesterases are selectively involved in regulating many different physiological processes. Accordingly, selective phosphodiesterase inhibitors may with fine specificity regulate different physiological and pathophysiological processes.

PDE2 and PDE10 hydrolyse both, cGMP and cAMP (Menniti et al., 2006; Soderling et al., 1999; Kotera et al., 1999).

They are both abundantly expressed in the brain indicating their relevance in CNS function (Bolger et al., 1994; Menniti et al., 2001).

PDE2 mRNA is mainly distributed in olfactory bulb, olfactory tubercle, cortex, amygdala, striatum, and hippocampus (Lakics et al., 2005; van Staveren et al., 2003). PDE10 (PDE10A) is primarily expressed in the nucleus accumbens and the caudate putamen. Areas with moderate expression are the thalamus, hippocampus, frontal cortex and olfactory tubercle (Menniti et al., 2001).

Although there are certainly fine differences in the function and expression patterns of PDE2 and 10, the expression of PDE2 in the hippocampus, the cortex and in the striatum and the expression of PDE10 in striatum, hippocampus and frontal cortex indicate an involvement in the mechanism of learning and memory/cognition. This is further supported by the fact that increased levels of both cGMP and cAMP are involved in the process of short and long term potentiation (LTP) forming (Blokland et al., 2006; Prickaerts et al., 2002). LTP is regarded as the electrophysiological basis of long term memory (Baddeley, 2003). Boess et al. (2004) showed that PDE2 inhibitors amplify the generation of LTP. Additionally, it is reported that the selective PDE2 inhibitor BAY60-7550 enhances learning and memory in rats and mice in different animal models (Boess et al., 2004; Rutten et al., 2006). Similar pro-cognitive effects are described for selective PDE10 inhibitors, such as papaverine and MP-10. Rodefer et al. (2005) have found that papaverine reverses attentional set-shifting deficits induced by subchronic administration of phencyclidine, an NMDA antagonist, in rats. Grauer et al. (2009) could show a positive effect of papaverine and MP-10 on cognitive deficits in the novel object recognition and in prepulse inhibition of acoustic startle response in rats. These data support the procognitive effect of PDE2 and/or 10 and a synergistic effect of PDE2 and 10 on cognition.

Furthermore, the expression of PDE2 in the nucleus accumbens (part of the striatum), the olfactory bulb, the olfactory tubercle and the amygdala and the expression of PDE10 in the nucleus accumbens, the olfactory tubercle and the thalamus supports additional involvement of PDE2 and 10 in the pathophysiology of anxiety and depression (Modell et al., 1990). This is supported by in vivo studies. The selective PDE2 inhibitors BAY60-7550 and ND-7001 are described to be effective in animal models of anxiety and stress-induced behavior (Masood et al., 2008, 2009).

In addition to the pro-cognitive and antidepressant potential of PDE10 inhibition there is evidence for an additional antipsychotic potential of PDE10 inhibitors. In the striatum PDE10 is predominately found postsynaptic in the medium spiny neurons (Xie et al., 2006). By this location, PDE10 may have an important influence on the signal cascade induced by dopaminergic and glutamatergic input on the striatum, two neurotransmitter systems playing a predominate role in the pathomechanism of psychosis. Focusing on the dopaminergic input on the medium spiny neurons, PDE10A inhibitors by up-regulating cAMP and cGMP levels act as D1 agonists and D2 antagonists because the activation of Gs-protein coupled dopamine D1 receptor increases intracellular cAMP, whereas the activation of the Gi-protein coupled dopamine D2 receptor decreases intracellular cAMP levels through inhibition of adenylyl cyclase activity (Mutschler et al., 2001). Accordingly, PDE10 inhibitors are reported to be active in several animal models of schizophrenia (Schmidt et al., 2008; Siuciak et al., 2006; Grauer et al., 2009).

PDE10 inhibitors have been disclosed recently in J. Med. Chem, 2011, 54, 7621-7638.

For drugs with an intended action in the central nervous system (CNS), it is assumed that unbound drug in interstitial spaces in the brain is in direct contact or in equilibrium with the site of action (de Lange and Danhof, 2002).

It is commonly accepted that unbound or free drug is the species available for interaction with drug targets within the body, and this is referred to as the free drug hypothesis.

Because cerebrospinal fluid (CSF) is in direct contact with the brain tissue, it is assumed to readily equilibrate with brain interstitial fluid concentration (Meineke et al., 2002; Shen et al., 2004) so that CSF concentration is used as a common surrogate measure for drug unbound concentration in clinical pharmacology studies (Bonati et al., 1982; Cherubin et al., 1989; Garver, 1989; Reiter and Doron, 1996; Ostermann et al., 2004). Accordingly, for compounds with an intended action in the central nervous system it is important that they reach a high CSF concentration and a high CSF to plasma ratio in order to have high pharmacological activity in the CNS.

Inhibition of the hERG channel by xenobiotics and subsequent delayed cardiac repolarization is associated with an increased risk for a specific polymorphic ventricular tachyarrhythmia, torsade de pointes, as established by Sanguinetti et al. (1995, Cell, April 21, 81(2):299-307) and a large body of subsequent evidence. As such, low hERG channel inhibition, such as that shown by the compounds of the present invention, is highly desirable for therapeutics.

Several families of PDE2 inhibitors are known. Imidazotriazinones are claimed in WO 2002/068423 for the treatment of e.g. memory deficiency, cognitive disorders, dementia and Alzheimer's disease. Oxindoles are described in WO 2005/041957 for the treatment of dementia. Further inhibitors of PDE2 are known from WO 2007/121319 for the treatment of anxiety and depression, from WO 2013/034761, WO 2012/104293 and WO2013/000924 for the treatment of neurological and psychiatric disorders, from WO 2006/072615, WO 2006/072612, WO 2006/024640 and WO 2005/113517 for the treatment of arthritis, cancer, edema and septic shock, from WO 2005/063723 for the treatment of renal and liver failure, liver dysfunction, restless leg syndrome, rheumatic disorders, arthritis, rhinitis, asthma and obesity, from WO 2005/041957 for the treatment of cancer and thrombotic disorders, from WO 2006/102728 for the treatment of angina pectoris and hypertension from WO 2008/043461 for the treatment of cardiovascular disorders, erectile dysfunction, inflammation and renal failure and from WO 2005/061497 for the treatment of e.g. dementia, memory disorders, cancer and osteoporosis.

Finally, benzodiazepines are described in WO 2005/063723 for the general treatment of CNS diseases including anxiety, depression, ADHD, neurodegeneration, Alzheimer's disease and psychosis.

AIM OF THE INVENTION

It has now been found that compounds of the present invention according to general formula I are effective inhibitors of phosphodiesterase 2 and/or 10. Besides the inhibition property toward phosphodiesterase 2 and/or 10 enzymes, the compounds of the present invention provide further advantageous pharmacokinetic properties. For example the compounds of the present invention show high concentration in cerebrospinal fluid (CSF) and have a high CSF to plasma ratio, which translates in lower efficacious doses of the compounds for disease treatment and as a consequence in further potential advantages such as minimization of side effects. Furthermore, compounds of the present inventions show good metabolic stability and low potential of formation of biologically active metabolite and low hERG potassium channel inhibition.

Accordingly, one aspect of the invention refers to compounds according to formula I, the tautomers thereof, the stereoisomers thereof, the mixtures thereof, the solvates thereof, the hydrates thereof and salts thereof as inhibitors of phosphodiesterase 2 and/or 10.

Another aspect of the invention refers to compounds according to formula I, the tautomers thereof, the stereoisomers thereof, the mixtures thereof, the solvates thereof, the hydrates thereof and the physiologically acceptable salts thereof as inhibitors of phosphodiesterase 2 and/or 10 and reaching high concentrations in cerebrospinal fluid (CSF) and/or having high CSF to plasma ratio.

Another aspect of the invention refers to compounds according to formula I, the tautomers thereof, the stereoisomers thereof, the mixtures thereof, the solvates thereof, the hydrates thereof and the physiologically acceptable salts thereof as inhibitors of phosphodiesterase 2 and/or 10 and showing good metabolic stability.

Another aspect of the invention refers to compounds according to formula I, the tautomers thereof, the stereoisomers thereof, the mixtures thereof, the solvates thereof, the hydrates thereof and the physiologically acceptable salts thereof as inhibitors of phosphodiesterase 2 and/or 10 with low hERG channel inhibition.

Another aspect of the invention refers to compounds according to formula I, the tautomers thereof, the stereoisomers thereof, the mixtures thereof, the solvates thereof, the hydrates thereof and the physiologically acceptable salts thereof as inhibitors of phosphodiesterase 2 and/or 10 with low potential of forming biologically active metabolite.

In a further aspect this invention relates to pharmaceutical compositions, containing at least one compound according to formula I, the tautomers thereof, the stereoisomers thereof, the mixtures thereof, the solvates thereof, the hydrates thereof and the physiologically acceptable salts thereof optionally together with one or more inert carriers and/or diluents.

A further aspect of the present invention relates to compounds according to formula I, the tautomers thereof, the stereoisomers thereof, the mixtures thereof, the solvates thereof, the hydrates thereof and the physiologically acceptable salts thereof or pharmaceutical compositions comprising compounds according to formula I, the tautomers thereof, the stereoisomers thereof, the mixtures thereof, the solvates thereof, the hydrates thereof and the physiologically acceptable salts thereof for the use in the prevention and/or treatment of disorders associated with PDE2 and/or 10 hyperactivity and/or cAMP and/or cGMP hypofunction.

Another aspect of the invention relates to processes of manufacture of the compounds of the present invention.

A further aspect of the present invention relates to compounds according to formula I, the tautomers thereof, the stereoisomers thereof, the mixtures thereof, the solvates thereof, the hydrates thereof and the physiologically acceptable salts thereof or pharmaceutical compositions comprising compounds according to formula I, the tautomers thereof, the stereoisomers thereof, the mixtures thereof, the solvates thereof, the hydrates thereof and the physiologically acceptable salts thereof for the use in the prevention and/or treatment of diseases or conditions which can be influenced by inhibition of PDE2 and/or 10 hyperactivity and/or cAMP and/or cGMP hypofunction, such as (1) disorders comprising the symptom of cognitive deficiency; (2) organic, including symptomatic, mental disorders, dementia; (3) mental retardation; (4) mood affective disorders; (5) neurotic, stress-related and somatoform disorders including anxiety disorders; (6) behavioural and emotional disorders with onset usually occurring in childhood and adolescence, attention deficit hyperactivity syndrome (ADHD) including Autism spectrum disorders; (7) disorders of psychological development, developmental disorders of scholastic skills; (8) schizophrenia and other psychotic disorders; (9) disorders of adult personality and behaviour; (10) mental and behavioural disorders due to psychoactive substance use; (11) extrapyramidal and movement disorders; (12) episodic and paroxysmal disorders, epilepsy; (13) Systemic atrophies primarily affecting the central nervous system, ataxia; (14) Behavioural syndromes associated with physiological disturbances and physical factors; (15) sexual dysfunction comprising excessive sexual drive; (16) factitious disorders.

In addition, the compounds of the present invention can be used for the treatment, amelioration and/or prevention of cognitive impairment being related to perception, concentration, cognition, learning or memory.

In addition, the compounds of the present invention can be used for the treatment amelioration and/or prevention of cognitive impairment being related to age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, schizophrenia with dementia or Korsakoff's psychosis.

In addition, the compounds of the present invention can be used for the treatment of Alzheimer's disease.

In addition compounds of the present invention can be used for the treatment of pain disorders, including but not limited to inflammatory, neuropatic and osteoarthritic pain.

In addition, the compounds of the present invention can be used for the treatment of sleep disorders, bipolar disorder, metabolic syndrome, obesity, diabetis mellitus, hyperglycemia, dyslipidemia, impaired glucose tolerance, or a disease of the testes, brain, small intestine, skeletal muscle, heart, lung, thymus or spleen.

Other aims of the present invention will become apparent to the skilled man directly from the foregoing and following remarks.

DETAILED DESCRIPTION

In a first aspect the present invention relates to compounds of general formula I

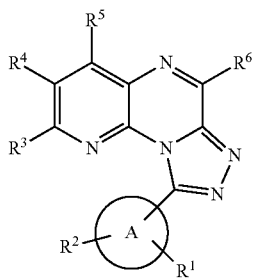

I wherein
A is selected from the group $A^a$ consisting of

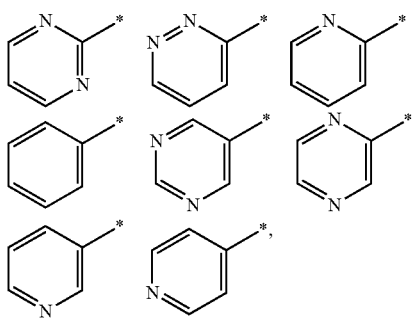

wherein above mentioned phenyl-, pyridinyl-, pyrimidinyl-, pyridazinyl and pyrazinyl groups are substituted with $R^1$ and $R^2$;

$R^1$ is selected from the group $R^{1a}$ consisting of
H, halogen, NC—, $C_{1-6}$-alkyl-, $C_{1-6}$-alkyl-O—, $C_{3-6}$-cycloalkyl and $R^8$—$(CH_2)_n$—O— with n=0, 1, 2, 3 or 4,
wherein above mentioned $C_{1-6}$-alkyl-, $C_{1-6}$-alkyl-O—, $C_{3-6}$-cycloalkyl and $R^8$—$(CH_2)_n$—O— groups may optionally be substituted with 1 to 5 substituents independently selected from the group consisting of halogen, HO— and optionally with 1 to 7 fluorine atoms substituted $C_{1-3}$-alkyl-;

$R^2$ is selected from the group $R^{2a}$ consisting of
H, HO—, halogen, $C_{1-6}$-alkyl-, $C_{1-6}$-alkyl-O—, $C_{3-6}$-cycloalkyl, heterocyclyl, heterocyclyl-$C_{1-3}$-alkyl-, phenyl, heteroaryl, $R^8$—$(CH_2)_n$—O— with n=0, 1, 2, 3 or 4, and $R^8$—$(CH_2)_m$—$(CH)(CH_3)$—$(CH_2)_o$—O— with m=0, 1 or 2 and o=0, 1 or 2,
wherein above mentioned $C_{1-6}$-alkyl-, $C_{1-6}$-alkyl-O—, $C_{3-6}$-cycloalkyl, heterocyclyl, heterocyclyl-$C_{1-3}$-alkyl-, phenyl, heteroaryl, $R^8$—$(CH_2)_n$—O— and $R^8$—$(CH_2)_m$—$(CH)(CH_3)$—$(CH_2)_o$—O-groups may optionally be substituted with 1 to 5 substituents independently selected from the group consisting of halogen, HO—, optionally with 1 to 7 fluorine atoms substituted $C_{1-3}$-alkyl-O—, and optionally with 1 to 7 fluorine atoms substituted $C_{1-3}$-alkyl-;

$R^3$ is selected from the group $R^{3a}$ consisting of
H, halogen, NC—, $C_{1-4}$-alkyl- and $C_{3-6}$-cycloalkyl-,
wherein the above mentioned $C_{1-4}$-alkyl- and $C_{3-6}$-cycloalkyl-groups may optionally be substituted with 1 to 9 substituents independently selected from the group consisting of halogen, NC—, HO—, $C_{1-3}$-alkyl- and $C_{1-3}$-alkyl-O—;

$R^4$, $R^5$ are selected independently of each other from the group $R^{4a}/R^{5a}$ consisting of
H, halogen, NC—, HO—, $C_{1-6}$-alkyl-, $C_{1-6}$-alkyl-O—, $C_{3-8}$-cycloalkyl-, $C_{3-8}$-cycloalkyl-$C_{1-3}$-alkyl-, $C_{3-8}$-cycloalkyl-O—, heterocyclyl-O—, heterocyclyl, heteroaryl, $R^7$—$CH_2$—O— and $R^7$—$(CH_2)_2$—O—,
wherein above mentioned $C_{1-6}$-alkyl-, $C_{1-6}$-alkyl-O—, $C_{3-8}$-cycloalkyl-, $C_{3-8}$-cycloalkyl-$C_{1-3}$-alkyl-, $C_{3-8}$-cycloalkyl-O—, heterocyclyl-O—, heterocyclyl, heteroaryl, $R^7$—$CH_2$—O— and $R^7$—$(CH_2)_2$—O-groups, may optionally be substituted with 1 to 5 substituents independently selected from the group consisting of halogen, optionally with 1 to 5 halogen atoms, substituted $C_{1-2}$-alkyl-, and optionally with 1 to 5 halogen atoms substituted $C_{1-2}$-alkyl-O—;

$R^6$ is selected from the group $R^{6a}$ consisting of
H, NC—, $C_{1-6}$-alkyl-, $C_{3-8}$-cycloalkyl-, $C_{3-8}$-cycloalkyl-$C_{1-3}$-alkyl- and $C_{3-8}$-cycloalkyl-O—
wherein above mentioned $C_{1-6}$-alkyl- groups may optionally be substituted with 1-3 halogen atoms;

$R^7$ is selected from the group $R^{7a}$ consisting of
H, carbocyclyl, heterocyclyl and heteroaryl,
wherein above mentioned carbocyclyl, heterocyclyl and heteroaryl-groups may optionally be substituted with 1 to 4 substituents independently selected from the group consisting of HO—, optionally with 1 to 3 halogen atoms substituted $C_{1-4}$-alkyl-, optionally with 1 to 3 halogen atoms substituted $C_{1-4}$-alkyl-O— and halogen;

$R^8$ is selected from the group $R^{8a}$ consisting of
$C_{3-6}$-cycloalkyl, heterocyclyl, heterocyclyl-$C_{1-3}$-alkyl-, phenyl and pyridyl,
wherein above mentioned $C_{3-6}$-cycloalkyl, heterocyclyl, heterocyclyl-$C_{1-3}$-alkyl-, phenyl and pyridyl groups may optionally be substituted with 1 to 5 substituents independently selected from the group consisting of HO—, fluorine and optionally with 1 to 7 halogen atoms substituted $C_{1-3}$-alkyl-;

the tautomers thereof, the stereoisomers thereof, the mixtures thereof, the solvates thereof, the hydrates thereof and the salts thereof.

Unless otherwise stated, the groups, residues, and substituents, particularly $R^1$, $R^2$, $R^3$, $R^{4/5}$, $R^6$, $R^7$, $R^8$ and A are defined as above and hereinafter. If residues, substituents, or groups occur several times in a compound they may have the same or different meanings. Some preferred meanings of groups and substituents of the compounds according to the invention will be given hereinafter.

In a further embodiment of the present invention
A is selected from the group $A^b$ consisting of

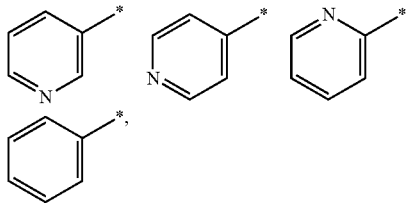

wherein above mentioned phenyl- and pyridinyl- groups are substituted with $R^1$ and $R^2$.

In a further embodiment of the present invention
A is selected from the group $A^c$ consisting of

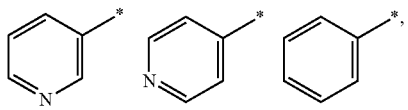

wherein above mentioned phenyl- and pyridinyl- groups are substituted with $R^1$ and $R^2$.

In a further embodiment of the present invention
A is selected from the group $A^d$ consisting of

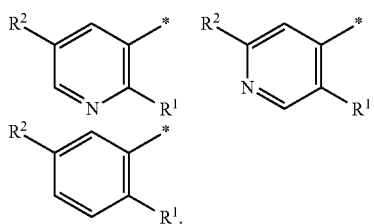

In a further embodiment of the present invention
A is selected from the group $A^e$ consisting of

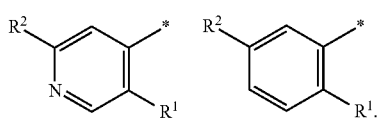

In a further embodiment of the present invention
A is selected from the group $A^f$ consisting of

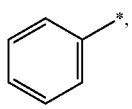

wherein above mentioned phenyl-group is substituted with $R^1$ and $R^2$.

In a further embodiment of the present invention
A is selected from the group $A^g$ consisting of

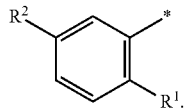

In a further embodiment of the present invention
$R^1$ is selected from the group $R^{1b}$ consisting of
H, halogen, $C_{1-6}$-alkyl- and $C_{3-6}$-cycloalkyl
wherein above mentioned $C_{1-6}$-alkyl- and $C_{3-6}$-cycloalkyl-groups may optionally be substituted with 1 to 5 substituents independently selected from the group consisting of halogen, HO— and optionally with 1 to 7 fluorine atoms substituted $C_{1-3}$-alkyl-.

In a further embodiment of the present invention
$R^1$ is selected from the group $R^{1c}$ consisting of
H, $H_3C$—, $F_3C$—, $F_2HC$—, $FH_2C$—, fluorine, chlorine and bromine.

In a further embodiment of the present invention
$R^1$ is selected from the group $R^{1c1}$ consisting of
$H_3C$—, fluorine and chlorine.

In a further embodiment of the present invention
$R^1$ is selected from the group $R^{1d}$ consisting of
H, fluorine and chlorine.

In a further embodiment of the present invention
$R^2$ is selected from the group $R^{2a1}$ consisting of
HO—, $C_{1-6}$-alkyl-, $C_{1-6}$-alkyl-O—, $C_{3-6}$-cycloalkyl, $C_{3-6}$-cycloalkyl-$C_{1-3}$-alkyl-, heterocyclyl, heterocyclyl-$C_{1-3}$-alkyl-, phenyl, heteroaryl, $R^8$—$(CH_2)_n$—O— with n=0, 1, 2, 3 or 4, and $R^8$—$(CH_2)_m$—$(CH)(CH_3)$—$(CH_2)_o$—O— with m=0, 1 or 2 and o=0, 1 or 2
wherein above mentioned $C_{1-6}$-alkyl- and $C_{1-6}$-alkyl-O- groups are substituted with 1 to 5 substituents independently selected from the group consisting of HO—, and optionally with 1 to 7 fluorine atoms substituted $C_{1-3}$-alkyl-O—,
and
wherein above mentioned $C_{1-6}$-alkyl- and $C_{1-6}$-alkyl-O- groups may optionally be substituted with 1 to 5 substituents independently selected from the group consisting of halogen, and optionally with 1 to 7 fluorine atoms substituted $C_{1-3}$-alkyl-,
and
wherein above mentioned $C_{3-6}$-cycloalkyl, $C_{3-6}$-cycloalkyl-$C_{1-3}$-alkyl-, heterocyclyl, heterocyclyl-$C_{1-3}$-alkyl-, phenyl, heteroaryl, $R^8$—$(CH_2)_n$—O— and $R^8$—$(CH_2)_m$—$(CH)(CH_3)$—$(CH_2)_o$—O-groups may optionally be substituted with 1 to 5 substituents independently selected from the group consisting of halogen, HO—, optionally with 1 to 7 fluorine atoms substituted $C_{1-3}$-alkyl-O—, and optionally with 1 to 7 fluorine atoms substituted $C_{1-3}$-alkyl-.

In a further embodiment of the present invention
$R^2$ is selected from the group $R^{2b}$ consisting of
H, HO—, $C_{1-4}$-alkyl-, $C_{1-4}$-alkyl-O—, $C_{3-6}$-cycloalkyl, heterocyclyl, heterocyclyl-$C_{1-3}$-alkyl-, phenyl, heteroaryl, $R^8$—$(CH_2)_n$—O— with n=0, 1, 2 or 3 and $R^8$—$(CH_2)_m$—$(CH)(CH_3)$—$(CH_2)_o$—O— with m=0 or 1 and o=0 or 1
wherein above mentioned $C_{1-4}$-alkyl-, $C_{1-4}$-alkyl-O—, $C_{3-6}$-cycloalkyl, heterocyclyl, heterocyclyl-$C_{1-3}$-alkyl-, $R^8$—$(CH_2)_n$—O— and $R^8$—$(CH_2)_m$—$(CH)(CH_3)$—$(CH_2)_o$—O-groups may optionally be substituted with 1 to 3 substituents independently selected from the group consisting of halogen, HO—, optionally with 1 to 7 fluorine atoms substituted $C_{1-3}$-alkyl-O—, and optionally with 1 to 7 fluorine atoms substituted $C_{1-3}$-alkyl-.

In a further embodiment of the present invention
$R^2$ is selected from the group $R^{2b1}$ consisting of
HO—, $C_{1-4}$-alkyl-, $C_{1-4}$-alkyl-O—, $C_{3-6}$-cycloalkyl, $C_{3-6}$-cycloalkyl-$C_{1-3}$-alkyl-, heterocyclyl, heterocyclyl-$C_{1-3}$-alkyl-, phenyl, heteroaryl, $R^8$—$(CH_2)_n$—O— with n=0, 1, 2 or 3 and $R^8$—$(CH_2)_m$—$(CH)(CH_3)$—$(CH_2)_o$—O— with m=0 or 1 and o=0 or 1
  wherein above mentioned $C_{1-4}$-alkyl- and $C_{1-4}$-alkyl-O— groups are substituted with 1 to 3 substituents independently selected from the group consisting of HO— and optionally with 1 to 7 fluorine atoms substituted $C_{1-3}$-alkyl-O—,
  and
  wherein above mentioned $C_{1-4}$-alkyl- and $C_{1-4}$-alkyl-O- groups may optionally be substituted with 1 to 3 substituents independently selected from the group consisting of halogen, and optionally with 1 to 7 fluorine atoms substituted $C_{1-3}$-alkyl-,
  and
  wherein above mentioned $C_{3-6}$-cycloalkyl-, $C_{3-6}$-cycloalkyl-$C_{1-3}$-alkyl-, heterocyclyl, heterocyclyl-$C_{1-3}$-alkyl-, $R^8$—$(CH_2)_n$—O— and $R^8$—$(CH_2)_m$—$(CH)(CH_3)$—$(CH_2)_o$—O-groups may optionally be substituted with 1 to 3 substituents independently selected from the group consisting of halogen, HO—, optionally with 1 to 7 fluorine atoms substituted $C_{1-3}$-alkyl-O—, and optionally with 1 to 7 fluorine atoms substituted $C_{1-3}$-alkyl-.

In a further embodiment of the present invention
$R^2$ is selected from the group $R^{2c}$ consisting of
H, HO—, $C_{1-4}$-alkyl-, $C_{1-4}$-alkyl-O—, $C_{3-6}$-cycloalkyl, heterocyclyl, $R^8$—$(CH_2)_n$—O— with n=0, 1, 2, or 3, and $R^8$—$(CH_2)_m$—$(CH)(CH_3)$—$(CH_2)_o$—O— with m=0 or 1 and o=0 or 1
  wherein above mentioned $C_{1-4}$-alkyl-, $C_{1-4}$-alkyl-O—, $C_{3-6}$-cycloalkyl, heterocyclyl, $R^8$—$(CH_2)_n$—O— and $R^8$—$(CH_2)_m$—$(CH)(CH_3)$—$(CH_2)_o$—O— groups may optionally be substituted with 1 to 5 substituents independently selected from the group consisting of halogen, HO—, optionally with 1 to 7 fluorine atoms substituted $C_{1-3}$-alkyl-O—, and optionally with 1 to 7 fluorine atoms substituted $C_{1-3}$-alkyl-.

In a further embodiment of the present invention
$R^2$ is selected from the group $R^{2c1}$ consisting of
HO—, $C_{1-4}$-alkyl-, $C_{1-4}$-alkyl-O—, $C_{3-6}$-cycloalkyl, $C_{3-6}$-cycloalkyl-$C_{1-3}$-alkyl-, heterocyclyl, $R^8$—$(CH_2)_n$—O— with n=0, 1, 2, or 3, and $R^8$—$(CH_2)_m$—$(CH)(CH_3)$—$(CH_2)_o$—O— with m=0 or 1 and o=0 or 1
  wherein above mentioned $C_{1-4}$-alkyl- and $C_{1-4}$-alkyl-O- groups are substituted with 1 to 5, preferably 1 to 3, substituents independently selected from the group consisting of HO—, and optionally with 1 to 7 fluorine atoms substituted $C_{1-3}$-alkyl-O—,
  and
  wherein above mentioned $C_{1-4}$-alkyl- and $C_{1-4}$-alkyl-O- groups may optionally be substituted with 1 to 5, preferably 1 to 3, substituents independently selected from the group consisting of halogen, and optionally with 1 to 7 fluorine atoms substituted $C_{1-3}$-alkyl-,
  and
  wherein above mentioned $C_{3-6}$-cycloalkyl-, $C_{3-6}$-cycloalkyl-$C_{1-3}$-alkyl-, heterocyclyl, $R^8$—$(CH_2)_n$—O— and $R^8$—$(CH_2)_m$—$(CH)(CH_3)$—$(CH_2)_o$—O— groups may optionally be substituted with 1 to 5, preferably 1 to 3, substituents independently selected from the group consisting of halogen, HO—, optionally with 1 to 7 fluorine atoms substituted $C_{1-3}$-alkyl-O—, and optionally with 1 to 7 fluorine atoms substituted $C_{1-3}$-alkyl-.

In a further embodiment of the present invention
$R^2$ is selected from the group $R^{2d}$ consisting of
H, HO—, $C_{1-4}$-alkyl-, $C_{1-4}$-alkyl-O—, a saturated 6 membered monocyclic heterocycle containing one heteroatom selected from N or O, $R^8$—$(CH_2)_n$—O— with n=0, 1 or 2, and $R^8$—$(CH_2)_m$—$(CH)(CH_3)$—$(CH_2)_o$—O— with m=0 or 1 and o=0 or 1
  wherein above mentioned $C_{1-4}$-alkyl-, $C_{1-4}$-alkyl-O—, saturated 6 membered monocyclic heterocycle containing one heteroatom selected from N or O, $R^8$—$(CH_2)_n$—O— and $R^8$—$(CH_2)_m$—$(CH)(CH_3)$—$(CH_2)_o$—O— groups may optionally be substituted with 1 to 5 substituents independently selected from the group consisting of halogen, HO—, optionally with 1 to 7 fluorine atoms substituted $C_{1-3}$-alkyl-O—, and optionally with 1 to 7 fluorine atoms substituted $C_{1-3}$-alkyl-.

In a further embodiment of the present invention
$R^2$ is selected from the group $R^{2d1}$ consisting of
HO—, $C_{1-4}$-alkyl-, $C_{1-4}$-alkyl-O—, $C_{3-6}$-cycloalkyl, $C_{3-6}$-cycloalkyl-$C_{1-3}$-alkyl-, a saturated 5 or 6 membered monocyclic heterocycle containing one heteroatom selected from N or O, $R^8$—$(CH_2)_n$—O— with n=0, 1 or 2, and $R^8$—$(CH_2)_m$—$(CH)(CH_3)$—$(CH_2)_o$—O— with m=0 or 1 and o=0 or 1
  wherein above mentioned $C_{1-4}$-alkyl- and $C_{1-4}$-alkyl-O- groups are substituted with 1 to 5, preferably 1 to 3, substituents independently selected from the group consisting of HO—, and optionally with 1 to 7 fluorine atoms substituted $C_{1-3}$-alkyl-O—,
  and
  wherein above mentioned $C_{1-4}$-alkyl- and $C_{1-4}$-alkyl-O- groups may optionally be substituted with 1 to 5, preferably 1 to 3, substituents independently selected from the group consisting of halogen, and optionally with 1 to 7 fluorine atoms substituted $C_{1-3}$-alkyl-,
  and
  wherein above mentioned $C_{3-6}$-cycloalkyl-, $C_{3-6}$-cycloalkyl-$C_{1-3}$-alkyl-, saturated 5 or 6 membered monocyclic heterocycle containing one heteroatom selected from N or O, $R^8$—$(CH_2)_n$—O— and $R^8$—$(CH_2)_m$—$(CH)(CH_3)$—$(CH_2)_o$—O— groups may optionally be substituted with 1 to 5, preferably 1 to 3, substituents independently selected from the group consisting of halogen, HO—, optionally with 1 to 7 fluorine atoms substituted $C_{1-3}$-alkyl-O—, and optionally with 1 to 7 fluorine atoms substituted $C_{1-3}$-alkyl-.

In a further embodiment of the present invention
$R^2$ is selected from the group $R^{2e}$ consisting of

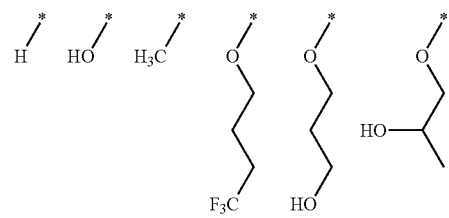

In a further embodiment of the present invention R² is selected from the group R²ᵉ¹ consisting of -continued

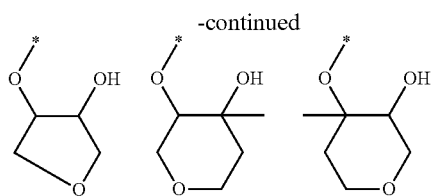

In a further embodiment of the present invention R² is selected from the group R²ᶠ consisting of

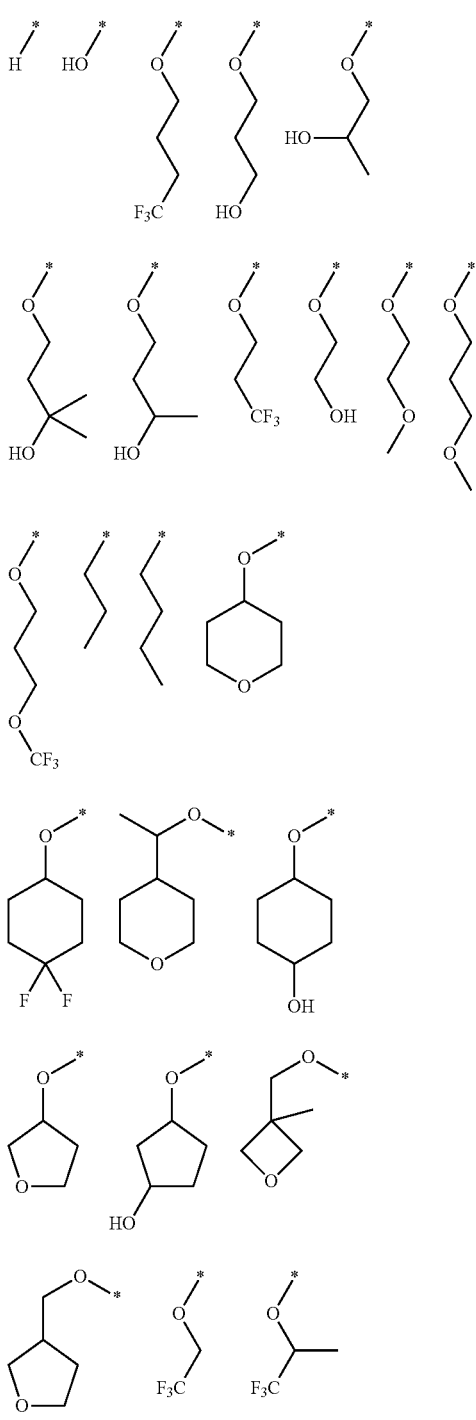

In a further embodiment of the present invention R² is selected from the group R²ᶠ¹ consisting of

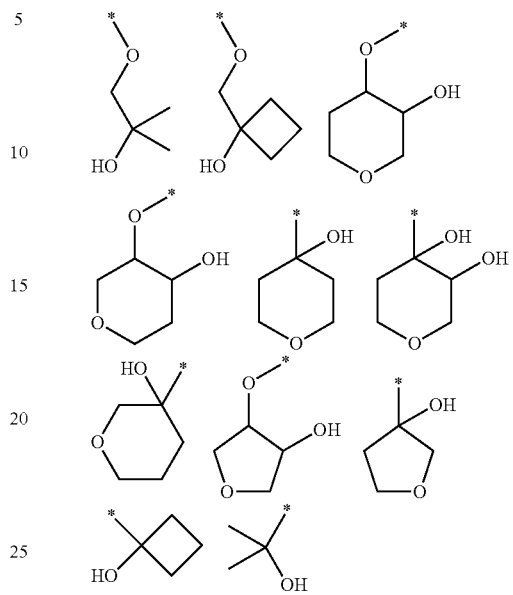

In a further embodiment of the present invention
R³ is selected from the group R³ᵃ¹ consisting of
$C_{3-6}$-cycloalkyl-,
  wherein the above mentioned $C_{3-6}$-cycloalkyl-group may optionally be substituted with 1 to 9 substituents independently selected from the group consisting of halogen, NC—, HO—, $C_{1-3}$-alkyl- and $C_{1-3}$-alkyl-O—.

In a further embodiment of the present invention
R³ is selected from the group R³ᵇ consisting of
H, $C_{1-3}$-alkyl-, cyclobutyl- and cyclopropyl-,
  wherein the above mentioned $C_{1-3}$-alkyl-, cyclobutyl- and cyclopropyl-groups may optionally be substituted with 1 to 7 substituents independently selected from the group consisting of halogen, $C_{1-3}$-alkyl-O—, NC— and HO—.

In a further embodiment of the present invention
R³ is selected from the group R³ᶜ consisting of
H, and $H_3C$— and cyclopropyl-,
  wherein the above mentioned $H_3C$— and cyclopropyl-groups may optionally be substituted with 1 to 3 fluorine atoms.

In a further embodiment of the present invention
R³ is selected from the group R³ᵈ consisting of
H and $H_3C$—,
  wherein the above mentioned $H_3C$-group may optionally be substituted with 1 to 3 fluorine atoms.

In a further embodiment of the present invention
R³ is selected from the group R³ᵉ consisting of
H.

In a further embodiment of the present invention
R³ is selected from the group R³ᶠ consisting of
$H_3C$—,
  wherein the above mentioned $H_3C$-group may optionally be substituted with 1 to 3 fluorine atoms.

In a further embodiment of the present invention
$R^3$ is selected from the group $R^{3g}$ consisting of
cyclopropyl-,
wherein the above mentioned cyclopropyl-group may optionally be substituted with 1 to 7 substituents independently selected from the group consisting of halogen, $C_{1-3}$-alkyl-O—, NC— and HO—.

In a further embodiment of the present invention
$R^4$, $R^5$ are selected independently of each other from the group $R^{4b}/R^{5b}$ consisting of
H, halogen, HO—, $H_3C$—, $F_3C$—, $H_3C$—O—, $F_2HC$—O—, $FH_2C$—O—, $F_3C$—O—, $C_{1-4}$-alkyl-O—, $R^7$—$CH_2$—O— and $R^7$—$(CH_2)_2$—O—,
wherein above mentioned $C_{1-4}$-alkyl-O—, $R^7$—$CH_2$—O— and $R^7$—$(CH_2)_2$—O— groups, may optionally be substituted with 1 to 5 substituents independently selected from the group consisting of halogen, optionally with 1 to 5 halogen atoms substituted $C_{1-2}$-alkyl-, and optionally with 1 to 5 halogen atoms substituted $C_{1-2}$-alkyl-O—.

In a further embodiment of the present invention
$R^4$, $R^5$ are selected independently of each other from the group $R^{4c}/R^{5c}$ consisting of
H, fluorine, chlorine, bromine, HO—, $H_3C$—, $F_3C$—, $H_3C$—O—, $F_3C$—O— and $R^7$—$CH_2$—O—.

In a further embodiment of the present invention
$R^4$, $R^5$ are selected from the group $R^{4d}/R^{5d}$ consisting of
H—.

In a further embodiment of the present invention
$R^6$ is selected from the group $R^{6b}$ consisting of
H, $C_{1-4}$-alkyl- and cyclopropyl-,
wherein above mentioned $C_{1-4}$-alkyl-group may optionally be substituted with 1-9 fluorine and/or chlorine atoms.

In a further embodiment of the present invention
$R^6$ is selected from the group $R^{6c}$ consisting of
H and $C_{1-2}$-alkyl-,
wherein above mentioned $C_{1-2}$-alkyl- group may optionally be substituted with 1-5 fluorine and/or chlorine atoms.

In a further embodiment of the present invention
$R^6$ is selected from the group $R^{6d}$ consisting of
H, $H_3C$—, $FH_2C$—, $F_2HC$— and $F_3C$—.

In a further embodiment of the present invention
$R^6$ is selected from the group $R^{6e}$ consisting of
$H_3C$—, $FH_2C$—, $F_2HC$— and $F_3C$—.

In a further embodiment of the present invention
$R^6$ is selected from the group $R^{6f}$ consisting of
$H_3C$—.

In a further embodiment of the present invention
$R^7$ is selected from the group $R^{7b}$ consisting of
H, phenyl, heteroaryl, cycloalkyl and heterocyclyl
wherein above mentioned phenyl, heteroaryl, cycloalkyl and heterocyclyl-groups may optionally be substituted with 1 to 4 substituents independently selected from the group consisting of halogen, and optionally with 1 to 3 halogen atoms substituted $C_{1-3}$-alkyl-O—.

In a further embodiment of the present invention
$R^7$ is selected from the group $R^{7c}$ consisting of
H and phenyl,
wherein above mentioned phenyl group may optionally be substituted with 1 to 4 substituents independently selected from the group consisting of halogen and optionally with 1 to 3 halogen atoms substituted $C_{1-3}$-alkyl-O—.

In a further embodiment of the present invention
$R^7$ is selected from the group $R^{7d}$ consisting of
H—.

In a further embodiment of the present invention
$R^8$ is selected from the group $R^{8b}$ consisting of
$C_{3-6}$-cycloalkyl, heterocyclyl and heterocyclyl-$C_{1-3}$-alkyl-,
wherein above mentioned $C_{3-6}$-cycloalkyl, heterocyclyl and heterocyclyl-$C_{1-3}$-alkyl-groups may optionally be substituted with 1 to 5 substituents independently selected from the group consisting of HO—, fluorine and optionally with 1 to 7 halogen atoms substituted $C_{1-3}$-alkyl-.

In a further embodiment of the present invention
$R^8$ is selected from the group $R^{8c}$ consisting of
$C_{3-6}$-cycloalkyl and heterocyclyl,
wherein above mentioned $C_{3-6}$-cycloalkyl and heterocyclyl-groups may optionally be substituted with 1 to 5 substituents independently selected from the group consisting of HO—, fluorine and optionally with 1 to 7 halogen atoms substituted $C_{1-3}$-alkyl-.

In a further embodiment of the present invention
$R^8$ is selected from the group $R^{8c1}$ consisting of
$C_{3-6}$-cycloalkyl and a saturated 4 to 6 membered monocyclic heterocycle containing one or two heteroatoms selected from N or O,
wherein above mentioned $C_{3-6}$-cycloalkyl and heterocyclyl-groups may optionally be substituted with 1 to 5 substituents independently selected from the group consisting of HO—, fluorine and optionally with 1 to 7 halogen atoms substituted $C_{1-3}$-alkyl-.

In a further embodiment of the present invention
$R^8$ is selected from the group $R^{8d}$ consisting of

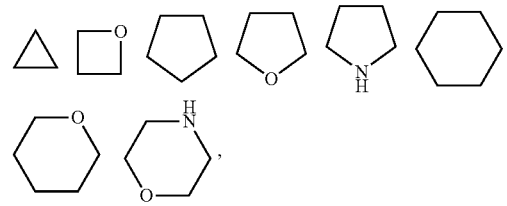

wherein above mentioned groups may optionally be substituted with 1 to 5 substituents independently selected from the group consisting of HO—, fluorine and optionally with 1 to 5 halogen atoms substituted $C_{1-3}$-alkyl-.

In a further embodiment of the present invention
$R^8$ is selected from the group $R^{8d1}$ consisting of

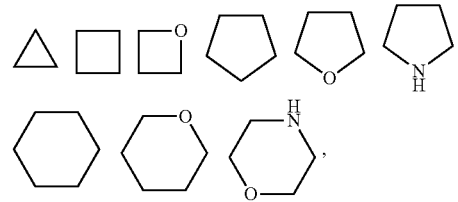

wherein above mentioned groups may optionally be substituted with 1 to 5 substituents independently selected from the group consisting of HO—, fluorine and optionally with 1 to 5 halogen atoms substituted $C_{1-3}$-alkyl-.

In a further embodiment of the present invention R$^8$ is selected from the group R$^{8e}$ consisting of

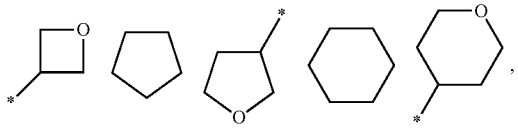

wherein above mentioned groups may optionally be substituted with 1 to 3 substituents independently selected from the group consisting of HO—, fluorine and optionally with 1 to 3 halogen atoms substituted C$_{1-3}$-alkyl-.

In a further embodiment of the present invention R$^8$ is selected from the group R$^{8e1}$ consisting of

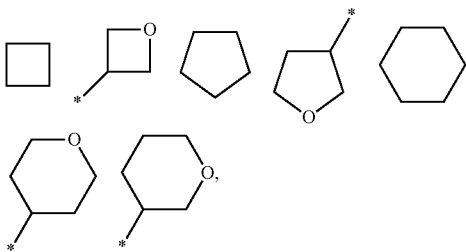

wherein above mentioned groups may optionally be substituted with 1 to 3 substituents independently selected from the group consisting of HO—, fluorine and optionally with 1 to 3 halogen atoms substituted C$_{1-3}$-alkyl-.

In a further embodiment of the present invention R$^8$ is selected from the group R$^{8f}$ consisting of

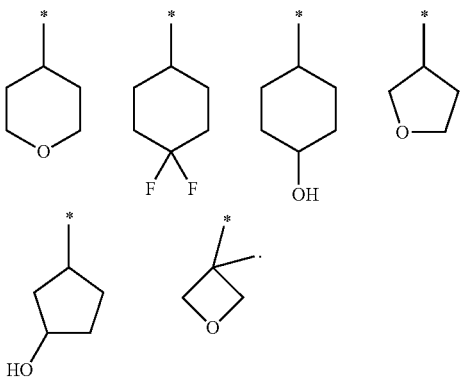

In a further embodiment of the present invention R is selected from the group R$^{8f1}$ consisting of

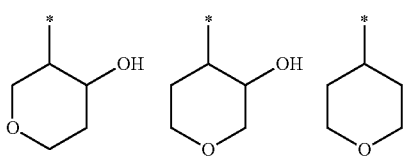

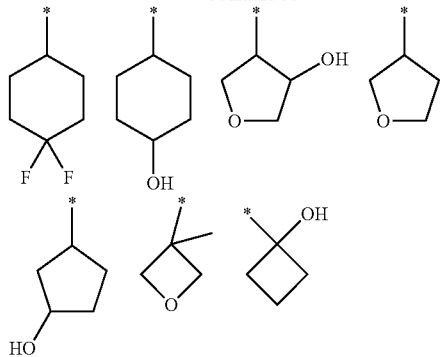

Each R$^{1x}$, R$^{2x}$, R$^{3x}$, R$^{4x/5x}$, R$^{8x}$, R$^{7x}$, R$^{8x}$ and A$^x$ represents a characterized, individual embodiment for the corresponding substituent as described above. Thus given the above definitions, preferred individual embodiments of the first aspect of the invention are fully characterized by the term (R$^{1x}$, R$^{2x}$, R$^{3x}$, R$^{4x/5x}$, R$^{8x}$, R$^{7x}$, R$^{8x}$ and A$^x$), wherein for each index x an individual figure is given that ranges from "a" to the highest letter given above. All individual embodiments described by the term in parentheses with full permutation of the indices x, referring to the definitions above, shall be comprised by the present invention.

The following Table 1 shows, exemplarily and in the order of increasing preference from the first line to the last line, such embodiments E-1 to E-37 of the invention that are considered preferred. This means that embodiment E-37, represented by the entries in the last row of Table 1, is the most preferred embodiment.

TABLE 1

Preferred embodiments E-1 to E-37 of the invention

| | A$^x$ | R$^{1x}$ | R$^{2x}$ | R$^{3x}$ | R$^{4x}$/R$^{5x}$ | R$^{6x}$ | R$^{7x}$ | R$^{8x}$ |
|---|---|---|---|---|---|---|---|---|
| E-1 | A$^b$ | R$^{1b}$ | R$^{2a}$ | R$^{3b}$ | R$^{4b}$/R$^{5b}$ | R$^{6b}$ | R$^{7b}$ | R$^{8a}$ |
| E-2 | A$^c$ | R$^{1b}$ | R$^{2a}$ | R$^{3b}$ | R$^{4b}$/R$^{5b}$ | R$^{6b}$ | R$^{7b}$ | R$^{8a}$ |
| E-3 | A$^c$ | R$^{1c}$ | R$^{2b}$ | R$^{3b}$ | R$^{4b}$/R$^{5b}$ | R$^{6b}$ | R$^{7c}$ | R$^{8b}$ |
| E-4 | A$^c$ | R$^{1c}$ | R$^{2b}$ | R$^{3c}$ | R$^{4c}$/R$^{5c}$ | R$^{6b}$ | R$^{7c}$ | R$^{8c}$ |
| E-5 | A$^c$ | R$^{1c}$ | R$^{2b}$ | R$^{3c}$ | R$^{4c}$/R$^{5c}$ | R$^{6b}$ | R$^{7d}$ | R$^{8c}$ |
| E-6 | A$^c$ | R$^{1c}$ | R$^{2c}$ | R$^{3c}$ | R$^{4c}$/R$^{5c}$ | R$^{6c}$ | R$^{7c}$ | R$^{8c}$ |
| E-7 | A$^c$ | R$^{1c}$ | R$^{2d}$ | R$^{3c}$ | R$^{4c}$/R$^{5c}$ | R$^{6c}$ | R$^{7c}$ | R$^{8d}$ |
| E-8 | A$^d$ | R$^{1c}$ | R$^{2d}$ | R$^{3d}$ | R$^{4d}$/R$^{5d}$ | R$^{6c}$ | — | R$^{8d}$ |
| E-9 | A$^e$ | R$^{1d}$ | R$^{2d}$ | R$^{3d}$ | R$^{4d}$/R$^{5d}$ | R$^{6e}$ | — | R$^{8f}$ |
| E-10 | A$^e$ | R$^{1d}$ | R$^{2e}$ | R$^{3d}$ | R$^{4d}$/R$^{5d}$ | R$^{6f}$ | — | — |
| E-11 | A$^f$ | R$^{1d}$ | R$^{2d}$ | R$^{3d}$ | R$^{4d}$/R$^{5d}$ | R$^{6e}$ | — | R$^{8f}$ |
| E-12 | A$^f$ | R$^{1d}$ | R$^{2e}$ | R$^{3d}$ | R$^{4d}$/R$^{5d}$ | R$^{6f}$ | — | — |
| E-13 | A$^f$ | R$^{1d}$ | R$^{2f}$ | R$^{3d}$ | R$^{4d}$/R$^{5d}$ | R$^{6e}$ | — | — |
| E-14 | A$^f$ | R$^{1d}$ | R$^{2f}$ | R$^{3d}$ | R$^{4d}$/R$^{5d}$ | R$^{6f}$ | — | — |
| E-15 | A$^a$ | R$^{1a}$ | R$^{2a}$ | R$^{3a1}$ | R$^{4a}$/R$^{5a}$ | R$^{6a}$ | R$^{7a}$ | R$^{8a}$ |
| E-16 | A$^b$ | R$^{1c}$ | R$^{2c}$ | R$^{3a1}$ | R$^{4b}$/R$^{5b}$ | R$^{6b}$ | R$^{7b}$ | R$^{8b}$ |
| E-17 | A$^d$ | R$^{1c}$ | R$^{2d}$ | R$^{3a1}$ | R$^{4c}$/R$^{5c}$ | R$^{6b}$ | — | R$^{8c}$ |
| E-18 | A$^e$ | R$^{1c}$ | R$^{2d}$ | R$^{3a1}$ | R$^{4d}$/R$^{5d}$ | R$^{6b}$ | — | R$^{8d}$ |
| E-19 | A$^g$ | R$^{1c}$ | R$^{2d}$ | R$^{3a1}$ | R$^{4d}$/R$^{5d}$ | R$^{6b}$ | — | R$^{8f}$ |
| E-20 | A$^d$ | R$^{1c}$ | R$^{2d}$ | R$^{3g}$ | R$^{4d}$/R$^{5d}$ | R$^{6b}$ | — | R$^{8c1}$ |
| E-21 | A$^e$ | R$^{1c}$ | R$^{2d}$ | R$^{3g}$ | R$^{4d}$/R$^{5d}$ | R$^{6b}$ | — | R$^{8d}$ |
| E-22 | A$^g$ | R$^{1c}$ | R$^{2d}$ | R$^{3g}$ | R$^{4d}$/R$^{5d}$ | R$^{6b}$ | — | R$^{8f}$ |
| E-23 | A$^a$ | R$^{1a}$ | R$^{2a1}$ | R$^{3a}$ | R$^{4a}$/R$^{5a}$ | R$^{6a}$ | R$^{7a}$ | R$^{8a}$ |
| E-24 | A$^b$ | R$^{1b}$ | R$^{2d1}$ | R$^{3a}$ | R$^{4c}$/R$^{5c}$ | R$^{6b}$ | R$^{7c}$ | R$^{8b}$ |
| E-25 | A$^c$ | R$^{1c}$ | R$^{2d1}$ | R$^{3a}$ | R$^{4d}$/R$^{5d}$ | R$^{6c}$ | — | R$^{8c1}$ |
| E-26 | A$^d$ | R$^{1c}$ | R$^{2d}$ | R$^{3b}$ | R$^{4d}$/R$^{5d}$ | R$^{6c}$ | — | R$^{8d1}$ |
| E-27 | A$^d$ | R$^{1c}$ | R$^{2d1}$ | R$^{3c}$ | R$^{4d}$/R$^{5d}$ | R$^{6d}$ | — | R$^{8e1}$ |
| E-28 | A$^d$ | R$^{1c1}$ | R$^{2c1}$ | R$^{3c}$ | R$^{4d}$/R$^{5d}$ | R$^{6d}$ | — | R$^{8f1}$ |
| E-29 | A$^e$ | R$^{1c}$ | R$^{2d1}$ | R$^{3b}$ | R$^{4d}$/R$^{5d}$ | R$^{6c}$ | — | R$^{8c1}$ |
| E-30 | A$^e$ | R$^{1c}$ | R$^{2d1}$ | R$^{3b}$ | R$^{4d}$/R$^{5d}$ | R$^{6d}$ | — | R$^{8d1}$ |
| E-31 | A$^e$ | R$^{1c1}$ | R$^{2e1}$ | R$^{3c}$ | R$^{4d}$/R$^{5d}$ | R$^{6e}$ | — | — |
| E-32 | A$^f$ | R$^{1c}$ | R$^{2d1}$ | R$^{3b}$ | R$^{4d}$/R$^{5d}$ | R$^{6c}$ | — | R$^{8e1}$ |
| E-33 | A$^f$ | R$^{1c1}$ | R$^{2e1}$ | R$^{3c}$ | R$^{4d}$/R$^{5d}$ | R$^{6e}$ | — | — |

TABLE 1-continued

Preferred embodiments E-1 to E-37 of the invention

| | $A^x$ | $R^{1x}$ | $R^{2x}$ | $R^{3x}$ | $R^{4x}/R^{5x}$ | $R^{6x}$ | $R^{7x}$ | $R^{8x}$ |
|---|---|---|---|---|---|---|---|---|
| E-34 | $A^f$ | $R^{1c1}$ | $R^{2f1}$ | $R^{3c}$ | $R^{4d}/R^{5d}$ | $R^{6f}$ | — | — |
| E-35 | $A^g$ | $R^{1c}$ | $R^{2c1}$ | $R^{3b}$ | $R^{4d}/R^{5d}$ | $R^{6c}$ | — | $R^{8e1}$ |
| E-36 | $A^g$ | $R^{1c}$ | $R^{2d1}$ | $R^{3c}$ | $R^{4d}/R^{5d}$ | $R^{6e}$ | — | $R^{8f1}$ |
| E-37 | $A^g$ | $R^{1c1}$ | $R^{2f1}$ | $R^{3c}$ | $R^{4d}/R^{5d}$ | $R^{6f}$ | — | — |

Accordingly, for example E-15 covers compounds of formula I, wherein
A is selected from the group $A^a$ consisting of

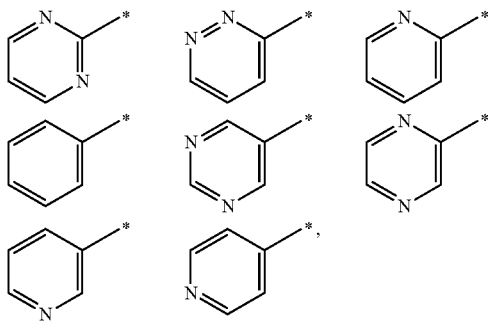

wherein above mentioned phenyl-, pyridinyl-, pyrimidinyl-, pyridazinyl- and pyrazinyl- groups are substituted with $R^1$ and $R^2$;
$R^1$ is selected from the group $R^{1a}$ consisting of
H, halogen, NC—, $C_{1-6}$-alkyl-, $C_{1-6}$-alkyl-O—, $C_{3-6}$-cycloalkyl and $R^8$—$(CH_2)_n$—O— with n=0, 1, 2, 3 or 4,
wherein above mentioned $C_{1-6}$-alkyl-, $C_{1-6}$-alkyl-O—, $C_{3-6}$-cycloalkyl and $R^8$—$(CH_2)_n$—O— groups may optionally be substituted with 1 to 5 substituents independently selected from the group consisting of halogen, HO— and optionally with 1 to 7 fluorine atoms substituted $C_{1-3}$-alkyl-;
$R^2$ is selected from the group $R^{2a}$ consisting of
H, HO—, halogen, $C_{1-6}$-alkyl-, $C_{1-6}$-alkyl-O—, $C_{3-6}$-cycloalkyl, heterocyclyl, heterocyclyl-$C_{1-3}$-alkyl-, phenyl, heteroaryl, $R^8$—$(CH_2)_n$—O— with n=0, 1, 2, 3 or 4, and $R^8$—$(CH_2)_m$—$(CH)(CH_3)$—$(CH_2)_o$—O— with m=0, 1 or 2 and o=0, 1 or 2,
wherein above mentioned $C_{1-6}$-alkyl-, $C_{1-6}$-alkyl-O—, $C_{3-6}$-cycloalkyl, heterocyclyl, heterocyclyl-$C_{1-3}$-alkyl-, phenyl, heteroaryl, $R^8$—$(CH_2)_n$—O— and $R^8$—$(CH_2)_m$—$(CH)(CH_3)$—$(CH_2)_o$—O-groups
may optionally be substituted with 1 to 5 substituents independently selected from the group consisting of halogen, HO—, optionally with 1 to 7 fluorine atoms substituted $C_{1-3}$-alkyl-O—, and optionally with 1 to 7 fluorine atoms substituted $C_{1-3}$-alkyl-;
$R^3$ is selected from the group $R^{3a1}$ consisting of
$C_{3-6}$-cycloalkyl-,
wherein the above mentioned $C_{3-6}$-cycloalkyl-group may optionally be substituted with 1 to 9 substituents independently selected from the group consisting of halogen, NC—, HO—, $C_{1-3}$-alkyl- and $C_{1-3}$-alkyl-O—;
$R^4$, $R^5$ are selected independently of each other from the group $R^{4a}/R^{5a}$ consisting of
H, halogen, NC—, HO—, $C_{1-6}$-alkyl-, $C_{1-6}$-alkyl-O—, $C_{3-8}$-cycloalkyl-, $C_{3-8}$-cycloalkyl-$C_{1-3}$-alkyl-, $C_{3-8}$-cycloalkyl-O—, heterocyclyl-O—, heterocyclyl, heteroaryl, $R^7$—$CH_2$—O— and $R^7$—$(CH_2)_2$—O—,
wherein above mentioned $C_{1-6}$-alkyl-, $C_{1-6}$-alkyl-O—, $C_{3-8}$-cycloalkyl-, $C_{3-8}$-cycloalkyl-$C_{1-3}$-alkyl-, $C_{3-8}$-cycloalkyl-O—, heterocyclyl-O—, heterocyclyl, heteroaryl, $R^7$—$CH_2$—O— and $R^7$—$(CH_2)_2$—O-groups, may optionally be substituted with 1 to 5 substituents independently selected from the group consisting of halogen, optionally with 1 to 5 halogen atoms, substituted $C_{1-2}$-alkyl-, and optionally with 1 to 5 halogen atoms substituted $C_{1-2}$-alkyl-O—;
$R^6$ is selected from the group $R^{6a}$ consisting of
H, NC—, $C_{1-6}$-alkyl-, $C_{3-8}$-cycloalkyl-, $C_{3-8}$-cycloalkyl-$C_{1-3}$-alkyl- and $C_{3-8}$-cycloalkyl-O—
wherein above mentioned $C_{1-6}$-alkyl- groups may optionally be substituted with 1-3 halogen atoms;
$R^7$ is selected from the group $R^{7a}$ consisting of
H, carbocyclyl, heterocyclyl and heteroaryl,
wherein above mentioned carbocyclyl, heterocyclyl and heteroaryl-groups may optionally be substituted with 1 to 4 substituents independently selected from the group consisting of HO—, optionally with 1 to 3 halogen atoms substituted $C_{1-4}$-alkyl-, optionally with 1 to 3 halogen atoms substituted $C_{1-4}$-alkyl-O— and halogen;
$R^8$ is selected from the group $R^{8a}$ consisting of
$C_{3-6}$-cycloalkyl, heterocyclyl, heterocyclyl-$C_{1-3}$-alkyl-, phenyl and pyridyl,
wherein above mentioned $C_{3-6}$-cycloalkyl, heterocyclyl, heterocyclyl-$C_{1-3}$-alkyl-, phenyl and pyridyl groups may optionally be substituted with 1 to 5 substituents independently selected from the group consisting of HO—, fluorine and optionally with 1 to 7 halogen atoms substituted $C_{1-3}$-alkyl-;
the tautomers thereof, the stereoisomers thereof, the mixtures thereof, the solvates thereof, the hydrates thereof and the salts thereof.

Accordingly, for example E-23 covers compounds of formula I, wherein
A is selected from the group $A^a$ consisting of

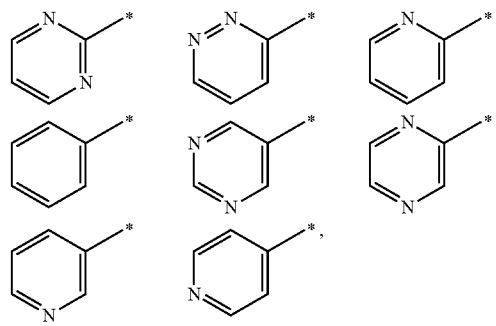

wherein above mentioned phenyl-, pyridinyl-, pyrimidinyl-, pyridazinyl- and pyrazinyl- groups are substituted with $R^1$ and $R^2$;
$R^1$ is selected from the group $R^{1a}$ consisting of
H, halogen, NC—, $C_{1-6}$-alkyl-, $C_{1-6}$-alkyl-O—, $C_{3-6}$-cycloalkyl and $R^8$—$(CH_2)_n$—O— with n=0, 1, 2, 3 or 4,
wherein above mentioned $C_{1-6}$-alkyl-, $C_{1-6}$-alkyl-O—, $C_{3-6}$-cycloalkyl and $R^8$—$(CH_2)_n$—O— groups may optionally be substituted with 1 to 5 substituents independently selected from the group consisting of halogen, HO— and optionally with 1 to 7 fluorine atoms substituted $C_{1-3}$-alkyl-;

$R^2$ is selected from the group $R^{2a1}$ consisting of
  HO—, $C_{1-6}$-alkyl-, $C_{1-6}$-alkyl-O—, $C_{3-6}$-cycloalkyl, $C_{3-6}$-cycloalkyl-$C_{1-3}$-alkyl-, heterocyclyl, heterocyclyl-$C_{1-3}$-alkyl-, phenyl, heteroaryl, $R^8$—$(CH_2)_n$—O— with n=0, 1, 2, 3 or 4, and $R^8$—$(CH_2)_m$—(CH)(CH$_3$)—$(CH_2)_o$—O— with m=0, 1 or 2 and o=0, 1 or 2
    wherein above mentioned $C_{1-6}$-alkyl- and $C_{1-6}$-alkyl-O- groups are substituted with 1 to 5 substituents independently selected from the group consisting of HO—, and optionally with 1 to 7 fluorine atoms substituted $C_{1-3}$-alkyl-O—,
    and
    wherein above mentioned $C_{1-6}$-alkyl- and $C_{1-6}$-alkyl-O- groups may optionally be substituted with 1 to 5 substituents independently selected from the group consisting of halogen, and optionally with 1 to 7 fluorine atoms substituted $C_{1-3}$-alkyl-,
    and
    wherein above mentioned $C_{3-6}$-cycloalkyl, $C_{3-6}$-cycloalkyl-$C_{1-3}$-alkyl-, heterocyclyl, heterocyclyl-$C_{1-3}$-alkyl-, phenyl, heteroaryl, $R^8$—$(CH_2)_n$—O— and $R^8$—$(CH_2)_m$—(CH)(CH$_3$)—$(CH_2)_o$—O-groups may optionally be substituted with 1 to 5 substituents independently selected from the group consisting of halogen, HO—, optionally with 1 to 7 fluorine atoms substituted $C_{1-3}$-alkyl-O—, and optionally with 1 to 7 fluorine atoms substituted $C_{1-3}$-alkyl-;
$R^3$ is selected from the group $R^{3a}$ consisting of
  H, halogen, NC—, $C_{1-4}$-alkyl- and $C_{3-6}$-cycloalkyl-,
    wherein the above mentioned $C_{1-4}$-alkyl- and $C_{3-6}$-cycloalkyl-groups may optionally be substituted with 1 to 9 substituents independently selected from the group consisting of halogen, NC—, HO—, $C_{1-3}$-alkyl- and $C_{1-3}$-alkyl-O—;
$R^4$, $R^5$ are selected independently of each other from the group $R^{4a}/R^{5a}$ consisting of
  H, halogen, NC—, HO—, $C_{1-6}$-alkyl-, $C_{1-6}$-alkyl-O—, $C_{3-8}$-cycloalkyl-, $C_{3-8}$-cycloalkyl-$C_{1-3}$-alkyl-, $C_{3-8}$-cycloalkyl-O—, heterocyclyl-O—, heterocyclyl, heteroaryl, $R^7$—$CH_2$—O— and $R^7$—$(CH_2)_2$—O—,
    wherein above mentioned $C_{1-6}$-alkyl-, $C_{1-6}$-alkyl-O—, $C_{3-8}$-cycloalkyl-, $C_{3-8}$-cycloalkyl-$C_{1-3}$-alkyl-, $C_{3-8}$-cycloalkyl-O—, heterocyclyl-O—, heterocyclyl, heteroaryl, $R^7$—$CH_2$—O— and $R^7$—$(CH_2)_2$—O- groups, may optionally be substituted with 1 to 5 substituents independently selected from the group consisting of halogen, optionally with 1 to 5 halogen atoms, substituted $C_{1-2}$-alkyl-, and optionally with 1 to 5 halogen atoms substituted $C_{1-2}$-alkyl-O—;
$R^6$ is selected from the group $R^{6a}$ consisting of
  H, NC—, $C_{1-6}$-alkyl-, $C_{3-8}$-cycloalkyl-, $C_{3-8}$-cycloalkyl-$C_{1-3}$-alkyl- and $C_{3-8}$-cycloalkyl-O—
    wherein above mentioned $C_{1-6}$-alkyl- groups may optionally be substituted with 1-3 halogen atoms;
$R^7$ is selected from the group $R^{7a}$ consisting of
  H, carbocyclyl, heterocyclyl and heteroaryl,
    wherein above mentioned carbocyclyl, heterocyclyl and heteroaryl-groups may optionally be substituted with 1 to 4 substituents independently selected from the group consisting of HO—, optionally with 1 to 3 halogen atoms substituted $C_{1-4}$-alkyl-, optionally with 1 to 3 halogen atoms substituted $C_{1-4}$-alkyl-O— and halogen;
$R^8$ is selected from the group $R^{8a}$ consisting of
  $C_{3-6}$-cycloalkyl, heterocyclyl, heterocyclyl-$C_{1-3}$-alkyl-, phenyl and pyridyl,
    wherein above mentioned $C_{3-6}$-cycloalkyl, heterocyclyl, heterocyclyl-$C_{1-3}$-alkyl-, phenyl and pyridyl groups may optionally be substituted with 1 to 5 substituents independently selected from the group consisting of HO—, fluorine and optionally with 1 to 7 halogen atoms substituted $C_{1-3}$-alkyl-;

the tautomers thereof, the stereoisomers thereof, the mixtures thereof, the solvates thereof, the hydrates thereof and the salts thereof.

Accordingly, for example E-29 covers compounds of formula I,
wherein
A is selected from the group $A^e$ consisting of

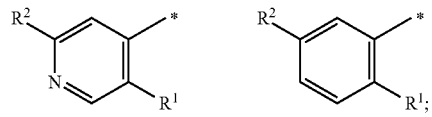

$R^1$ is selected from the group $R^{1c}$ consisting of
  H, $H_3C$—, $F_3C$—, $F_2HC$—, $FH_2C$—, fluorine, chlorine and bromine:
$R^2$ is selected from the group $R^{2d1}$ consisting of
  HO—, $C_{1-4}$-alkyl-, $C_{1-4}$-alkyl-O—, $C_{3-6}$-cycloalkyl, $C_{3-6}$-cycloalkyl-$C_{1-3}$-alkyl-, a saturated 5 or 6 membered monocyclic heterocycle containing one heteroatom selected from N or O, $R^8$—$(CH_2)_n$—O— with n=0, 1 or 2, and $R^8$—$(CH_2)_m$—(CH)(CH$_3$)—$(CH_2)_o$—O— with m=0 or 1 and o=0 or 1
    wherein above mentioned $C_{1-4}$-alkyl- and $C_{1-4}$-alkyl-O- groups are substituted with 1 to 5, preferably 1 to 3, substituents independently selected from the group consisting of HO—, and optionally with 1 to 7 fluorine atoms substituted $C_{1-3}$-alkyl-O—,
    and
    wherein above mentioned $C_{1-4}$-alkyl- and $C_{1-4}$-alkyl-O- groups may optionally be substituted with 1 to 5, preferably 1 to 3, substituents independently selected from the group consisting of halogen, and optionally with 1 to 7 fluorine atoms substituted $C_{1-3}$-alkyl-,
    and
    wherein above mentioned $C_{3-6}$-cycloalkyl-, $C_{3-6}$-cycloalkyl-$C_{1-3}$-alkyl-, saturated 5 or 6 membered monocyclic heterocycle containing one heteroatom selected from N or O, $R^8$—$(CH_2)_n$—O— and $R^8$—$(CH_2)_m$—(CH)(CH$_3$)—$(CH_2)_o$—O— groups may optionally be substituted with 1 to 5, preferably 1 to 3, substituents independently selected from the group consisting of halogen, HO—, optionally with 1 to 7 fluorine atoms substituted $C_{1-3}$-alkyl-O—, and optionally with 1 to 7 fluorine atoms substituted $C_{1-3}$-alkyl-;
$R^3$ is selected from the group $R^{3b}$ consisting of
  H, $C_{1-3}$-alkyl-, cyclobutyl- and cyclopropyl-,
    wherein the above mentioned $C_{1-3}$-alkyl-, cyclobutyl-, and cyclopropyl-groups may optionally be substituted with 1 to 7 substituents independently selected from the group consisting of halogen, $C_{1-3}$-alkyl-O—, NC— and HO—;

$R^4$, $R^5$ are selected from the group $R^{4d}/R^{5d}$ consisting of
H;
$R^6$ is selected from the group $R^{6c}$ consisting of
H and $C_{1-2}$-alkyl-,
wherein above mentioned $C_{1-2}$-alkyl- group may optionally be substituted with 1-5 fluorine and/or chlorine atoms;
$R^8$ is selected from the group $R^{8c1}$ consisting of
$C_{3-6}$-cycloalkyl and a saturated 4 to 6 membered monocyclic heterocycle containing one or two heteroatoms selected from N or O,
wherein above mentioned $C_{3-6}$-cycloalkyl and heterocyclyl-groups may optionally be substituted with 1 to 5 substituents independently selected from the group consisting of HO—, fluorine and optionally with 1 to 7 halogen atoms substituted $C_{1-3}$-alkyl-;
the tautomers thereof, the stereoisomers thereof, the mixtures thereof, the solvates thereof, the hydrates thereof and the salts thereof.

Accordingly, for example E-37 covers compounds of formula I,
wherein
A is selected from the group $A^9$ consisting of

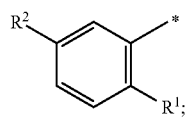

$R^1$ is selected from the group $R^{1c1}$ consisting of
$H_3C$—, fluorine and chlorine;
$R^2$ is selected from the group $R^{2f1}$ consisting of

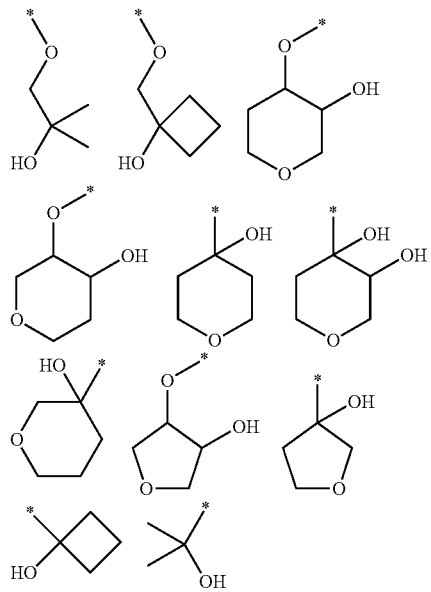

$R^3$ is selected from the group $R^{3c}$ consisting of
H, and $H_3C$— and cyclopropyl-,
wherein the above mentioned $H_3C$— and cyclopropyl- groups may optionally be substituted with 1 to 3 fluorine atoms;

$R^4$, $R^5$ are selected from the group $R^{4d}/R^{5d}$ consisting of
H;
$R^6$ is selected independently of each other from the group $R^{6f}$ consisting of
$H_3C$—;
the tautomers thereof, the stereoisomers thereof, the mixtures thereof, the solvates thereof, the hydrates thereof and the salts thereof.

Further preferred are the following compounds listed in table 2:

| No. | Structure |
|---|---|
| I | ![structure I] |
| II | ![structure II] |
| III | ![structure III] |
| IV | ![structure IV] |
| V | ![structure V] |

-continued
| No. | Structure |
|---|---|
| VI | 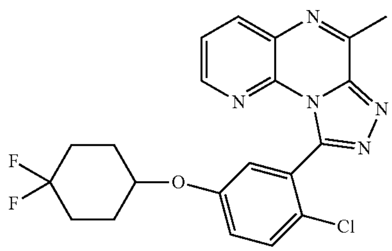 [SMILES: Cc1nc2cccnc2n2c(-c3cc(OC4CCC(F)(F)CC4)ccc3Cl)nnc12] |
| VII | 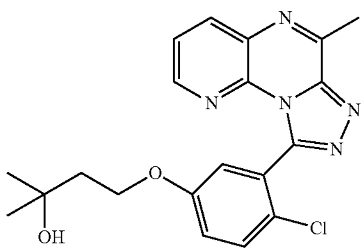 [SMILES: Cc1nc2cccnc2n2c(-c3cc(OCCC(C)(C)O)ccc3Cl)nnc12] |
| VIII | 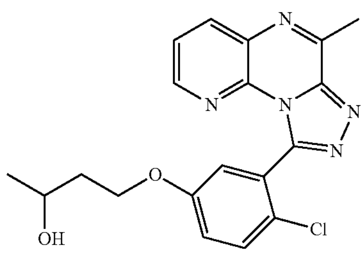 [SMILES: Cc1nc2cccnc2n2c(-c3cc(OCCC(C)O)ccc3Cl)nnc12] |
| IX | 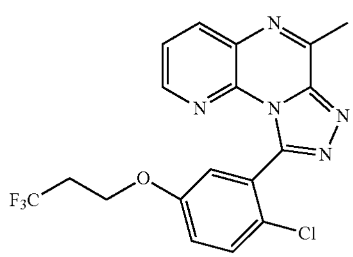 [SMILES: Cc1nc2cccnc2n2c(-c3cc(OCCC(F)(F)F)ccc3Cl)nnc12] |
| X | 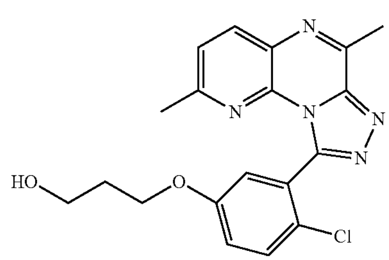 [SMILES: Cc1ccc2nc(C)c3nnc(-c4cc(OCCCO)ccc4Cl)n3c2n1] |
| XI | 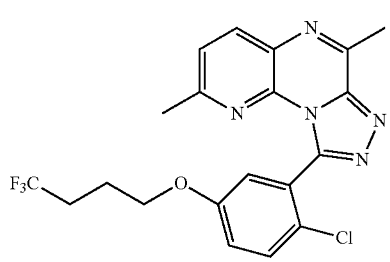 [SMILES: Cc1ccc2nc(C)c3nnc(-c4cc(OCCCC(F)(F)F)ccc4Cl)n3c2n1] |
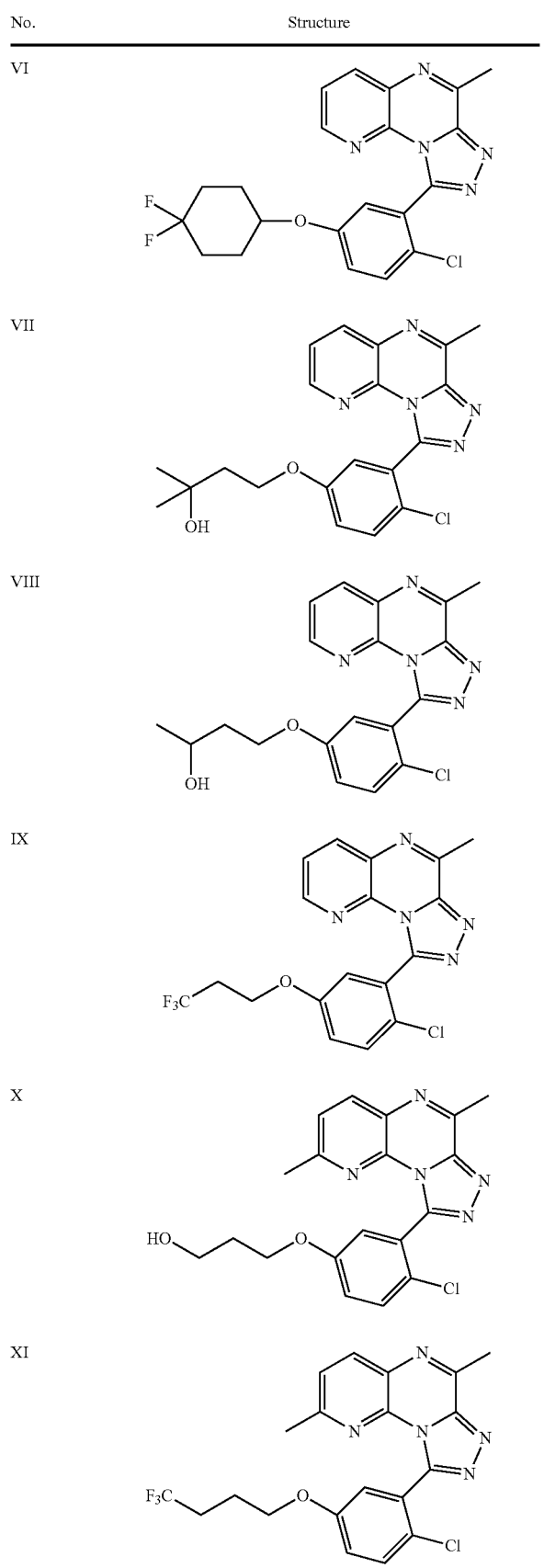
-continued
| No. | Structure |
|---|---|
| XII | 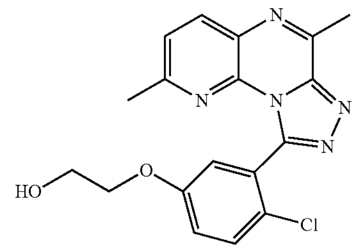 [SMILES: Cc1ccc2nc(C)c3nnc(-c4cc(OCCO)ccc4Cl)n3c2n1] |
| XIII | 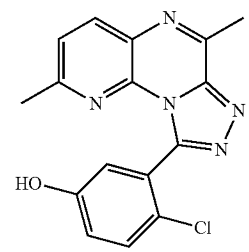 |
| XIV | 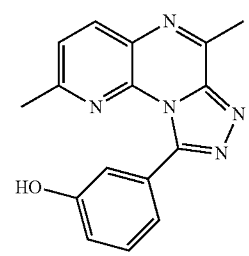 |
| XV | 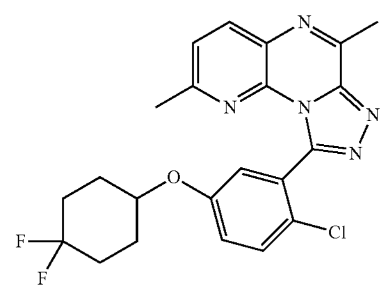 [SMILES: Cc1ccc2nc(C)c3nnc(-c4cc(OC5CCC(F)(F)CC5)ccc4Cl)n3c2n1] |
| XVI | 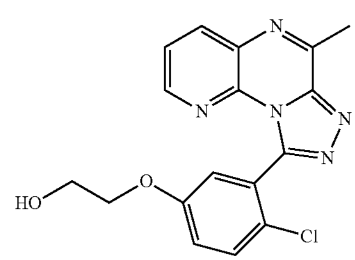 [SMILES: Cc1nc2cccnc2n2c(-c3cc(OCCO)ccc3Cl)nnc12] |
| XVII | 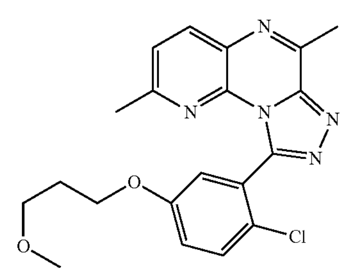 [SMILES: COCCCOc1ccc(Cl)c(-c2nnc3c(C)nc4ccc(C)nc4n23)c1] |
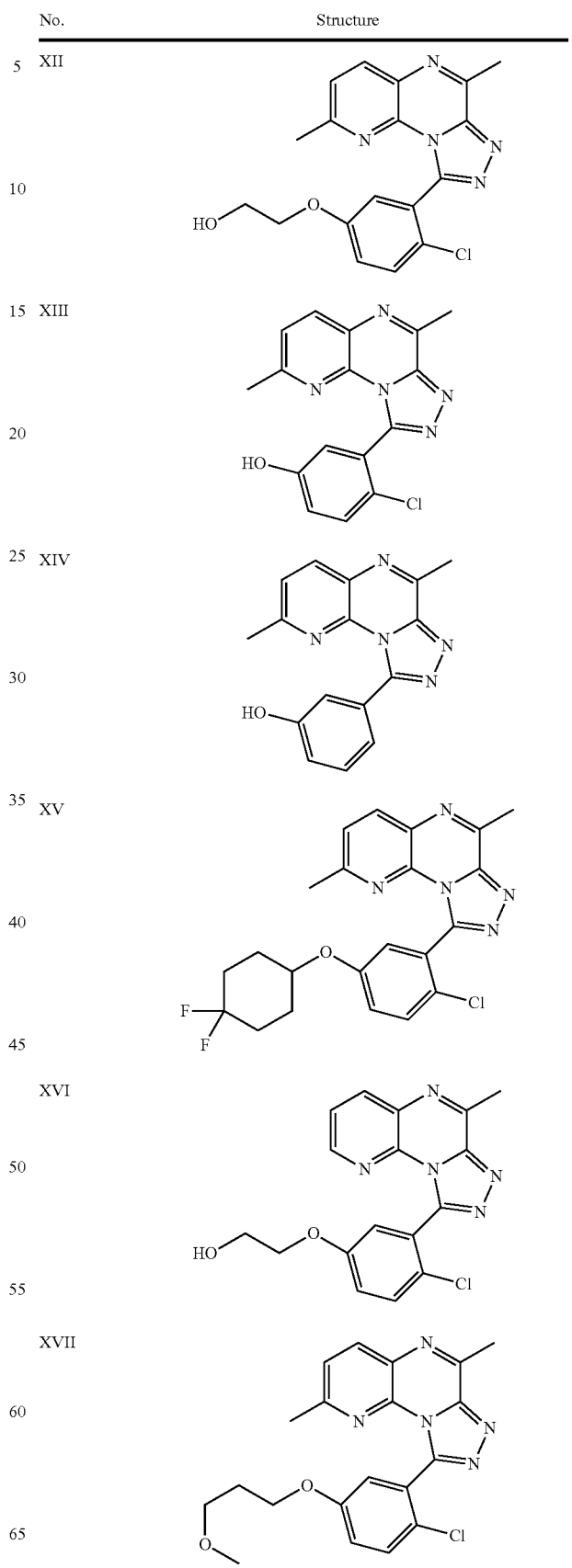

| No. | Structure |
|---|---|
| XVIII | 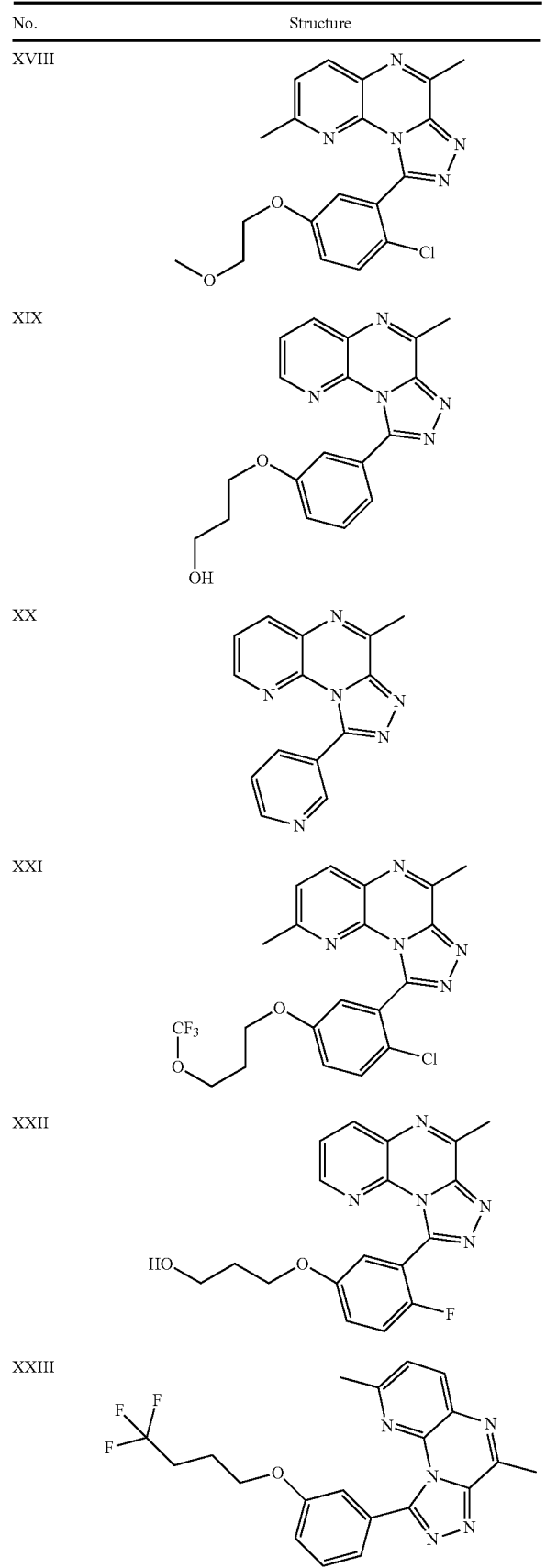 |
| XIX | |
| XX | |
| XXI | |
| XXII | |
| XXIII | |
| No. | Structure |
|---|---|
| XXIV | 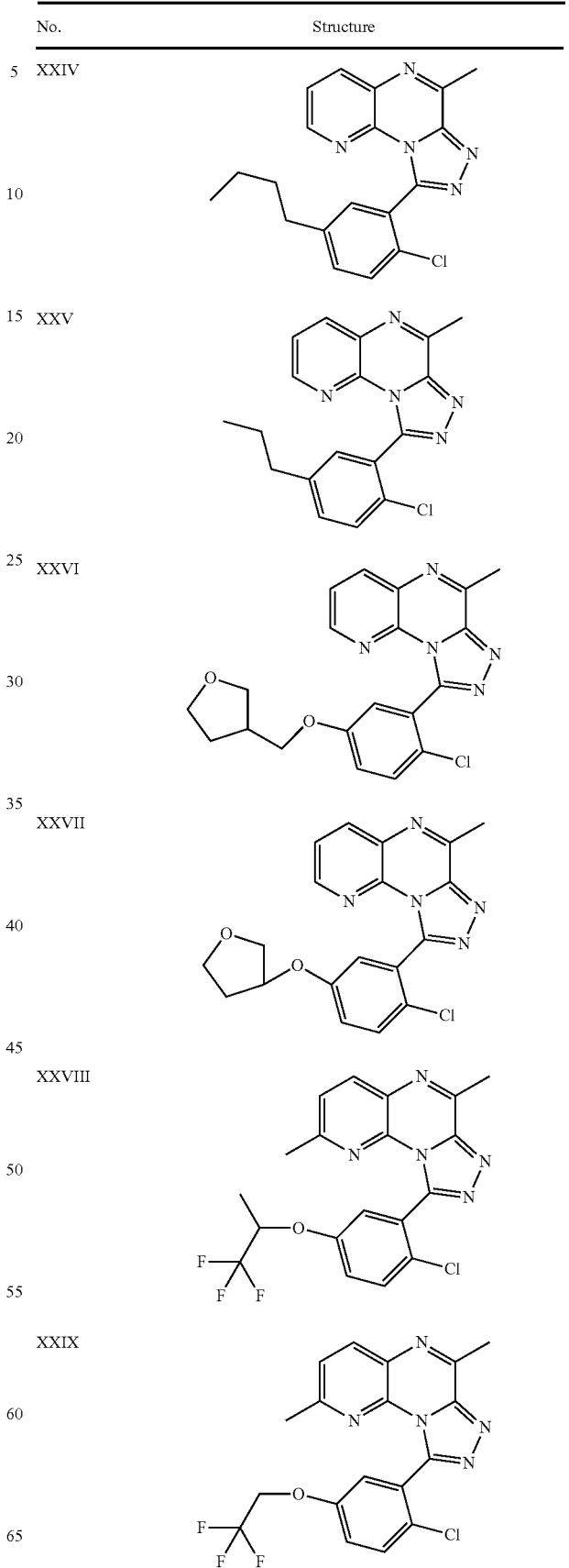 |
| XXV | |
| XXVI | |
| XXVII | |
| XXVIII | |
| XXIX | |

-continued

| No. | Structure |
|---|---|
| XXX | 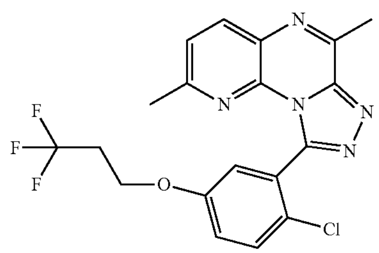 [SMILES: Cc1ccc2nc(C)c3nnc(-c4cc(OCCC(F)(F)F)ccc4Cl)n3c2n1] |
| XXXI | 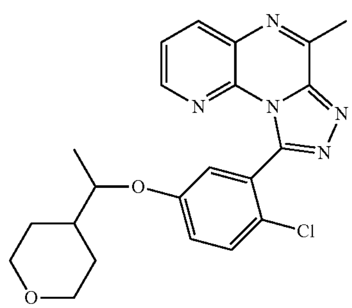 [SMILES: Cc1nc2cccnc2n2c(-c3cc(OC(C)C4CCOCC4)ccc3Cl)nnc12] |
| XXXII | 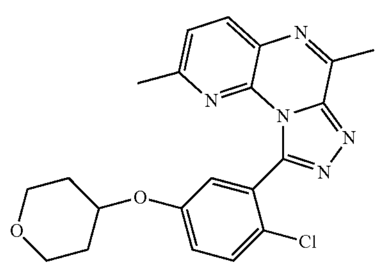 [SMILES: Cc1ccc2nc(C)c3nnc(-c4cc(OC5CCOCC5)ccc4Cl)n3c2n1] |
| XXXIII | 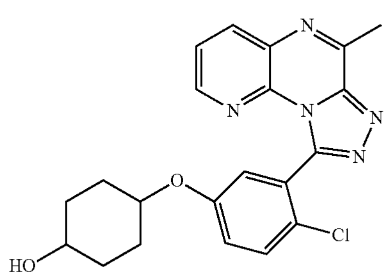 [SMILES: Cc1nc2cccnc2n2c(-c3cc(OC4CCC(O)CC4)ccc3Cl)nnc12] |
| XXXIV | 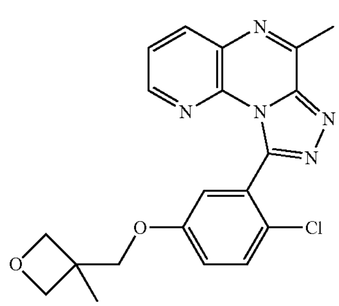 [SMILES: Cc1nc2cccnc2n2c(-c3cc(OCC4(C)COC4)ccc3Cl)nnc12] |

-continued

| No. | Structure |
|---|---|
| XXXV | 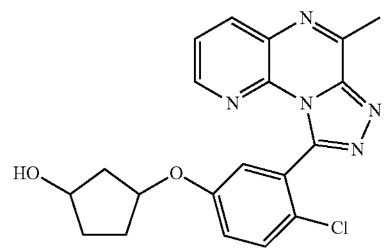 [SMILES: Cc1nc2cccnc2n2c(-c3cc(OC4CCC(O)C4)ccc3Cl)nnc12] |
| XXXVI | 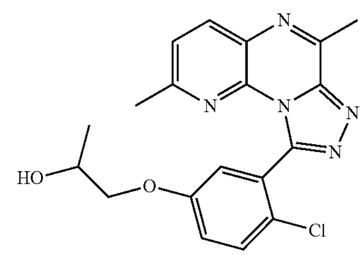 [SMILES: Cc1ccc2nc(C)c3nnc(-c4cc(OCC(C)O)ccc4Cl)n3c2n1] |
| XXXVII | 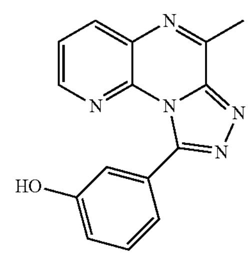 [SMILES: Cc1nc2cccnc2n2c(-c3cccc(O)c3)nnc12] |
| XXXVIII | 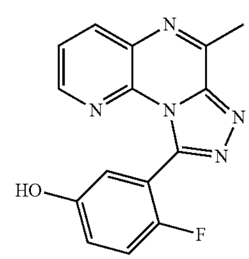 [SMILES: Cc1nc2cccnc2n2c(-c3cc(O)ccc3F)nnc12] |
| XXXIX | 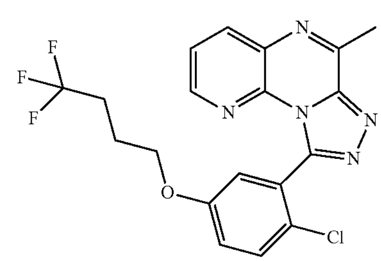 [SMILES: Cc1nc2cccnc2n2c(-c3cc(OCCCC(F)(F)F)ccc3Cl)nnc12] |
| XL | 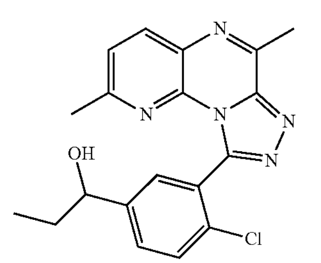 [SMILES: CCC(O)c1ccc(Cl)c(-c2nnc3c(C)nc4ccc(C)nc4n23)c1] |

| No. | Structure |
|---|---|
| XLI | 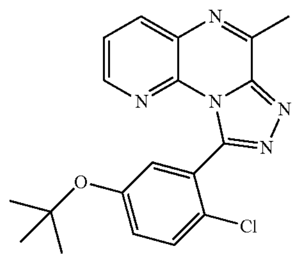 [SMILES: Cc1nc2cccnc2n2c(-c3cc(OC(C)(C)C)ccc3Cl)nnc12] |
| XLII | 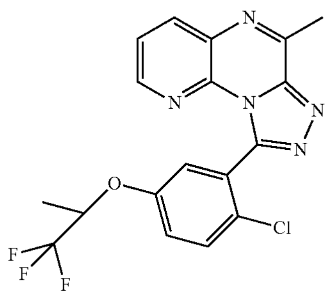 [SMILES: Cc1nc2cccnc2n2c(-c3cc(OC(C)C(F)(F)F)ccc3Cl)nnc12] |
| XLIII | 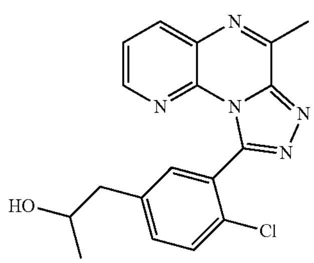 [SMILES: Cc1nc2cccnc2n2c(-c3cc(CC(C)O)ccc3Cl)nnc12] |
| XLIV | 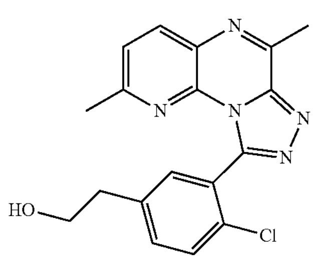 [SMILES: Cc1ccc2nc(C)c3nnc(-c4cc(CCO)ccc4Cl)n3c2n1] |
| XLV | 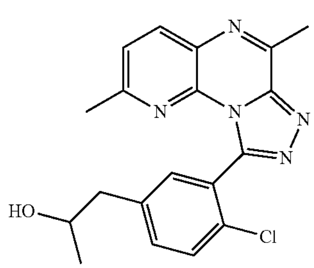 [SMILES: Cc1ccc2nc(C)c3nnc(-c4cc(CC(C)O)ccc4Cl)n3c2n1] |
| XLVI | 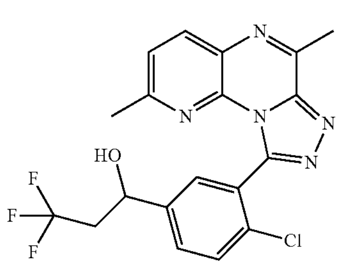 [SMILES: Cc1ccc2nc(C)c3nnc(-c4cc(C(O)CC(F)(F)F)ccc4Cl)n3c2n1] |
| XLVII | |
| XLVIII | |
| XLIX | |
| L | |
| LI | |
| LII | |

-continued
| No. | Structure |
|---|---|
| LIII | 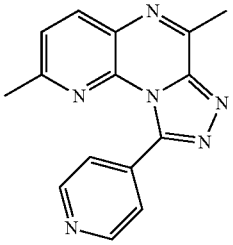 |
| LIV | 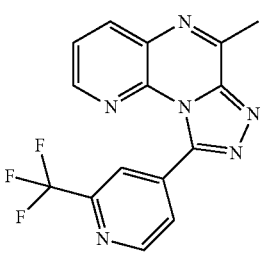 [SMILES: Cc1nc2cccnc2n2c(-c3ccnc(C(F)(F)F)c3)nnc12] |
| LV | 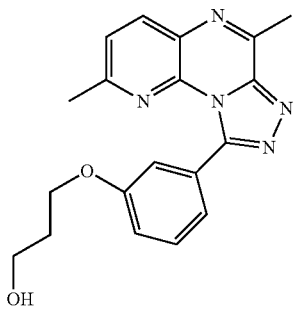 [SMILES: Cc1ccc2nc(C)c3nnc(-c4cccc(OCCCO)c4)n3c2n1] |
| LVI | 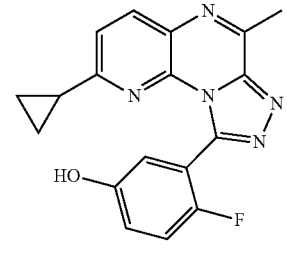 [SMILES: Cc1nc2ccc(C3CC3)nc2n2c(-c3cc(O)ccc3F)nnc12] |
| LVII | 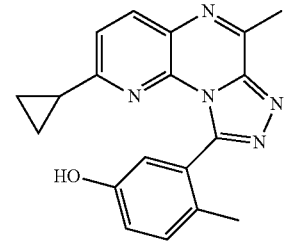 |
| LVIII | 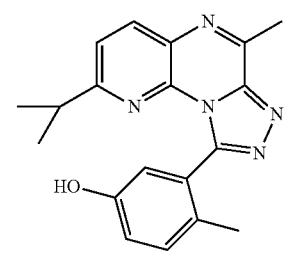 [SMILES: Cc1ccc(O)cc1-c1nnc2c(C)nc3ccc(C(C)C)nc3n12] |
-continued
| No. | Structure |
|---|---|
| LIX | 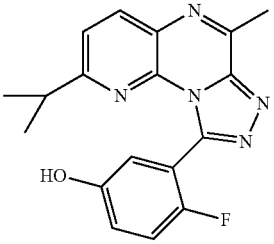 [SMILES: Cc1nc2ccc(C(C)C)nc2n2c(-c3cc(O)ccc3F)nnc12] |
| LX | 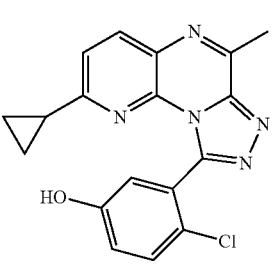 [SMILES: Cc1nc2ccc(C3CC3)nc2n2c(-c3cc(O)ccc3Cl)nnc12] |
| LXI | 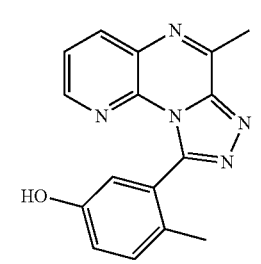 [SMILES: Cc1ccc(O)cc1-c1nnc2c(C)nc3cccnc3n12] |
| LXII | 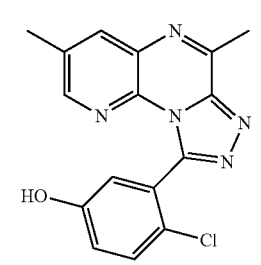 |
| LXIII | 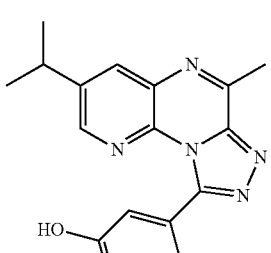 |
| LXIV | 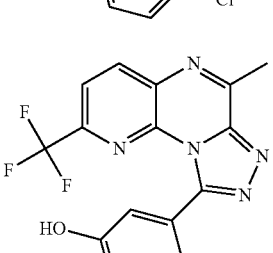 |

| No. | Structure |
|---|---|
| LXV | 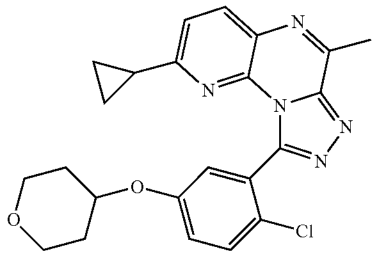 [SMILES: Cc1nc2ccc(C3CC3)nc2n2c(-c3cc(OC4CCOCC4)ccc3Cl)nnc12] |
| LXVI | 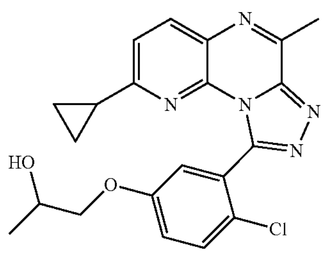 [SMILES: Cc1nc2ccc(C3CC3)nc2n2c(-c3cc(OCC(C)O)ccc3Cl)nnc12] |
| LXVII | 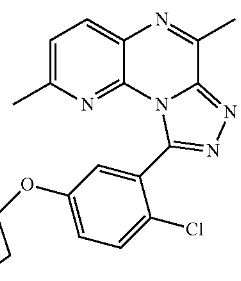 |
| LXVIII | 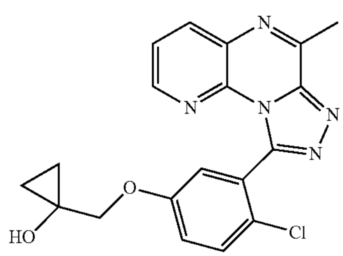 [SMILES: Cc1nc2cccnc2n2c(-c3cc(OCC4(O)CC4)ccc3Cl)nnc12] |
| LXIX | 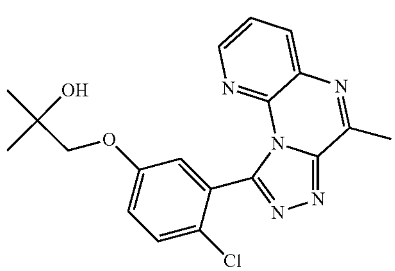 [SMILES: Cc1nc2cccnc2n2c(-c3cc(OCC(C)(C)O)ccc3Cl)nnc12] |
| LXX | 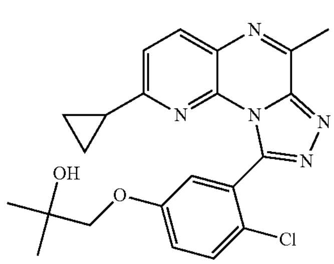 |
| LXXI | |
| LXXII | |
| LXXIII | |
| LXXIV | |
| LXXV | |
| LXXVI | |

| No. | Structure |
|---|---|
| LXXVII | 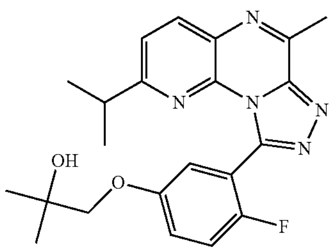 |
| LXXVIII | 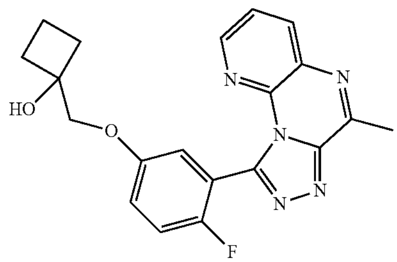 [SMILES: Cc1nc2cccnc2n2c(-c3cc(OCC4(O)CCC4)ccc3F)nnc12] |
| LXXIX | 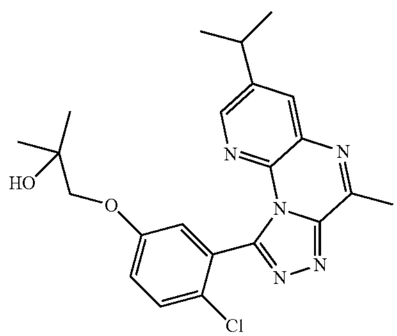 [SMILES: Cc1nc2cc(C(C)C)cnc2n2c(-c3cc(OCC(C)(C)O)ccc3Cl)nnc12] |
| LXXX | 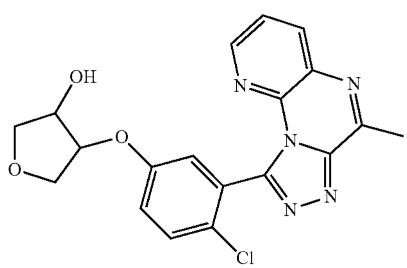 [SMILES: Cc1nc2cccnc2n2c(-c3cc(OC4COCC4O)ccc3Cl)nnc12] |
| LXXXI | 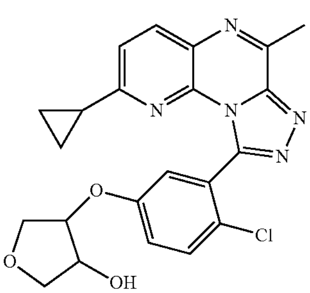 [SMILES: Cc1nc2ccc(C3CC3)nc2n2c(-c3cc(OC4COCC4O)ccc3Cl)nnc12] |

| No. | Structure |
|---|---|
| LXXXII | 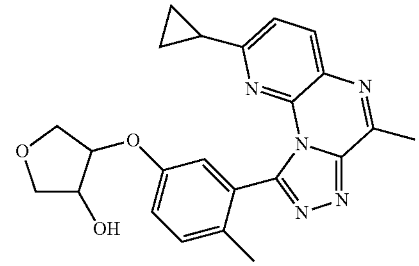 [SMILES: Cc1ccc(OC2COCC2O)cc1-c1nnc2c(C)nc3ccc(C4CC4)nc3n12] |
| LXXXIII | 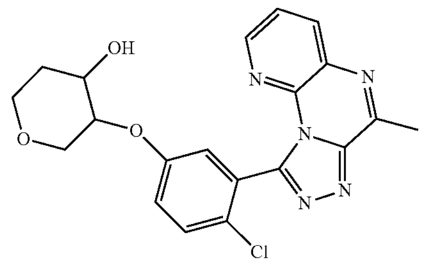 [SMILES: Cc1nc2cccnc2n2c(-c3cc(OC4COCCC4O)ccc3Cl)nnc12] |
| LXXXIV | 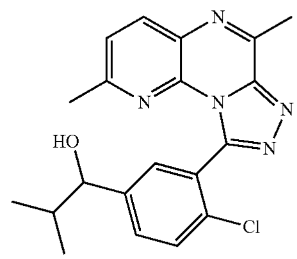 [SMILES: Cc1ccc2nc(C)c3nnc(-c4cc(C(O)C(C)C)ccc4Cl)n3c2n1] |
| LXXXV | 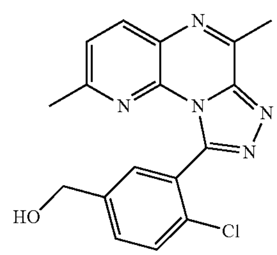 [SMILES: Cc1ccc2nc(C)c3nnc(-c4cc(CO)ccc4Cl)n3c2n1] |
| LXXXVI | 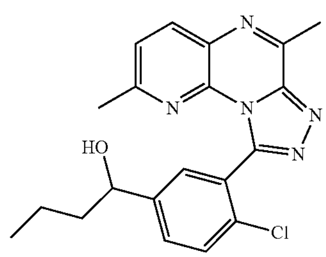 [SMILES: CCCC(O)c1ccc(Cl)c(-c2nnc3c(C)nc4ccc(C)nc4n23)c1] |
| LXXXVII | 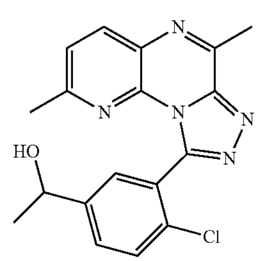 [SMILES: Cc1ccc2nc(C)c3nnc(-c4cc(C(C)O)ccc4Cl)n3c2n1] |

| No. | Structure |
|---|---|
| LXXXVIII | 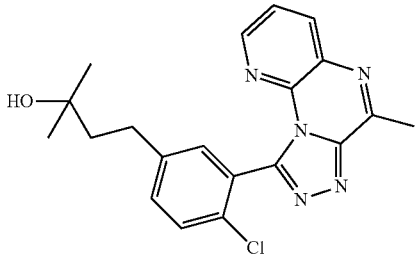 [SMILES: Cc1nc2cccnc2n2c(-c3cc(CCC(C)(C)O)ccc3Cl)nnc12] |
| LXXXIX | 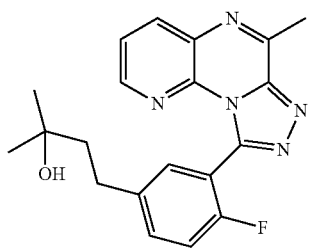 [SMILES: Cc1nc2cccnc2n2c(-c3cc(CCC(C)(C)O)ccc3F)nnc12] |
| XC | 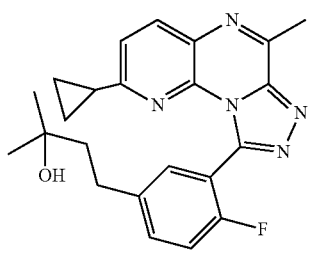 [SMILES: Cc1nc2ccc(C3CC3)nc2n2c(-c3cc(CCC(C)(C)O)ccc3F)nnc12] |
| XCI | 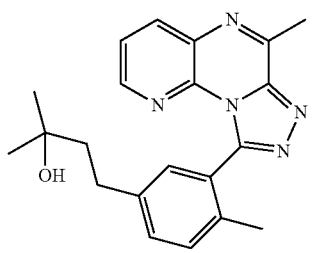 [SMILES: Cc1ccc(CCC(C)(C)O)cc1-c1nnc2c(C)nc3cccnc3n12] |
| XCII | 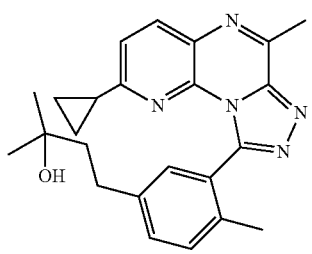 [SMILES: Cc1ccc(CCC(C)(C)O)cc1-c1nnc2c(C)nc3ccc(C4CC4)nc3n12] |
| XCIII | 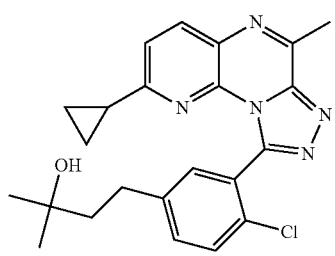 [SMILES: Cc1nc2ccc(C3CC3)nc2n2c(-c3cc(CCC(C)(C)O)ccc3Cl)nnc12] |
| No. | Structure |
|---|---|
| XCIV | 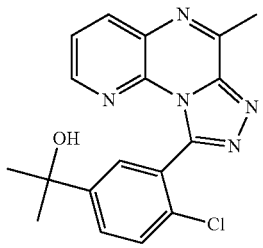 [SMILES: Cc1nc2cccnc2n2c(-c3cc(C(C)(C)O)ccc3Cl)nnc12] |
| XCV | 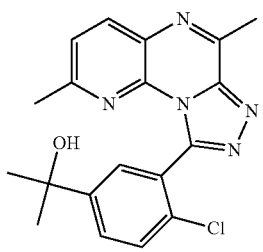 [SMILES: Cc1ccc2nc(C)c3nnc(-c4cc(C(C)(C)O)ccc4Cl)n3c2n1] |
| XCVI | 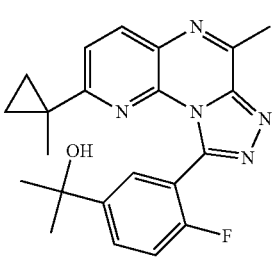 [SMILES: Cc1nc2ccc(C3(C)CC3)nc2n2c(-c3cc(C(C)(C)O)ccc3F)nnc12] |
| XCVII | 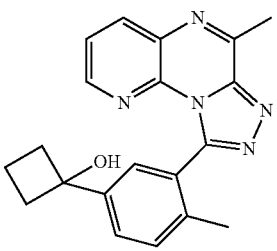 [SMILES: Cc1ccc(C2(O)CCC2)cc1-c1nnc2c(C)nc3cccnc3n12] |
| XCVIII | 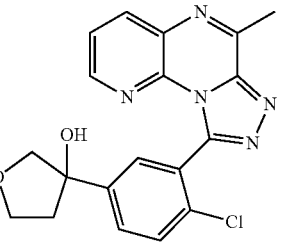 |
| XCIX | 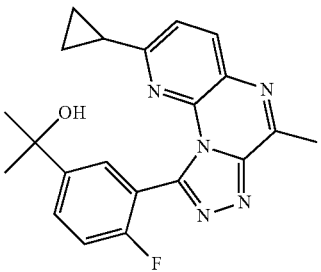 [SMILES: Cc1nc2ccc(C3CC3)nc2n2c(-c3cc(C(C)(C)O)ccc3F)nnc12] |

| No. | Structure |
|---|---|
| C | 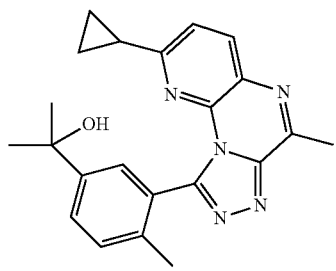 [SMILES: Cc1ccc(C(C)(C)O)cc1-c1nnc2c(C)nc3ccc(C4CC4)nc3n12] |
| CI | 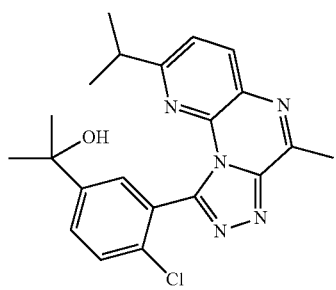 [SMILES: Cc1nc2ccc(C(C)C)nc2n2c(-c3cc(C(C)(C)O)ccc3Cl)nnc12] |
| CII | 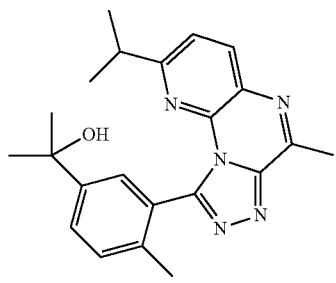 [SMILES: Cc1ccc(C(C)(C)O)cc1-c1nnc2c(C)nc3ccc(C(C)C)nc3n12] |
| CIII | 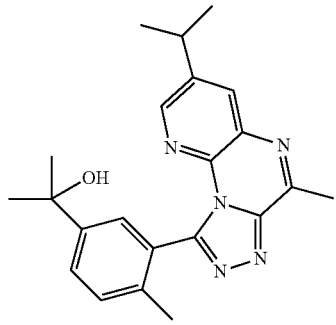 [SMILES: Cc1ccc(C(C)(C)O)cc1-c1nnc2c(C)nc3cc(C(C)C)cnc3n12] |
| CIV | 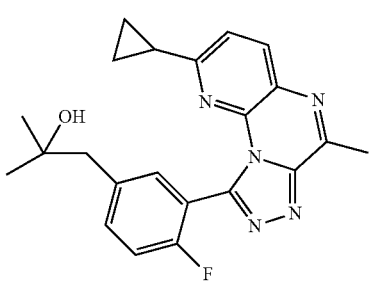 [SMILES: Cc1nc2ccc(C3CC3)nc2n2c(-c3cc(CC(C)(C)O)ccc3F)nnc12] |
| CV | 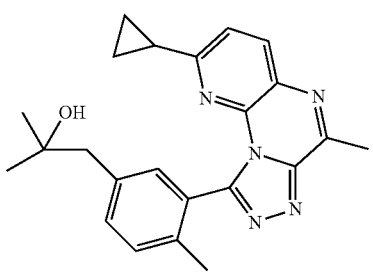 [SMILES: Cc1ccc(CC(C)(C)O)cc1-c1nnc2c(C)nc3ccc(C4CC4)nc3n12] |
| CVI | 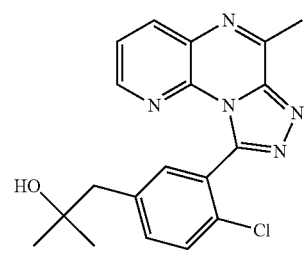 [SMILES: Cc1nc2cccnc2n2c(-c3cc(CC(C)(C)O)ccc3Cl)nnc12] |
| CVII | 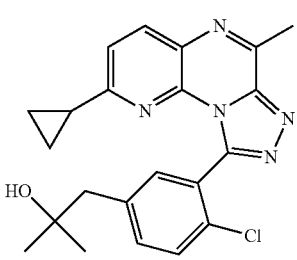 [SMILES: Cc1nc2ccc(C3CC3)nc2n2c(-c3cc(CC(C)(C)O)ccc3Cl)nnc12] |
| CVIII | 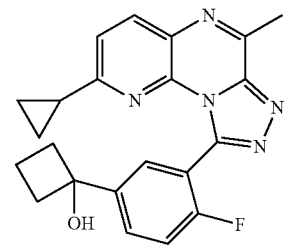 [SMILES: Cc1nc2ccc(C3CC3)nc2n2c(-c3cc(C4(O)CCC4)ccc3F)nnc12] |
| CIX | 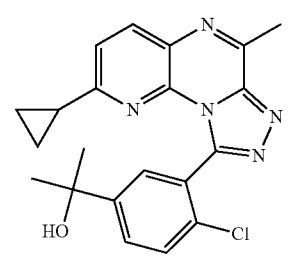 [SMILES: Cc1nc2ccc(C3CC3)nc2n2c(-c3cc(C(C)(C)O)ccc3Cl)nnc12] |
| CX | 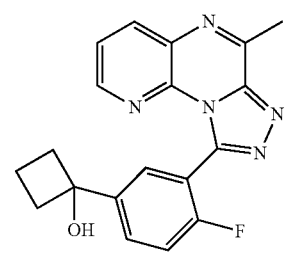 [SMILES: Cc1nc2cccnc2n2c(-c3cc(C4(O)CCC4)ccc3F)nnc12] |

| No. | Structure |
|---|---|
| CXI | 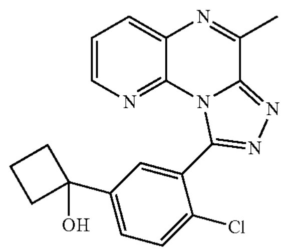 [SMILES: Cc1nc2cccnc2n2c(-c3cc(C4(O)CCC4)ccc3Cl)nnc12] |
| CXII | 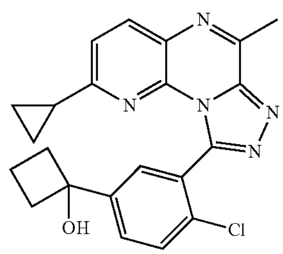 [SMILES: Cc1nc2ccc(C3CC3)nc2n2c(-c3cc(C4(O)CCC4)ccc3Cl)nnc12] |
| CXIII | 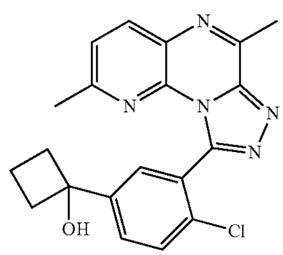 [SMILES: Cc1ccc2nc(C)c3nnc(-c4cc(C5(O)CCC5)ccc4Cl)n3c2n1] |
| CXIV | 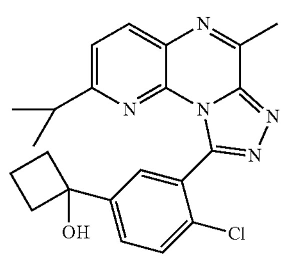 [SMILES: Cc1nc2ccc(C(C)C)nc2n2c(-c3cc(C4(O)CCC4)ccc3Cl)nnc12] |
| CXV | 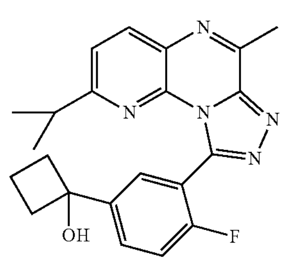 [SMILES: Cc1nc2ccc(C(C)C)nc2n2c(-c3cc(C4(O)CCC4)ccc3F)nnc12] |
| CXVI | 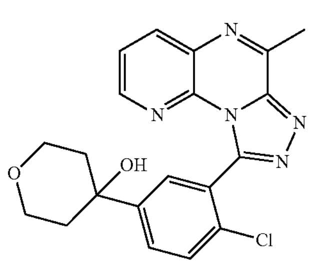 [SMILES: Cc1nc2cccnc2n2c(-c3cc(C4(O)CCOCC4)ccc3Cl)nnc12] |
| CXVII | |
| CXVIII | |
| CXIX | |
| CXX | |
| CXXI | |
| CXXII | |

| No. | Structure |
|---|---|
| CXXIII | 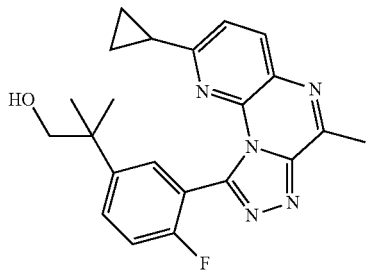 [SMILES: Cc1nc2ccc(C3CC3)nc2n2c(-c3cc(C(C)(C)CO)ccc3F)nnc12] |
| CXXIV | 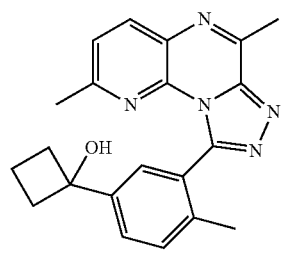 [SMILES: Cc1ccc2nc(C)c3nnc(-c4cc(C5(O)CCC5)ccc4C)n3c2n1] |
| CXXV | 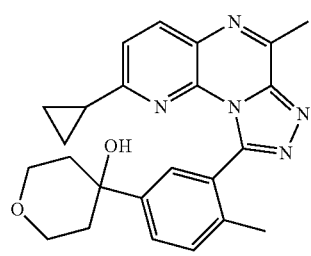 [SMILES: Cc1ccc(C2(O)CCOCC2)cc1-c1nnc2c(C)nc3ccc(C4CC4)nc3n12] |
| CXXVI | 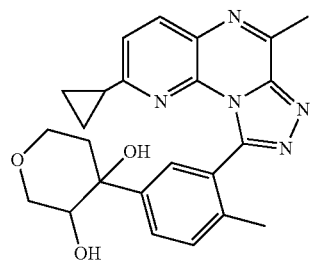 [SMILES: Cc1ccc(C2(O)CCOCC2O)cc1-c1nnc2c(C)nc3ccc(C4CC4)nc3n12] |
| CXXVII | 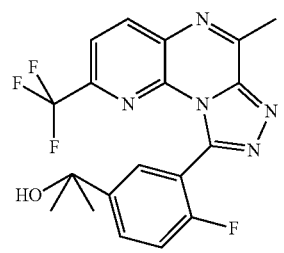 [SMILES: Cc1nc2ccc(C(F)(F)F)nc2n2c(-c3cc(C(C)(C)O)ccc3F)nnc12] |
| CXXVIII | 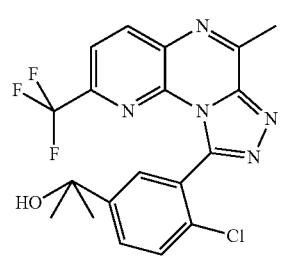 [SMILES: Cc1nc2ccc(C(F)(F)F)nc2n2c(-c3cc(C(C)(C)O)ccc3Cl)nnc12] |
| No. | Structure |
|---|---|
| CXXIX | 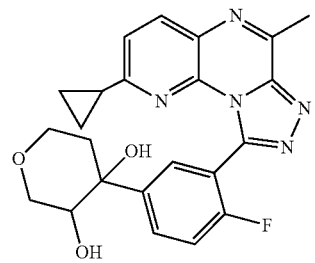 [SMILES: Cc1nc2ccc(C3CC3)nc2n2c(-c3cc(C4(O)CCOCC4O)ccc3F)nnc12] |
| CXXX | 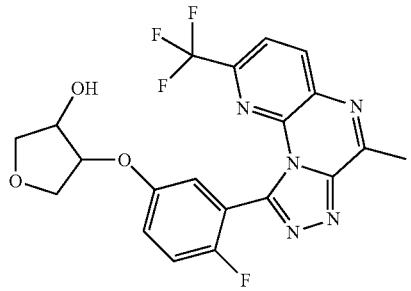 [SMILES: Cc1nc2ccc(C(F)(F)F)nc2n2c(-c3cc(OC4COCC4O)ccc3F)nnc12] |
| CXXXI | 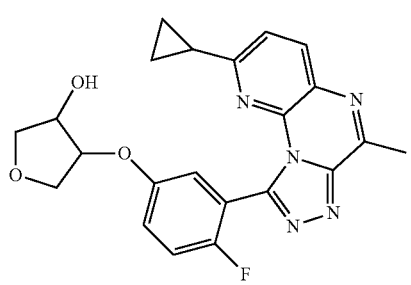 [SMILES: Cc1nc2ccc(C3CC3)nc2n2c(-c3cc(OC4COCC4O)ccc3F)nnc12] |
| CXXXII | 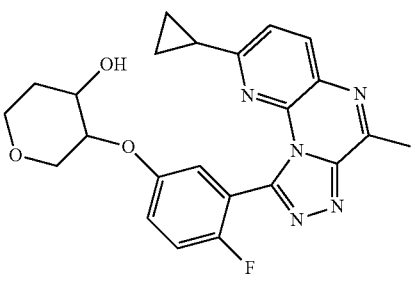 [SMILES: Cc1nc2ccc(C3CC3)nc2n2c(-c3cc(OC4COCCC4O)ccc3F)nnc12] |
| CXXXIII | 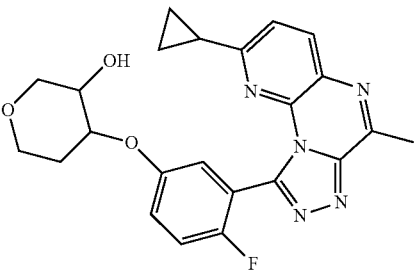 [SMILES: Cc1nc2ccc(C3CC3)nc2n2c(-c3cc(OC4CCOCC4O)ccc3F)nnc12] |

| No. | Structure |
|---|---|
| CXXXIV | 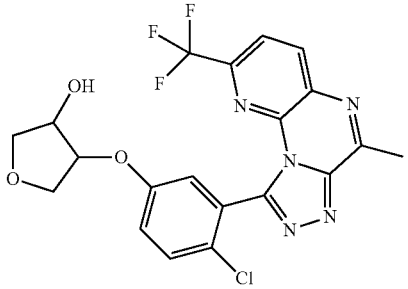 |
| CXXXV | 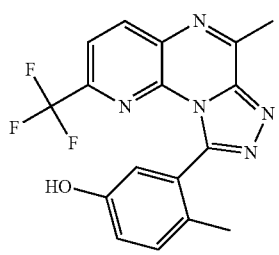 [SMILES: Cc1ccc(O)cc1-c1nnc2c(C)nc3ccc(C(F)(F)F)nc3n12] |
| CXXXVI | 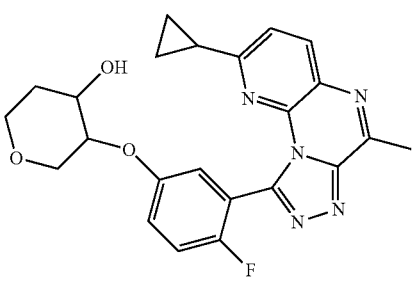 [SMILES: Cc1nc2ccc(C3CC3)nc2n2c(-c3cc(OC4COCCC4O)ccc3F)nnc12] |
| CXXXVII | 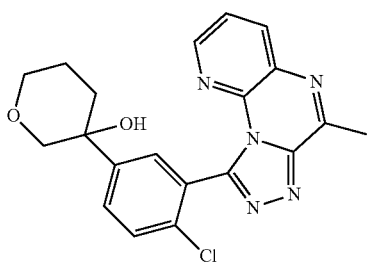 [SMILES: Cc1nc2cccnc2n2c(-c3cc(C4(O)CCCOC4)ccc3Cl)nnc12] |
| CXXXVIII | 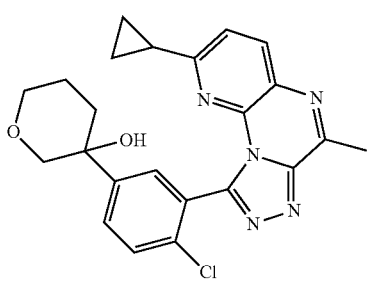 [SMILES: Cc1nc2ccc(C3CC3)nc2n2c(-c3cc(C4(O)CCCOC4)ccc3Cl)nnc12] |// 
| CXXXIX | 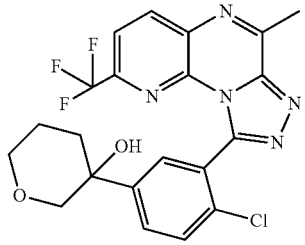 [SMILES: Cc1nc2ccc(C(F)(F)F)nc2n2c(-c3cc(C4(O)CCCOC4)ccc3Cl)nnc12] |
| CXL | 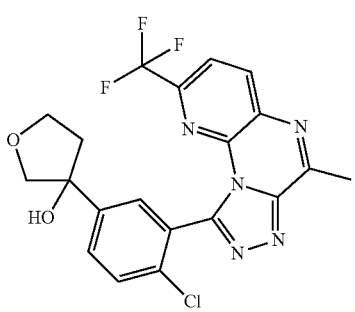 [SMILES: Cc1nc2ccc(C(F)(F)F)nc2n2c(-c3cc(C4(O)CCOC4)ccc3Cl)nnc12] | the tautomers thereof, the stereoisomers thereof, the mixtures thereof, the solvates thereof, the hydrates thereof and the salts thereof.

Some terms used above and hereinafter to describe the compounds according to the invention will now be defined more closely.

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl group, the latter of which is bound to the core molecule or to the group to which the substituent is attached.

Within the present invention, the term "core molecule" is defined by the following structure:

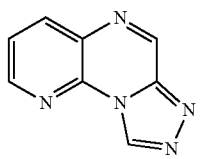

In general, the attachment site of a given residue to another group shall be variable, i.e. any capable atom, bearing hydrogens to be replaced, within this residue may be the linking spot to the group being attached, unless otherwise indicated.

In case a compound of the present invention is depicted in form of a chemical name and as a formula in case of any discrepancy the formula shall prevail.

An asterisk may be used in sub-formulas to indicate the bond which is connected to the core molecule or to the substituent to which it is bound as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" or "physiologically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" or "physiologically acceptable salts" refer to derivatives of the disclosed compounds wherein the parent compound is modified by making acid or base salts thereof. Examples of pharmaceutically acceptable salts or physiologically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2', 2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "substituted" as used herein means that any one or more hydrogens on the designated atom is replaced with a selection from the indicated group, provided that the designated atom's viable valence number is not exceeded, and that the substitution results in a stable compound.

The term "partially unsaturated" as used herein means that in the designated group or moiety 1, 2, or more, preferably 1 or 2, double bonds are present. Preferably, as used herein, the term "partially unsaturated" does not cover fully unsaturated groups or moieties.

Terms like " . . . optionally with 1 to 7 fluorine atoms substituted $C_{1-3}$-alkyl-O— . . . " or " . . . optionally with 1 to 7 fluorine atoms substituted $C_{1-3}$-alkyl-" in a section like " . . . groups may optionally be substituted with 1 to 5 substituents independently selected from the group consisting of halogen, HO—, optionally with 1 to 7 fluorine atoms substituted $C_{1-3}$-alkyl-O—, and optionally with 1 to 7 fluorine atoms substituted $C_{1-3}$-alkyl-" means that the referenced group may be substituted with 1 to 5 substituents, wherein these substituents can be halogen, HO—, $C_{1-3}$-alkyl-O— which may be optionally fluorinated with 1 to 7 fluoro atoms, and $C_{1-3}$-alkyl-O— which may be optionally fluorinated with 1 to 7 fluoro atoms.

The term "halogen" generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The terms "carbocyclyl" and "carbocycle" as used either alone or in combination with another radical, mean, if not mentioned otherwise, a mono- bi- or tricyclic ring structure consisting of 3 to 14 carbon atoms. The terms, if not mentioned otherwise, refers to fully saturated, partially saturated and aromatic ring systems. The terms encompass fused, bridged and spirocyclic systems.

Thus, the terms include the following exemplary structures which are not depicted as radicals as each form may be attached through a covalent bond to any atom so long as appropriate valences are maintained:

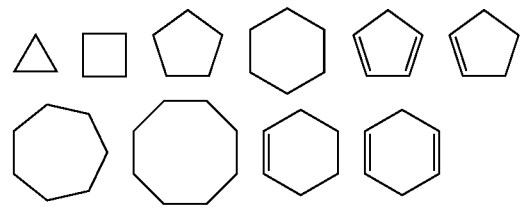

-continued

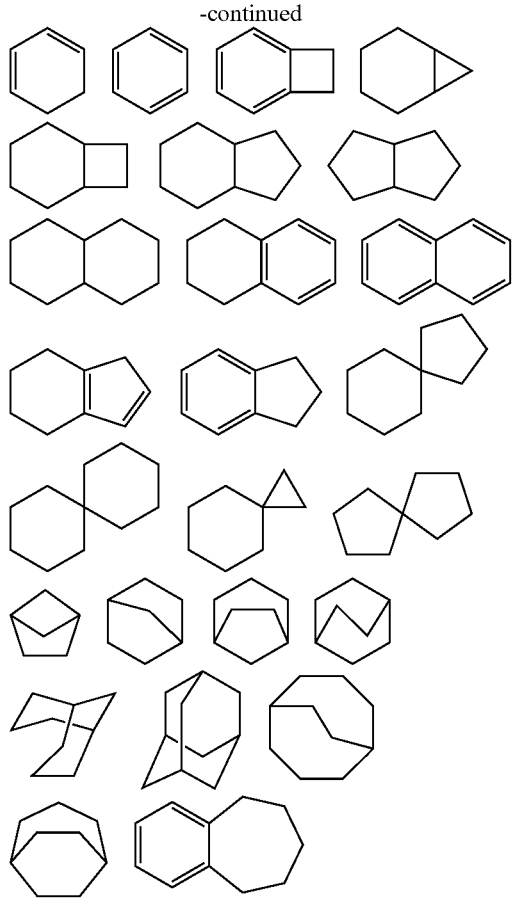

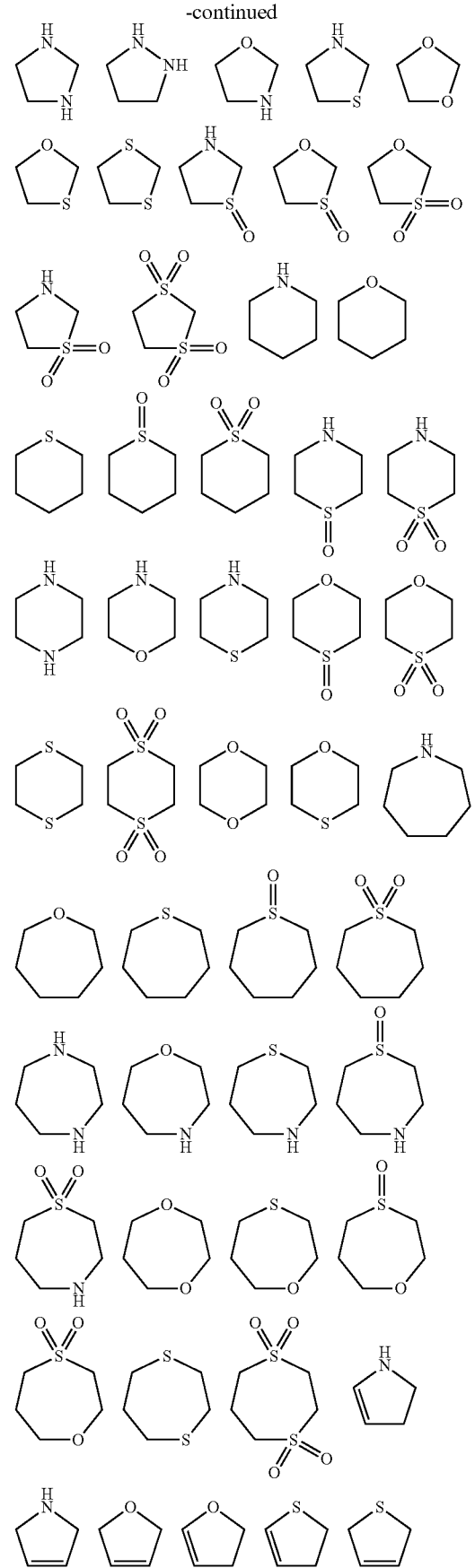

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The terms "heterocyclyl" and "heterocycle" as used either alone or in combination with another radical, mean a saturated or unsaturated mono- or polycyclic ring system containing one or more heteroatoms selected from N, O or $S(O)_r$, wherein r=0, 1 or 2, which may contain aromatic rings consisting of, if not mentioned otherwise, 3 to 14 ring atoms wherein none of the heteroatoms is part of an aromatic ring. The terms encompass fused, bridged and spirocyclic systems. The terms are intended to include all the possible isomeric forms.

Thus, the terms include the following exemplary structures which are not depicted as radicals as each form may be attached through a covalent bond to any atom so long as appropriate valences are maintained:

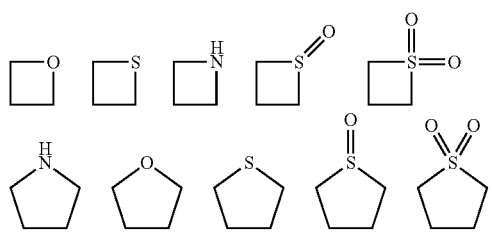

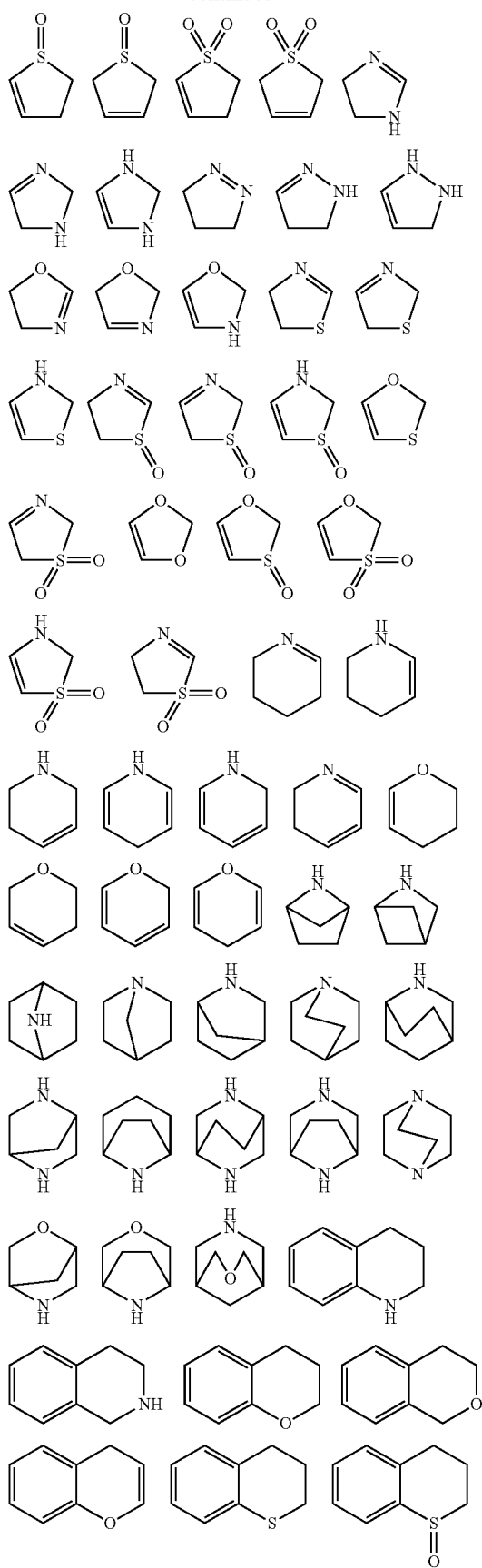
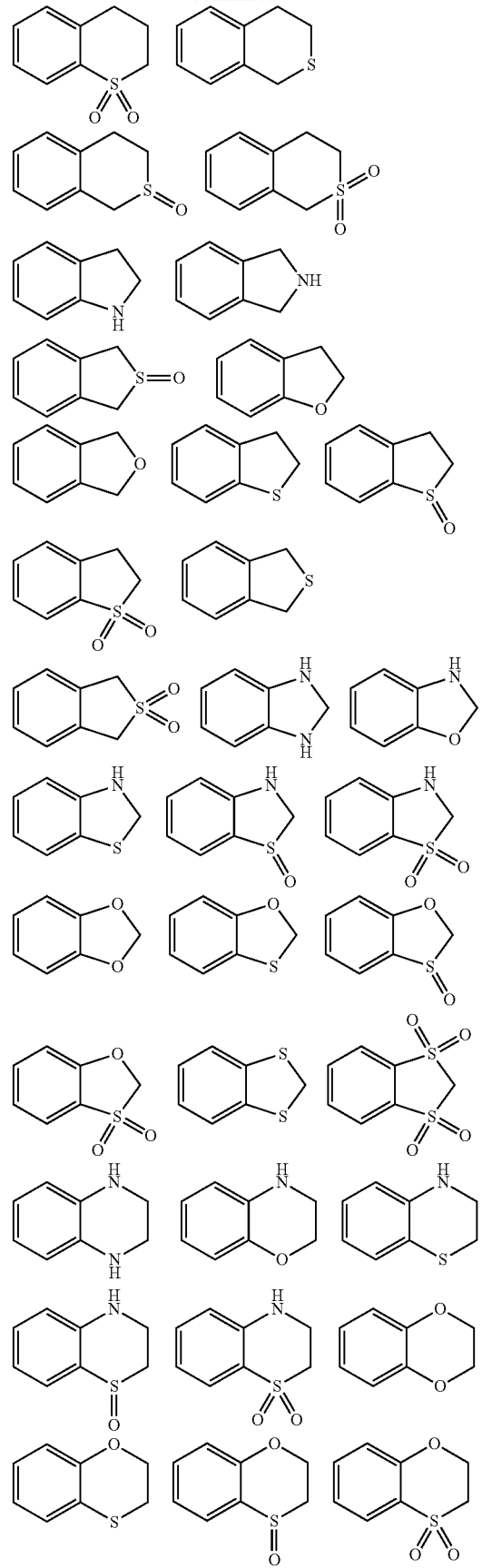

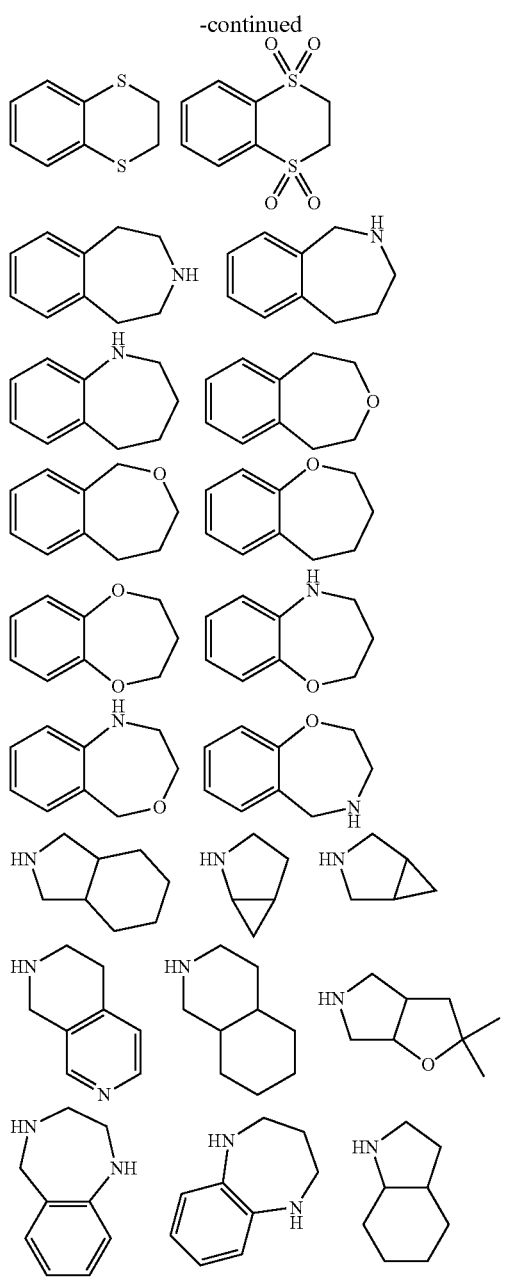

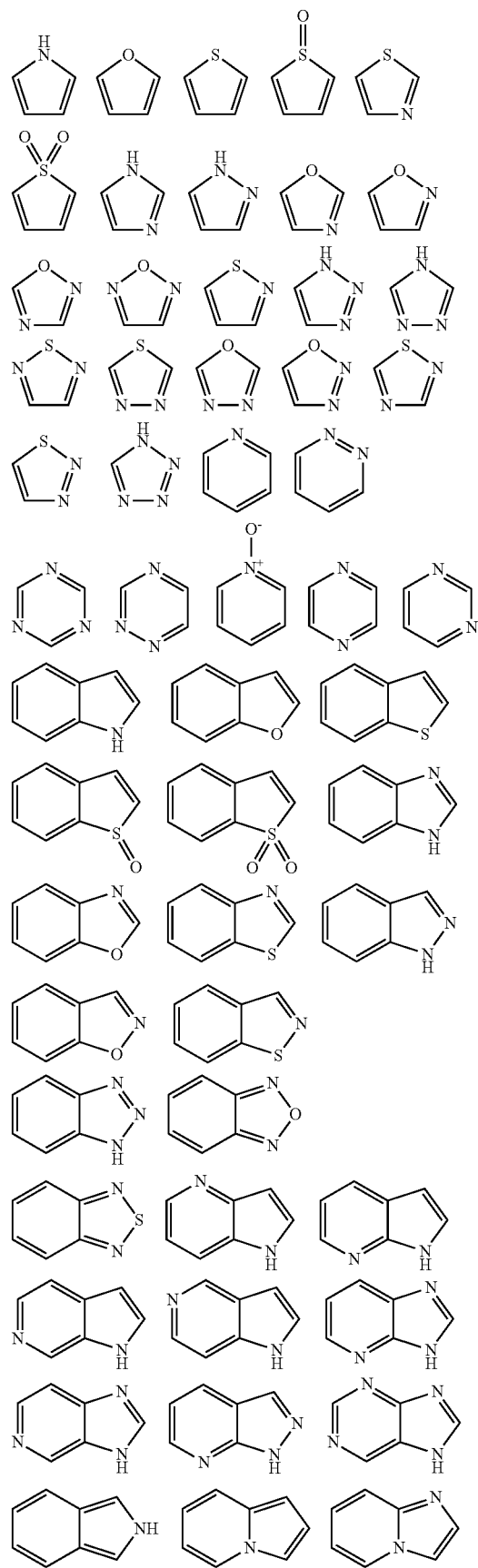

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of an aromatic ring. The term "heteroaryl" is intended to include all the possible isomeric forms. Thus, the term "heteroaryl" includes the following exemplary structures which are not depicted as radicals as each form may be attached through a covalent bond to any atom so long as appropriate valences are maintained:

-continued

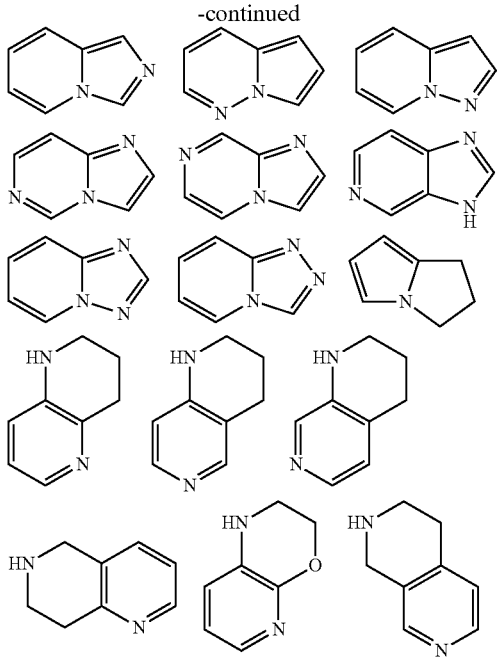
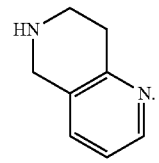

Many of the terms given above may be used repeatedly in the definition of a formula or group and in each case have one of the meanings given above, independently of one another.

The compounds according to the invention may be obtained using methods of synthesis known in principle. Preferably, the compounds are obtained by the following methods according to the invention which are described in more detail hereinafter.

Preparation

The following schemes illustrate generally how to manufacture the compounds of the present invention by way of example. The abbreviated substituents may be as defined above if not defined otherwise within the context of the schemes:

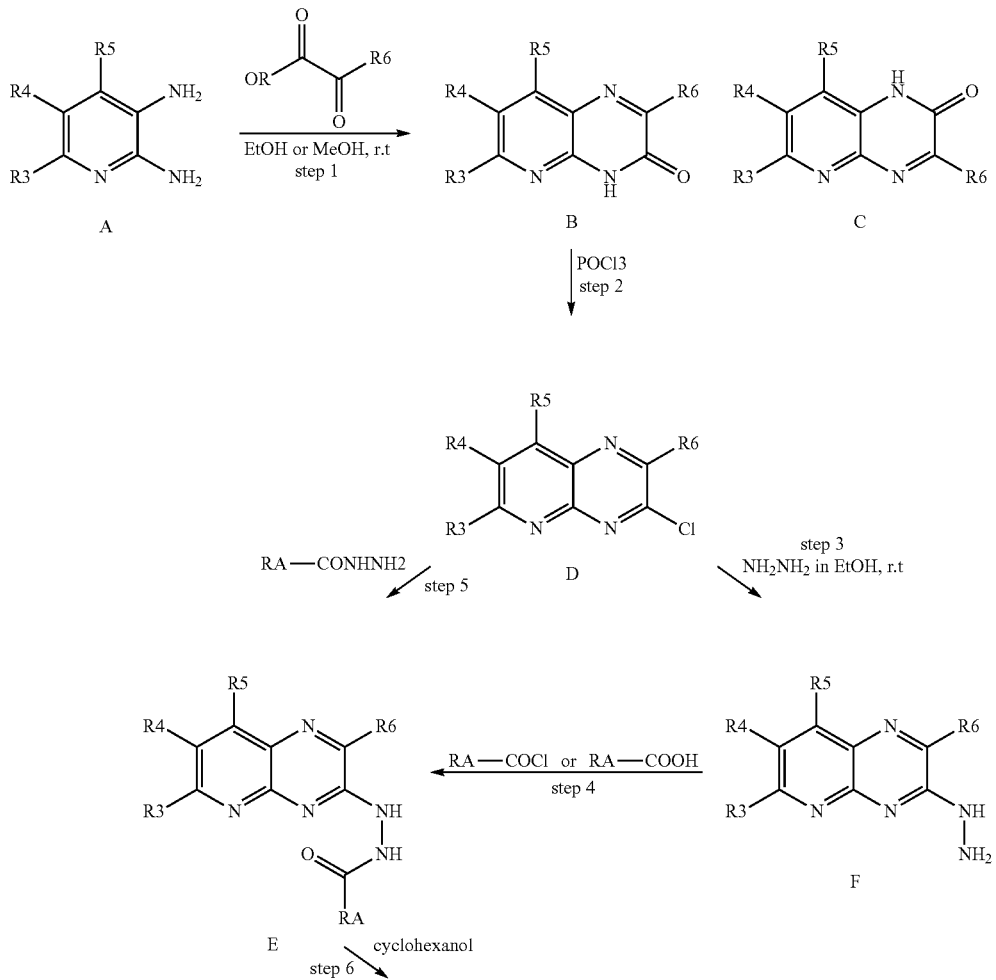

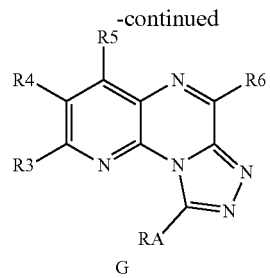

G

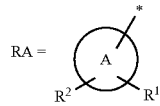

Scheme 1: In a first step, substituted 1,2-pyrido-diamines (A), commercially available or prepared following well known reported procedures, were reacted with the appropriate 1,2 - keto ester or acid in EtOH or MeOH as solvents at room temperature, to form the corresponding pyrido[2,3-b] pyrazinone intermediates (B,C). Where required, regioisomers were seperated by flash cromatography and treated with POCl₃ under heating to obtain the 2-chloro-pyridopyrazines(D).

Nucleophilic substitution was performed using hydrazine hydrate in appropriate solvents (e.g. EtOH) at room temperature to form the corresponding pyrido[2,3-b]-pyrazin-3yl-idrazines derivatives (F). Reaction with appropriate acyl chlorides or carboxylic acids in the presence of a coupling agent (e.g. HATU or TBTU) and a base (e.g. TEA or DIPEA), gave the corresponding hydrazides (E) which were submitted to in situ cyclization to triazoles core by heating in appropriate solvent (e.g. cyclohexanol).

Alternatively, in step 5, preformed hydrazides derivative were reacted with 2-chloro-pyridopyrazines (D) in appropriate solvents (such as DMF) to gave intermediates hydrazides (E) which were then converted to compounds G as described before or heating directly the 2-chloro-pyridopyrazines (D) with the appropriate hydrazides in appropriate solvent such as cyclohexanol at high temperature.

Further examples of the present invention were prepared following Scheme 2:

Scheme 2:

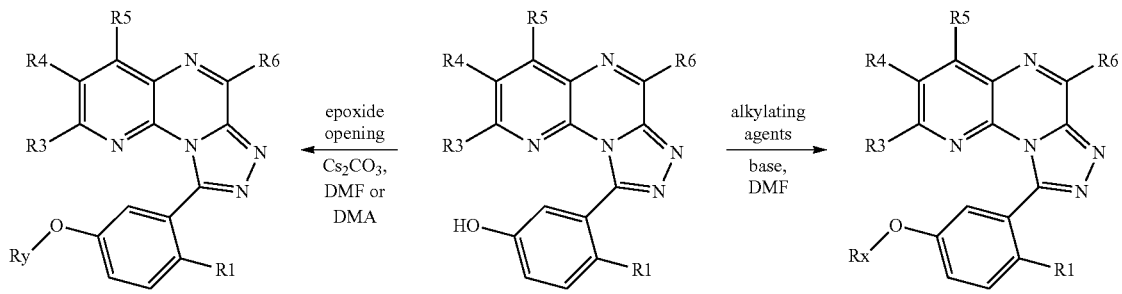

Further examples of the present invention were prepared by alkylation of the appropriate phenol derivative (obtained as described in Scheme 1) with alkylating agents (e.g. chloride, bromide or tosylates derivatives) in the presence of a suitable base (e.g. tBuOK or Cs₂CO₃) in a solvent like DMF under heating or by ring opening of the appropriate epoxides in the presence of a suitable base (e.g. Cs₂CO₃) in a solvent like DMF or DMA under conventional heating or microwave irradation.

Rx and Ry: Examples 13, 15, 16, 17, 18, 19, 20, 21, 22, 23, 24, 25, 26, 27, 28, 29, 30, 31, 32, 32a, 33, 34, 35, 35a, 36, 37, 38, 39, 40, 41, 42, 43, 44, 45, 46, 47, 48, 49, 50, 51, 52, 53, 54, 55, 56, 57, 58, 106, 107, 108a, 108b, 108c, 108d, 109a, 109b, 109c, 109d, 110b, 110d, 111 were prepared following the above described procedures.

Scheme 3:

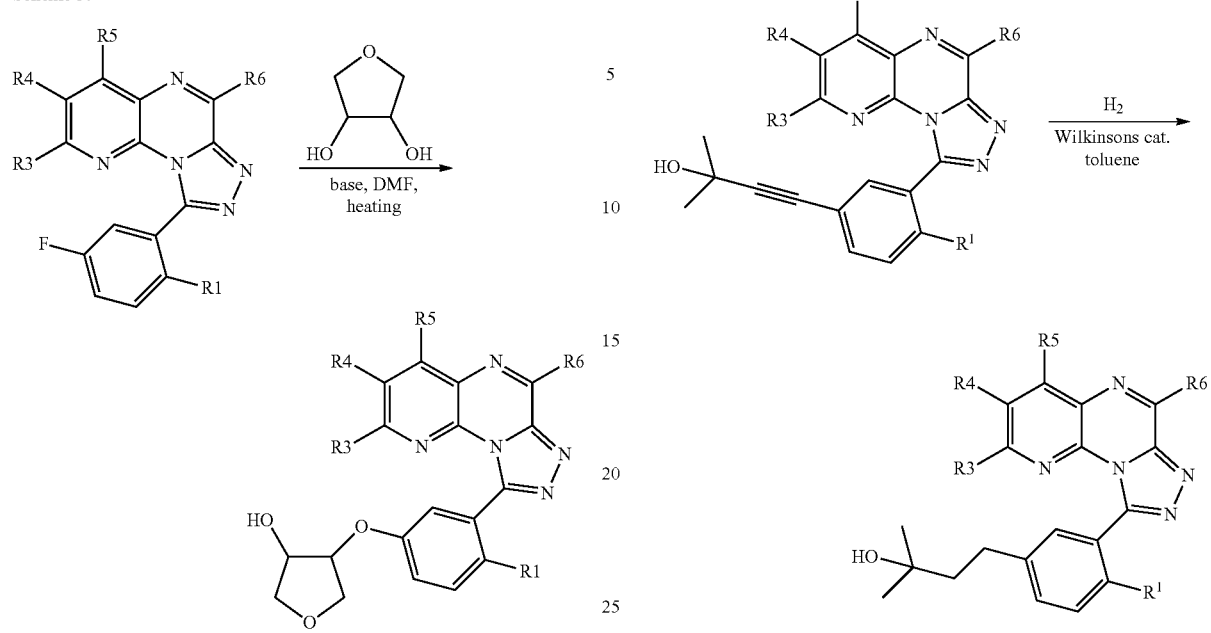

Further examples of the present invention were prepared by aromatic nucleophilic substitution, reacting the appropriate aromatic fluoro derivatives (prepared as described in Scheme 1) with primary or secondary alcohols in the presence of a suitable base (e.g tBuOK or $Cs_2CO_3$), in a solvent like DMF under heating. Examples 58a, 58b, 58c were prepared following the above described procedure.

Scheme 4:

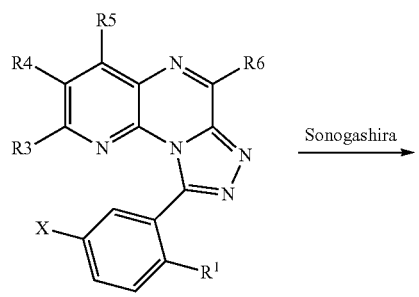

Further examples of the present invention were prepared by well-known cross coupling reaction (i.e Sonogashira, see for example Organic Letters, 2007, vol. 9, p. 4057-4060) starting from appropriate aromatic halogen intermediates (X=Br,I).

The resulting unsaturated triple bond intermediates were then converted to final compounds by appropriate reduction with Wilkinson's catalyst $RhCl(TPP)_3$ under hydrogen atmosphere in toluene as solvent.

Examples 66, 67, 68, 69 were prepared following the above described procedure. Alternatively, the same synthetic approach was applied for the preparation of preformed hydrazydes which were then reacted with intermediate D as described in Scheme 1

Scheme 5

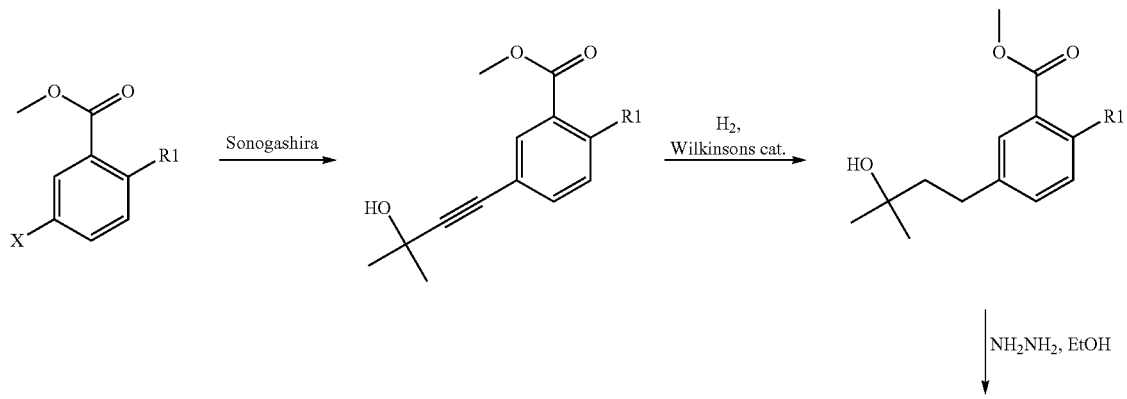

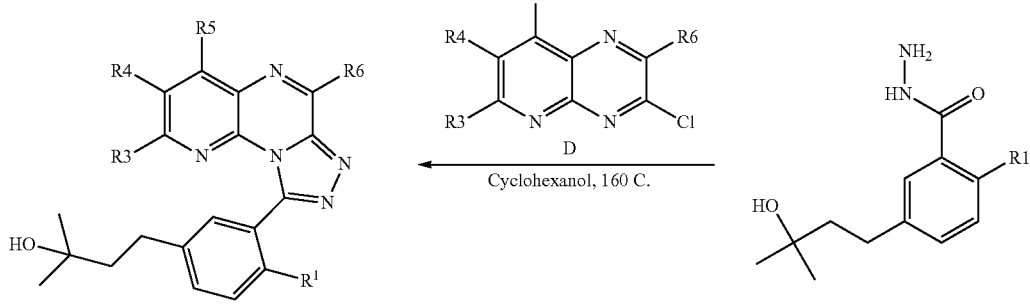

Examples 64 and 65 were prepared following the above described procedure.

Scheme 6:

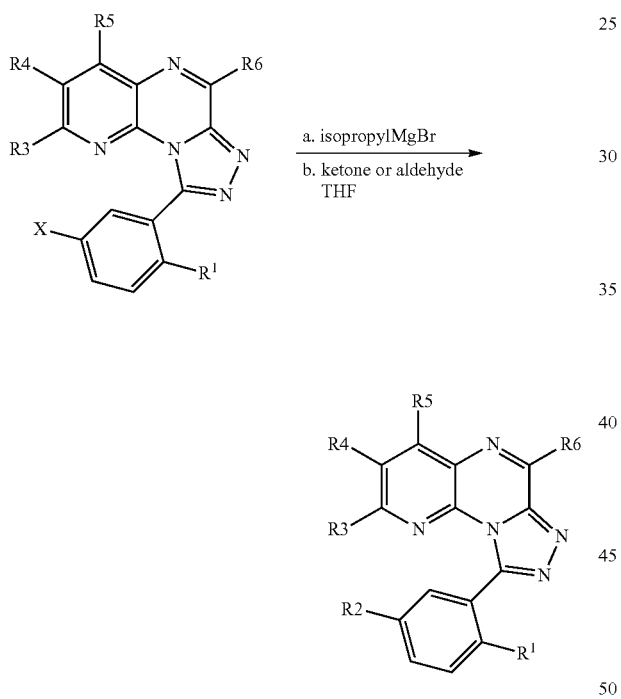

Further examples of the present invention were prepared as described in Scheme 6: in a first step the appropriate aromatic alogen derivatives (X=I) was treated with isopropyl magnesium bromide in a suitable solvent (like THF) at low temperature followed by addition of the appropriate ketone or aldehyde derivatives.

Examples 70, 71, 72, 73, 74 were prepared following the above described procedure.

Alternatively, the same synthetic approach was applied for the preparation of preformed hydrazydes which were then reacted with intermediate D as described in Scheme 1.

Scheme 7

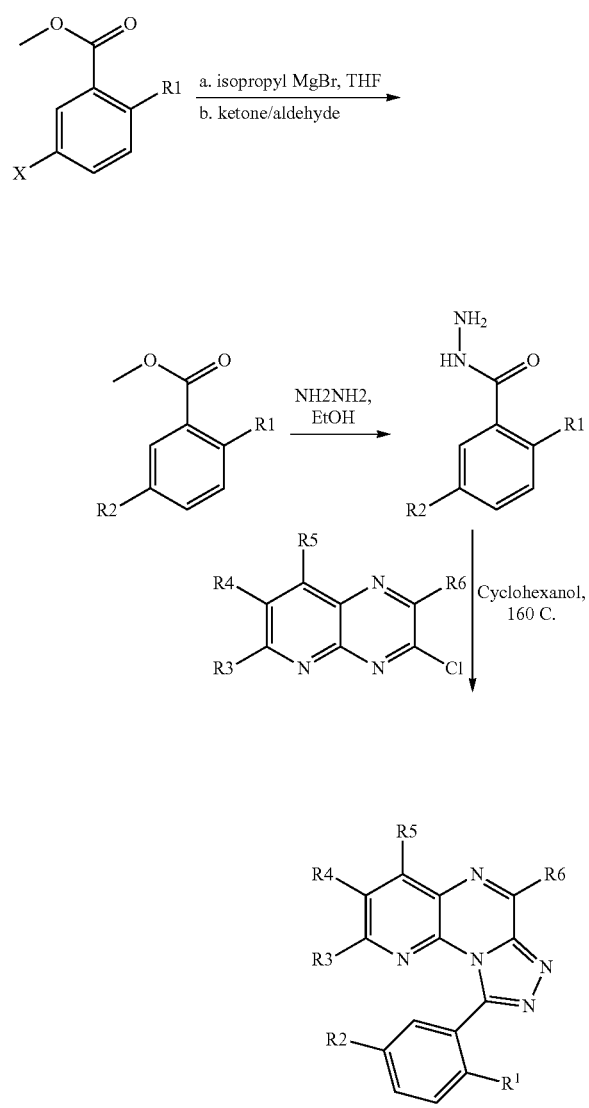

Examples 84, 85, 86, 87, 88, 89, 90, 91, 92, 93, 94, 95, 96, 96a, 96b, 96c, 97 were prepared following the above described procedure.

Scheme 8:

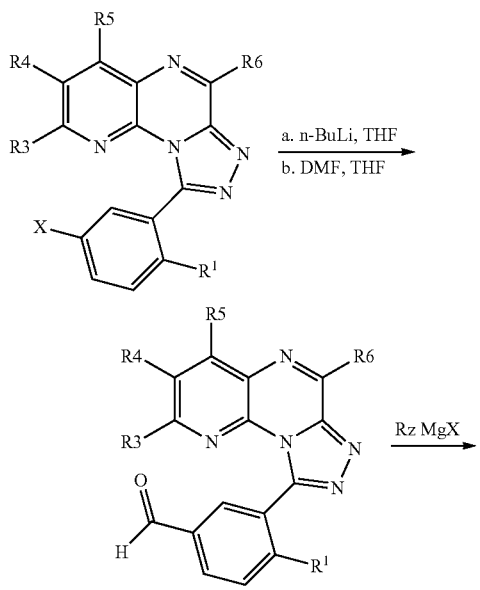

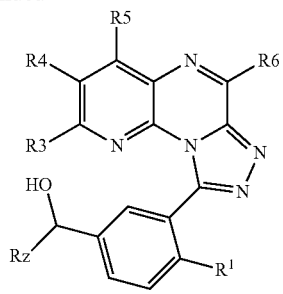

Further examples of the present invention were prepared as described in Scheme 8: in a first step the appropriate aromatic aldehyde is obtained by reaction of alogen derivatives (X=I) with n-BuLi in a suitable solvent (like THF) at low temperature followed by addition of dry DMF in THF. In a second step the suitable commercially available Grignard reagent is added at low temperature.

Rz: Examples 59, 61, 62, 63 were prepared following the above reported procedure.

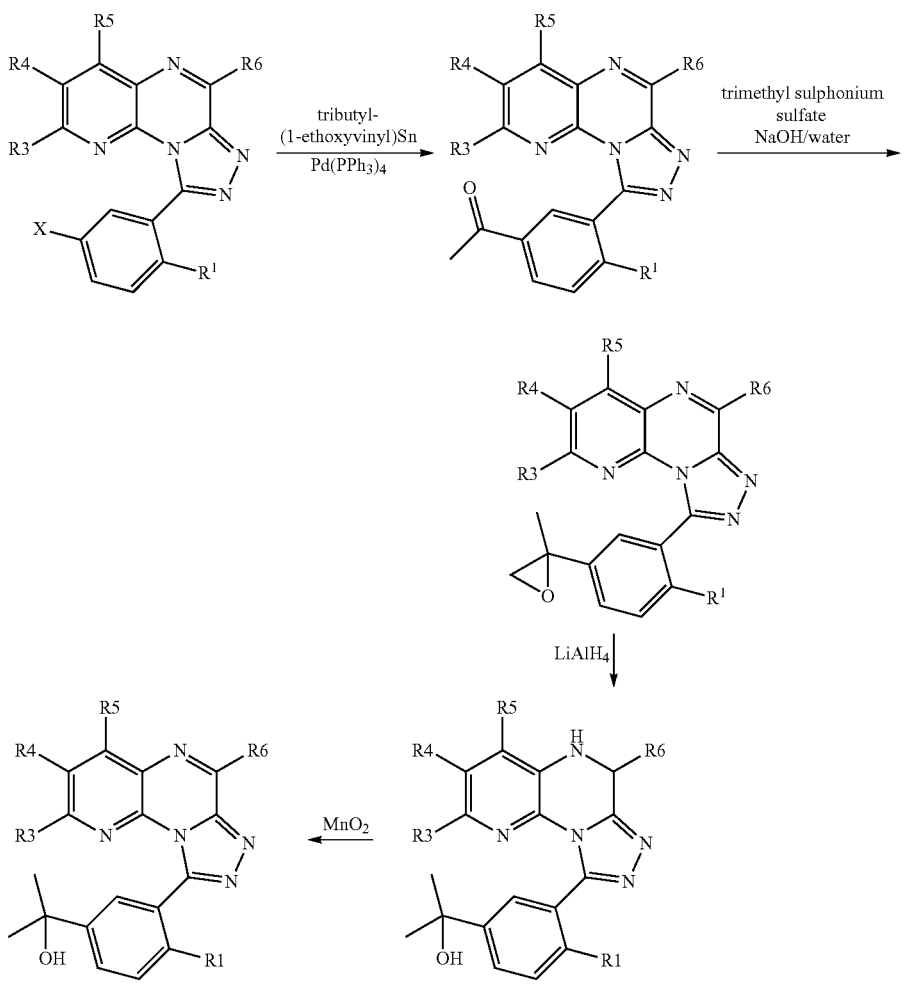

Further examples of the present invention were prepared as described in Scheme 9: in a first step the appropriate ketone is obtained by reaction of alogen derivatives (X=I,Br) with tributyl-(1-ethoxyvinyl-)tin in the presence of Pd(PPh₃)₄. The epoxide obtained by reaction with appropriate trimethyl sulphonium ylide was then subjected to ring opening with hydride and subsequent oxidation with suitable agents such as manganese dioxide in appropriate solvents (DCM).

Examples 76, 77, 78, 79 were prepared following the above reported procedure.

In analogy, the omologated derivatives Examples 80, 81 were obtained performing the first step as described in Scheme 9a.

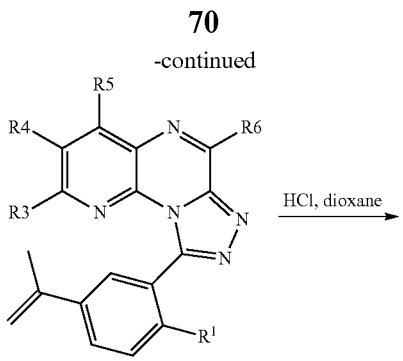

Scheme 9

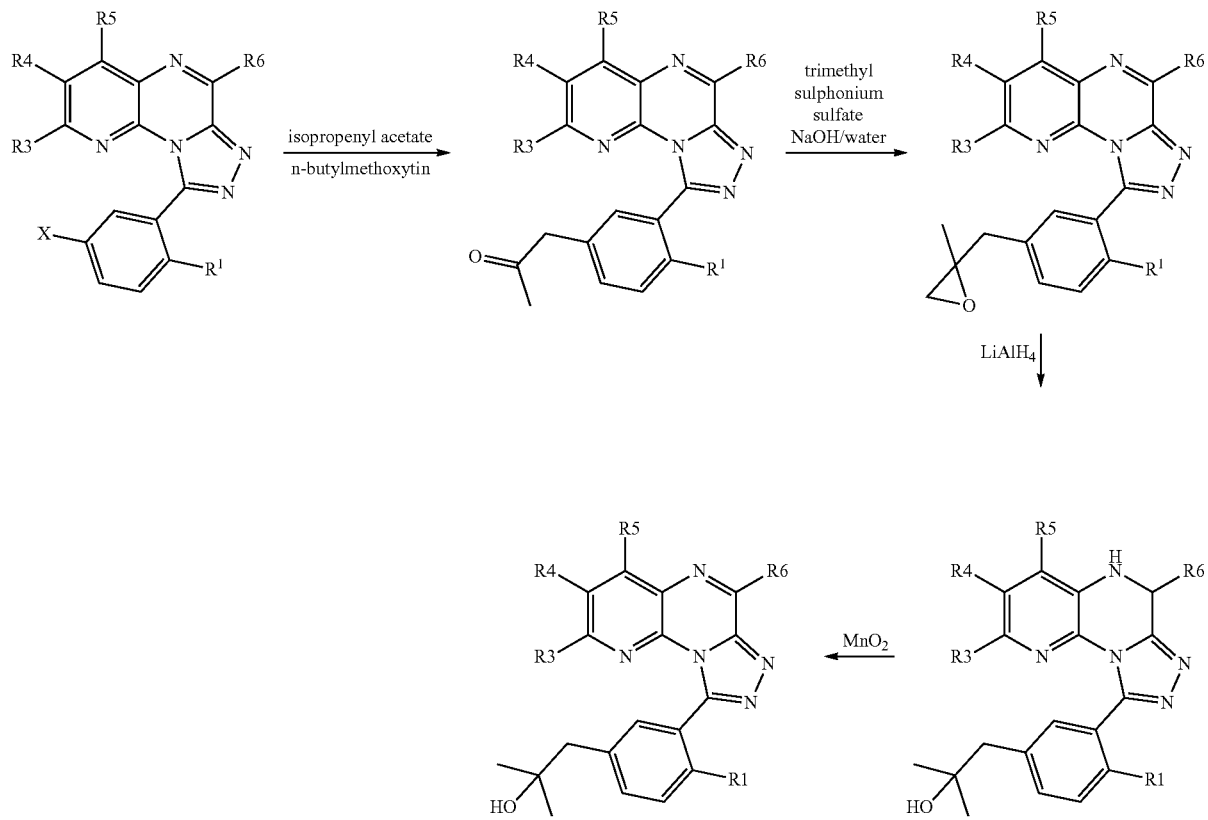

Scheme 10

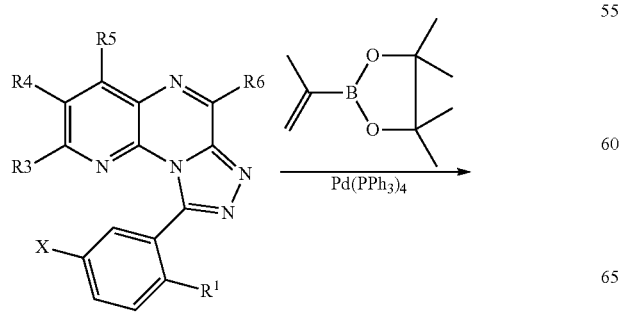

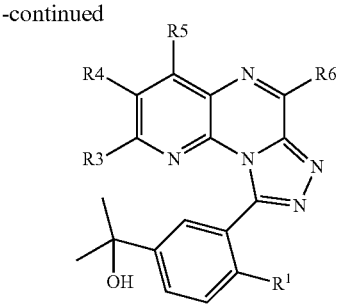

Further examples of the present invention were prepared as described in Scheme 10: in a first step the appropriate double bond is installed by Suzuki coupling with suitable boronic acids or esters (such as for example 2-isopropenyl-dioxaborolane, Scheme 10). In a second step, the hydration of the double bond (HCl/dioxane) allowed to introduce hydroxylic function.

Example 103,103b,103c were prepared following the above described procedure.

The compounds according to the invention are advantageously also obtainable using the methods described in the examples that follow, which may also be combined for this purpose with methods known to the skilled man from the literature.

As already mentioned, the compounds of general formula I according to the invention and the physiologically acceptable salts thereof have valuable pharmacological properties, particularly as inhibitors of phosphodiesterase 2 and/or 10.

BIOLOGICAL EXAMPLES

In-vitro Effect:

The in-vitro effect of the active compounds of the invention can be shown with the following biological assays.

a) Radioactive PDE2 Assay Protocol:

For all experiments the Phosphodiesterase [$^3$H]cAMP SPA Enzyme Assay (TRKQ7090, GE Healthcare Europe GmbH) were used. The enzymatic activity of the PDE2 and the inhibitory potency of compounds was measured by the conversion of [$^3$H]cAMP to [$^3$H]AMP. [$^3$H]AMP associate to the scintillator soaked yttrium-silicate beads resulting in an increase in scintillation events. Compounds that inhibit the respective enzymes decrease the generation of [$^3$H]AMP and accordingly the number of counts detected.

SF9 lysate containing PDE2A is incubated at room temperature for 1 h with [$^3$H]cAMP and the reaction is terminated by addition of SPA beads in 18 mM zinc sulphate. The [$^3$H] AMP bound to SPA beads is determined after at least 3 hours of sedimentation of the beads, the signal is recorded using the TopCount with a recording time of 3 min/well.

PDE 2A protein is expressed upon baculovirus infection in SF9 cells. The cells have been incubated upon infection for ~3 days and protein production was confirmed by Western Blot. The cells were collected by centrifugation and the pellet frozen in liquid nitrogen before it was resuspended in PBS containing 1% Triton X-100 and protease inhibitors. After 45 min incubation on ice, the cell debris was removed by centrifugation (13.000 rpm, 30 min).

The assay conditions were as follows:

| | |
|---|---|
| total assay volume: | 40 µl |
| protein amount: | 5 ng |
| protein concentration: | 500 pg/µl |
| substrate concentration: | 20 nM; ~1.08 mCi/l |
| incubation time: | 60 min |

The buffer used for above described assay buffer was:

| |
|---|
| 50 mM Tris/HCl, pH 7.4 |
| 8.3 mM MgCl$_2$ |
| 1.7 mM EGTA |
| 0.1% (w/v) BSA |
| 0.05% (v/v) Tween 20 |

In detail the protocol is as follows:

Into a 384 well plate (OptiPlate, white), the following components are pipetted (either manually or using automated pipetting devices):

20 µl test-compound solution (test compound diluted in assay buffer at twofold the desired concentration)

+10 µl PDE 2A preparation (enzyme diluted in assay buffer to a concentration of 0.5 ng/µl protein)

+10 µl [$^3$H]cAMP (diluted in assay buffer to a concentration of 80 nM cAMP)

Controls included into each experiment:

positive control: no inhibitor, DMSO at the concentration as used in the compound dilutions negative control: no PDE 2 (SF9 lysate instead of SF9/PDE 2A lysate)

Calculation of % Inhibition:

The activity of the positive control (minus the negative control=background) is set to 100% and activity in the presence of compound is expressed relative to these 100%.

Calculation of IC50:

IC50 are calculated with GraphPadPrism or other suited software setting the positive control as 100 and the negative control as 0. For calculation of IC50 usually 11 dilutions of the test compound are selected.

b) Radioactive PDE10 Assay Protocol:

For assessing activity of compounds on PDE10 inhibition, the following modifications of the protocol described above are applied:

protein amount: 3 ng protein concentration: 75 µg/µl

In detail the protocol is as follows:

Into a 384 well plate (OptiPlate, white), the following components are pipetted (either manually or using automated pipetting devices):

20 µl test-compound solution (test compound diluted in assay buffer at twofold the desired concentration)

+10 µl PDE 10A preparation (enzyme diluted in assay buffer to a concentration of 0.3 ng/µl protein)

+10 µl cAMP tracer (diluted in assay buffer to a concentration of 80 nM cAMP, specific activity ~4 mCi/l)

After addition of all 3 components the plates are shortly spun and incubated at room temperature for 60 min. The reaction is stopped by the addition of 20 µl Yttrium SPA PDE Beads containing 18 mM zinc sulphate in water After at least 3 hours sedimentation of the beads, the signal is recorded using the TopCount with a recording time of 3 min/well.

PDE 10A protein is expressed upon baculovirus infection in SF9 cells. The cells have been incubated upon infection for ~3 days and protein production was confirmed by Western Blot. The cells were collected by centrifugation and the pellet frozen in liquid nitrogen before it was resuspended in PBS containing 1% Triton X-100 and protease inhibitors. After 45 min incubation on ice, the cell debris was removed by centrifugation (13.000 rpm, 30 min).

In the following table the results of the above described experiments are listed.

TABLE 3

Activity of the examples (Ex) compiled in the experimental part, based on above described assays (cAMPA SPA radioactive).

| Ex. | PDE2 IC$_{50}$ [µM] | PDE10 IC$_{50}$ [µM] |
|---|---|---|
| 1 | 0.016 | 0.421 |
| 2 | 0.004 | 0.040 |
| 3 | 0.155 | 0.411 |
| 4 | 0.138 | 0.441 |
| 13 | 0.053 | 2.190 |
| 14 | 0.202 | 3.580 |

TABLE 3-continued

Activity of the examples (Ex) compiled in the experimental part, based on above described assays (cAMPA SPA radioactive).

| Ex. | PDE2 IC$_{50}$ [μM] | PDE10 IC$_{50}$ [μM] |
|---|---|---|
| 15 | 0.040 | >10 |
| 16 | 0.058 | 1.876 |
| 17 | 0.098 | 5.72 |
| 18 | 0.071 | 3.01 |
| 19 | 0.146 | 3.01 |
| 20 | 0.028 | 2.76 |
| 21 | 0.070 | 2.82 |
| 22 | 0.115 | >5 |
| 23 | 0.071 | 5.10 |
| 24 | 0.138 | 6.69 |
| 25 | 0.055 | 3.26 |
| 26 | 0.116 | 1.38 |
| 27 | 0.004 | 0.97 |
| 28 | 0.009 | >10 |
| 29 | 0.017 | 2.38 |
| 30 | 0.027 | 3.92 |
| 31 | 0.007 | 1.90 |
| 32 | 0.003 | 1.76 |
| 33 | 0.004 | 2.50 |
| 34 | 0.009 | 1.89 |
| 35 | 0.009 | 1.30 |
| 36 | 0.219 | 0.85 |
| 37 | 0.171 | 3.08 |
| 38 | 0.417 | 1.96 |
| 39 | 0.914 | 2.10 |
| 40 | 0.080 | 3.47 |

Another, non radioactive, in-vitro assay was performed as follows c) Phosphodiesterase (PDE) 2A and 10 Assay with Fluorescent Substrate Assay Principle:

The PDE reaction cleaves cAMP to AMP. The IMAP system (Molecular Device) using fluorescence polarization (FP) as detection principle was used to measure enzyme activity. A fluorescent labeled cAMP was used as substrate for the reaction, generating a labeled AMP. The fluorescent AMP binds specifically to the large M(III)-based nano-particles which reduces the rotational speed of the substrate and thus increases its polarization.

Detailed Method:

The inhibition of PDE 2A or 10 enzyme activity was assessed using IMAP-Phosphodiesterase-cAMP fluorescence labeled substrate (Molecular Devices, Order No. R7506), IMAP TR-FRET screening express (Molecular Devices, Order No. R8160, the TR-FRET component will not be used) and PDE 2A or PDE10 protein expressed upon baculovirus infection in SF9 cells. The cells were incubated after infection for ~3 days and protein production was confirmed by Western Blot. The cells were collected by centrifugation and the pellet frozen in liquid nitrogen before it was resuspended in PBS containing 1% Triton X-100 and protease inhibitors. After 45 min incubation on ice, the cell debris was removed by centrifugation (13.000 rpm, 30 min). Since SF 9 cells do not express cAMP hydrolyzing enzymes to a high extent, no further purification of the protein was needed.

All reactions were performed in 384 well plates, Perkin Elmer black optiplates and IMAP reaction buffer with 0.1% Tween20 (kit component)

Compounds were serial diluted in DMSO. With an intermediate dilution step with reaction buffer DMSO concentration was reduced to achieve 1% DMSO in the assay reaction. Setup of the assay started with 10 μl enzyme (~10 ng/well, depending on prep. batch), 5 μl compound, reaction was started by addition of 5 μl labeled cAMP (30 nM, final concentration), immediately mixed for 15 seconds on a Eppendorf mixmate (2000 rpm) followed by an incubation at room temperature for 90 minutes in the dark. Reaction is stopped by adding of 60 μl binding buffer for FP/cAMP (kit component). After at least 90 min of further incubation (room temperature, dark) the assay was measured at 485 nm excitation/525 nm emission in an Envision multilabel reader (PerkinElmer).

Each assay plate contained wells with vehicle controls (1% DMSO) for the measurement of non-inhibited reaction (=100% control) and wells without enzyme as 0% controls.

The analysis of the data was performed by calculation of the percentage of inhibition in the presence of test compound compared to the vehicle control samples (100% control, no inhibition) and a low control (0% control, no enzyme). IC50 values are calculated with Assay Explorer or other suited software based on curve fitting of results of at least 8 different compound concentrations. The compound concentrations may vary according to the needed range, but typically cover the range between 10 μM and 0.1 pM.

TABLE 3a

Activity of the examples (Ex) compiled in the experimental part, based on above described assays (IMAP fluorescent).

| Ex. | PDE2 IC$_{50}$ [μM] | PDE10 IC$_{50}$ [μM] |
|---|---|---|
| 1 | 0.041 | 0.355 |
| 2 | 0.003 | 0.033 |
| 4 | 0.120 | 0.256 |
| 5 | 0.003 | 0.005 |
| 6 | 0.003 | 0.010 |
| 7 | 0.003 | 0.016 |
| 8 | 0.002 | 0.008 |
| 9 | 0.001 | 0.015 |
| 10 | 0.229 | 0.254 |
| 11 | 0.059 | 0.123 |
| 12 | 0.009 | 0.044 |
| 12a | 0.036 | 0.170 |
| 13 | 0.095 | 6.363 |
| 15 | 0.112 | 1.118 |
| 16 | 0.098 | 8.700 |
| 17 | 0.162 | 10.200 |
| 18 | 0.090 | 8.418 |
| 20 | 0.077 | 8.162 |
| 21 | 0.022 | 7.047 |
| 22 | 0.207 | 9.317 |
| 23 | 0.216 | 9.193 |
| 25 | 0.038 | 7.333 |
| 27 | 0.018 | 0.958 |
| 28 | 0.020 | 0.299 |
| 29 | 0.037 | 5.097 |
| 30 | 0.020 | 2.573 |
| 31 | 0.008 | 2.897 |
| 32 | 0.026 | 6.703 |
| 32a | 0.006 | 7.390 |
| 33 | 0.005 | 3.417 |
| 34 | 0.017 | 2.143 |
| 35 | 0.017 | 1.477 |
| 35a | 0.003 | 0.822 |
| 40 | 0.077 | 8.707 |
| 41 | 0.050 | 2.770 |
| 42 | 0.035 | 2.520 |
| 43 | 0.057 | 3.015 |
| 43a | 0.109 | 4.510 |
| 44 | 0.156 | 6.037 |
| 45 | 0.005 | 1.488 |
| 46 | 0.050 | 1.035 |
| 47 | 0.008 | 0.852 |
| 48 | 0.008 | 1.520 |
| 49 | 0.033 | 3.760 |
| 50 | 0.194 | 7.120 |
| 51 | 0.009 | 2.150 |
| 52 | 0.011 | 1.195 |
| 53 | 0.140 | 2.830 |
| 54 | 0.058 | 0.798 |

TABLE 3a-continued

Activity of the examples (Ex) compiled in the experimental part, based on above described assays (IMAP fluorescent).

| Ex. | PDE2 IC$_{50}$ [μM] | PDE10 IC$_{50}$ [μM] |
|---|---|---|
| 55 | 0.080 | 5.298 |
| 55a | 0.033 | 2.435 |
| 56 | 0.002 | 0.061 |
| 56a | 0.008 | 0.061 |
| 56b | 0.001 | 0.066 |
| 57 | 0.006 | 0.045 |
| 57a | 0.012 | 0.167 |
| 57b | 0.003 | 0.091 |
| 58 | 0.143 | 0.663 |
| 58a | 0.054 | 0.713 |
| 58b | 0.045 | 0.663 |
| 58c | 0.037 | 0.241 |
| 59 | 0.008 | 0.936 |
| 60 | 0.019 | 0.285 |
| 61 | 0.004 | 0.534 |
| 62 | 0.011 | 1.300 |
| 63 | 0.060 | 1.710 |
| 64 | 0.045 | 3.870 |
| 65 | 0.214 | 3.545 |
| 66 | 0.003 | 0.674 |
| 67 | 0.175 | 3.905 |
| 68 | 0.002 | 1.007 |
| 69 | 0.001 | 0.891 |
| 70 | 0.163 | 8.620 |
| 71 | 0.109 | 2.080 |
| 72 | 0.032 | 2.865 |
| 73 | 0.189 | 10.000 |
| 74 | 0.131 | 2.340 |
| 75 | 0.012 | 2.403 |
| 76 | 0.021 | 1.105 |
| 77 | 0.004 | 1.400 |
| 78 | 0.010 | 2.845 |
| 79 | 0.144 | 0.305 |
| 80 | 0.010 | 5.405 |
| 81 | 0.007 | 5.384 |
| 82 | 0.199 | 5.615 |
| 83 | 0.004 | 8.815 |
| 84 | 0.006 | 0.565 |
| 85 | 0.006 | 4.325 |
| 86 | 0.434 | 5.750 |
| 87 | 0.074 | 2.594 |
| 88 | 0.001 | 0.302 |
| 89 | 0.018 | 0.187 |
| 90 | 0.103 | 0.485 |
| 91 | 0.001 | 0.077 |
| 92 | 0.002 | 0.553 |
| 93 | 0.086 | 6.107 |
| 94 | 0.001 | 2.719 |
| 95 | 0.005 | 1.369 |
| 96 | 0.043 | 5.945 |
| 96a | 0.199 | 10.000 |
| 96b | 0.087 | 10.000 |
| 96c | 0.591 | 7.460 |
| 97 | 0.004 | 2.142 |
| 97a | 0.004 | 5.945 |
| 97b | 0.004 | 0.891 |
| 98 | 0.139 | 1.560 |
| 99 | 0.125 | 1.510 |
| 100 | 0.017 | 3.856 |
| 101 | 0.047 | 1.125 |
| 102 | 0.103 | 2.265 |
| 103 | 0.003 | 1.007 |
| 103b | 0.100 | 10.000 |
| 103c | 0.622 | 7980 |
| 104 | 0.036 | 7.715 |
| 104a | 0.040 | 3.229 |
| 104b | 0.030 | 9.765 |
| 105 | 0.023 | 1.540 |
| 105a | 0.104 | 3.630 |
| 105b | 0.038 | 3.410 |
| 106 | 0.160 | 1.940 |
| 106a | 0.429 | 1.410 |
| 106b | 0.050 | 2.500 |
| 107 | 0.007 | 0.022 |
| 111 | 0.022 | 3.980 |
| 108a | 0.011 | 0.548 |
| 108b | 0.059 | 0.594 |
| 108c | 0.024 | 0.262 |
| 108d | 0.046 | 0.630 |
| 109a | 0.014 | 1.670 |
| 109b | 0.009 | 1.090 |
| 109c | 0.009 | 1.360 |
| 109d | 0.004 | 1.830 |
| 110b | 0.388 | >10 |
| 110d | 0.467 | 7.600 |
| 111a | 0.065 | 1.830 |
| 111b | 0.011 | 2.130 |
| 112 | 0.018 | 7.000 |
| 112a | 0.025 | 2.600 |
| 112b | 0.068 | 2.500 |
| 113 | 0.0002 | 3.190 |
| 114 | 0.022 | 10.000 |
| 114a | 0.009 | 10.000 |
| 114b | 0.011 | 10.000 |
| 115 | 0.039 | 10.000 |
| 115a | 0.082 | 10.000 |
| 115b | 0.045 | 10.000 |

In-vivo Effect:

Animal Experiments and Sample Analysis (CSF):

Test compounds were administered to animals (rat) different routes at doses of 10.0 or 5 μmol/kg, (both oral and intravenous). After compound administration, the animals were sacrificed in a $CO_2$ chamber and CSF samples were carefully collected by puncture of the cisterna magna. Immediately after CSF sampling, blood was taken by heart puncture and brains were dissected out. Blood was collected in EDTA-coated microvettes and plasma was prepared by centrifugation. Concentration of the test compounds in plasma, CSF or brain homogenate was determined using HPLC-MS-MS.

TABLE 4

Plasma, brain and CSF concentration

| Ex. | Time(*) (h) | conc plasma (nmol/L) | conc brain (nmol/L) | c(brain)/ c(plasma) | conc CSF (nmol/L) | c(CSF)/ c(plasma) |
|---|---|---|---|---|---|---|
| 44 | 0.5 | 2187 | 670 | 0.31 | 228 | 0.10 |
| 34 | 0.5 | 223 | 146 | 0.7 | 19 | 0.09 |
| 18 | 0.5 | 1225 | 351 | 0.3 | 163 | 0.13 |
| 20 | 0.5 | 338 | 272 | 0.82 | 37 | 0.11 |
| 45 | 2 | 801 | 183 | 0.20 | 25 | 0.03 |
| 64 | 2 | 783 | 254 | 0.5 | 37 | 0.06 |
| 76 | 2 | 463 | 218 | 0.5 | 18 | 0.04 |
| 75 | 2 | 1130 | 383 | 0.34 | 31 | 0.03 |
| 70 | 2 | 2377 | 695 | 0.29 | 276 | 0.12 |
| 47 | 2 | 622 | 441 | 0.7 | 22 | 0.04 |
| 49 | 2 | 239 | 47 | 0.2 | 13 | 0.06 |

(*)Time between administration and CSF sampling

For the skilled in the art it is evident from the experimental results shown above that the compounds of the present invention are not only very potent phosphodiesterase 2 and/or 10 inhibitors but also reach high CSF concentrations and adequate CSF to plasma ratios.

Metabolic Stability

The metabolic stability of the compounds according to the invention has been investigated as follows:

The metabolic degradation of the test compound was assayed at 37° C. with pooled liver microsomes from various species. The final incubation volume of 100 µl per time point contains TRIS buffer pH 7.6 at room temperature (0.1 M), magnesium chloride (5 mM), microsomal protein (1 mg/mL for human and dog, 0.5 mg/mL for other species) and the test compound at a final concentration of 1 µM. Following a short preincubation period at 37° C., the reactions were initiated by addition of betanicotinamide adenine dinucleotide phosphate, reduced form (NADPH, 1 mM), and terminated by transferring an aliquot into solvent after different time points. After centrifugation (10000 g, 5 min), an aliquot of the supernatant was assayed by $LC_{10}$ MS/MS for the amount of parent compound. The half-life was determined by the slope of the semi-logarithmic plot of the concentration-time profile.

TABLE 4

Stability of compounds of the present invention in human liver microsomes.

| Ex. | Half-life - $t^{1/2}$ [min] |
|---|---|
| 1 | 130 |
| 5 | 43 |
| 6 | 66 |
| 9 | 41 |
| 12 | 63 |
| 13 | 130 |
| 17 | 130 |
| 18 | 130 |
| 20 | 130 |
| 21 | 130 |
| 30 | 130 |
| 32 | 130 |
| 32a | 36 |
| 34 | 130 |
| 35 | 130 |
| 35a | 130 |
| 42 | 130 |
| 43 | 130 |
| 44 | 130 |
| 45 | 130 |
| 46 | 130 |
| 47 | 130 |
| 48 | 130 |
| 49 | 130 |
| 50 | 130 |
| 51 | 130 |
| 52 | 130 |
| 54 | 130 |
| 55 | 130 |
| 55a | 130 |
| 56 | 120 |
| 56a | 110 |
| 56b | 62 |
| 57 | 130 |
| 57a | 130 |
| 57b | 93 |
| 58 | 130 |
| 58a | 130 |
| 58b | 130 |
| 58c | 130 |
| 59 | 49 |
| 61 | 65 |
| 62 | 130 |
| 63 | 130 |
| 64 | 130 |
| 66 | 57 |
| 67 | 130 |
| 68 | 39 |
| 69 | 53 |
| 70 | 130 |
| 71 | 130 |

TABLE 4-continued

Stability of compounds of the present invention in human liver microsomes.

| Ex. | Half-life - $t^{1/2}$ [min] |
|---|---|
| 72 | 130 |
| 73 | 130 |
| 75 | 130 |
| 76 | 130 |
| 77 | 90 |
| 78 | 79 |
| 80 | 83 |
| 81 | 26 |
| 82 | 130 |
| 83 | 100 |
| 84 | 39 |
| 85 | 130 |
| 87 | 130 |
| 88 | 53 |
| 89 | 130 |
| 91 | 28 |
| 92 | 23 |
| 93 | 130 |
| 94 | 38 |
| 96 | 110 |
| 97 | 51 |
| 99 | 130 |
| 100 | 12 |
| 101 | 22 |
| 102 | 130 |
| 104 | 130 |
| 104a | 130 |
| 104b | 130 | hERG (Human Ether-à-go-go-Related Gene)-Channel Assay hERG channel inhibition of compounds of the present invention has been investigated as follows:

HEK (human embryonic kidney) 293 cells were stably transfected with hERG cDNA.

Cells were superfused with a bath solution containing (mM): NaCl (137), KCl (4.0), MgCl2 (1.0), CaCl2 (1.8), Glucose (10), HEPES (10), pH 7.4 with NaOH. Patch pipettes were made from borosilicate glass tubing using a horizontal puller and filled with pipette solution containing (mM): K-aspartate (130), MgCl2 (5.0), EGTA (5.0), K2ATP (4.0), HEPES (10.0), pH 7.2 with KOH. Resistance of the microelectrodes was in the range between 2 and 5 MΩ.

Stimulation and recording:

Membrane currents were recorded using an EPC-10 patch clamp amplifier and PatchMaster software. hERG-mediated membrane currents were recorded at 35° C., using the whole-cell configuration of the patch-clamp technique. Transfected HEK293 cells were clamped at a holding potential of −60 mV and hERG-mediated inactivating tail currents were elicited using a pulse pattern with fixed amplitudes (activation/inactivation: 40 mV for 2000 ms; recovery: 120 mV for 2 ms; ramp to 40 mV in 2 ms; inactivating tail current: 40 mV for 50 ms) repeated at 15 s intervals. During each inter-pulse interval 4 pulses scaled down by a factor of 0.2 were recorded for a P/n leak subtraction procedure. Rs compensation was employed up to a level that safely allowed recording devoid of ringing.

Compound preparation and application:

The different concentrations of the test compound were applied sequentially on each of the different cells investigated. A steady state level of baseline current was measured for at least 6 sweeps prior to the application of the first test compound concentration.

The test compound was dissolved in DMSO to yield a master stock solution which was diluted further in DMSO to stock solutions needed for the lower concentrations. Final dilutions in extracellular buffer were prepared freshly from these stocks by a 1:1000 dilution step each before starting the experiments.

Data analysis and IC50 determination:

Peak current amplitudes were measured 3 ms after the ramp to +40 mV. For baseline and each concentration the peak currents of the three last sweeps before application of the next concentration were averaged. Residual currents (I/I0) were calculated for each cell as the fraction of actual average peak current and average baseline peak current.

The logistic concentration-response curve of the following form was fitted to the residual current data using a genetic algorithm:

$$I/I0 = 1 - 1/(1 + (C/IC50)^{**}p)$$

C: actual concentration of compound (in μM)
IC50: half-inhibitory concentration (in μM)
p: Hill slope

TABLE 4 hERG channel inhibition of compounds of the present invention.

| Ex. | hERG IC$_{50}$ [μM] |
|---|---|
| 13 | >10 |
| 18 | >10 |
| 20 | >10 |
| 21 | >10 |
| 27 | >10 |
| 28 | >10 |
| 32 | >10 |
| 32a | >10 |
| 34 | >10 |
| 35a | >10 |
| 45 | >10 |
| 47 | >10 |
| 48 | >10 |
| 49 | >10 |
| 55 | >10 |
| 64 | >10 |
| 66 | >10 |
| 68 | 8.3 |
| 75 | >10 |
| 76 | >10 |
| 80 | >10 |
| 82 | >10 |
| 83 | >10 |
| 84 | 6.3 |
| 85 | >10 |
| 87 | >10 |
| 88 | >10 |
| 93 | >10 |

In view of their ability to inhibit the activity of phosphodiesterase 2 and/or 10 activity, their CSF values and their metabolic stability and their low inhibition of the hERG channel, the compounds of general formula I according to the invention, including the tautomers thereof, the stereoisomers thereof, the mixtures thereof, the hydrates thereof, the solvates and the physiologically acceptable salts thereof, are suitable for the treatment and/or preventative treatment of all those diseases or conditions which can be influenced by inhibition of PDE2 and/or 10 hyperactivity and/or cAMP and/or cGMP hypofunction. Therefore, compounds according to the invention, including the physiologically acceptable salts thereof, are particularly suitable for the prevention or treatment of diseases, particularly (1) disorders comprising the symptom of cognitive deficiency; (2) organic, including symptomatic, mental disorders, dementia; (3) mental retardation; (4) mood [affective] disorders; (5) neurotic, stress-related and somatoform disorders including anxiety disorders; (6) behavioural and emotional disorders with onset usually occurring in childhood and adolescence, attention deficit hyperactivity syndrome (ADHD) and Autism spectrum disorders; (7) disorders of psychological development, developmental disorders of scholastic skills; (8) schizophrenia and other psychotic disorders; (9) disorders of adult personality and behaviour; (10) mental and behavioural disorders due to psychoactive substance use; (11) extrapyramidal and movement disorders; (12) episodic and paroxysmal disorders, epilepsy; (13) Systemic atrophies primarily affecting the central nervous system, ataxia; (14) Behavioural syndromes associated with physiological disturbances and physical factors; (15) sexual dysfunction comprising excessive sexual drive; (16) factitious disorders.

In addition, the compounds according to the invention can be used for the treatment, amelioration and/or prevention of cognitive impairment being related to perception, concentration, cognition, learning or memory.

In addition, the compounds according to the invention can be used for the treatment amelioration and/or prevention of cognitive impairment being related to age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, schizophrenia with dementia or Korsakoff's psychosis. In addition, the compounds of the present invention can be used for the treatment of Alzheimer's disease.

In addition compounds according toe the invention can be used for the treatment of pain disorders including but not limited to inflammatory, neuropatic and osteoarthritic pain.

In addition, the compounds according to the invention can be used for the treatment of sleep disorders, bipolar disorder, metabolic syndrome, obesity, diabetis mellitus, hyperglycemia, dyslipidemia, impaired glucose tolerance, or a disease of the testes, brain, small intestine, skeletal muscle, heart, lung, thymus or spleen.

Preferably the compounds according to the invention are suitable for the treatment of Alzheimer's Disease and for the treatment schizophrenia.

More preferably the compounds according to the invention are suitable for symptomatic treatment of Alzheimer's Disease and for the treatment of cognitive impairment associated with schizophrenia.

In particular the compounds according to the invention are suitable for symptomatic treatment of prodromal and mild-to-moderate Alzheimer's Disease and for the treatment of cognitive impairment associated with schizophrenia.

In a further aspect of the present invention the present invention relates to methods for the treatment or prevention of above mentioned diseases and conditions, which method comprises the administration of an effective amount of a compound of general formula I, the tautomers thereof, the stereoisomers thereof, the mixtures thereof, the hydrates thereof, the solvates and the physiologically acceptable salts thereof, to a human being.

The dose range of the compounds of general formula I applicable per day is usually from 0.1 to 1000 mg, preferably from 1 to 500 mg by oral route, in each case administered 1 to 4 times a day.

Each dosage unit may conveniently contain from 0.1 to 500 mg, preferably 1 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Suitable preparations for administering the compounds of formula I, including the physiologically acceptable salts thereof, will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, citric acid, tartaric acid, water, polyvinylpyrrolidone, water/ethanol, water/glycerol, water/sorbitol, water/polyethylene glycol, propylene glycol, cetylstearyl alcohol, carboxymethylcellulose or fatty substances such as hard fat or suitable mixtures thereof.

The compounds according to the invention may also be used in conjunction with other active substances, particularly for the treatment and/or prevention of the diseases and conditions mentioned above. Other active substances which are suitable for such combinations include, for example, BACE inhibitors; amyloid aggregation inhibitors (e.g. ELND-005); directly or indirectly acting neuroprotective and/or disease-modifying substances; anti-oxidants (e.g. vitamin E or ginkolide); anti-inflammatory substances (e.g. Cox inhibitors, NSAIDs additionally or exclusively having Abeta lowering properties); HMG-CoA reductase inhibitors (statins); acetylcholinesterase inhibitors (e.g., donepezil, rivastigmine, tacrine, galantamine); NMDA receptor antagonists (e.g. memantine); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, glycine transporter 1 inhibitors, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced. The compounds according to the invention may also be used in combination with immunotherapies (e.g., active immunisation with Abeta or parts thereof or passive immunisation with humanised anti-Abeta antibodies or nanobodies) for the treatment of the above-mentioned diseases and conditions.

The dosage for the combination partners mentioned above is usefully ⅕ of the lowest dose normally recommended up to 1/1 of the normally recommended dose.

Therefore, in another aspect, this invention relates to the use of a compound according to the invention or a physiologically acceptable salt thereof combined with at least one of the active substances described above as a combination partner, for preparing a pharmaceutical composition which is suitable for the treatment or prevention of diseases or conditions which can be affected by inhibitors of phosphodiesterase 2 and/or 10. These are preferably pathologies related to PDE2 and/or 10 hyperactivity and/or cAMP and/or cGMP hypofunction, particularly one of the diseases or conditions listed above, most particularly prodromal and mild-to-moderate Alzheimer's Disease and cognitive impairment associated with schizophrenia.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

EXAMPLES

The following examples are intended to illustrate the invention, without restricting its scope.
Chemical Manufacture
Abbreviations
ACN acetonitrile
APCI Atmospheric pressure chemical ionization
d day
Cy cyclohexane
DCM dichloromethane
DIPEA diisopropylethylamine
DMF dimethylformamide
DMA dimethylacetamide
ESI electrospray ionization (in MS)
EtOAc ethylacetate
EtOH ethanol
Ex. example h hour(s)
HATU O-(7-azabenzotriazol-1-yl)-N,N,N',N'-tetramethyluronium-hexafluorophosphate
HPLC high performance liquid chromatography
HPLC-MS coupled high performance liquid chromatography-mass spectrometry
M molar (mol/L)
MeOH methanol
min minute(s)
MS mass spectrometry
NMP 1-methyl-2-pyrrolidinone
rt room temperature
$R_t$ retention time (in HPLC)
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
UPLC-MS ultra performance liquid chromatography-mass spectrometry Methods:
UPLC-MS methods:
Method 1
Instrument: LC/MS Waters Acquity UPLC System DAD, SQD single quadrupole; column: HSS C18 1.8 μm 2.1×50 mm, Temp 35° C.; mobile phase: A=$H_2O$ 90%+10% $CH_3CN$+$CF_3COOH$ 0.1%, B=$CH_3CN$ 90%+$H_2O$ 10%; gradient: 0.0 min 0% B→1.20 min 100% B→1.45 min 100% B→1.55 min 0% B→1.75 min 0% B; flow rate: 0.70 mL/min; detection: UV 254 nm; detection: SQD, single quadrupole; ion source: ES+/ES−; scan range: 90-900 amu.

Method 2
Instrument: LC/MS Waters Acquity UPLC System DAD, SQD single quadrupole; column: BEH C18 1.7 μm 2.1×50 mm, Temp 35° C.; mobile phase: A=$H_2O$ 90%+10% $CH_3CN$+$NH_4COOH$ 5 mmol, B=$CH_3CN$ 90%+$H_2O$ 10%; gradient: 0.0 min 0% B→1.20 min 100% B→1.45 min 100% B→1.55 min 0% B→1.75 min 0% B; flow rate: 0.70 mL/min; detection: UV 254 nm; detection: SQD, single quadrupole; ion source: ES+/ES−; scan range: 90-900 amu.

Method 3
Instrument: LC/MS Waters Acquity UPLC System DAD, ELSD detector, SQD single quadrupole; column: HSS C18 1.8 μm 2.1×50 mm, Temp 35° C.; mobile phase: A=$H_2O$ 90%+10% $CH_3CN$+$CF_3COOH$ 0.1%, B=$CH_3CN$ 90%+$H_2O$ 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ES+/ES−; scan range: 90-900 amu.

Method 4
Instrument: LC/MS Waters Acquity UPLC System DAD, ELSD detector, SQD single quadrupole; column: HSS C18 1.8 μm 2.1×50 mm, Temp 35° C.; mobile phase: A=$H_2O$ 90%+10% $CH_3CN$+$NH_4COOH$ 5 mmol, B=$CH_3CN$ 90%+$H_2O$ 10%; gradient: 0.0 min 0% B→2.40 min 100% B→2.70 min 100% B →2.80 min 0% B→3.00 min 0% B; flow rate: 0.70 mL/min; detection: UV 254 nm; detection: ELSD detector; detection: SQD, single quadrupole; ion source: ES+/ES−; scan range: 90-900 amu.

HPLC-MS Methods:
Method 5
Instrument: LC/MS ThermoFinnigan. Hplc Surveyor DAD, MSQ Quadrupole; column: Synergi Hydro-RP80A, 4 um, 4.60×100 mm; eluent A: 90% water+10% ACN+ammonium formate 10 mM; eluent B=ACN 90%+10% $H_2O$+$NH_4COOH$ 10 mM; gradient: A (100) for 1.5 min, then to B (100) in 10 min for 1.5 min; flow rate: 1.2 mL/min; UV Detection: 254 nm; Ion source: APCI.

Method 6
Instrument: LC/MS ThermoFinnigan HPLC Surveyor DAD, LCQ Fleet Ion Trap; column:
Simmetry Shield RPB, 5 μm, 4.6×150 mm; eluent A: 90% water+10% ACN+HCOOH 0.1%; eluent B=ACN 90%+10% $H_2O$+HCOOH 0.1%; gradient: 0.0 min 5% B→1.5 min 5% B→11.5 min 95% B→13.0 min 95% B→13.3 min 5% B→15.0 min 5% B; flow rate: 1.0 mL/min; UV Detection: 254 nm; Detection: Finnigan Fleet, Ion Trap; ion source: ES+; scan range: 100-900 amu.

Method 7
Instrument: LC/MS ThermoFinnigan. Hplc Surveyor DAD, MSQ Quadrupole; column: Synergi Hydro-RP8, 4 um, 4.60×100 mm; eluent A: 90% water+10% ACN+ammonium formate 10 mM; eluent B=ACN 90%+10% $H_2O$+$NH_4COOH$ 10 mM; gradient: 0.0 min 30% B→1.50 min 50% B→8.50 min 100% B→13.50 min 100% B→14.00 min 30% B→15.00 min 30% B; flow rate: 0.85 mL/min; UV Detection: 254 nm; Ion source: ES+.

Method 8
Instrument: LC/MS ThermoFinnigan. Hplc Surveyor DAD, MSQ Quadrupole; column: Synergi Hydro-RP100A, 2.5 um, 3×50 mm; eluent A: 90% water+10% ACN+ammonium formate 10 mM; eluent B=ACN 90%+10% $H_2O$+$NH_4COOH$ 10 mM; gradient: A (100) for 1.5 min, then to B (100) in 10 min for 1.5 min; flow rate: 0.7 mL/min; UV Detection: 254 nm; Ion source: APCI.

Method 9
Instrument: LC/MS ThermoFinnigan. Hplc Surveyor DAD, MSQ Quadrupole; column: Synergi Hydro-RP100A, 2.5 um, 3×50 mm; eluent A: 90% water+10% ACN+ $NH_4COOH$ 5 mM; eluent B=ACN 90%+10% $H_2O$; gradient: A (100), then to B (100) in 4 min for 1.3 min; flow rate: 1.2 mL/min; UV Detection: 254 nm; Ion source: APCI.

Method 13
Instrument: LC/MS ThermoFinnigan HPLC Surveyor DAD, LCQ Fleet Ion Trap; column: Xselect CSH, 2.5 um, 4.6×50 mm; eluent A: 90% water+10% ACN+HCOOH 0.1%; eluent B=ACN 90%+10% $H_2O$+HCOOH 0.1%; gradient: A (100), then to B (100) in 4 min for 1.3 min; then to A(100) in 1.6 min. flow rate: 1.4 mL/min; UV Detection: 254 nm; Ion source: ESI.

Method 16
Instrument: LC/MS Waters Alliance 2695 HPLC System DAD, Quattro Micro Triple quadrupole; Column: Atlantis dC18 5 μm 4.6×50 mm, Temp 35° C.: Mobile phase: A=$H_2O$ 90%+10% $CH_3CN$+$CF_3COOH$ 0.05%; B=$CH_3CN$ 90%+10% $H_2O$; flow rate: 1.3 mL/min; UV Detection: 254 nm; Ion source: ESI.

Gradient:

| Time in min | % A | % B |
| --- | --- | --- |
| 0.00 | 100 | 0 |
| 0.70 | 100 | 0 |
| 4.5 | 0 | 100 |
| 5.80 | 0 | 100 |
| 6.00 | 100 | 0 |

Method 17
Instrument: LC/MS ThermoFinnigan HPLC Surveyor DAD, LCQ Fleet Ion Trap; column: Xselect CSH, 2.5 um, 4.6×50 mm; eluent A: 90% water+10% ACN+HCOOH 0.1%;

eluent B=ACN 90%+10% H₂O+HCOOH 0.1%; flow rate: 1.4 mL/min; UV Detection: 254 nm; Ion source: ESI.
Gradient:

| Time in min: | % A | % B |
|---|---|---|
| 0.00 | 100 | 0 |
| 1.00 | 100 | 0 |
| 8.50 | 0 | 100 |
| 10.0 | 0 | 100 |
| 10.2 | 100 | 0 |
| 11.0 | 100 | 0 |

GC-MS Methods:
Method 10 (3A.2)
Instrument: GC/MS Thermo Scientific TRACE GC ULTRA, DSQ II MS single quadrupole; column: Agilent DB-5MS, 25m×0.25 mmol×0.25 µm; carrier gas: Helium, 1 mL/min costant flow; oven program: 50° C., to 100° C. in 10° C./min, to 200° C. in 20° C./min, to 320° C. in 30° C./min (hold 10 min); detection: DSQ II MS single quadrupole; ion source: EI; scan range: 50-450 amu.
Preparative HPLC Methods:
Method 11:
Instrument: Waters Autopurification HPLC/MS System; column: Sunfire C18, ODB 5.0 µm, 19×100 mm. MS Zq single quadropole; eluent A: 90% water+0.05% TFA; eluent B=ACN gradient: 0.0 min 20% B→6.5 min 60% B→7.0 min 95% B→8.5 min 20% B flow rate: 40 mL/min; UV Detection: 254 nm; Ion source: ES+.
Method 12:
Instrument: Waters Autopurification HPLC/MS System; column: Sunfire C18, ODB 5.0 µm, 19×100 mm. MS Zq single quadropole; eluent A: 90% water+0.05% TFA; eluent B=ACN gradient: 0.0 min 50% B→6.5 min 90% B→7.0 min 95% B→8.5 min 50% B flow rate: 40 mL/min; UV Detection: 254 nm; Ion source: ES+.
Method 14:
Instrument: Waters Autopurification HPLC/MS System; column: Xbridge, C18 5 µm, 19×100 mm. MS Zq single quadropole; eluent A: 90% water+NH₄COOH 5 mM, eluent B=ACN gradient: 0.0 min 40% B→6.5 min 80% B→7.0 min 95% B→8.0 min 95% B→8.5 min 40% B flow rate: 40 mL/min; UV Detection: 254 nm; Ion source: ES+.
Method 15
Instrument: Waters Autopurification HPLC/MS System; column: Xbridge, C18 5 µm, 19×100 mm. MS Zq single quadropole; eluent A: 90% water+NH₄COOH 5 mM, eluent B=ACN gradient: 0.0 min 30% B→6.5 min 80% B→6.50 min 70% B→8.0 min 95% B→8.5 min 30% B flow rate: 40 mL/min; UV Detection: 254 nm; Ion source: ES+.
Chiral HPLC Methods:
Instrument: HPLC Agilent 1100 (DAD equipped; UV Detection: 230 nm); flow rate: 15 mL/min; column temperature: 25° C.
Method C1
column: Daicel Chiralpack AS-H; eluent: Hexane:EtOH=70:30
Method C1a
column: Daicel Chiralpack AS-H; eluent: Hexane:EtOH=80:20
Method C2
column: Daicel Chiralpack AD-H; eluent: Hexane:Isopropanol=70:30
Method C2a
column: Daicel Chiralpack AD-H; eluent: Hexane:Isopropanol=75:25

Method C2b
column: Daicel Chiralpack AD-H; eluent: Hexane:Isopropanol=80:20
Method C2c
column: Daicel Chiralpack AD-H; eluent: Hexane:Isopropanol=60:40
Method C3
column: Daicel Chiralcel OJ-H; eluent: Hexane:EtOH=80:20

The most suitable purification techniques applied for the purification of compounds of the present invention are direct phase silica gel flash chromatography and reverse phase chromatography or preparative HPLC, General Comment Concerning the Presentation of the Structures Compounds with stereogenic centre(s): The structures depicted in the experimental section will not necessarily show all the stereochemical possibilities of the compounds but only one.

The structural presentation of the compounds in the experimental section will show a stereochemical bond only in case where the absolute stereochemistry is known.

The structural presentation of the compounds in the experimental section with unknown absolute stereochemistry will show a planar bond plus an additional comment that indicates if the described compound is a racemic mixture, a single stereoisomer and where applicable the relative stereochemistry.

Two examples are given below.

Example 1 the Presented Chemical Structure is Depicted as

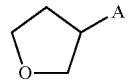

Racemic Mixture

The added term racemic mixture points to the two stereochemical options and thus the manufactured compounds is a mixture of:

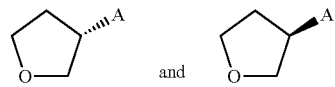

When racemic mixtures of above depicted structures are separated, the single stereoisomers are depicted as:

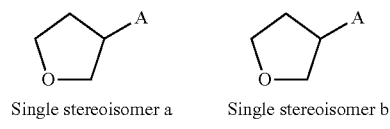

Single stereoisomer a        Single stereoisomer b

The added term 'single stereoisomer' indicates that the absolute configuration is unknown.

Single stereoisomer a is assigned to the first eluting isomer in chiral HPLC, single stereoisomer b is assigned to the second eluting isomer in chiral HPLC.

Example 2 the Presented Chemical Structure is Depicted as

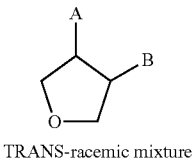

TRANS-racemic mixture

The added term 'TRANS-racemic mixture' points to the two stereochemical options and thus the manufactured compounds is a mixture of:

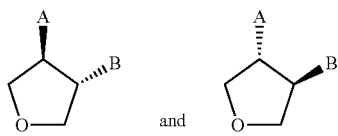

The same principles applies to 'CIS-racemic mixture'.

When racemic mixtures of above depicted structures are separated, the single stereoisomers are depicted as:

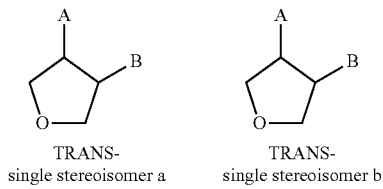

| TRANS- | TRANS- |
| single stereoisomer a | single stereoisomer b |

The added term 'TRANS-single stereoisomer' indicates a relative configuration known (trans) and the planar bond indicates the unknown absolute configuration. The same principles applies to 'CIS-single stereoisomer'.

Single stereoisomer a is assigned to the first eluting isomer in chiral HPLC, single stereoisomer b is assigned to the second eluting isomer in chiral HPLC.

INTERMEDIATES

Intermediate 1

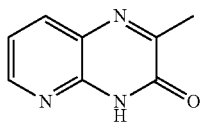

To a stirred solution of 2-oxo-propanoic acid (157 mL, 2.23 mmol) in dry MeOH (100 mL) at 0° C., pyridine-2,3-diamine (20 g, 18 mmol) was added portionwise. The resulting solution was stirred at room temperature overnight, solvent was evaporated under reduced pressure and the suspension filtered. The solid was washed with MeOH, dried to obtain 14 g of title compound.

HPLC-MS (Method 6): $R_t$=5 min
MS: m/z=162 (M+H)$^+$

Intermediate 2

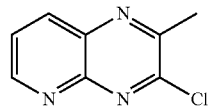

A mixture of Intermediate 1 (1 g) and phosphorus oxychloride (15 mL) was heated to 90° C. for 2.5 h. After cooling, the reaction mixture was carefully poured on ice, then neutralized with a saturated solution of $Na_2CO_3$ and diluted with DCM. Phases were separated, organics washed with a saturated solution of NaCl, dried over sodium sulphate and evaporated to obtain 0.95 g of the title compound.

HPLC-MS (Method 8): $R_t$=4.54 min
MS: m/z=180 (M+H)$^+$

Intermediate 3

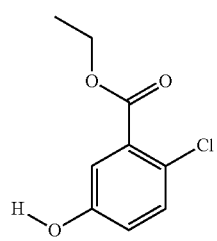

To a mixture of commercially available 2-chloro-5-hydroxybenzoic acid (4 g, 23.18 mmol) in dry EtOH (90 mL), concentrated sulphuric acid (1 mL, 17.62 mmol) was added. The mixture was stirred under reflux overnight, then solvent evaporated under reduced pressure and the residue dissolved with DCM. A saturated solution of $NaHCO_3$ was added, phases were separated, organics dried over sodium sulphate, filtered and evaporated to obtain 5 g of the corresponding 2-chloro-5-hydroxy-benzoic acid ethyl ester.

HPLC-MS (Method 2): $R_t$=1.0 min
MS: m/z=201.6 (M+H)$^+$

Intermediate 4

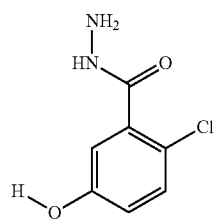 [SMILES: NNC(=O)c1cc(O)ccc1Cl]

Intermediate 3 (5 g, 23.62 mmol) was dissolved in EtOH (100 mL) and hydrazine hydrate (13.0 mL, 262.12 mmol) was added. Mixture was stirred under reflux for 24 h, solvent evaporated and the crude treated with 20 mL of water. The white solid formed was filtered and washed with water and dried for 3 h at 60° C. over $P_2O_5$ to obtain 3.0 g of title compound.

HPLC-MS (Method 2): $R_t$=0.53 min
MS: m/z=180 (M+H)$^+$

Intermediate 5

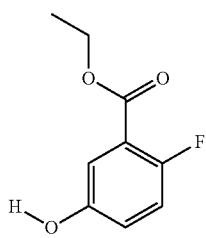

Intermediate 5 was prepared as described for Intermediate 3 starting from commercially available 2-fluoro-5-hydroxybenzoic acid (1 g, 6.41 mmol) to obtain 1.17 g of the title compound.

HPLC-MS (Method 2): $R_t$=0.94 min

MS: m/z=185.16 (M+H)$^+$

The following Ester Intermediates were prepared in analogy to Intermediate 3 starting from commercially available benzoic acids.

| Starting benzoic acid | | Ester Intermediate | MS m/z | $R_t$ (min) | Method |
|---|---|---|---|---|---|
| (HO, 2-methyl-5-hydroxybenzoic acid) | 5a | (ethyl 2-methyl-5-hydroxybenzoate) | 180 [M]$^+$ | 9.73 | 10 |
| (2-chloro-5-fluorobenzoic acid) | 5b | (ethyl 2-chloro-5-fluorobenzoate) | 203 [M + H]$^+$ | 1.2 | 2 |
| (5-bromo-2-chlorobenzoic acid) | 5c | (ethyl 5-bromo-2-chlorobenzoate) | 263 [M]$^+$ | 9.90 | 10 |
| (2-chloro-5-iodobenzoic acid) | 5d | (ethyl 2-chloro-5-iodobenzoate) | 310 [M]$^+$ | 10.47 | 10 |
| (2-fluoro-5-iodobenzoic acid) | 5e | (ethyl 2-fluoro-5-iodobenzoate) | 294 [M]$^+$ | 9.52 | 10 |

| Starting benzoic acid | | Ester Intermediate | MS m/z | R$_t$ (min) | Method |
|---|---|---|---|---|---|
| | 5f | | 242 [M]$^+$ | 9.42 | 10 |
| | 5g | | 246 [M]$^+$ | 8.84 | 10 |
| | 5h | | 290 [M]$^+$ | 10.15 | 10 |

Intermediate 5i

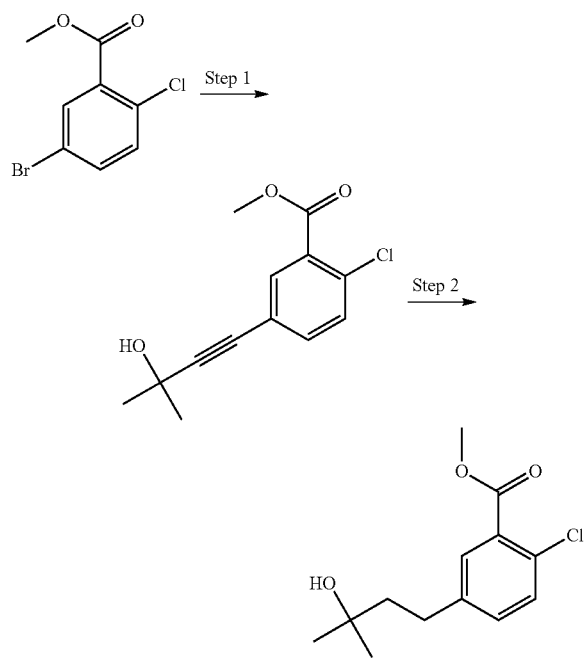

Step 1:
Step 1 was performed in analogy to what reported in literature reference: Li, Yuanzhen et al. Organic Letters, 2007 vol. 9, #20 p. 4057-4060, starting from Ester Intermediate 5c.

Step 2:
Intermediate obtained from Step 1 (0.5 g), was dissolved in toluene (10 mL). Wilkinson's catalyst RhCl(TPP)$_3$ (0.1 g) was added and the reaction mixture stirred at 60° C. under hydrogen atmosphere for 18 h. The reaction mixture was filtered on a celite pad and the solvent was removed under vacuum to obtain the desired product (0.4 g).
GC-MS (Method 10) R$_t$=11.55 min
MS: m/z=256 [M]+

Intermediate 5j

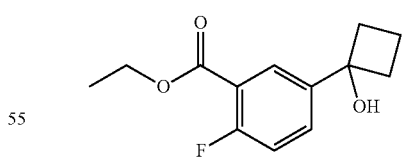

Under nitrogen atmosphere, starting Ester Intermediate 5e (5.0 g, 15.3 mmol) was dissolved in THF (40 mL), the reaction mixture was cooled to −50° C. and stirred for 10 minutes. Isopropyl-magnesium-chloride (11 mL of a 2M solution in THF) was added dropwise and the reaction mixture was stirred at −50° C. for 2 h. The reaction mixture was cooled to −78° C. and a solution of cyclobutanone (2.15 g, 30.6 mmol) in THF (10 mL) was added dropwise. The reaction mixture was stirred at −78° C. for 1 h, then warmed to room temperature and stirred for 18 h. The solvent was removed under vacuum, dichloromethane was added and the reaction mixture was washed with a saturated solution of NaHCO₃. The organic phase was concentrated under vacuum and the crude product obtained was purified by flash chromatography (eluent from 90:10 to 80:20 Cy/EtOAc) to obtain the desired product (3.0 g).

GC-MS (Method 10): $R_t$=10.91 min

MS: m/z=210 (M−28)⁺

The following Ester Intermediates were prepared in analogy to Intermediate 5j and purified applying the most suitable purification technique, starting from the corresponding Starting Esters Intermediates and commercially available ketones.

| Starting Ester intermediate | Starting ketone | | Ester intermediate Structure | MS m/z | $R_t$ (min) | Method |
|---|---|---|---|---|---|---|
| 5d |  | 5k | 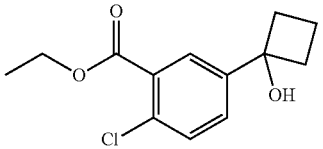 [SMILES: CCOC(=O)c1cc(C2(O)CCC2)ccc1Cl] | 255 [M + H]⁺ | 4.23 | 16 |
| 5d | 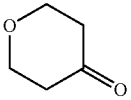 | 5l | 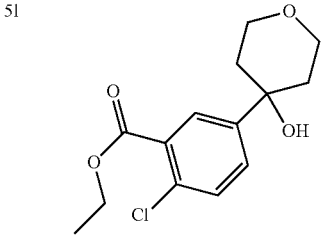 | 284 [M]⁺ | 12.58 | 10 |
| 5d |  | 5m | 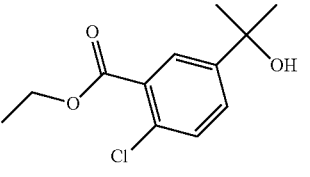 [SMILES: CCOC(=O)c1cc(C(C)(C)O)ccc1Cl] | 243 [M + H]⁺ | 1.04 | 2 |
| 5e | 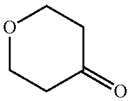 | 5n | 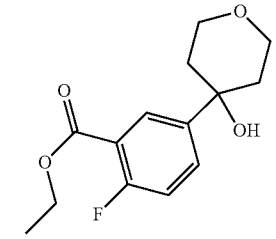 [SMILES: CCOC(=O)c1cc(C2(O)CCOCC2)ccc1F] | 268 [M]⁺ | 11.97 | 10 |
| 5h | 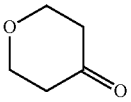 | 5na | 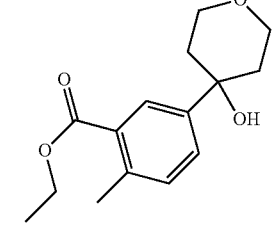 | 264 [M]⁺ | 12.18 | 10 |
| 5d | 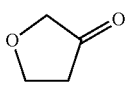 | 5q | 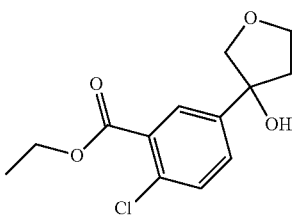 [SMILES: CCOC(=O)c1cc(C2(O)CCOC2)ccc1Cl] | 253 [M + H]⁺ | 2.84 | 13 |

-continued

| Starting Ester intermediate | Starting ketone | | Ester intermediate Structure | MS m/z | $R_t$ (min) | Method |
|---|---|---|---|---|---|---|
| 5e | (tetrahydrofuran-3-one) | 5r | (ethyl 2-fluoro-5-(3-hydroxytetrahydrofuran-3-yl)benzoate) | 237 [M − 17]⁺ | 2.68 | 13 |
| 5d | (tetrahydro-2H-pyran-3-one) | 5s | (ethyl 2-chloro-5-(3-hydroxytetrahydro-2H-pyran-3-yl)benzoate) | 284 [M]⁺ | 12.42 | 10 |

Intermediate 5o

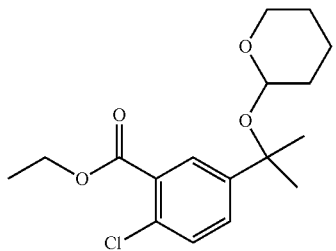 [SMILES: CCOC(=O)c1cc(C(C)(C)OC2CCCCO2)ccc1Cl]

To a solution of Ester Intermediate 5m (0.37 g, 1.52 mmol) in dichloromethane (9 mL), pyridinium-para-toluenesulfonate (0.06 mg, 0.23 mmol) and 3,4-dihydro-2H-pyran (0.2 mL, 2.29 mmol) were added and the reaction mixture was stirred at room temperature for 4 h. The reaction mixture was washed with water and the organic phase was concentrated under vacuum. Crude was purified by flash chromatography (eluent from 100:0 to 80:20 Cy/EtOAc) to obtain the desired product (0.4 g).

GC-MS (Method 10): $R_t$=12.52 min

MS: m/z=326 (M)⁺

Intermediate 5p

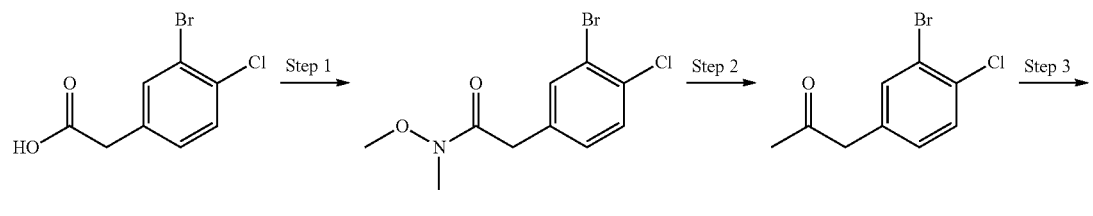

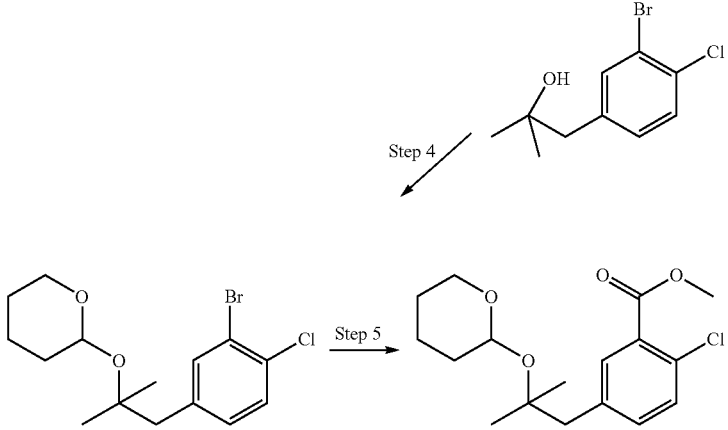

Step 1:
Step 1 was performed in analogy to what reported in the literature reference: Duong, Hung A.; et al. Angewandte Chemie, International Edition, 2011 vol. 50, p. 463-466, starting from commercially available (3-bromo-4-chloro-phenyl)-acetic acid.

Step 2:
Under nitrogen atmosphere, a solution of Intermediate from Step 1 (0.24 g) in THF (10 mL) was stirred at −60° C., methylmagnesium bromide was added dropwise and the reaction mixture was stirred at −78° C. to r.t. for 2 h. The reaction mixture was quenched with saturated ammonium chloride water solution and extracted with ethyl acetate twice, dried over sodium sulfate and concentrated under vacuum to get the crude product as colour-less oil.

Step 3:
Step 3 was performed in analogy to Step 2 starting from Intermediate obtained in Step 2.

Step 4:
Step 4 was performed in analogy to preparation of Intermediate 50, starting from Intermediate obtained in Step 3.

Step 5:
To a solution of the Intermediate obtained from Step 4 (15 g) in MeOH (150 mL), [1,1'-bis(diphenylphosphino)ferrocene]dichloropalladium(II)] (3.088 g) and triethylamine (22 g, 21.4 mL) were added and the reaction mixture was stirred at 80° C. under CO atmosphere for 36 h.

The solvent was removed under vacuum and the crude product obtained was purified by flash chromatography to get the desired product.

Intermediate 6

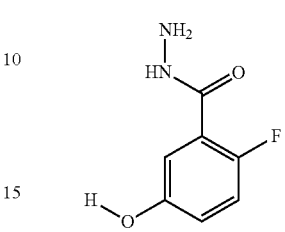

Intermediate 6 (4,4 g) was prepared as described for Intermediate 4 and purified applying the most suitable purification technique, starting from Intermediate 5 (5.84 g, 0.03 mmol).

HPLC-MS (Method 2): $R_t$=0.42 min
MS: m/z=171.2 (M+H)$^+$

The following Hydrazide Intermediates were prepared in analogy to Intermediate 4 and purified applying the most suitable purification technique, starting from the corresponding Ester Intermediates.

| Starting Ester intermediate | | Hydrazide Intermediate Structure | MS m/z | $R_t$ (min) | Method |
|---|---|---|---|---|---|
| 5a | 6a | | 167 [M + H]$^+$ | 0.47 | 17 |
| 5b | 6b | | 188 [M]$^+$ | 9.47 | 10 |
| 5c | 6c | | 249 [M + H]$^+$ | 1.98 | 13 |
| 5d | 6d | | 296 [M]$^+$ | 11.78 | 10 |

-continued

| Starting Ester intermediate | Hydrazide Intermediate | Structure | MS m/z | R$_t$ (min) | Method |
|---|---|---|---|---|---|
| 5e | 6e | 2-fluoro-5-iodobenzohydrazide | 281 [M + H]$^+$ | 1.83 | 9 |
| 5f | 6f | 5-bromo-2-methylbenzohydrazide | 229 [M + H]$^+$ | 1.80 | 9 |
| 5g | 6g | 5-bromo-2-fluorobenzohydrazide | 233 [M + H]$^+$ | 1.55 | 9 |
| 5h | 6h | 5-iodo-2-methylbenzohydrazide | 277 [M + H]$^+$ | 1.94 | 9 |
| 5i | 6i | 2-chloro-5-(3-hydroxy-3-methylbutyl)benzohydrazide | 256 [M + H]$^+$ | 0.68 | 2 |
| 5j | 6j | 2-fluoro-5-(1-hydroxycyclobutyl)benzohydrazide | 225 [M + H]$^+$ | 0.56 | 2 |
| 5k | 6k | 2-chloro-5-(1-hydroxycyclobutyl)benzohydrazide | 241 [M + H]$^+$ | 0.59 | 2 |

-continued

| Starting Ester intermediate | Hydrazide Intermediate | | MS m/z | R$_t$ (min) | Method |
|---|---|---|---|---|---|
| 5l | 6l | (structure) | 271 [M + H]$^+$ | 0.57 | 2 |
| 5m | 6m | (structure) | 228 [M]$^+$ | 11.79 | 10 |
| 5n | 6n | (structure) | 255 [M + H]$^+$ | 0.43 | 2 |
| 5na | 6na | (structure) | 251 [M + H]$^+$ | 0.57 | 2 |
| 5o | 6o | (structure) | 313 [M + H]$^+$ | 0.85 | 2 |
| 5p | 6p | (structure) | 327 [M + H]$^+$ | 0.90 | 2 |
| 5q | 6q | (structure) | 257 [M + H]$^+$ | 0.49 | 13 |

| Starting Ester intermediate | Hydrazide Intermediate Structure | MS m/z | $R_t$ (min) | Method |
|---|---|---|---|---|
| 5r | 6r | 241 [M + H]$^+$ | 0.44 | 2 |
| 5s | 6s | 271 [M + H]$^+$ | 0.58 | 2 |

Intermediate 7

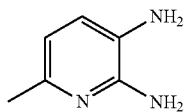

Commercially available 2-amino-6-methyl-3-nitropyridine (12 g, 78.36 mmol) was dissolved in a mixture of dry THF/MeOH (1:1, 60 mL) and hydrogenated in the presence of Pd/C (10%, 1.2 g) under 5 bar hydrogen atmosphere for 5 h. Catalyst was filtered, solvent evaporated under reduced pressure to obtain 7 g of the title compound.

HPLC-MS (Method 2): $R_t$=0.77 min
MS: m/z=154 (M+H)$^+$

Intermediate 7a

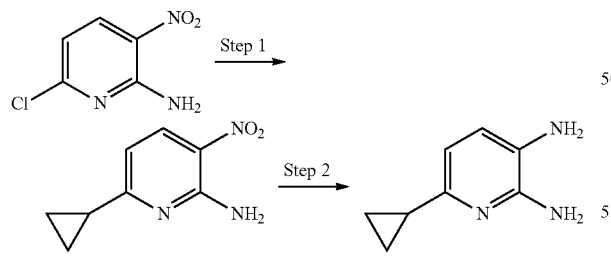

Step 1:
2-Amino-6-chloro-3-nitro-pyridine (20 g, 115 mmol), cyclopropylboronic acid (12.8 g, 150 mmol), tricyclohexylphosphine (3.2 g, 11.5 mmol), 2,6-ditert-butyl-4-methylphenol (5.08 g, 23 mmol), palladium acetate (1.3 g, 5.7 mmol) and tri-potassium-phosphate (73 g, 346 mmol) were suspended in toluene (40 mL) and water (2 mL). The reaction mixture was stirred at reflux for 18 h, diluted with ethyl acetate and washed with water. The organic phase was separated, concentrated under vacuum and dried over sodium sulfate. The crude product obtained was purified by flash chromatography (eluent from 90:10 to 45:55 Cy/EtOAc) to obtain the desired product (10.6 g).

GC-MS (Method 10): $R_t$=10.54 min
MS: m/z=179 (M)$^+$

Step 2:
To a solution of Intermediate from Step 1 (6 g, 19 mmol) in absolute EtOH (120 mL), zinc (13.7 g, 209 mmol) and ammonium chloride (30.8 g, 573 mmol) were added and the reaction mixture was stirred at room temperature for 18 h. The reaction mixture was filtered on a celite pad, the solvent was removed under vacuum and the crude product obtained was purified by flash chromatography (eluent 90:10 dichloromethane/MeOH) to obtain the desired product (2.4 g).

HPLC-MS (Method 9): $R_t$=1.42 min
MS: m/z=150 (M+H)$^+$

Intermediate 7b

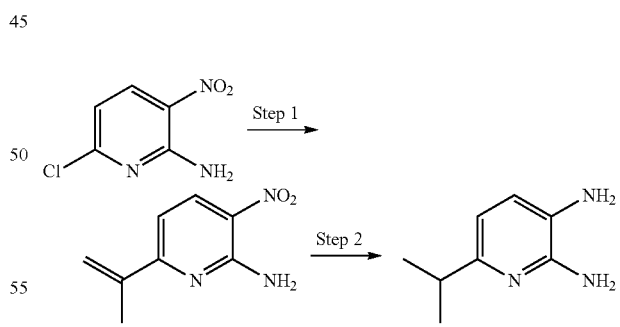

Step 1:
Step 1 was performed in analogy to what described in Step 1 in the preparation of Intermediate 7a, starting from commercially available 2-Isopropenyl-4,4,5,5-tetramethyl-[1,3,2]dioxaborolane.

Step 2:
Intermediate from Step 1 (5 g, 26.5 mmol) was dissolved in 20 mL of methanol, Pd/C (0.25 g) was added and the reaction mixture was stirred under hydrogen atmosphere (4 bar) for 2 h at room temperature. The reaction mixture was filtered on a celite pad and the solvent was removed under vacuum to give the desired product (3 g).

GC-MS (Method 10): $R_t$=8.91 min
MS: m/z=151 (M)$^+$

Intermediate 7c

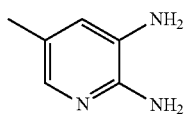

Intermediate 7c (3.99 g) was prepared in analogy to Intermediate 7 and purified applying the most suitable purification technique, starting from commercially available 2-amino-3-nitro-5-picoline (5.0 g, 32.65 mmol).

Intermediate 7d

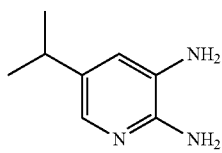

Intermediate 7d (4 g) was prepared in analogy to Intermediate 7b and purified applying the most suitable purification technique, starting from commercially available 2-amino-5-chloro-3-nitro-pyridine (5 g, 26.5 mmol).

HPLC-MS (Method 2): $R_t$=0.6 min
MS: m/z=152 (M+H)$^+$

Intermediate 8

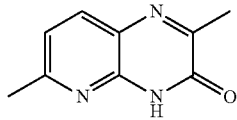

To stirred solution of 2-oxo-propanoic acid (40.8 mL, 587 mmol) in dry MeOH (130 mL) at 0° C., 6-methyl-pyridine-2,3-diamine (Intermediate 7, 6.8 g, 55.2 mmol) dissolved in dry MeOH (40 mL) was added dropwise. The solution was stirred at room temperature overnight then solvent was evaporated under reduced pressure and the resulting suspension filtered. The solid was washed with MeOH, dried to obtain 1.35 g of title compound.

HPLC-MS (Method 9): $R_t$=1.31 min
MS: m/z=176 (M+H)$^+$

Intermediate 8a

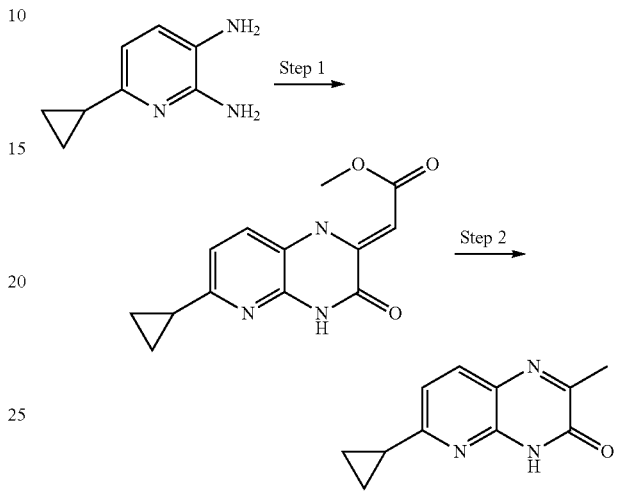

Step 1:
Intermediate 7a (2.4 g, 15.2 mmol) was dissolved in absolute EtOH and stirred at 0° C., Dimethylacetylenedicarboxylate (2.4 g, 16.8 mmol) was added dropwise and the reaction mixture was allowed to react room temperature for 18 h. The solid formed was filtered, washed with EtOH, Ethyl Ether and dried in vacuum to give the desired product (3 g).

HPLC-MS (Method 13): $R_t$=3.16 min
MS: m/z=260 (M+H)$^+$

Step 2:
Intermediate obtained from Step 1 (3 g 0.01 mol) was dissolved in a sodium hydroxide water solution (1.36 g, 0.03 mol in 50 mL) and the reaction mixture was reflux for 2 h. pH was adjusted to 2-3 and the reaction mixture was extracted with ethyl acetate. The organic phase was dried over sodium sulfate, concentrated under vacuum. The crude product obtained was purified by flash chromatography (eluent from 80:20 to 20:80 Cy/EtOAc) to obtained the desired product (2.0 g).

HPLC-MS (Method 13): $R_t$=2.46 min
MS: m/z=202 (M+H)$^+$

The following Amide Intermediates were prepared in analogy to Amide Intermediate 8a and purified applying the most suitable purification technique, starting from the corresponding Di-amine Intermediates.

| Starting Di-amine Intermediate | Amide Intermediate | | MS m/z | $R_t$ (min) | Method |
| --- | --- | --- | --- | --- | --- |
| | Structure | | | | |
| 7b | 8b | | 204 [M + H]$^+$ | 2.48 | 13 |

-continued

| Starting Di-amine Intermediate | Amide Intermediate | Structure | MS m/z | $R_t$ (min) | Method |
|---|---|---|---|---|---|
| 7c | 8c | | 176 [M + H]$^+$ | 1.88 | 13 |
| 7d | 8d | | 204 [M + H]$^+$ | 0.78 | 2 |
| 6-(1-Methyl-cyclopropyl)-pyridine-2,3-diamine (commercially available) | 8e | | 216 [M + H]$^+$ | 4.96 | 17 |
| 6-trifluoromethyl-pyridine-2,3-di-amine (commercially available) | 8f | | 229 [M]$^+$ | 9.42 | 10 |

Intermediate 9

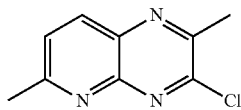

A mixture of Amide intermediate 8 (1.35 g, 7.71 mmol) and phosphorus oxychloride (16 mL) was heated to 90° C. for 3 h. After cooling, solvent was reduced under reduced pressure, the reaction mixture was carefully poured on ice and neutralized with a saturated solution of Na$_2$CO$_3$. DCM was added, phases were separated, organics washed with a saturated solution of NaCl, dried over sodium sulphate and evaporated to obtain 1.39 g of the title compound.

HPLC-MS (Method 8): R$_t$=0.84 min
MS: m/z=194.6 (M+H)$^+$

The following Chloride Intermediates were prepare in analogy to Chloride Intermediate 9 and purified applying the most suitable purification technique, starting from the corresponding Amide Intermediates. Heating temperature reported in Table.

| Starting Amide Intermediate | Chloride Intermediate | Structure | Heating Temperature | MS m/z | R$_t$ (min) | Method |
|---|---|---|---|---|---|---|
| 8a | 9a | | 55° C. | 220 [M + H]$^+$ | 1.01 | 2 |
| 8b | 9b | | 80° C. | 222 [M + H]$^+$ | 3.18 | 13 |
| 8c | 9c | | 90° C. | 194 [M + H]$^+$ | 2.52 | 13 |

-continued

| Starting Amide Intermediate | Chloride Intermediate | Structure | Heating Temperature | MS m/z | $R_t$ (min) | Method |
|---|---|---|---|---|---|---|
| 8d | 9d | | 55° C. | 222 [M + H]$^+$ | 3.19 | 13 |
| 8e | 9e | | 80° C. | 234 [M + H]$^+$ | 1.15 | 2 |

Intermediate 9f

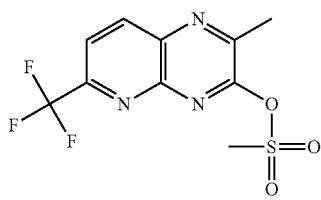 [SMILES: Cc1nc2ccc(C(F)(F)F)nc2nc1OS(C)(=O)=O]

Intermediate 8f (1.35 g, 5.9 mmol) and N,N-diisopropyl-ethylamine (2.28 g, 3 mmol) were dissolved in DMF (10 mL). The reaction mixture was cooled to 0° C. and methanesulfonylchloride (0.74 g, 6.48 mmol) was added dropwise. The reaction mixture was allowed to reach room temperature and stirred for 4 h. Ammonium chloride saturated water solution was added and the reaction mixture was extracted with dichloromethane. The organic phase was washed with citric acid (10% water solution), dried over sodium sulfate and concentrated under vacuum, to give the desired product (1.5 g).

HPLC-MS (Method 13): $R_t$=3.09 min
MS: m/z=308 (M+H)$^+$

The following Intermediates were prepared based on well known reported procedures starting from commercially available starting materials.

| Intermediate | | Structure | Reference |
|---|---|---|---|
| 10 | Toluene-4-sulfonic acid 3-hydroxy-3-methyl-butyl ester | 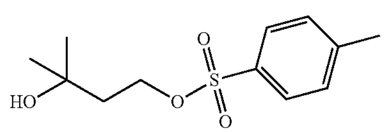 [SMILES: Cc1ccc(S(=O)(=O)OCCC(C)(C)O)cc1] | Bioorganic & Medicinal Chemistry Letters (2007), 17(22), 6164-6168 |
| 11 | Toluene-4-sulfonic acid 3-hydroxy-butyl ester | 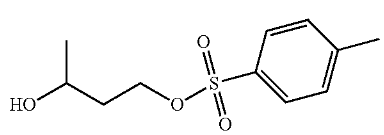 [SMILES: Cc1ccc(S(=O)(=O)OCCC(C)O)cc1] | Bioorganic & Medicinal Chemistry, 18(4), 1665-1675; 2010 |
| 12 | Toluene-4-sulfonic acid 3,3,3-trifluoro-propyl ester | 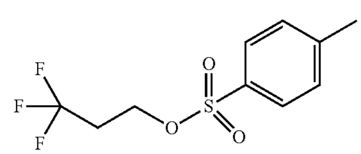 [SMILES: Cc1ccc(S(=O)(=O)OCCC(F)(F)F)cc1] | US 2009-564132 |
| 13 | Toluene-4-sulfonic acid tetrahydropyran-4-yl ester | 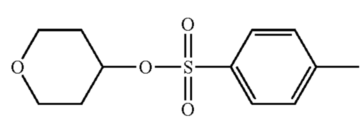 [SMILES: Cc1ccc(S(=O)(=O)OC2CCOCC2)cc1] | WO 2011-20767 |
| 14 | Toluene-4-sulfonic acid 4,4-difluoro-cyclohexyl ester | 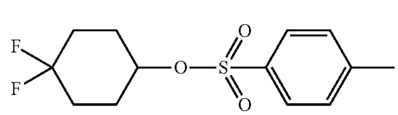 [SMILES: Cc1ccc(S(=O)(=O)OC2CCC(F)(F)CC2)cc1] | WO 2008-119663 |

-continued

| Intermediate | | Structure | Reference |
|---|---|---|---|
| 15 | Toluene-4-sulfonic acid tetrahydro-furan-3-yl ester | 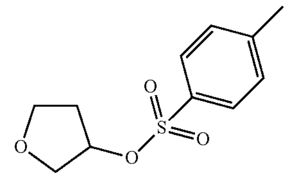 [SMILES: Cc1ccc(S(=O)(=O)OC2CCOC2)cc1] | WO 2010-023594 |
| 16 | Toluene-4-sulfonic acid (S)-(tetrahydro-furan-3-yl) ester | 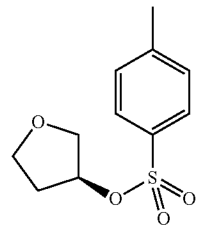 [SMILES: Cc1ccc(S(=O)(=O)O[C@H]2CCOC2)cc1] | WO 2011-061590 |
| 17 | Toluene-4-sulfonic acid (R)-(tetrahydro-furan-3-yl) ester | 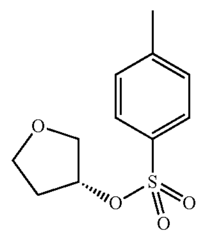 [SMILES: Cc1ccc(S(=O)(=O)O[C@@H]2CCOC2)cc1] | WO 2010-102512 |
| 18 | Toluene-4-sulfonic acid tetrahydro-furan-3-ylmethyl ester | 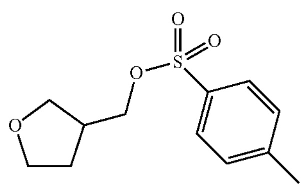 [SMILES: Cc1ccc(S(=O)(=O)OCC2CCOC2)cc1] | WO 2011-084402 |
| 19 | tert-Butyl-(R)-2-chloro-1-methyl-ethoxy)-diphenyl-silane | 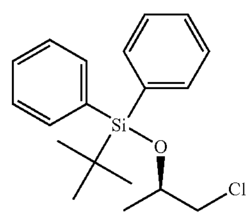 [SMILES: C[C@H](CCl)O[Si](c1ccccc1)(c1ccccc1)C(C)(C)C] | Tetrahedron Letters (1982), 23(25), 2543-6. |
| 20 | tert-Butyl-(S)-2-chloro-1-methyl-ethoxy)-diphenyl-silane | 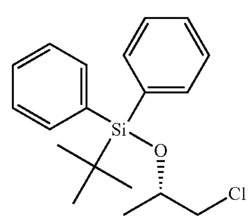 [SMILES: C[C@@H](CCl)O[Si](c1ccccc1)(c1ccccc1)C(C)(C)C] | Tetrahedron Letters (1982), 23(25), 2543-6. |
| 21 | 2-((S)-2-Chloro-1-methyl-ethoxy)-tetrahydro-pyran | 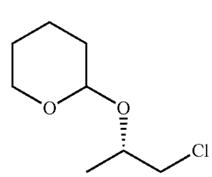 | Tetrahedron Letters (1982), 23(25), 2543-6. |
| 26 | Toluene-4-sulfonic acid 3-methyl-oxetan-3-ylmethyl ester | 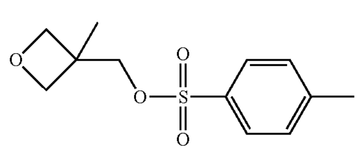 [SMILES: Cc1ccc(S(=O)(=O)OCC2(C)COC2)cc1] | Synthetic Communications (2011), 41(17), 2539-2543 |

| Intermediate | | Structure | Reference |
|---|---|---|---|
| 27 | Toluene-4-sulfonic acid 1-(tetrahydro-pyran-4-yl)-ethyl ester | 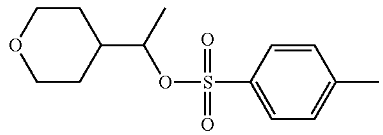 [SMILES: Cc1ccc(S(=O)(=O)OC(C)C2CCOCC2)cc1] | Journal of Organometallic Chemistry (1978), 150(2), 179-85 |
| 28 | Toluene-4-sulfonic acid 1,4-dioxa-spiro[4.5]dec-8-yl ester | 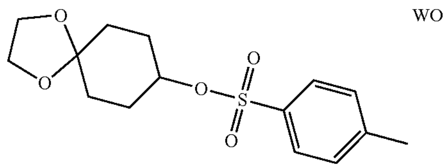 | WO 2010-006086 |
| 29 | Toluene-4-sulfonic acid 3-hydroxy-cyclopentyl ester | 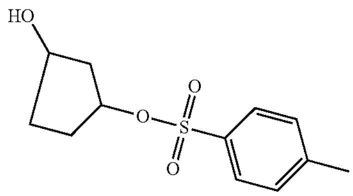 [SMILES: Cc1ccc(S(=O)(=O)OC2CCC(O)C2)cc1] | US 2007-0049537 |

Intermediate 29a

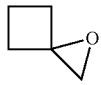

Literature Reference: Journal of Organic Chemistry USSR (English Translation), 1989 vol. 25, #6.1 p. 1019-1025).
Epoxide Intermediate 29a (4 g) was prepared in analogy to what described in WO2010/47956 A1, starting from methylene cyclobutane (5 g, 73 mmol).
GC-MS (Method 10) $R_t$=2.70 min
$[M]^+$=83

Intermediate 29b

Epoxide Intermediate 29b (1 g) was prepared in analogy to what described in WO2013/55577 A1 starting from 3,6-Dihydro-2H-pyran (2 g, 23.78 mmol).
GC-MS (Method 10) $R_t$=8.10 min
$[M]^+$=99

Intermediate 29c

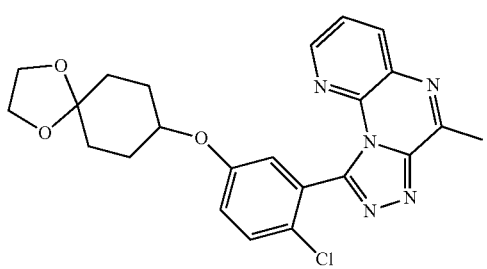 [SMILES: Cc1nc2cccnc2n2c(-c3cc(OC4CCC5(CC4)OCCO5)ccc3Cl)nnc12]

To a solution of Example 1 (0.2 g, 0.67 mmol) in dry DMF (3 mL), cesium carbonate (0.63 g, 1.92 mmol) and Intermediate 28 (0.41 g, 1.28 mmol) were added. Mixture was heated at 80° C. for 1 h, then solvent evaporated under reduced pressure and the residue dissolved in DCM and washed with a saturated solution of NaCl. Phases were separated, organics dried over sodium sulphate and evaporated. The residue was purified by flash chromatography (eluent from 100:0 to 50:50 Cy/EtOAc) to obtain 0.21 g of the title compound.

HPLC-MS (Method 2): $R_t$=1.12 min

MS: m/z=452 (M+H)$^+$

Intermediate 30

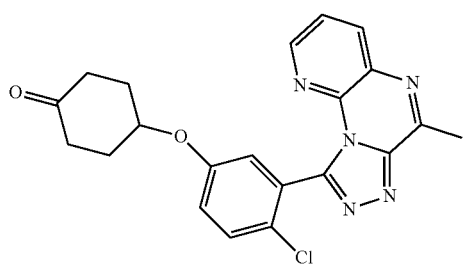 [SMILES: Cc1nc2cccnc2n2c(-c3cc(OC4CCC(=O)CC4)ccc3Cl)nnc12]

To a solution of Intermediate 29c (0.21 g, 0.46 mmol) in acetone (10 mL), a 4M solution of HCl (1 mL) was added and mixture stirred at room temperature for 2 h. Solvent was evaporated under reduced pressure, the residue treated with DCM, washed with a saturated solution of NaHCO$_3$. Phases were separated, organics dried over sodium sulphate and evaporated. The residue was purified by flash chromatography (eluent from 90:10 to 50:50 Cy/EtOAc) to obtain 0.18 g of the title compound.

HPLC-MS (Method 2): $R_t$=1.09 min

MS: m/z=410 (M+H)$^+$

The following intermediates were prepared in analogy to Example 1 and purified applying the most suitable purification technique, starting from the corresponding Chloride and Idrazide intermediates:
| Chloride Intermediate | Hydrazide | | Intermediate Structure | MS m/z | R$_t$ (min) | Method |
|---|---|---|---|---|---|---|
| 9 | 6c | 30a | 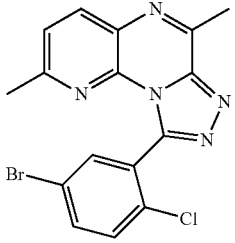 | 388 [M + H]$^+$ | 3.58 | 13 |
| 2 | 6d | 30b | 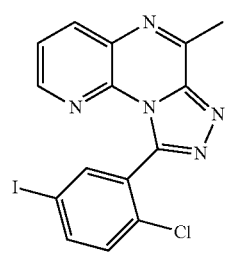 [SMILES: Cc1nc2cccnc2n2c(-c3cc(I)ccc3Cl)nnc12] | 422 [M + H]$^+$ | 1.07 | 2 |
| 2 | 6h | 30c | 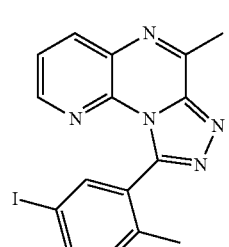 | 402 [M + H]$^+$ | 3.00 | 9 |
| 2 | 6e | 30d | 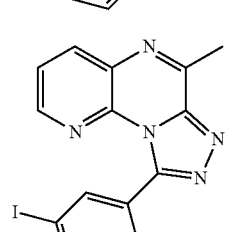 | 406 [M + H]$^+$ | 3.02 | 9 |
| 9a | 6e | 30e | 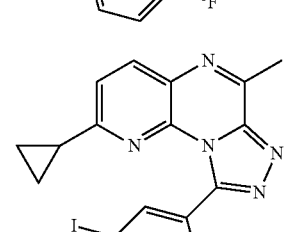 | 446 [M + H]$^+$ | 3.78 | 13 |
| 2 | 6f | 30f | 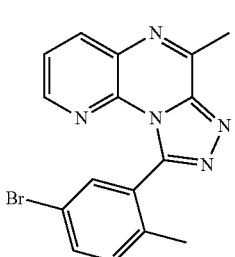 | 354 [M + H]$^+$ | 3.35 | 13 |

-continued
| Chloride Intermediate | Hydrazide | | Intermediate Structure | MS m/z | R$_t$ (min) | Method |
|---|---|---|---|---|---|---|
| 9a | 6f | 30g | 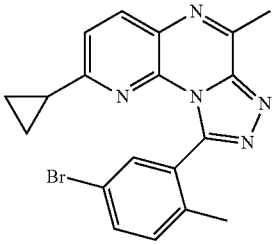 [SMILES: Cc1ccc(Br)cc1-c1nnc2c(C)nc3ccc(C4CC4)nc3n12] | 394 [M + H]$^+$ | 3.69 | 13 |
| 9a | 6d | 30h | 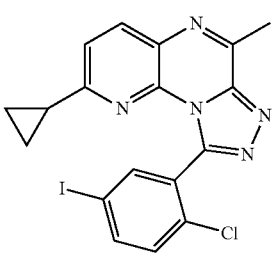 [SMILES: Cc1nc2ccc(C3CC3)nc2n2c(-c3cc(I)ccc3Cl)nnc12] | 462 [M + H]$^+$ | 3.81 | 13 |
| 9a | 6g | 30i | 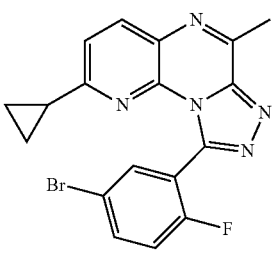 | 398 [M + H]$^+$ | 3.72 | 13 |
| 9 | 6d | 30j | 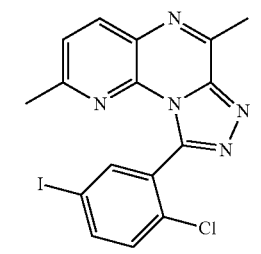 | 436 [M + H]$^+$ | 3.64 | 13 |
| 9b | 6d | 30k | 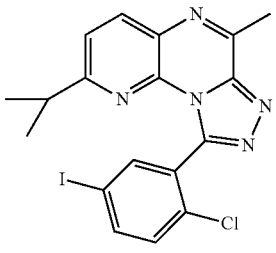 [SMILES: Cc1nc2ccc(C(C)C)nc2n2c(-c3cc(I)ccc3Cl)nnc12] | 464 [M + H]$^+$ | 3.99 | 13 |
| 9b | 6f | 30l | 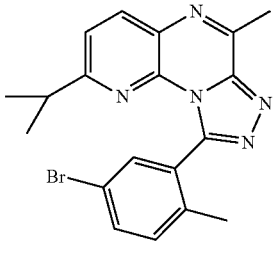 | 396 [M + H]$^+$ | 3.85 | 13 |

-continued

| Chloride Intermediate | Hydrazide | | Intermediate Structure | MS m/z | R_t (min) | Method |
|---|---|---|---|---|---|---|
| 9e | 6e | 30m | | 460 [M + H]+ | 1.29 | 2 |
| 9d | 6f | 30n | | 397 [M + H]+ | 1.27 | 2 |
| 9a | 6b | 30o | | 354 [M + H]+ | 3.53 | 13 |
| 9f | 6d | 30r | | 490 [M + H]+ | 1.25 | 2 |
| 9f | 6g | 30s | | 427 [M + H]+ | 1.15 | 2 |

Intermediate 30p

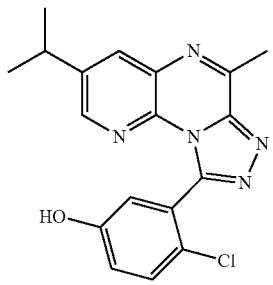 [SMILES: Cc1nc2cc(C(C)C)cnc2n2c(-c3cc(O)ccc3Cl)nnc12]

Intermediate 30p (0.26 g) was prepared in analogy to Example 1 and purified applying the most suitable purification technique, starting from Chloride Intermediate 9d (0.25 g, 1.01 mmol) and Hydrazide Intermediate 4 (0.19 g, 1.01 mmol).
HPLC-MS (Method 2): $R_t$=1.01 min
MS: m/z=354 (M+H)$^+$

Intermediate 31

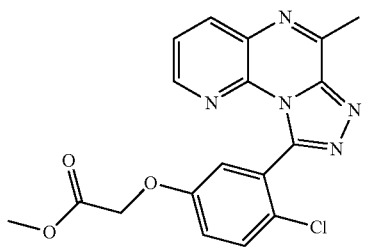

To a solution of Example 1 (0.4 g, 1.3 mmol) in dry DMF (4 mL), cesium carbonate (0.85 g, 2.62 mmol) and methylbromoacetate (0.152 mL, 1.56 mmol) were added. Mixture was stirred at room temperature overnight, solvent evaporated and the residue treated with EtOAc. A saturated solution of NH$_4$Cl was added, phases were separated and evaporated. The crude was purified by flash chromatography (eluent from 50:50 to 0:100 Cy/EtOAc) to obtain 0.29 g of the title compound.
HPLC-MS (Method 13): $R_t$=3.06 min
MS: m/z=384 (M+H)$^+$

Intermediate 32

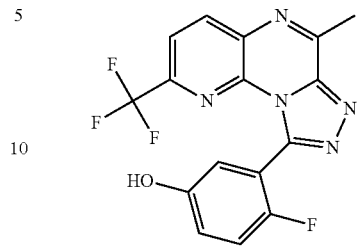

Intermediate 32 (0.5 g) was prepared in analogy to Example 1 and purified applying the most suitable purification technique, starting from Intermediate 9f (0.9 g, 2.52 mmol) and Hydrazide Intermediate 6 (0.47 g, 2.77 mmol).
HPLC-MS (Method 13) $R_t$=3.11 min
MS: m/z=380 (M+H)$^+$ Exemplary Embodiments:

Example 1

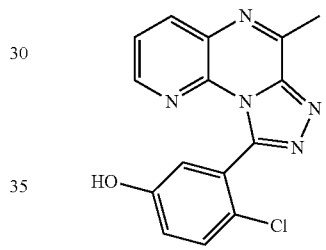

Intermediate 2 (0.60 g, 3.34 mmol) and Intermediate 4 (0.62 g, 3.34 mmol) were suspended in cyclohexanol (5 mL) and heated under reflux for 2 h. The resulting solution was cooled and solvent evaporated under reduced pressure and the residue purified by flash chromatography (eluent 95:5 DCM/EtOH) to obtain 0.95 g of the title compound.
HPLC-MS (Method 9): $R_t$=2.17 min
MS: m/z=312 (M+H)$^+$ The following Examples were prepared in analogy to Example 1 and purified applying the most suitable purification technique, starting from the corresponding Chloride Intermediates and Hydrazide Intermediates:

| Starting Chloride Intermediate | Starting Hydrazide Intermediate | Ex. | Structure | MS m/z [M + H]$^+$ | $R_t$ (min) | Method |
|---|---|---|---|---|---|---|
| 9 | 4 | 2 | 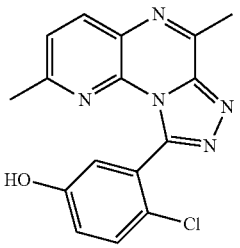 | 326 | 0.93 | 2 |

-continued

| Starting Chloride Intermediate | Starting Hydrazide Intermediate | Ex. | Structure | MS m/z [M + H]$^+$ | R$_t$ (min) | Method |
|---|---|---|---|---|---|---|
| 9 | 3-hydroxy-benzhydrazide (commercially available) | 3 | 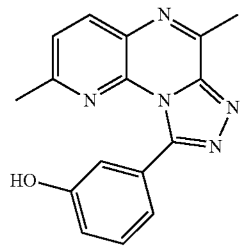 | 292 | 2.62 | 13 |
| 2 | 6 | 4 | 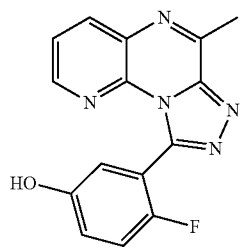 | 296 | 0.79 | 13 |
| 9a | 6 | 5 | | 336 | 2.97 | 13 |
| 9a | 6a | 6 | | 226 | 2.93 | 13 |
| 9b | 6a | 7 | | 334 | 3.16 | 13 |
| 9b | 6 | 8 | | 338 | 3.14 | 13 |

-continued

| Starting Chloride Intermediate | Starting Hydrazide Intermediate | Ex. | Structure | MS m/z [M + H]+ | R_t (min) | Method |
|---|---|---|---|---|---|---|
| 9a | 4 | 9 | 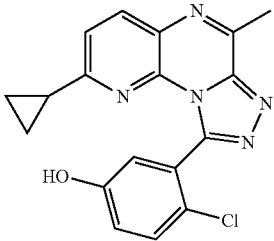 | 352 | 2.59 | 9 |
| 2 | 6a | 10 | 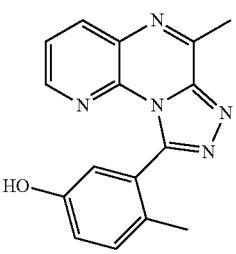 | 292 | 2.03 | 13 |
| 9c | 4 | 11 | 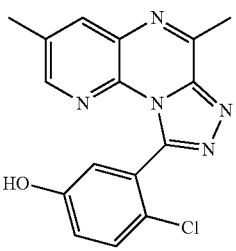 | 326 | 2.96 | 13 |

Example 12

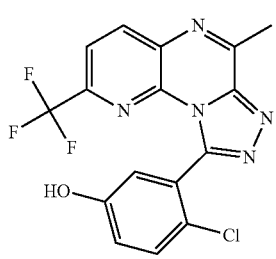 [SMILES: Cc1nc2ccc(C(F)(F)F)nc2n2c(-c3cc(O)ccc3Cl)nnc12]

Example 12 (0.04 g) was prepared in analogy to Example 1 and purified applying the most suitable purification technique, starting from Intermediate 9f (0.3 g, 0.68 mmol) and Hydrazide Intermediate 4 (0.27, 0.68 mmol).

HPLC-MS (Method 13) R_t=3.11 min

MS: m/z=380 (M+H)+

Example 12a

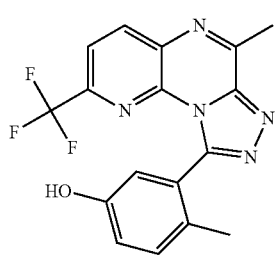 [SMILES: Cc1ccc(O)cc1-c1nnc2c(C)nc3ccc(C(F)(F)F)nc3n12]

Example 12a (0.15 g) was prepared in analogy to Example 12 and purified applying the most suitable purification technique, starting from the Hydrazide Intermediate 6a (0.23 g, 1.45 mmol).

HPLC-MS (Method) R_t=3.00 min

MS: m/z=360 (M+H)+

Example 13

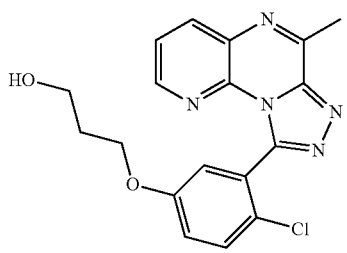 [SMILES: Cc1nc2cccnc2n2c(-c3cc(OCCCO)ccc3Cl)nnc12]

To a solution of Example 1 (0.1 g, 0.24 mmol) in dry ACN (3 mL), cesium carbonate (0.2 g) and commercially available 3-chloro-1-propanol (0.04 mL) were added. Mixture was heated at 80° C. for 1 h, then solvent evaporated under reduced pressure and the residue dissolved in DCM and washed with a saturated solution of NaCl. Phases were separated, organics dried over sodium sulphate and evaporated. The residue was purified by flash chromatography (eluent from 100:0 to 94:6 DCM/EtOH) to obtain 0.02 g of the title compound.

HPLC-MS (Method 8) $R_t$=5.23 min

MS: m/z=370 (M+H)$^+$

Example 14

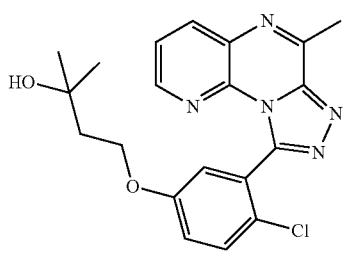 [SMILES: Cc1nc2cccnc2n2c(-c3cc(OCCC(C)(C)O)ccc3Cl)nnc12]

To a solution of Example 1 (0.05 g, 0.16 mmol) in dry DMF (3 mL), Intermediate 10 (0.05 g, 0.018 mmol) and cesium carbonate (0.08 g, 0.24 mmol) were added and mixture heated at 100° C. for 2 h. Solvent was evaporated, the residue was dissolved with DCM, washed with a saturated solution of NaCl. Phases were separated, organics dried over sodium sulphate and evaporated. The residue was purified by flash chromatography (eluent from 70:30 to 20:80 Cy/EtOAc) to obtain 0.025 g of the title compound.

HPLC-MS (Method 9): $R_t$=2.57 min

MS: m/z=398 (M+H)$^+$

Example 15

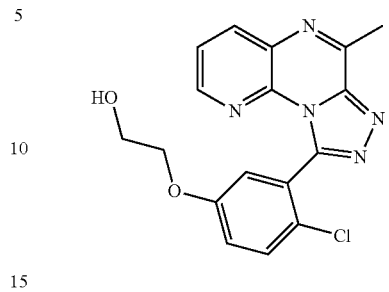

To a solution of Example 1 (0.08 g, 0.16 mmol) in dry ACN (3 mL), commercially available 2-bromo-ethanol (0.65 g, 0.52 mmol) and cesium carbonate (0.5 g, 1.54 mmol) were added and mixture heated at 80° C. for 48 h. Solvent was evaporated, the residue was dissolved with DCM, washed with 1N solution of NaOH and then with a saturated solution of NaCl. Phases were separated, organics dried over sodium sulphate and evaporated. The residue was purified by flash chromatography (eluent from 100:0 to 97:3 DCM/EtOH) to obtain 0.04 g of the title compound.

HPLC-MS (Method 6): $R_t$=8.75 min

MS: m/z=356 (M+H)$^+$

Example 16

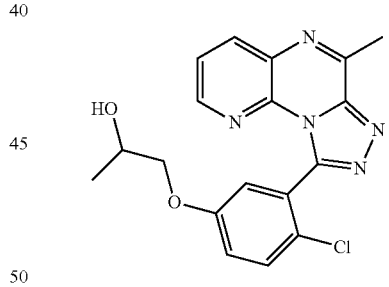

To a solution of Example 1 (0.05 g, 0.16 mmol) in dry DMF (3 mL), commercially available 1-bromo-2-propanol (0.09 g, 0.64 mmol) and potassium tert-butoxide (0.1 g, 0.96 mmol) were added and mixture heated at 130° C. for 8 h. Solvent was evaporated, the residue was dissolved with DCM, washed with 1N solution of NaOH and then with a saturated solution of NaCl. Phases were separated, organics dried over sodium sulphate and evaporated. The residue was purified by flash chromatography (eluent from 100:0 to 97:3 DCM/EtOH) to obtain 0.05 g of the title compound.

HPLC-MS (Method 9): $R_t$=2.23 min

MS: m/z=370 (M+H)$^+$

Example 17

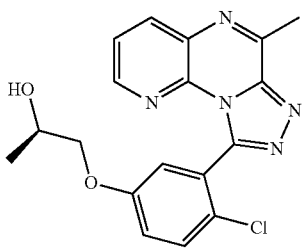 [SMILES: Cc1nc2cccnc2n2c(-c3cc(OC[C@@H](C)O)ccc3Cl)nnc12]

To a solution of Example 1 (0.085 g, 0.27 mmol) in dry DMF (3 mL), commercially available (R)-1-chloro-2-propanol (0.052 g, 0.55 mmol) and potassium tert-butoxide (0.093 g, 0.82 mmol) were added and mixture heated at 130° C. for 48 h. Solvent was evaporated, the residue was dissolved with DCM, washed with 1N solution of NaOH and then with a saturated solution of NaCl. Phases were separated, organics dried over sodium sulphate and evaporated. The residue was purified by flash chromatography (eluent from 100:0 to 97:3 DCM/EtOH) to obtain 0.0085 g of the title compound.

HPLC-MS (Method 9): $R_t$=2.22 min
MS: m/z=370 (M+H)$^+$

Example 18

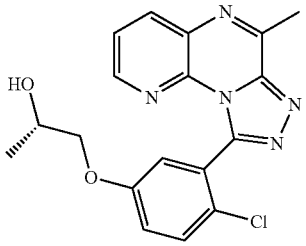 [SMILES: Cc1nc2cccnc2n2c(-c3cc(OC[C@H](C)O)ccc3Cl)nnc12]

Example 18 was prepared as described for Example 17 starting from Example 1 (0.085 g, 0.27 mmol) and commercially available (S)-1-chloro-2-propanol. The residue was purified by flash chromatography (eluent from 100:0 to 90:10 DCM/MeOH) to obtain 0.045 g of the title compound.

HPLC-MS (Method 9): $R_t$=2.19 min
MS: m/z=370 (M+H)$^+$

Example 19

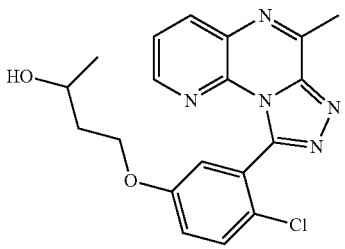 [SMILES: Cc1nc2cccnc2n2c(-c3cc(OCCC(C)O)ccc3Cl)nnc12]

To a solution of Example 1 (0.115 g, 0.37 mmol) in dry DMF (3 mL), cesium carbonate (0.36 g, 1.11 mmol) and Intermediate 11 (0.09 g, 0.37 mmol) were added and mixture heated at 100° C. for 4 h. Solvent was evaporated, the residue was dissolved with DCM, washed with a saturated solution of NaCl. Phases were separated, organics dried over sodium sulphate and evaporated. The residue was purified by flash chromatography (eluent from 100:0 to 80:20 DCM/EtOH) to obtain 0.025 g of the title compound.

HPLC-MS (Method 9): $R_t$=2.4 min
MS: m/z=384 (M+H)$^+$

Example 20

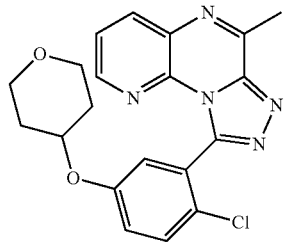 [SMILES: Cc1nc2cccnc2n2c(-c3cc(OC4CCOCC4)ccc3Cl)nnc12]

Example 20 was prepared as described for Example 19, starting from Example 1 (0.08 g, 0.26 mmol) and Intermediate 13 (0.2 g, 0.78 mmol). The residue was purified by flash chromatography (eluent from 100:0 to 50:50 Cy/EtOAc) to obtain 0.032 g of the title compound.

HPLC-MS (Method 9): $R_t$=2.65 min
MS: m/z=396 (M+H)$^+$

Example 21

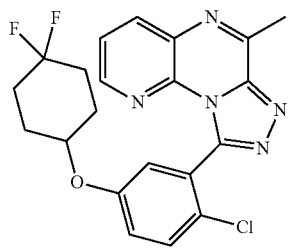 [SMILES: Cc1nc2cccnc2n2c(-c3cc(OC4CCC(F)(F)CC4)ccc3Cl)nnc12]

Example 21 was prepared as described for Example 20, starting from Example 1 (0.065 g, 0.21 mmol) and Intermediate 14 (0.12 g, 0.42 mmol). The residue was purified by flash chromatography (eluent from 100:0 to 50:50 Cy/EtOAc) to obtain 0.035 g of the title compound.

HPLC-MS (Method 9): $R_t$=3.32 min
MS: m/z=430 (M+H)$^+$

Example 22

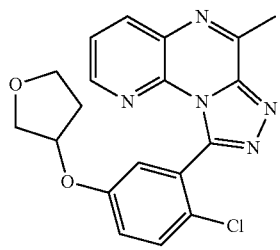 [SMILES: Cc1nc2cccnc2n2c(-c3cc(OC4CCOC4)ccc3Cl)nnc12]

Example 22 was prepared as described for Example 20, starting from Example 1 (0.1 g, 0.32 mmol) and Intermediate 15 (0.093 g, 0.38 mmol). The residue was purified by flash chromatography (eluent from 100:0 to 50:50 Cy/EtOAc) to obtain 0.032 g of the title compound.

HPLC-MS (Method 13): $R_t$=3.03 min
MS: m/z=382 (M+H)$^+$

Example 23

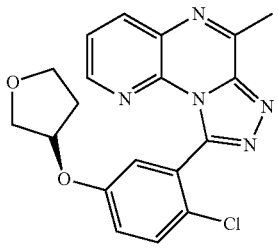

Example 23 was prepared as described for Example 20, starting from Example 1 (0.1 g, 0.32 mmol) and Intermediate 17 (0.093 g, 0.38 mmol). The residue was purified by flash chromatography (eluent from 100:0 to 50:50 Cy/EtOAc) to obtain 0.02 g of the title compound.

HPLC-MS (Method 13): $R_t$=3.07 min

MS: m/z=382 (M+H)$^+$

Example 24

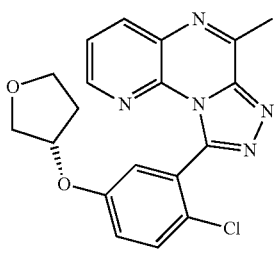

Example 24 was prepared as described for Example 20, starting from Example 1 (0.1 g, 0.32 mmol) and Intermediate 16 (0.093 g, 0.38 mmol). The residue was purified by flash chromatography (eluent from 100:0 to 50:50 Cy/EtOAc) to obtain 0.03 g of the title compound.

HPLC-MS (Method 13): $R_t$=3.05 min

MS: m/z=382 (M+H)$^+$

Example 25

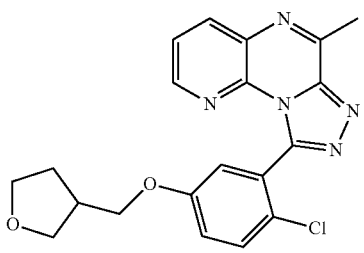 [SMILES: Cc1nc2cccnc2n2c(-c3cc(OCC4CCOC4)ccc3Cl)nnc12]

Example 25 was prepared as described for Example 20, starting from Example 1 (0.1 g, 0.32 mmol) and Intermediate 18 (0.097 g, 0.38 mmol). The residue was purified by flash chromatography (eluent from 100:0 to 50:50 Cy/EtOAc) to obtain 0.03 g of the title compound.

HPLC-MS (Method 13): $R_t$=3.18 min

MS: m/z=396 (M+H)$^+$

Example 26

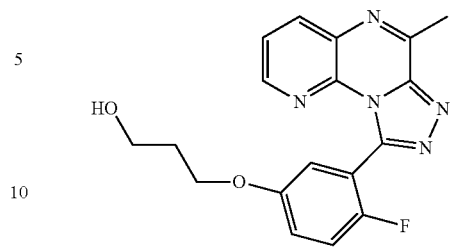

Example 26 was prepared as described for Example 20, starting from Example 4 (0.08 g, 0.27 mmol) and commercially available 3-chloro-1-propanol (0.052 g, 0.54 mmol). The crude was purified by flash chromatography (eluent from 100:0 to 97:3 DCM/EtOH) to obtain 0.052 g of the title compound.

HPLC-MS (Method 13): $R_t$=2.71 min

MS: m/z=354 (M+H)$^+$

Example 27

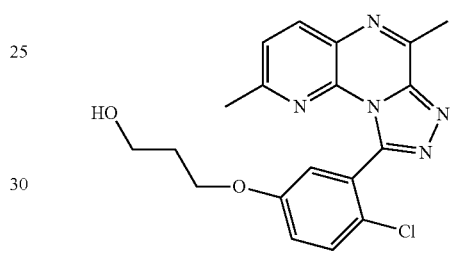

Example 27 was prepared as described for Example 20, starting from Example 2 (0.133 g, 80% content, 0.32 mmol) and commercially available 3-chloro-1-propanol (0.046 g, 0.49 mmol). The crude was purified by prep-HPLC (Method 11). Fractions containing the pure compound were combined and evaporated to reduced volume, diluted with DCM and treated with a saturated solution of sodium carbonate. Phases were separated, dried over sodium sulphate and evaporated under reduced pressure to obtain 0.039 g of the title compound.

HPLC-MS (Method 9): $R_t$=2.46 min

MS: m/z=384 (M+H)$^+$

Example 28

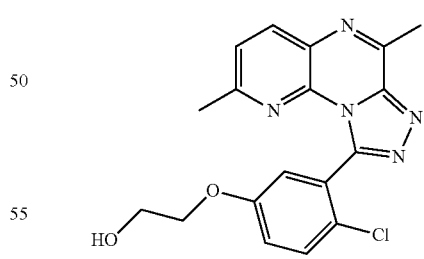

Example 28 was prepared as described for Example 20, starting from Example 2 (0.133 g, 80% content, 0.32 mmol) and commercially available 2-bromo-ethanol (0.061 g, 0.49 mmol). The crude was purified by prep-HPLC (Method 12). Fractions containing the pure compound are combined and evaporated to reduced volume, diluted with DCM and treated with a saturated solution of sodium carbonate. Phases were separated, dried over sodium sulphate and evaporated under reduced pressure to obtain 0.025 g of the title compound.

HPLC-MS (Method 9): $R_t$=2.35 min

MS: m/z=370 (M+H)$^+$

Example 29

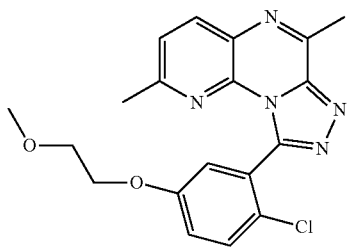

To a solution of Example 2 (0.07 g, 0.20 mmol) and commercially available 2-bromo-methylether (0.057 g, 0.41 mmol) in dry DMF (3 mL), cesium carbonate (0.199 g, 0.61 mmol) was added and the mixture heated at 100° C. for 1 h. Solvent was evaporated under reduced pressure, the residue dissolved with DCM and treated with water. Phases were separated, dried over sodium sulphate and the crude purified by flash cromatography (eluent from 80:20 to 40:60 hexane/EtOAc) to obtain 0.023 g of the title compound.

HPLC-MS (Method 9): $R_t$=2.82 min

MS: m/z=384 (M+H)$^+$

Example 30

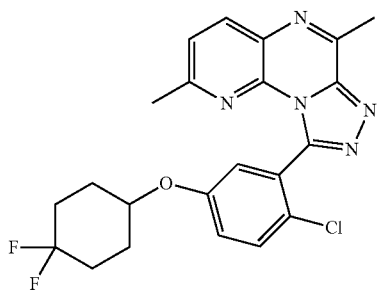 [SMILES: Cc1ccc2nc(C)c3nnc(-c4cc(OC5CCC(F)(F)CC5)ccc4Cl)n3c2n1]

To a solution of Example 2 (0.07 g, 0.20 mmol) and Intermediate 14 (0.12 g, 0.41 mmol) in dry DMF (3 mL), cesium carbonate (0.2 g, 0.61 mmol) was added and the mixture heated at 90° C. for 2 h. Solvent was evaporated under reduced pressure, the residue dissolved with DCM and treated with water. Phases were separated, dried over sodium sulphate and the crude purified by flash cromatography (eluent from 80:20 to 40:60 hexane/EtOAc) and then further purified by prep-HPLC (Method 14). Fractions containing the pure compound were combined and evaporated to reduced volume, diluted with DCM. Phases were separated, dried over sodium sulphate and evaporated under reduced pressure to obtain 0.047 g of the title compound.

HPLC-MS (Method 9): $R_t$=3.56 min

MS: m/z=444 (M+H)$^+$

Example 31

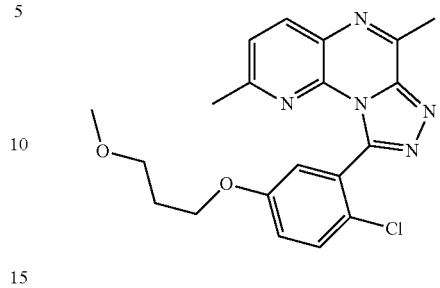

Example 31 was prepared as described for Example 30 starting from Example 2 (0.07 g, 0.20 mmol) and commercially available 1-bromo-3-methoxy-propane (0.063 g, 0.41 mmol). After heating for 3 h at 100° C. in dry DMF (3 mL), solvent was evaporated under reduced pressure, the residue dissolved with DCM and treated with water. Phases were separated, dried over sodium sulphate and the crude purified by flash cromatography (eluent from 88:12 to 0:100 Cy/EtOAc) to obtain 0.043 g of the title compound.

HPLC-MS (Method 13): $R_t$=3.55 min

MS: m/z=398 (M+H)$^+$

Example 32

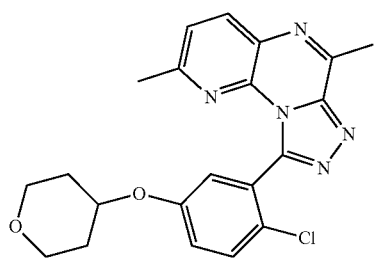 [SMILES: Cc1ccc2nc(C)c3nnc(-c4cc(OC5CCOCC5)ccc4Cl)n3c2n1]

Example 32 was prepared as described for Example 31 starting from Example 2 (0.09 g, 0.26 mmol) and Intermediate 13 (0.20 g, 0.78 mmol). Solvent was evaporated under reduced pressure, the residue dissolved with DCM and washed with 1N solution of NaOH. Phases were separated, dried over sodium sulphate and the crude purified by flash cromatography (eluent from 88:12 to 0:100 Cy/EtOAc) to obtain 0.037 g of the title compound.

HPLC-MS (Method 9): $R_t$=2.95 min

MS: m/z=410 (M+H)$^+$

Example 32a

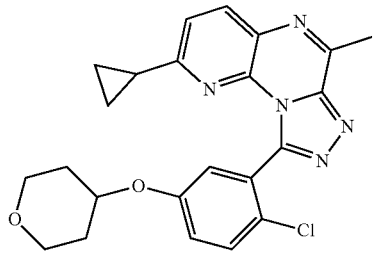 [SMILES: Cc1nc2ccc(C3CC3)nc2n2c(-c3cc(OC4CCOCC4)ccc3Cl)nnc12]

Example 32a (0.06 g) was prepared in analogy to Example 32 and purified applying the most suitable purification technique, starting from Example 9 (0.08 g, 0.23 mmol).

HPLC-MS (Method 16): $R_t$=4.51 min
MS: m/z=436 (M+H)$^+$

Example 33

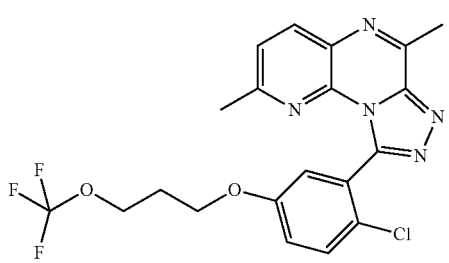 [SMILES: Cc1ccc2nc(C)c3nnc(-c4cc(OCCCOC(F)(F)F)ccc4Cl)n3c2n1]

Example 33 was prepared as described for Example 31 starting from Example 2 (0.07 g, 0.20 mmol) and commercially available 1-bromo-3-trifluoro-methoxypropane (0.084 g, 0.41 mmol). Solvent was evaporated under reduced pressure, the residue dissolved with DCM and washed with water. Phases were separated, dried over sodium sulphate and the crude purified by flash cromatography (eluent from 88:12 to 0:100 Cy/EtOAc) and then further purified by prep-HPLC (Method 14). Fractions containing the pure compound were combined and evaporated to reduced volume, diluted with DCM. Phases were separated, dried over sodium sulphate and evaporated under reduced pressure to obtain 0.047 g of the title compound. cromatography (eluent from 88:12 to 0:100 Cy/EtOAc) to obtain 0.037 g of the title compound.

HPLC-MS (Method 13): $R_t$=1.06 min
MS: m/z=452 (M+H)$^+$

Example 34

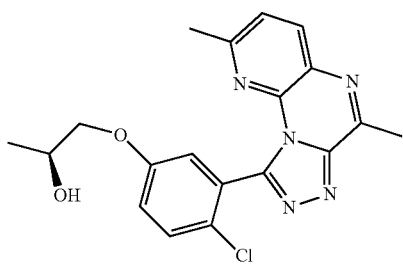 [SMILES: Cc1ccc2nc(C)c3nnc(-c4cc(OC[C@H](C)O)ccc4Cl)n3c2n1]

To a solution of Example 2 (0.082 g, 0.25 mmol) in dry DMF (3 mL), potassium tert-butoxide (0.084 g, 0.65 mmol) and Intermediate 20 (0.176 g, 0.50 mmol) were added. The resulting solution was heated at 120° C. for 5 h. The mixture was left at room temperature for 24 h. Solvent was evaporated under reduced pressure, the residue dissolved in DCM and treated with a 1N solution of NaOH. Phases were separated, dried over sodium sulphate and the crude purified by flash cromatography (eluent from 20:80 to 0:100 ACN/H$_2$O) to obtain 0.033 g of the title compound.

HPLC-MS (Method 9): $R_t$=2.98 min
MS: m/z=384 (M+H)$^+$

Example 35

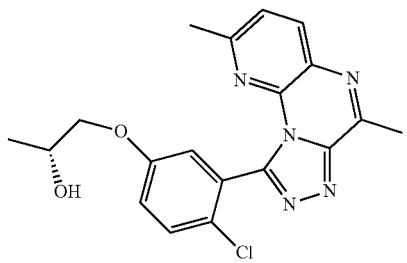 [SMILES: Cc1ccc2nc(C)c3nnc(-c4cc(OC[C@@H](C)O)ccc4Cl)n3c2n1]

To a solution of Example 2 (0.095 g, 0.29 mmol) in dry DMF (3 mL), potassium tert-butoxide (0.074 g, 0.22 mmol and Intermediate 19 (0.204 g, 0.58 mmol) were added. The resulting solution was heated at 120° C. for 5 h. Solvent was evaporated under reduced pressure, the residue dissolved in DCM and treated with a 1N solution of NaOH. Phases were separated, dried over sodium sulphate and the crude purified by flash cromatography (eluent from 80:20 to 0:100 Cy/EtOAc) to obtain 0.023 g of the title compound.

HPLC-MS (Method 13): $R_t$=2.98 min
MS: m/z=384 (M+H)$^+$

Example 35a

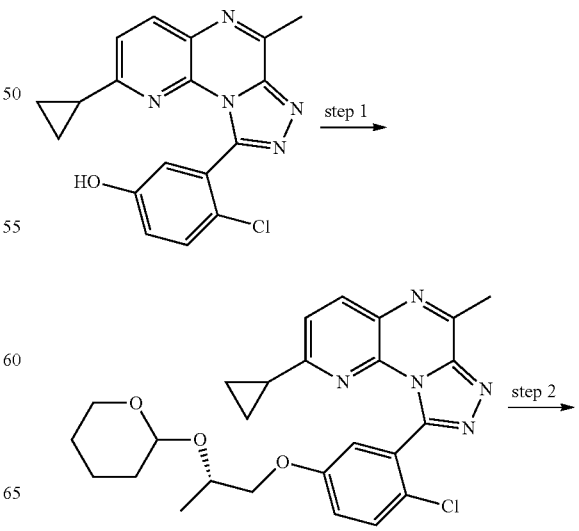

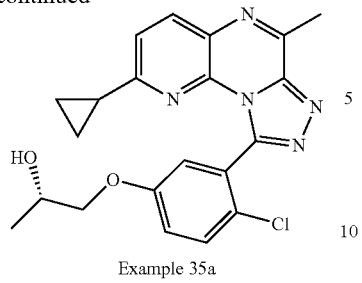

Example 35a

To a suspension of Intermediate 9a (0.08 g, 0.23 mmol) in dry DMF (4 mL), t-BuOK (0.076 g, 0.68 mmol) and Intermediate 21 (0.09 g, 0.45 mmol) were added and the reaction mixture was heated at 90° C. for 5 h. Dry DMF was then added and mixture heated at 110° C. overnight. Solvent was evaporated under reduced pressure, the residue dissolved in DCM and treated with a 1N solution of NaOH. Phases were separated, dried over sodium sulphate and the crude purified by flash cromatography (eluent from 80:20 to 0:100 Cy/EtOAc) to obtain 0.055 g of the protected intermediate 1-{2-chloro-5-[(S)-2-(tetrahydro-pyran-2-yloxy)-propoxy]-phenyl}-8-cyclopropyl-4-methyl-2,3,5,9,9b-pentaaza-cyclopenta[a]naphthalene.

The compound (0.055 g, 0.11 mmol) was then dissolved in dry MeOH (1 mL) and p-toluenesulfonic acid monohydrate (0.012 g, 0.06 mmol) was added. Mixture was stirred at room temperature for 1 h, solvent evaporated under reduced pressure and the residue purified by reverse phase flash cromatography (eluent ACN/H$_2$O from 10:100 to 100:0) and then by silica flash cromatography (eluent DCM/EtOH 90:10) to obtain 0.03 g of the title compound.

HPLC-MS (Method 9): R$_t$=2.69 min

MS: m/z=384 (M+H)$^+$

Example 36

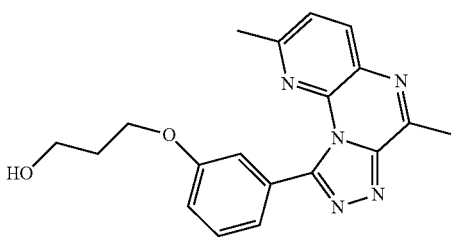 [SMILES: Cc1ccc2nc(C)c3nnc(-c4cccc(OCCCO)c4)n3c2n1]

To a solution of Example 3 (0.07 g, 0.24 mmol) in dry DMF (3 mL), cesium carbonate (0.23 g, 0.71 mmol) and commercially available 3-chloro-1-propanol (0.024 g, 0.26 mmol) were added and the mixture heated at 100° C. for 3 h. Solvent was evaporated under reduced pressure, the residue dissolved with DCM and washed with 1N solution of NaOH. Phases were separated, dried over sodium sulphate and the crude purified by prep-HPLC (Method 11). Fractions containing the pure compound were combined and evaporated to reduced volume, diluted with DCM and washed with a saturated solution of sodium carbonate. Phases were separated, dried over sodium sulphate and evaporated under reduced pressure to obtain 0.02 g of the title compound.

HPLC-MS (Method 13): R$_t$=2.71 min

MS: m/z=350 (M+H)$^+$

Example 37

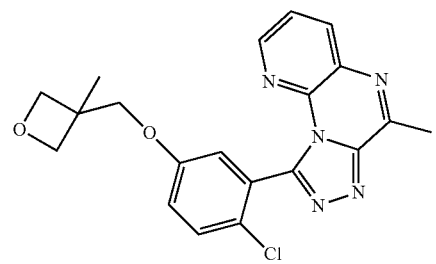 [SMILES: Cc1nc2cccnc2n2c(-c3cc(OCC4(C)COC4)ccc3Cl)nnc12]

Example 37 was prepared as described for Example 32 starting from Example 1 (0.07 g, 0.22 mmol) and Intermediate 26 (0.22 g, 067 mmol). The residue was purified by flash cromatography (eluent from 100:0 to 50:50 Cy/EtOAc) to obtain 0.046 g of the title compound.

HPLC-MS (Method 13): R$_t$=3.15 min

MS: m/z=396 (M+H)$^+$

Example 38

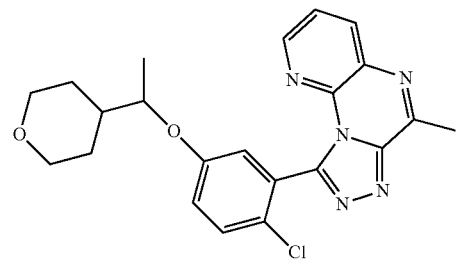 [SMILES: Cc1nc2cccnc2n2c(-c3cc(OC(C)C4CCOCC4)ccc3Cl)nnc12]

Example 38 was prepared as described for Example 32 starting from Example 1 (0.07 g, 0.22 mmol) and Intermediate 27 (0.127 g, 044 mmol). The residue was purified by flash cromatography (eluent from 100:0 to 50:50 Cy/EtOAc) to obtain 0.045 g of the title compound.

HPLC-MS (Method 13): R$_t$=3.45 min

MS: m/z=424 (M+H)$^+$

Example 39

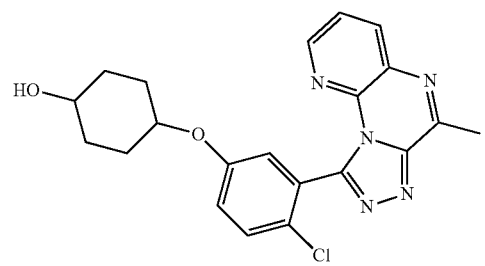 [SMILES: Cc1nc2cccnc2n2c(-c3cc(OC4CCC(O)CC4)ccc3Cl)nnc12]

To a solution of Intermediate 30 (0.18 g, 0.44 mmol) in absolute EtOH (10 mL) sodiumborohydride (0.008 g, 0.22 mmol) was added and the mixture stirred at room temperature for 30 min. Solvent was evaporated under reduced pressure, the residue treated with DCM and washed with a saturated solution of sodiumcarbonate. Phases were separated, dried over sodium sulphate and evaporated under reduced pressure to obtain 0.047 g of the title compound.
HPLC-MS (Method 13): R$_t$=2.96 min
MS: m/z=410 (M+H)$^+$ Example 40

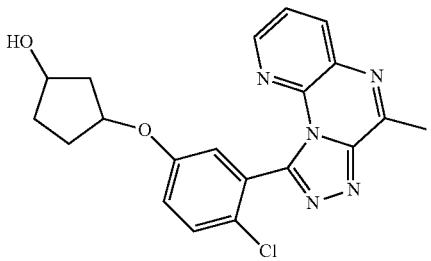 [SMILES: Cc1nc2cccnc2n2c(-c3cc(OC4CCC(O)C4)ccc3Cl)nnc12]

Example 40 was prepared as described Example 14, starting from Example 1 (0.075 g, 0.24 mmol) and Intermediate 31 (0.12 g, 0.48 mmol). Crude was purified by flash chromatography (eluent from 100:0 to 95:5 DCM/EtOH) to obtain 0.046 g of the title compound.
HPLC-MS (Method 13): R$_t$=2.87 min
MS: m/z=396 (M+H)$^+$ Example 41

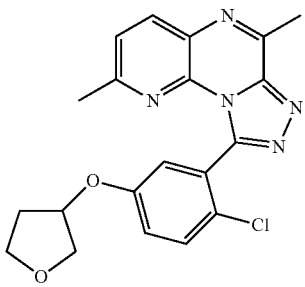 [SMILES: Cc1ccc2nc(C)c3nnc(-c4cc(OC5CCOC5)ccc4Cl)n3c2n1]

Example 41 (0.05 g) was prepared as described for Example 22 and purified applying the most suitable purification technique, starting from Example 2 (0.1 g, 0.3 mmol).
HPLC-MS (Method 13): R$_t$=3.21 min
MS: m/z=396 (M+H)$^+$ Example 42

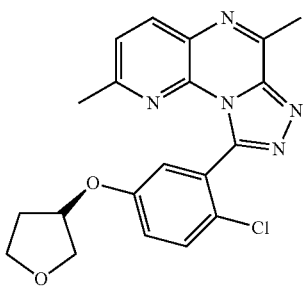

Example 42 (0.06 g) was prepared as described for Example 23 and purified applying the most suitable purification technique, starting from Example 2 (0.09 g, 0.28 mmol).

(HPLC-MS (Method 13): R$_t$=3.21 min
MS: m/z=396 (M+H)$^+$

Example 43

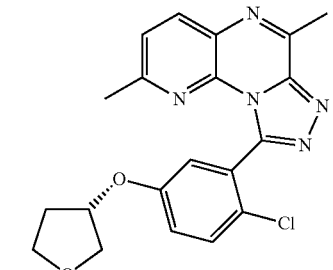

Example 43 (0.03 g) was prepared as described for Example 24 and purified applying the most suitable purification technique, starting from Example 2 (0.09 g, 0.28 mmol).
HPLC-MS (Method 13): R$_t$=3.21 min
MS: m/z=396 (M+H)$^+$ Example 43a

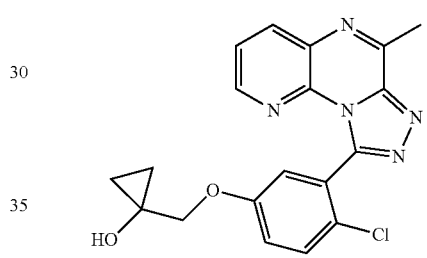

To a solution of ethylmagnesium bromide (0.7 mL of a 3M solution in diethyl ether) in dry DCM (2 mL) at −75° C., titanium(IV) isopropoxide (0.2 mL, 0.7 mmol) was added. Mixture was stirred for 10 min, then a solution of Intermediate 31 (0.28 g, 0.73 mmol) in dry DCM (8 mL) was added dropwise. Mixture was allowed to reach room temperature and stirred at room temperature overnight. Mixture was diluted with EtOAc, hydrochloric acid (1 N solution) was added and phases separated. Organics were dried over sodium sulphate and evaporated under reduced pressure and the crude purified by silica flash cromatography (eluent AcOEt/EtOH 90:10) followed by a reverse phase cromatography to obtain 0.006 g of the title compound.
HPLC-MS (Method 13): R$_t$=2.93 min
MS: m/z=382 (M+H)$^+$ Example 44

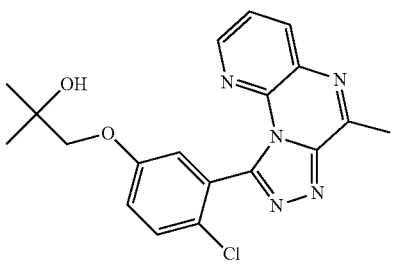 [SMILES: Cc1nc2cccnc2n2c(-c3cc(OCC(C)(C)O)ccc3Cl)nnc12]

Example 1 (0.07 mg, 0.2 mmol) was dissolved in DMF (3 mL), isobutylene oxide (0.03 mg, 0.43 mmol) and cesium carbonate (208 mg, 0.64 mmol) were added and the reaction mixture was warmed to 100° C. for 2 h. The solvent was removed, dichloromethane was added and the organic phase was washed with a 1M NaOH water solution, dried over sodium sulfate, concentrated under vacuum. The crude product obtained was purified by reverse phase chromatography to give the desired compound (29 mg).

HPLC-MS (Method 13): $R_t$=2.93 min
MS: m/z=386 (M+H)$^+$

The following Examples were prepared in analogy to Example 44 and purified applying the most suitable purification technique, starting from the corresponding Starting Example and the suitable epoxides.

| Starting Example of Starting Intermediate | Starting Epoxide | Ex. # | Structure | MS m/z [M + H]$^+$ | $R_t$ (min) | Method |
|---|---|---|---|---|---|---|
| 9 | | 45 | 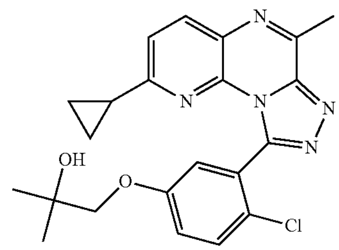 [SMILES: Cc1nc2ccc(C3CC3)nc2n2c(-c3cc(OCC(C)(C)O)ccc3Cl)nnc12] | 424 | 2.88 | 9 |
| 2 | | 46 | 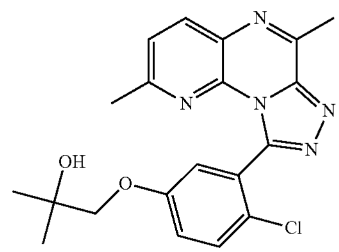 [SMILES: Cc1ccc2nc(C)c3nnc(-c4cc(OCC(C)(C)O)ccc4Cl)n3c2n1] | 398 | 3.01 | 9 |
| 5 | | 47 | 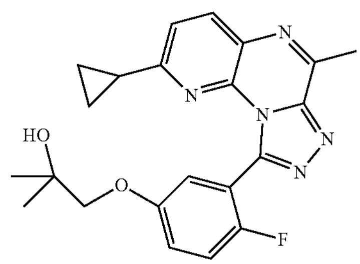 [SMILES: Cc1nc2ccc(C3CC3)nc2n2c(-c3cc(OCC(C)(C)O)ccc3F)nnc12] | 408 | 3.19 | 13 |
| 6 | | 48 | 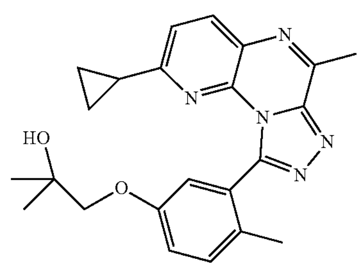 [SMILES: Cc1ccc(OCC(C)(C)O)cc1-c1nnc2c(C)nc3ccc(C4CC4)nc3n12] | 404 | 3.19 | 13 |
| 1 | 29a | 49 | 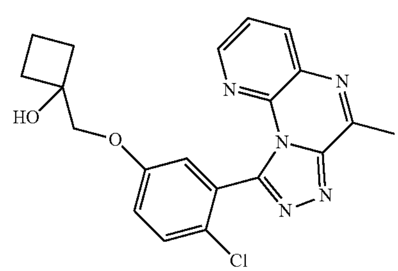 [SMILES: Cc1nc2cccnc2n2c(-c3cc(OCC4(O)CCC4)ccc3Cl)nnc12] | 396 | 3.04 | 13 |

-continued
| Starting Example of Starting Intermediate | Starting Epoxide | Ex. # | Structure | MS m/z [M + H]+ | R$_t$ (min) | Method |
|---|---|---|---|---|---|---|
| 10 | 29a | 50 | 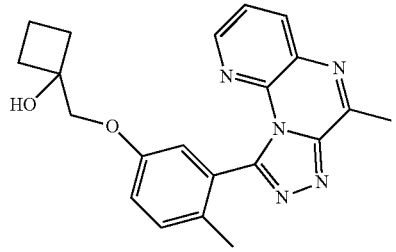 [SMILES: Cc1ccc(OCC2(O)CCC2)cc1-c1nnc2c(C)nc3cccnc3n12] | 376 | 2.88 | 13 |
| 7 |  | 51 | 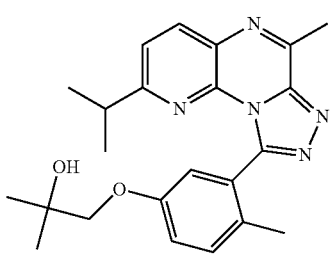 [SMILES: Cc1ccc(OCC(C)(C)O)cc1-c1nnc2c(C)nc3ccc(C(C)C)nc3n12] | 406 | 3.32 | 13 |
| 8 |  | 52 | 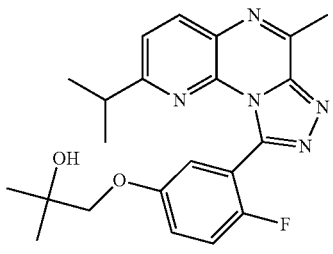 | 410 | 3.32 | 13 |
| 4 | 29a | 53 | 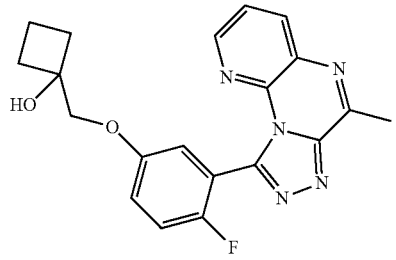 | 380 | 2.89 | 13 |
| 30p |  | 54 | 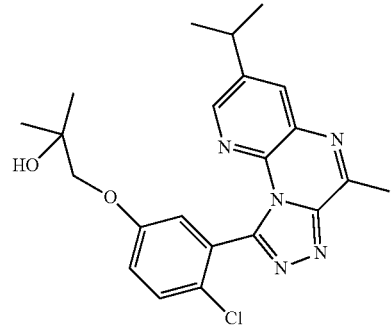 [SMILES: Cc1nc2cc(C(C)C)cnc2n2c(-c3cc(OCC(C)(C)O)ccc3Cl)nnc12] | 426 | 3.56 | 13 |

-continued

| Starting Example of Starting Intermediate | Starting Epoxide | Ex. # | Structure | MS m/z [M + H]+ | $R_t$ (min) | Method |
|---|---|---|---|---|---|---|
| 1 |  | 55 TRANS-racemic mixture | 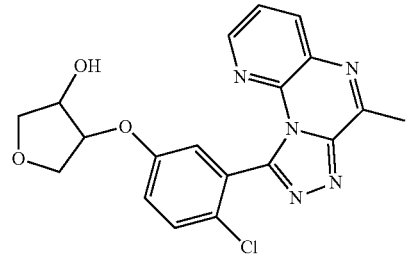 [SMILES: Cc1nc2cccnc2n2c(-c3cc(OC4COCC4O)ccc3Cl)nnc12] | 398 | 2.74 | 13 |
| 9 |  | 56 TRANS-racemic mixture | 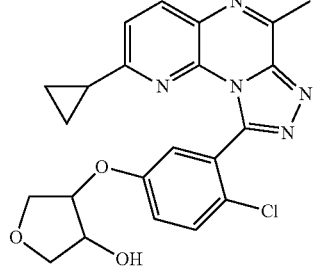 | 438 | 3.10 | 13 |
| 6 | | 57 TRANS-racemic mixture | 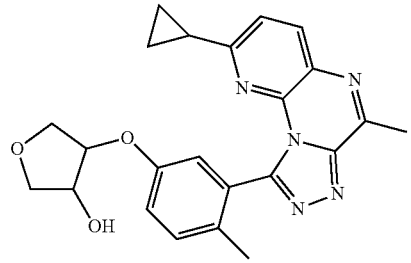 [SMILES: Cc1ccc(OC2COCC2O)cc1-c1nnc2c(C)nc3ccc(C4CC4)nc3n12] | 418 | 2.94 | 13 |

The following examples were obtained as single stereoisomers by chiral HPLC separation of the corresponding racemic mixture.

| Starting Racemic Mixture | Ex. # | Structure | MS m/z [M + H]+ | $R_t$ (min) [LC-MS Method] | $R_t$ (min) [Chiral HPLC Method] |
|---|---|---|---|---|---|
| 55 TRANS-racemic mixture | 55a TRANS-single stereoisomer a | 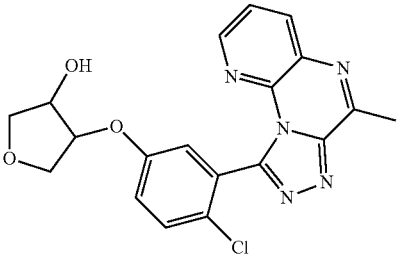 [SMILES: Cc1nc2cccnc2n2c(-c3cc(OC4COCC4O)ccc3Cl)nnc12] | 398 | 2.63 [13] | 8.23 [C1] |

-continued
| Starting Racemic Mixture | Ex. # | Structure | MS m/z [M + H]+ | R$_t$ (min) [LC-MS Method] | R$_t$ (min) [Chiral HPLC Method] |
|---|---|---|---|---|---|
| 56 TRANS- racemic mixture | 56a TRANS- single stereoisomer a | 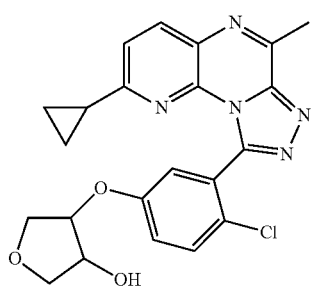 [SMILES: Cc1nc2ccc(C3CC3)nc2n2c(-c3cc(OC4COCC4O)ccc3Cl)nnc12] | 438 | 3.03 [13] | 12.13 [C2] |
| 56 TRANS- racemic mixture | 56b TRANS- single stereoisomer b | 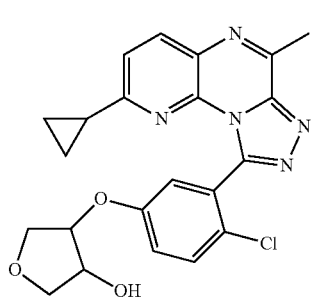 [SMILES: Cc1nc2ccc(C3CC3)nc2n2c(-c3cc(OC4COCC4O)ccc3Cl)nnc12] | 438 | 3.03 [13] | 16.56 [C2] |
| 57 TRANS- racemic mixture | 57a TRANS- single stereoisomer a | 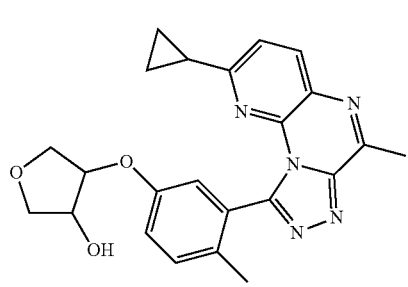 [SMILES: Cc1ccc(OC2COCC2O)cc1-c1nnc2c(C)nc3ccc(C4CC4)nc3n12] | 418 | 2.18 [13] | 17.66 [C2] |
| 57 TRANS- racemic mixture | 57b TRANS- single stereoisomer b | 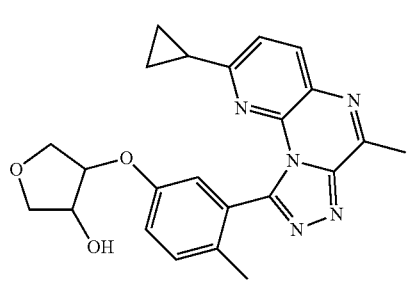 [SMILES: Cc1ccc(OC2COCC2O)cc1-c1nnc2c(C)nc3ccc(C4CC4)nc3n12] | 418 | 2.81 [13] | 19.81 [C2] |

Example 58

TRANS-single Stereoisomer a

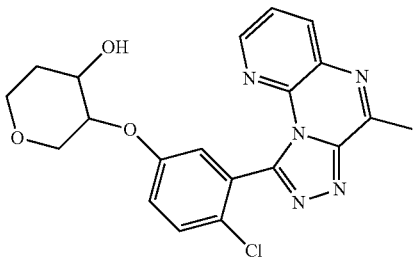 [SMILES: Cc1nc2cccnc2n2c(-c3cc(OC4COCCC4O)ccc3Cl)nnc12]

Example 58 (0.01 g) was prepared in analogy to example 44 starting from Example 1 (0.2 g, 0.61 mmol) and epoxide intermediate 29 (0.07 g, 0.73 mmol) after chiral HPLC separation HPLC-MS (Method 13): $R_t$=2.63 min MS: m/z=412 (M+H)$^+$ Chiral HPLC (Method C2): $R_t$=16.84 min

Example 58a

CIS-racemic Mixture

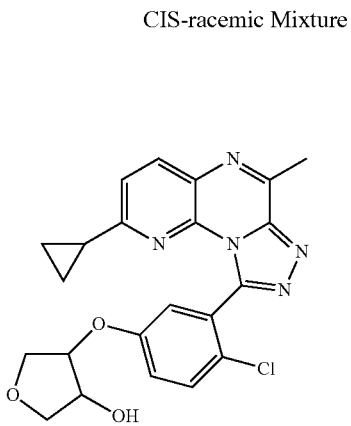

To a solution of Intermediate 30o (0.13 g, 0.37 mmol) in dry DMF (3 mL), potassium tert.butoxide (0.083 g, 0.73 mmol) and commercially available 1,4-anhydroerythritol (0.06 mL, 0.73 mmol) were added and mixture heated at 90 C for 6 h. Solvent was evaporated, DCM and water added. Organics were separated, washed with a saturated solution of ammonium chloride, evaporated. The crude was purified by flash chromatography (eluent Cy/EtOAc 90:10 to 0:100) to give the desired compound (0.055 g).

HPLC-MS (Method 13): $R_t$=2.94 min

MS: m/z=438 (M+H)$^+$

Example 58b

CIS-single Stereoisomer a

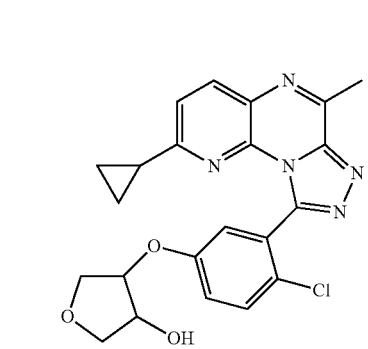 [SMILES: Cc1nc2ccc(C3CC3)nc2n2c(-c3cc(OC4COCC4O)ccc3Cl)nnc12]

Example 58b was obtained by chiral HPLC separation of Example 58.

HPLC-MS (Method 13): $R_t$=2.95 min

MS: m/z=438 (M+H)$^+$

Chiral HPLC (Method C1): $R_t$=7.65 min

Example 58c

CIS-single Stereoisomer b

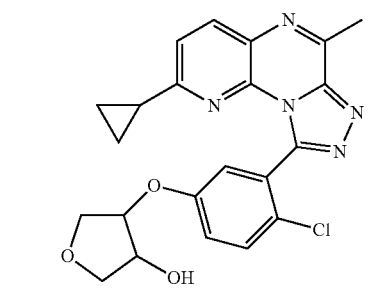 [SMILES: Cc1nc2ccc(C3CC3)nc2n2c(-c3cc(OC4COCC4O)ccc3Cl)nnc12]

Further elution from the chiral column in the purification of Example 58 gave Example 58c HPLC-MS (Method 13): $R_t$=2.95 min MS: m/z=438 (M+H)$^+$ Chiral HPLC (Method C1): $R_t$=9.54 min

Example 59 and Example 60

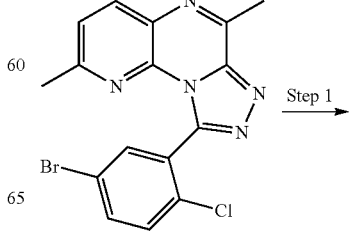

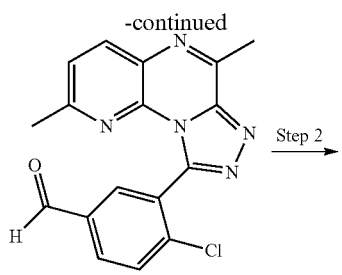

Step 2

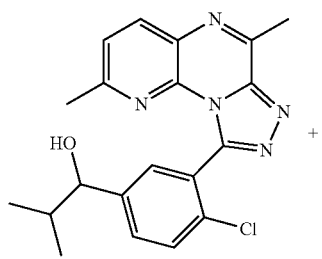

Example 59

+

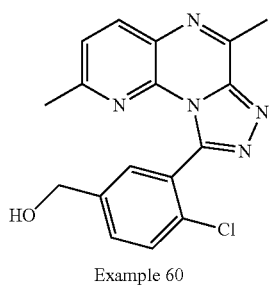

Example 60

Step 1:

Scaffold Intermediate 30a (1.4 g, 3.5 mmol) was suspended in THF (40 mL) and stirred at −78° C. under nitrogen atmosphere. N-Butyllithium (3 mL of a 2.5M solution in hexane) was added dropwise and the reaction mixture was stirred at −78° C. for 0.5 h. A solution of N,N.dimethylformamide (1.43 mL, 17.6 mmol) in THF (15 mL) was added dropwise and the reaction mixture was stirred at −78° C. for 30 minutes. Ammonium chloride saturated water solution (20 mL) was added and the reaction mixture was allowed to reach room temperature. The reaction mixture was diluted with ethyl acetate and washed with water. The organic phase was washed with brine, dried over sodium sulfate and concentrated under vacuum. The crude product obtained was purified by flash chromatography (eluent from 100:0 to 80:20 Cy/EtOAc) to obtain the title compound (0.3 g).

Step 2:

Intermediate obtained from Step 1 (0.07 g, 0.21 mmol) was suspended in THF (2 mL) and stirred at 0° C. A 2M solution of isopropylmagnesium chloride in THF (0.1 mL) was added an the reaction mixture was allowed to reach room temperature in 2 h. Ammonium chloride saturated water solution (20 mL) was added and the reaction mixture was allowed to reach room temperature. The reaction mixture was diluted with ethyl acetate and washed with water. The organic phase was washed with brine, dried over sodium sulfate and concentrated under vacuum. The crude product obtained was purified by flash chromatography (eluent 50:50 Cy/EtOAc) to obtain Example 60 (0.02 g).

HPLC-MS (Method 9): $R_t$=2.85 min

MS: m/z=382 (M+H)$^+$

Further elution from the column (eluent from 50:50 to 0:100 Cy/EtOAc) gave Example 60 (0.03 g)

HPLC-MS (Method 9): $R_t$=2.28 min

MS: m/z=340 (M+H)$^+$

The following examples were prepared in analogy to Example 59 and purified applying the most suitable purification technique, starting from Scaffold Intermediate 30a and the corresponding commercially available Grignard reagents.

| Grignard reagent | Ex. # | Structure | MS m/z (M + H)+ | $R_t$ (min) | Method |
|---|---|---|---|---|---|
| Cl—Mg~~~ | 61 | | 382 | 2.89 | 9 |
| Br—Mg~~ | 62 | | 368 | 3.12 | 13 |

| Grignard reagent | Ex. # | Structure | MS m/z (M + H)+ | $R_t$ (min) | Method |
|---|---|---|---|---|---|
| —Mg—Cl | 63 | 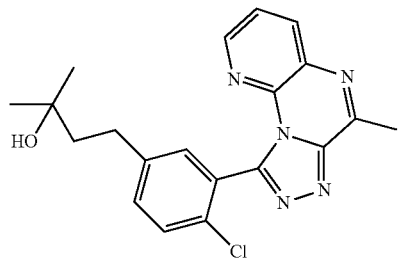 [SMILES: Cc1nc2cccnc2n2c(-c3cc(CCC(C)(C)O)ccc3Cl)nnc12] | 354 | 2.93 | 13 |

Example 64

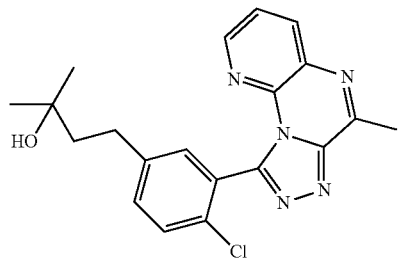 [SMILES: Cc1nc2cccnc2n2c(-c3cc(CCC(C)(C)O)ccc3Cl)nnc12]

Example 64 (0.03 g) was prepared in analogy to Example 1 and purified applying the most suitable purification technique, starting from Intermediate 2 (0.1 g, 0.55 mmol) and Hydrazide Intermediate 6i (0.15 g, 0.55 mmol).

HPLC-MS (Method 9): $R_t$=2.52 min

MS: m/z=382 (M+H)$^+$

Example 65

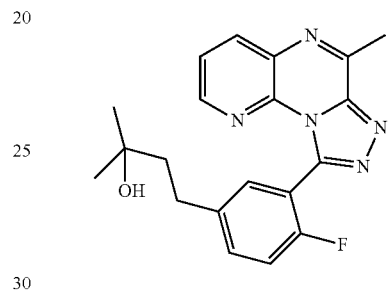

Example 65 (0.03 mg) was prepared in analogy to the preparation of Intermediate 5i and purified applying the most suitable purification technique, starting from Scaffold Intermediate 30d (0.1 g, 0.25 mmol).

HPLC-MS (Method 9): $R_t$=2.45 min

MS: m/z=366 (M+H)$^+$

The following examples were prepared in analogy to Example 65 and purified applying the most suitable purification technique, starting from the corresponding Scaffold Intermediates.

| Starting Intermediate | Ex. # | Structure | MS m/z (M + H)+ | $R_t$ (min) | Method |
|---|---|---|---|---|---|
| 30e | 66 | 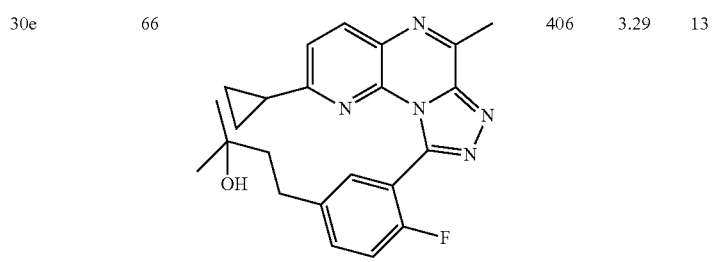 | 406 | 3.29 | 13 |
| 30f | 67 | 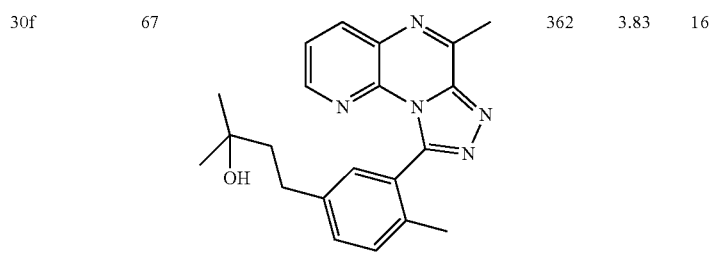 | 362 | 3.83 | 16 |

| Starting Intermediate | Ex. # | Structure | MS m/z (M + H)+ | R$_t$ (min) | Method |
|---|---|---|---|---|---|
| 30g | 68 | 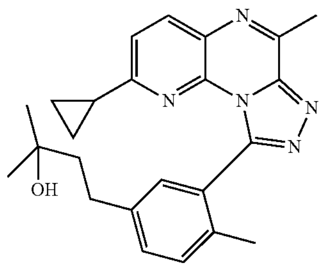 [SMILES: Cc1ccc(CCC(C)(C)O)cc1-c1nnc2c(C)nc3ccc(C4CC4)nc3n12] | 402 | 3.22 | 13 |
| 30h | 69 | 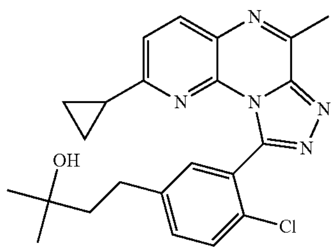 | 422 | 3.33 | 13 |

Example 70

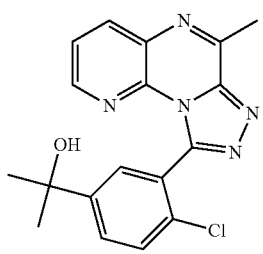

Example 70 (0.03 g) was prepared in analogy to the preparation of Intermediate 5j and purified applying the most suitable purification technique, starting from Scaffold Intermediate 30b (0.16 g, 0.38 mmol) and acetone (0.07 mg, 1.13 mmol).

HPLC-MS (Method 13): R$_t$=2.67 min

MS: m/z=354 (M+H)$^+$

The following examples were prepared in analogy to Example 70 and purified applying the most suitable purification technique, starting from the corresponding Scaffold Intermediates and commercially available ketons.

| Starting Intermediate | Ketone | Ex. # | Structure | MS m/z (M + H)+ | R$_t$ (min) | Method |
|---|---|---|---|---|---|---|
| 30j | | 71 | 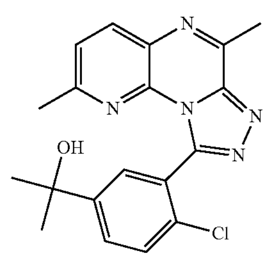 [SMILES: Cc1ccc2nc(C)c3nnc(-c4cc(C(C)(C)O)ccc4Cl)n3c2n1] | 368 | 2.95 | 13 |
| 30m | | 72 | 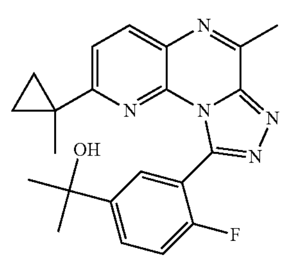 [SMILES: Cc1nc2ccc(C3(C)CC3)nc2n2c(-c3cc(C(C)(C)O)ccc3F)nnc12] | 392 | 3.32 | 13 |

-continued

| Starting Intermediate | Ketone | Ex. # | Structure | MS m/z (M + H)+ | $R_t$ (min) | Method |
|---|---|---|---|---|---|---|
| 30c | cyclobutanone | 73 | 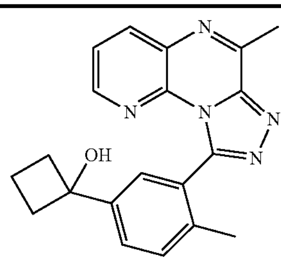 | 346 | 2.77 | 13 |
| 30b | cyclopentanone | 74 | 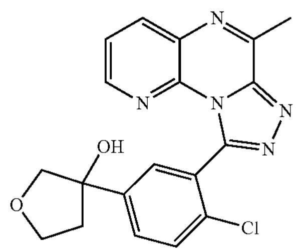 [SMILES: Cc1nc2cccnc2n2c(-c3cc(C4(O)CCOC4)ccc3Cl)nnc12] | 382 | 2.61 | 13 |

Example 75

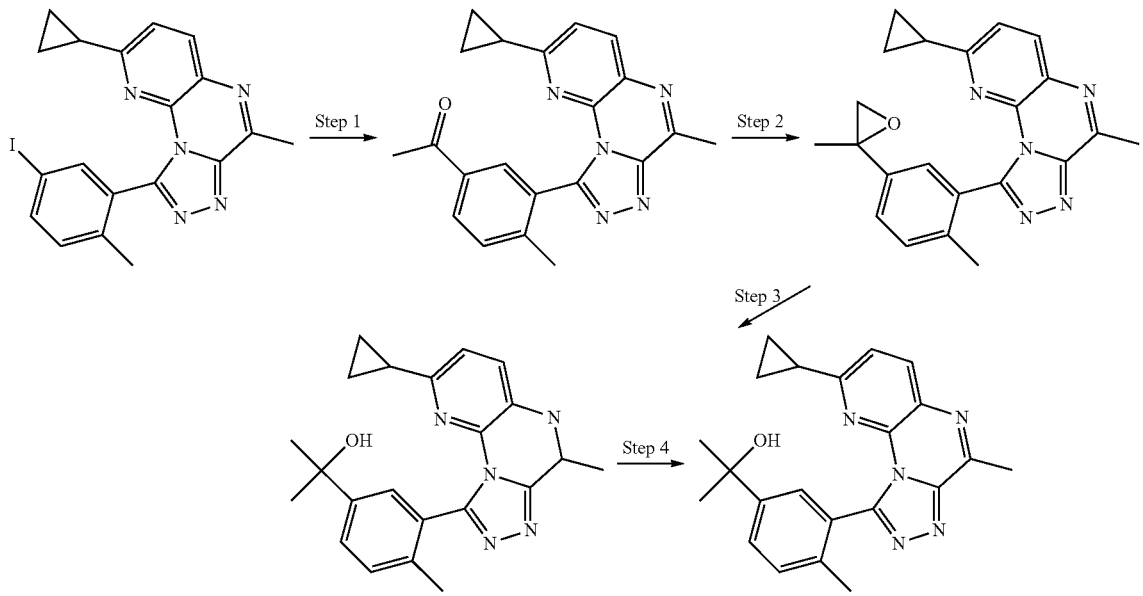

Step 1:
Under $N_2$ atmosphere, to a solution of Scaffold Intermediate 30 g (1.0 g, 2.54 mmol) in toluene (35 mL), tributyl-(1-ethoxyvinyl-)tin (1.3 mL, 3.04 mmol) and Pd tetrakis(triphenylphosphine) (580 mg, 0.51 mmol). The solution was stirred at 105° C. for 18 h. The reaction mixture was cooled at room temperature, concentrated in vacuo and the crude product obtained was dissolved in THF. A 2N water solution of HCl 2N (5 ml) was added and the reaction mixture was stirred for 30 mins. After dilution with ethyl acetate, phases were separated and organic layer was dried over sodium sulfate and concentrated. The crude product obtained was purified by flash chromatography (eluent from 90:10 to 75:25 Cy/EtOAc) to obtain the desired compound (0.8 g).
HPLC-MS (Method 13): $R_t$=3.09 min
MS: m/z=358 (M+H)$^+$ Step 2:
To a solution of the intermediate from Step 1 (0.8 g, 2.2 mmol) in DCM (20 mL) 50% NaOH/H2O solution (0.8 mL) was added and the reaction mixture was stirred for 10 minutes. Trimethylsulfonium methyl sulfate (0.4 g, 2.8 mmol) was added and the reaction mixture was refluxed for 2 h. The reaction mixture was diluted with DCM and washed with water. The organic layer was separated, dried over sodium sulfate and concentrated. The crude product obtained was purified by flash chromatography (eluent 85:15 Cy/EtOAc) to obtain the desired compound (0.5 g).
HPLC-MS (Method 13): $R_t$=3.33 min
MS: m/z=372 (M+H)$^+$ Step 3:

To a solution of lithiumaluminiumhydride (0.15 mL of a 2M solution in THF) in 15 mL of THF stirred at 0° C., the intermediate from step 2 (0.4 g, 0.4 mmol) was added slowly. The reaction mixture was stirred for 1 h and allowed to reach room temperature. Water (2 mL) and NaOH (1 mL of a 2M water solution) were added and the reaction mixture was diluted with ethyl acetate. Organic phase was separated, dried over sodium sulfate and concentrated to give the desired product (0.28 g).

HPLC-MS (Method 13): $R_t$=3.0 min
MS: m/z=376 (M+H)$^+$

Step 4:

Intermediate from step 3 (0.17 g, 0.38 mmol) was dissolved in DCM (10 mL), manganese dioxide (0.38 g, 3.38 mmol) was added and the suspension was stirred for 1 h at room temperature. The reaction mixture was filtered on a celite pad and the solvent was evaporated. The crude product obtained was purified by flash chromatography (eluent 90:10 DCM/MeOH) to obtain the desired compound (0.14 g).

HPLC-MS (Method 13): $R_t$=3.04 min
MS: m/z=374 (M+H)$^+$

The following examples were prepared in analogy to Example 75 and purified applying the most suitable purification technique, starting from the corresponding Intermediates.

| Starting Intermediate | Ex. | Structure | MS m/z (M + H)+ | $R_t$ (min) | Method |
|---|---|---|---|---|---|
| 30e | 76 | 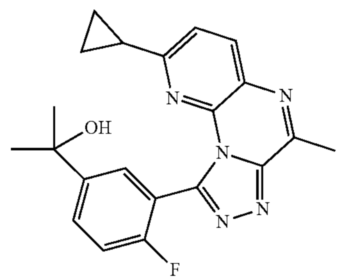 [SMILES: Cc1nc2ccc(C3CC3)nc2n2c(-c3cc(C(C)(C)O)ccc3F)nnc12] | 378 | 3.12 | 13 |
| 30k | 77 | 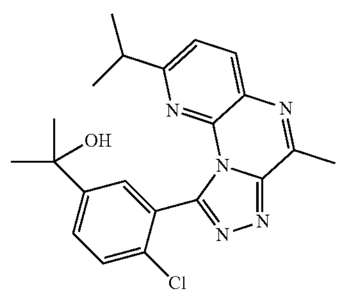 [SMILES: Cc1nc2ccc(C(C)C)nc2n2c(-c3cc(C(C)(C)O)ccc3Cl)nnc12] | 396 | 3.37 | 13 |
| 30l | 78 | 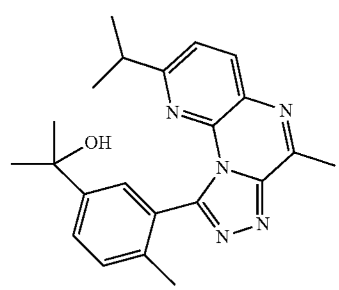 [SMILES: Cc1ccc(C(C)(C)O)cc1-c1nnc2c(C)nc3ccc(C(C)C)nc3n12] | 376 | 3.3 | 13 |
| 30n | 79 | 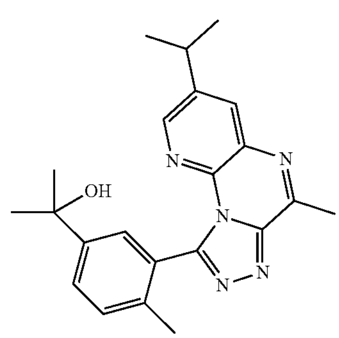 [SMILES: Cc1ccc(C(C)(C)O)cc1-c1nnc2c(C)nc3cc(C(C)C)cnc3n12] | 376 | 3.31 | 13 |

Example 80

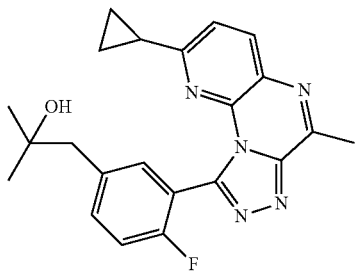 [SMILES: Cc1nc2ccc(C3CC3)nc2n2c(-c3cc(CC(C)(C)O)ccc3F)nnc12]

Example 80 (0.02 g) was prepared in step 2, step 3 and step 4 step in analogy to Example 75 and purified applying the most suitable purification technique, starting from the Intermediate obtained in step 1.

Step 1 was performed as follow:

Scaffold Intermediate 30i (1.35 g, 3.39 mmol) tri-n-butyl-methoxytin (1.51 mL, 5.08 mmol), isopropenyl acetate (5.6 mL, 51 mmol), tri-o-tolylphosphine (0.07 g, 0.25 mmol) and palladium acetate (0.03 g) were suspended in toluene (30 mL) under nitrogen atmosphere and stirred for 2 h at room temperature, then at 110° C. for 20 minutes. Water (10 mL) and a bicarbonate saturated water solution (3 mL) were added, toluene was removed under vacuum and DCM was added. The organic phase was separated, and concentrated. The crude product obtained was purified by flash chromatography (eluent from 30:70 to 0:100 cyclohexane/AcOEt) to obtain the desired compound (0.5 g).

Step 2, Step 3 and Step 4 were performed in analogy to Example 75.

HPLC-MS (Method 16): $R_t$=3.13 min

MS: m/z=392 (M+H)$^+$

The following example was prepared in analogy to Example 80 and purified applying the most suitable purification technique, starting from the corresponding Scaffold Intermediates.

| Intermediate | Ex. # | Structure | MS m/z (M + H)+ | $R_t$ (min) | Method |
|---|---|---|---|---|---|
| 30g | 81 | 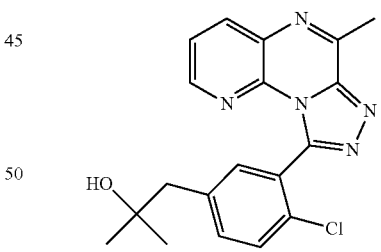 | 388 | 5.75 | 17 |

Example 82

Example 82 (0.09 g) was prepared in analogy to Example 1 starting from Chloride Intermediate 2 (0.1 g, 0.61 mmol) and Hydrazide Intermediate 6p (0.2 g, 0.61 mmol).

(HPLC-MS (Method 13): $R_t$ 2.80=min

MS: m/z=368 (M+H)$^+$

The following examples were prepared in analogy to Example 82 and purified applying the most suitable purification technique, starting from the corresponding Chloride and Hydrazide Intermediates.

| Starting Chloride Intermediate | Starting Hydrazide Intermediate | Ex. # | Structure | MS m/z (M + H)+ | R$_t$ (min) | Method |
|---|---|---|---|---|---|---|
| 9a | 6p | 83 | | 408 | 3.24 | 13 |
| 9a | 6j | 84 | | 390 | 3.18 | 13 |
| 9a | 6o | 85 | | 394 | 3.22 | 13 |
| 2 | 6j | 86 | | 350 | 2.76 | 13 |
| 2 | 6k | 87 | | 366 | 2.93 | 13 |
| 9a | 6k | 88 | | 406 | 3.33 | 13 |

-continued
| Starting Chloride Intermediate | Starting Hydrazide Intermediate | Ex. # | Structure | MS m/z (M + H)+ | R_t (min) | Method |
|---|---|---|---|---|---|---|
| 9 | 6k | 89 | 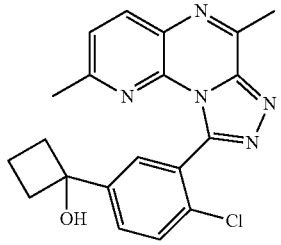 [SMILES: Cc1ccc2nc(C)c3nnc(-c4cc(C5(O)CCC5)ccc4Cl)n3c2n1] | 380 | 3.05 | 13 |
| 9 | 6j | 90 | 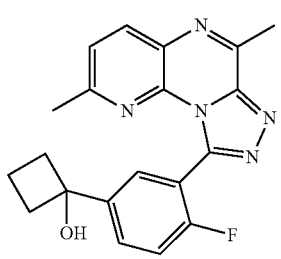 [SMILES: Cc1ccc2nc(C)c3nnc(-c4cc(C5(O)CCC5)ccc4F)n3c2n1] | 364 | 2.91 | 13 |
| 9b | 6k | 91 | 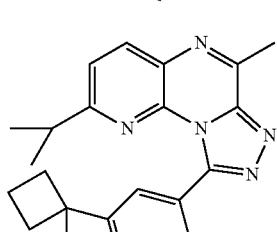 | 408 | 3.45 | 13 |
| 9b | 6j | 92 | 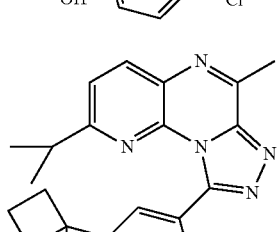 | 392 | 3.34 | 13 |
| 2 | 6l | 93 | 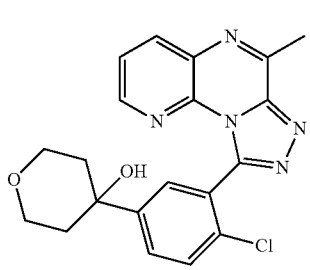 | 396 | 2.96 | 13 |
| 9a | 6l | 94 | 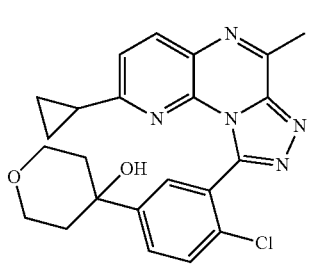 [SMILES: Cc1nc2ccc(C3CC3)nc2n2c(-c3cc(C4(O)CCOCC4)ccc3Cl)nnc12] | 436 | 3.08 | 13 |

-continued
| Starting Chloride Intermediate | Starting Hydrazide Intermediate | Ex. # | Structure | MS m/z (M + H)+ | R$_t$ (min) | Method |
|---|---|---|---|---|---|---|
| 9a | 6n | 95 | 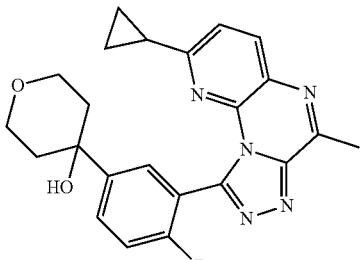 | 420 | 2.9 | 13 |
| 9f | 6l | 96 | 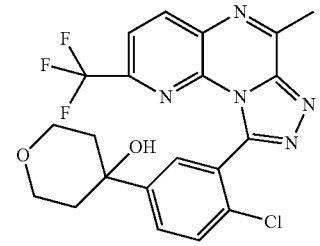 [SMILES: Cc1nc2ccc(C(F)(F)F)nc2n2c(-c3cc(C4(O)CCOCC4)ccc3Cl)nnc12] | 464 | 3.04 | 13 |
| 9f | 6n | 96a | 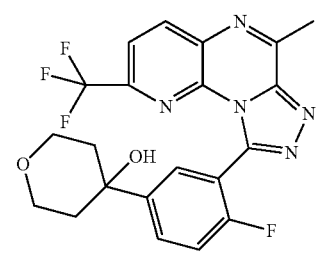 [SMILES: Cc1nc2ccc(C(F)(F)F)nc2n2c(-c3cc(C4(O)CCOCC4)ccc3F)nnc12] | 448 | 2.98 | 13 |
| 9f | 6na | 96b | 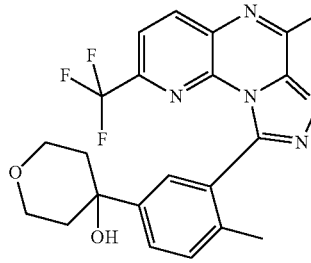 | 444 | 2.94 | 13 |
| 9f | 6r | 96c | 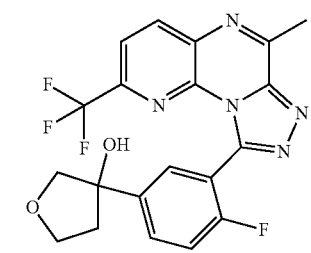 [SMILES: Cc1nc2ccc(C(F)(F)F)nc2n2c(-c3cc(C4(O)CCOC4)ccc3F)nnc12] | 434 | 2.91 | 13 |
| 9a | 6q | 97 | 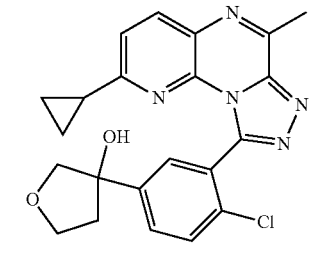 [SMILES: Cc1nc2ccc(C3CC3)nc2n2c(-c3cc(C4(O)CCOC4)ccc3Cl)nnc12] | 422 | 2.90 | 13 |

-continued

| Starting Chloride Intermediate | Starting Hydrazide Intermediate | Ex. # | Structure | MS m/z (M + H)+ | R_t (min) | Method |
|---|---|---|---|---|---|---|
| 2 | 6s | 112 | 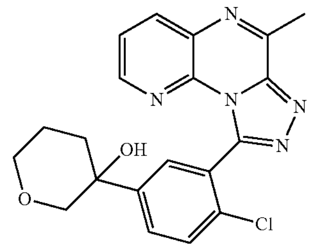 | 396 | 2.67 | 13 |
| 9a | 6s | 113 | 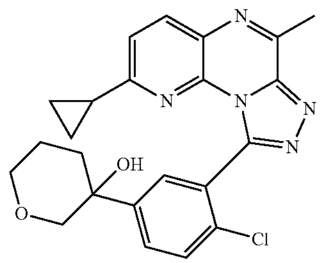 [SMILES: Cc1nc2ccc(C3CC3)nc2n2c(-c3cc(C4(O)CCCOC4)ccc3Cl)nnc12] | 436 | 3.10 | 13 |
| 9f | 6s | 114 | | 464 | 3.21 | 13 |
| 9f | 6r | 115 | | 450 | 3.90 | 13 |

The following examples were obtained as single stereoisomers by chiral HPLC separation of the corresponding racemic mixture.

| Starting Racemic Mixture | Ex. # | Structure | MS m/z [M + H]+ | R_t (min) [LC-MS Method] | R_t (min) [Chiral HPLC Method] |
|---|---|---|---|---|---|
| 97 Racemic mixture | 97a Single stereo-isomer b | 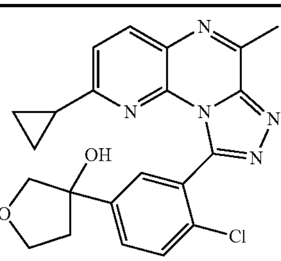 | 422 | 2.89 [13] | 15.75 [C2a] |

-continued

| Starting Racemic Mixture | Ex. # | Structure | MS m/z [M + H]+ | R$_t$ (min) [LC-MS Method] | R$_t$ (min) [Chiral HPLC Method] |
|---|---|---|---|---|---|
| 97 Racemic mixture | 97b Single stereoisomer a | 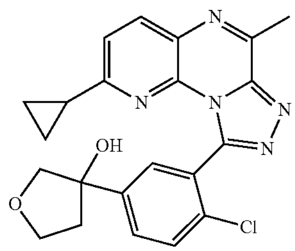 [SMILES: Cc1nc2ccc(C3CC3)nc2n2c(-c3cc(C4(O)CCOC4)ccc3Cl)nnc12] | 422 | 2.89 [13] | 13.32 [C2a] |
| 112 Racemic mixture | 112a Single stereoisomer a | | 396 | 2.85 [13] | 14.5 [C2a] |
| 112 Racemic mixture | 112b Single stereoisomer b | | 396 | 2.85 [13] | 15.6 [C2a] |
| 114 Racemic mixture | 114a Single stereoisomer a | | 464 | 3.21 [13] | 13.8 [C2] |
| 114 Racemic mixture | 114b Single stereoisomer b | | 464 | 3.21 [13] | 16.76 [C2] |

-continued

| Starting Racemic Mixture | Ex. # | Structure | MS m/z [M + H]+ | R_t (min) [LC-MS Method] | R_t (min) [Chiral HPLC Method] |
|---|---|---|---|---|---|
| 115 Racemic mixture | 115a Single stereo-isomer a | | 450 | 3.05 [13] | 28.0 [C2b] |
| 115 Racemic mixture | 115b Single stereo-isomer b | | 450 | 3.05 [13] | 31.2 [C2b] |

Example 98

Single Stereoisomer a

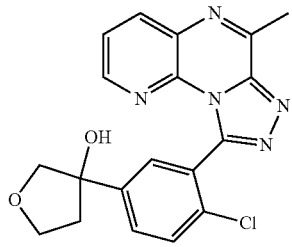 [SMILES: Cc1nc2cccnc2n2c(-c3cc(C4(O)CCOC4)ccc3Cl)nnc12]

Example 98 (0.026 g) was prepared in analogy to Example 1 starting from Chloride Intermediate 2 (0.3 g, 1.45 mmol) and Hydrazide Intermediate 6q (0.4 g, 1.56 mmol) after semi-preparative chiral purification.

HPLC-MS (Method 13): $R_t$=2.56 min
MS: m/z=382 (M+H)+
Chiral HPLC (Method C1a): $R_t$=9.55 min Example 99

Single Stereoisomer b

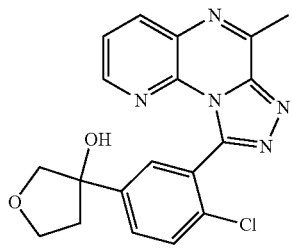 [SMILES: Cc1nc2cccnc2n2c(-c3cc(C4(O)CCOC4)ccc3Cl)nnc12]

Example 99 (0.028 g) was obtained via further elution from the column in the semipreparative chiral chromatographic purification of Example 98.

HPLC-MS (Method 13): $R_t$=2.52 min
MS: m/z=382 (M+H)+
Chiral HPLC (Method C1a): $R_t$=11.03 min Example 100

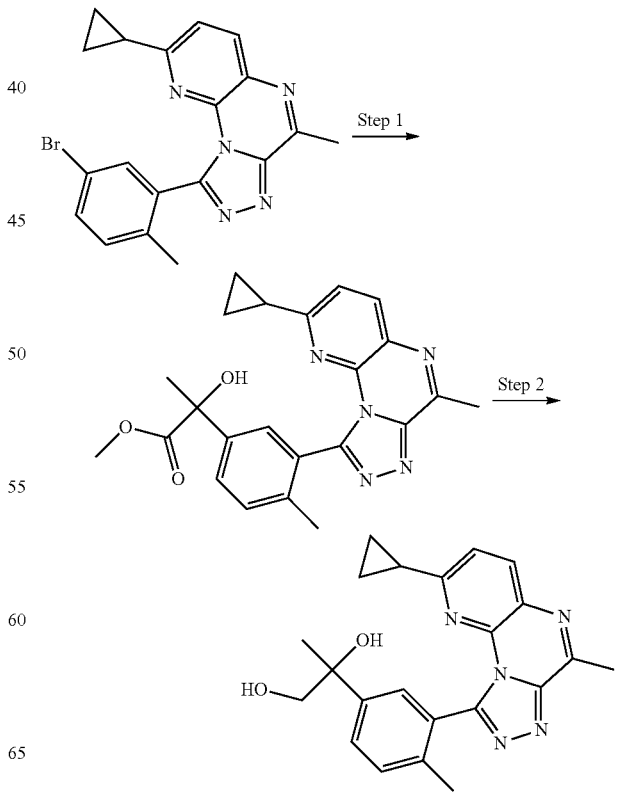

Step 1:
Scaffold Intermediate 30 g (0.5 g, 1.27 mmol), 1-methoxy-2-methyl-1-(trimethylsililoxy)propene (1.9 g, 11.4 mmol), bis(dibenzylideneacetone)palladium(0) (0.14 g, 0.25 mmol) and zinc fluoride (0.19 g, 1.9 mmol) were suspended in DMF (25 mL) and stirred under nitrogen atmosphere for 10 minutes. Tri-tert-butyl-phosphine (0.06 mL, 0.25 mmol) was added and the reaction mixture was stirred at 115° C. for 18 h. The reaction mixture was concentrated, an ammonium chloride water saturated solution was added and the reaction mixture was extracted with DCM. The organic phase was separated, dried over sodium sulfate and concentrated. The crude product obtained was purified by flash chromatography (eluent from 100:0 to 50:50 cyclohexane/AcOEt) to obtain the desired compound (0.4 g).

Step 2:
The intermediate obtained in Step 1 (0.4 g, 0.07 mmol) was dissolved in THF (6 mL) and stirred under nitrogen atmosphere at 0° C. for 5 minutes. Lithiumaluminium hydride (0.5 mL of a 2M solution in THF) was added. The reaction mixture was stirred at 0° C. for 10 minutes then allowed to reach room temperature and stirred for 0.5 h. The solvent was removed, the crude product was dissolved in DCM and the reaction mixture was washed with water (4 mL), bicarbonate saturated water solution (2 mL) and brine (2 mL). The organic phase was separated, dried over sodium sulfate and manganese dioxide (0.15 g, 1.73 mmol) was added. The reaction mixture was stirred for 0.5 h, filtered on a celite pad and concentrated. The crude product obtained was purified by flash chromatography (eluent from 100:0 to 95:5 DCM/MeOH) to obtain the desired compound (0.1 g).

(HPLC-MS (Method 13): $R_f$=3.29 min

MS: m/z=388 (M+H)$^+$

Example 101

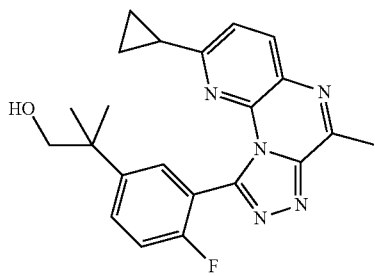 [SMILES: Cc1nc2ccc(C3CC3)nc2n2c(-c3cc(C(C)(C)CO)ccc3F)nnc12]

Example 101 (0.05 g) was prepared in analogy to Example 100 and purified applying the most suitable purification technique, starting from Scaffold Intermediate 30i (0.36 g, 0.9 mmol).

HPLC-MS (Method): $R_f$=3.3 min
MS: m/z=392 (M+H)$^+$

Example 102

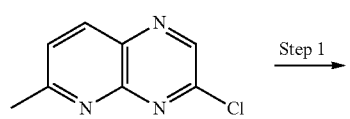

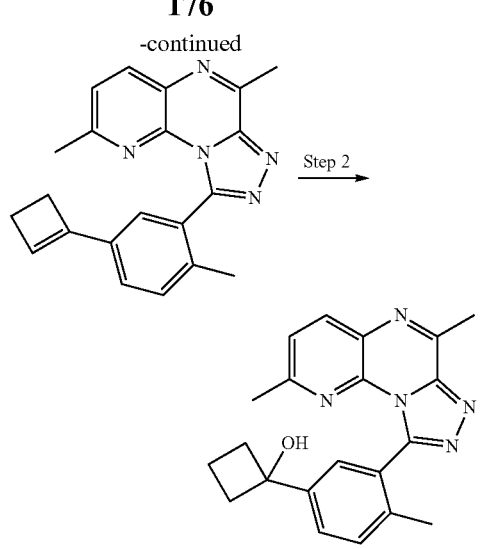

Step 1:
Step 1 was performed in analogy to preparation of Example 1 starting from Chloride Intermediate 9 (0.3 g, 1.39 mmol) and Hydrazide Intermediate 6o (0.47 g, 1.39 mmol).

Step 2:
Intermediate from step 1 (0.09 g, 0.26 mmol) and hydrochloric acid (10 mL of a 37% water solution) were dissolved in 10 mL of 1,4-dioxane. The reaction mixture was stirred at room temperature for 20 minutes. A bicarbonate saturated water solution was added, THF was removed in vacuum and the reaction mixture was extracted with DCM. The organic phase was separated, dried over sodium sulfate and concentrated. The crude product obtained was purified by flash chromatography (eluent from 100:0 to 90:10 DCM/MeOH) to obtain the title compound (0.03 g).

HPLC-MS (Method 13): $R_f$=2.95 min
MS: m/z=360 (M+H)$^+$

Example 103

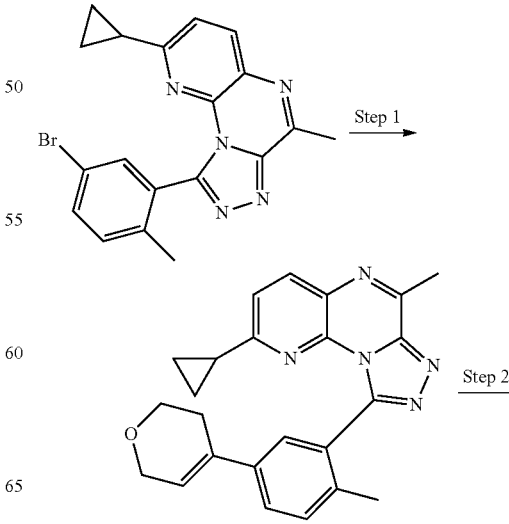

-continued

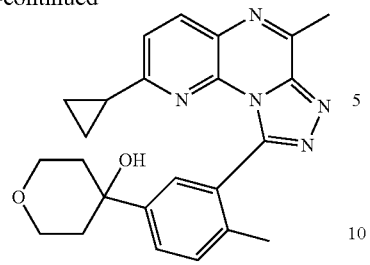

Step 1:
Under nitrogen atmosphere, Scaffold Intermediate 30 g (0.3 g, 0.61 mmol), potassium carbonate (0.34 g, 2.4 mmol) and [1,1'Bis(diphenylphosphino)ferrocene]dichloropalladium(II) (0.05 g) were suspended in toluene (150 mL) and stirred at room temperature for 10 minutes. 3,6-dihydro-2H-pyran-4-boronic acid pinacol ester (0.17 g, 0.79 mmol) was added and the reaction mixture was stirres at 100° C. for 4 h. Water (30 mL) was added and the reaction mixture was extracted with AcOEt. The organic phase was separated and concentrated. The crude product obtained was purified by flash chromatography (eluent from 100:0 to 90:10 DCM/MeOH) to obtain the title compound (0.02 g).

Step 2:
Step 2 was performed in analogy to Step 2 in the preparation of Example 102.

0.02 g of the desired product were obtained after purification by flash chromatography (eluent from 100:0 to 90:10 DCM/MeOH).

(HPLC-MS (Method 13): $R_t$=2.88 min
MS: m/z=416 (M+H)$^+$

The following examples were prepared in analogy to Example 103 and purified applying the most suitable purification technique, starting from the corresponding Scaffold Intermediate and the boronic ester 2-Isopropenyl-4,4,5,5-tetramethyl-[1,3,2]dioxaborolane.

| Starting Intermediate | Ex. # | Structure | MS m/z (M+H)+ | $R_t$ (min) | Method |
|---|---|---|---|---|---|
| 30r | 103b | 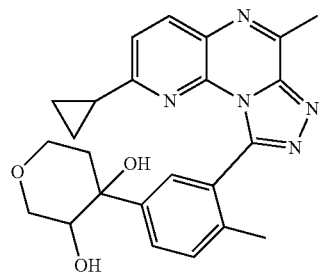 [SMILES: Cc1ccc(C2(O)CCOCC2O)cc1-c1nnc2c(C)nc3ccc(C4CC4)nc3n12] | 422 | 3.25 | 13 |
| 30s | 103c | 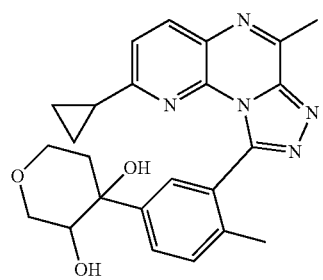 [SMILES: Cc1ccc(C2(O)CCOCC2O)cc1-c1nnc2c(C)nc3ccc(C4CC4)nc3n12] | 406 | 3.17 | 13 |

Example 104

CIS-racemic Mixture

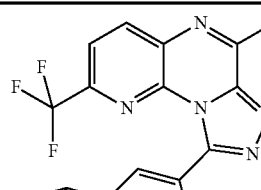

Intermediate obtained from Step 1 in preparation of Example 103 (50 mg, 0.13 mmol) was dissolved in DCM (5 mL). Osmium tetroxide (0.1 mL, 0.01 mmol) and 4-methylmorpholine-4-oxide (0.07 g, 0.63 mmol) were added and the reaction mixture was stirred at room temperature for 5 h. The solvent was removed and the crude product obtained was purified by flash chromatography (eluent from 100:0 to 80.20 DCM/MeOH) to obtain the title compound (0.03 g).
HPLC-MS (Method 13): $R_t$=2.73 min
MS: m/z=432 (M+H)$^+$ Example 104a CIS-single Stereoisomer a

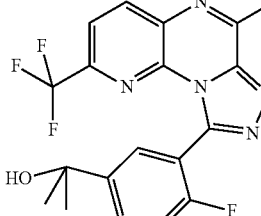

Example 104a was obtained via Chiral HPLC purification of Example 104.
HPLC-MS (Method 13): $R_t$=2.65 min
MS: m/z=432 (M+H)$^+$
Chiral HPLC (Method C2b): $R_t$=18.70 min Example 104b CIS-single Stereoisomer b

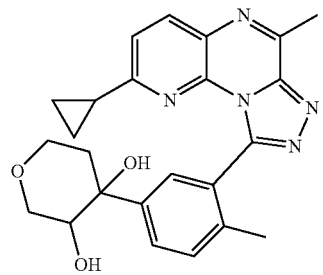 [SMILES: Cc1ccc(C2(O)CCOCC2O)cc1-c1nnc2c(C)nc3ccc(C4CC4)nc3n12]

Further elution from the chiral column gave Example 104b.
HPLC-MS (Method 13): $R_t$=2.65 min
MS: m/z=432 (M+H)$^+$
Chiral HPLC (Method C2b): $R_t$=21.04 min

Example 105

CIS-racemic Mixture

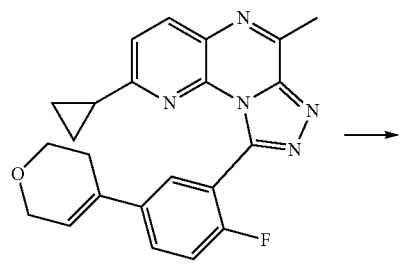 

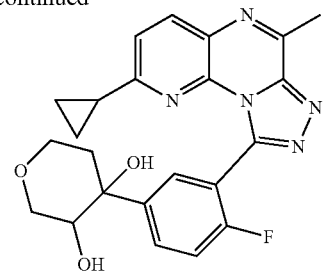

Example 105 (0.03 g) was prepared in analogy to Example 104, starting from 8-Cyclopropyl-1-[5-(3,6-dihydro-2H-pyran-4-yl)-2-fluoro-phenyl]-4-methyl-2,3,5,9,9b-pentaaza-cyclopenta[a]naphthalene (0.05 g, 0.12 mmol) which was obtained as by-product in the preparation of Example 95 and isolated from the same flash chromatograpy purification.

HPLC-MS (Method 13): $R_t$=2.68 min
MS: m/z=436 (M+H)$^+$

The following examples were obtained as single stereoisomers by chiral HPLC separation of the corresponding racemic mixture.

| Starting Racemic Mixture | Ex. # | Structure | MS m/z [M + H]$^+$ | $R_t$ (min) [LC-MS Method] | $R_t$ (min) [Chiral HPLC Method] |
|---|---|---|---|---|---|
| 105 CIS-Racemic mixture | 105a CIS-Single stereoisomer a | 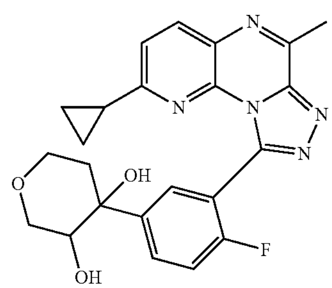 [SMILES: Cc1nc2ccc(C3CC3)nc2n2c(-c3cc(C4(O)CCOCC4O)ccc3F)nnc12] | 436 | 2.69 [13] | 15.05 [C2b] |
| 97 CIS-Racemic mixture | 105b CIS-Single stereoisomer b | 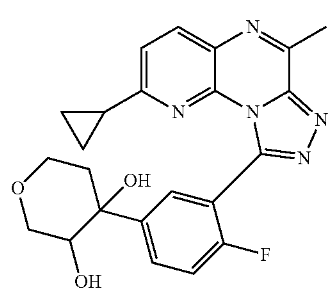 [SMILES: Cc1nc2ccc(C3CC3)nc2n2c(-c3cc(C4(O)CCOCC4O)ccc3F)nnc12] | 436 | 2.68 [13] | 18.47 [C2b] |

The following Examples were prepared in analogy to Example 44 and purified applying the most suitable purification technique, starting from the corresponding Starting Example and the corresponding epoxides.

| Starting Example or Starting Intermediate | Starting Epoxide | Ex. # | Structure | MS m/z (M + H)+ | $R_t$ (min) | Method |
|---|---|---|---|---|---|---|
| Intermediate 32 | | 106 TRANS- Racemic mixture | 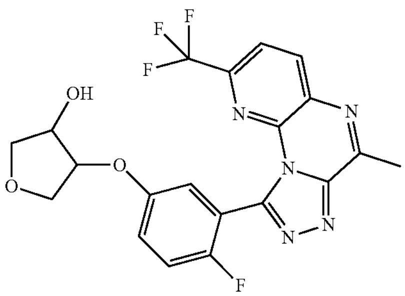 [SMILES: Cc1nc2ccc(C(F)(F)F)nc2n2c(-c3cc(OC4COCC4O)ccc3F)nnc12] | 450 | 2.97 | 13 |
| 5 | | 107 TRANS- Racemic mixture | 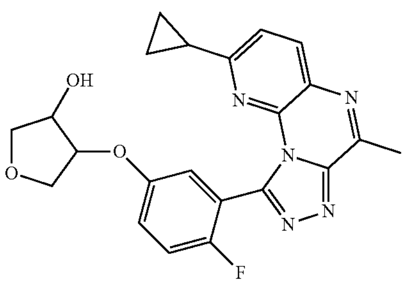 [SMILES: Cc1nc2ccc(C3CC3)nc2n2c(-c3cc(OC4COCC4O)ccc3F)nnc12] | 422 | 3.88 | 16 |
| 12 | | 111 TRANS- Racemic mixture | 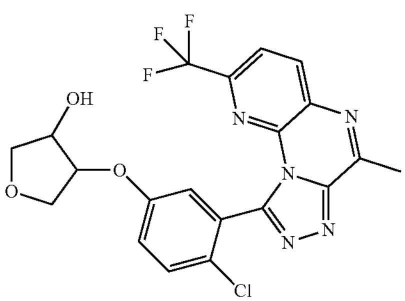 [SMILES: Cc1nc2ccc(C(F)(F)F)nc2n2c(-c3cc(OC4COCC4O)ccc3Cl)nnc12] | 466 | 3.09 | 13 |

45

The following examples were obtained as single stereoisomers by chiral HPLC separation of the corresponding racemic mixture.

| Starting Racemic Mixture | Ex. # | Structure | MS m/z [M + H]+ | $R_t$ (min) [LC-MS Method] | $R_t$ (min) [Chiral HPLC Method] |
|---|---|---|---|---|---|
| 106 TRANS- Racemic mixture | 106a TRANS- single stereo- isomer a | 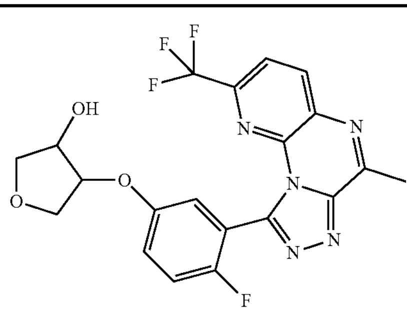 | 450 | 2.95 [13] | 7.77 [C2c] |

-continued

| Starting Racemic Mixture | Ex. # | Structure | MS m/z [M + H]+ | R$_t$ (min) [LC-MS Method] | R$_t$ (min) [Chiral HPLC Method] |
|---|---|---|---|---|---|
| 106 TRANS-Racemic mixture | 106b TRANS-single stereoisomer b | 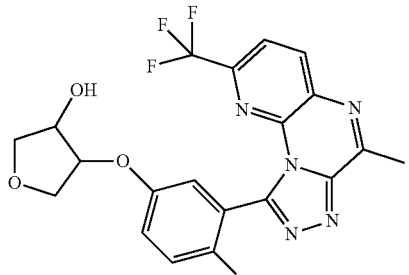 | 450 | 2.98 [13] | 11.58 [C2c] |
| 111 TRANS-Racemic mixture | 111a TRANS-single stereoisomer a | 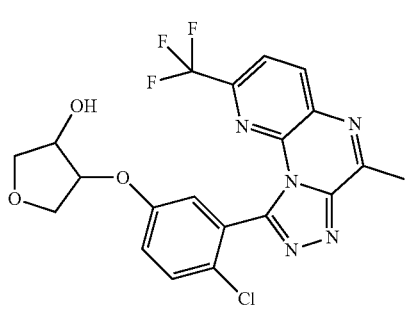 [SMILES: Cc1nc2ccc(C(F)(F)F)nc2n2c(-c3cc(OC4COCC4O)ccc3Cl)nnc12] | 466 | 3.10 [13] | 13.65 [C2] |
| 111 TRANS-Racemic mixture | 111b TRANS-single stereoisomer b | 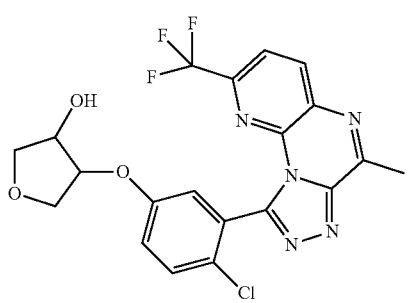 [SMILES: Cc1nc2ccc(C(F)(F)F)nc2n2c(-c3cc(OC4COCC4O)ccc3Cl)nnc12] | 466 | 3.10 [13] | 16.14 [C2] |

The following examples were obtained as single stereoisomers by chiral HPLC separation of the corresponding TRANS regioisomeric racemic mixtures. TRANS regioisomeric racemic mixtures were obtained in analogy to preparation of Example 44, starting from epoxide Intermediate 29 and the corresponding Starting Examples or Starting Intermediates.

| Starting Example or Starting Intermediate | Ex. # | Structure | MS m/z [M + H]+ | R$_t$ (min) [LC-MS Method] | R$_t$ (min) [Chiral HPLC Method] |
|---|---|---|---|---|---|
| 5 | 108a TRANS-single stereoisomer b | 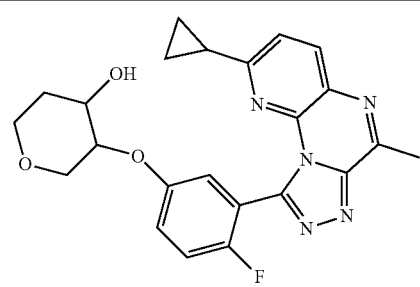 | 436 | 2.91 [13] | 31.54 [C3] |

-continued

| Starting Example or Starting Intermediate | Ex. # | Structure | MS m/z [M + H]+ | R$_t$ (min) [LC-MS Method] | R$_t$ (min) [Chiral HPLC Method] |
|---|---|---|---|---|---|
| 5 | 108c TRANS- single stereo- isomer b | | 436 | 2.91 [13] | 44.59 [C2c] |
| 5 | 108b TRANS- single stereo- isomer a | | 436 | 2.92 [13] | 27.61 [C3] |
| 5 | 108d TRANS- single stereo- isomer a | | 436 | 2.91 [13] | 22.06 [C2c] |
| 9 | 109a TRANS- single stereo- isomer a | | 452 | 3.03 [13] | 23.62 [C2] |
| 9 | 109c TRANS- single stereo- isomer a | | 452 | 3.03 [13] | 40.91 [C2] |

-continued

| Starting Example or Starting Intermediate | Ex. # | Structure | MS m/z [M + H]+ | R<sub>t</sub> (min) [LC-MS Method] | R<sub>t</sub> (min) [Chiral HPLC Method] |
|---|---|---|---|---|---|
| 9 | 109b TRANS- single stereo- isomer b | | 452 | 3.03 [13] | 89.29 [C2] |
| 9 | 109d TRANS- single stereo- isomer b | | 452 | 3.03 [13] | 25.61 [C2] |
| Intermediate 32 | 110b TRANS- single stereo- isomer b | | 464 | 3.00 [13] | 21.99 [C2] |
| Intermediate 32 | 110d TRANS- single stereo- isomer b | | 464 | 3.02 [13] | 62.95 [C2] |

The invention claimed is:
1. A compound of formula I

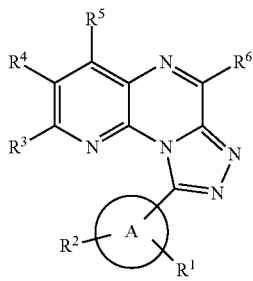

wherein
A is selected from the group $A^a$ consisting of

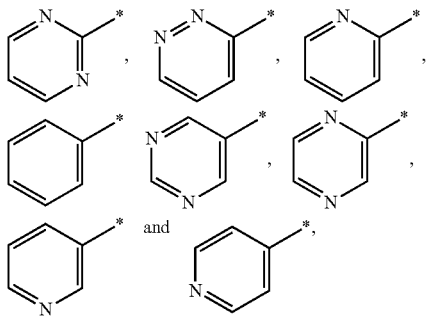

wherein the above mentioned phenyl-, pyridinyl-, pyrimidinyl-, pyridazinyl- and pyrazinyl-groups are substituted with $R^1$ and $R^2$;

$R^1$ is selected from the group $R^{1a}$ consisting of
H, halogen, NC—, $C_{1-6}$-alkyl-, $C_{1-6}$-alkyl-O—, $C_{3-6}$-cycloalkyl and $R^8$—$(CH_2)_n$—O— wherein n is 0, 1, 2, 3 or 4,
wherein the above mentioned $C_{1-6}$-alkyl-, $C_{1-6}$-alkyl-O—, $C_{3-6}$-cycloalkyl and $R^8$—$(CH_2)_n$—O— groups may optionally be substituted with 1 to 5 substituents independently selected from the group consisting of halogen, HO— and $C_{1-3}$-alkyl- optionally substituted with 1 to 7 fluorine atoms;

$R^2$ is selected from the group $R^{2a1}$ consisting of
HO—, $C_{1-6}$-alkyl-, $C_{1-6}$-alkyl-O—, $C_{3-6}$-cycloalkyl, $C_{3-6}$-cycloalkyl-$C_{1-3}$-alkyl-, heterocyclyl, heterocyclyl-$C_{1-3}$-alkyl-, phenyl, heteroaryl, $R^8$—$(CH_2)_n$—O— wherein n is 0, 1, 2, 3 or 4, and $R^8$—$(CH_2)_m$—$(CH)(CH_3)$—$(CH_2)_o$—O— wherein m is 0, 1 or 2 and o is 0, 1 or 2
wherein the above mentioned $C_{1-6}$-alkyl- and $C_{1-6}$-alkyl-O-groups are substituted with 1 to 5 substituents independently selected from the group consisting of HO— and $C_{1-3}$-alkyl-O— optionally substituted with 1 to 7 fluorine atoms,
and
wherein the above mentioned $C_{1-6}$-alkyl- and $C_{1-6}$-alkyl-O— groups may optionally be substituted with 1 to 5 substituents independently selected from the group consisting of halogen and $C_{1-3}$-alkyl- optionally substituted with 1 to 7 fluorine atoms,
and
wherein the above mentioned $C_{3-6}$-cycloalkyl, $C_{3-6}$-cycloalkyl-$C_{1-3}$-alkyl-, heterocyclyl, heterocyclyl-$C_{1-3}$-alkyl-, phenyl, heteroaryl, $R^8$—$(CH_2)_n$—O— and $R^8$—$(CH_2)_m$—$(CH)(CH_3)$—$(CH_2)_o$—O— groups may optionally be substituted with 1 to 5 substituents independently selected from the group consisting of halogen, HO—, $C_{1-3}$-alkyl-O— optionally substituted with 1 to 7 fluorine atoms, and $C_{1-3}$-alkyl- optionally substituted with 1 to 7 fluorine atoms;

$R^3$ is selected from the group $R^{3a}$ consisting of
H, halogen, NC—, $C_{1-4}$-alkyl- and $C_{3-6}$-cycloalkyl-,
wherein the above mentioned $C_{1-4}$-alkyl- and $C_{3-6}$-cycloalkyl-groups may optionally be substituted with 1 to 9 substituents independently selected from the group consisting of halogen, NC—, HO—, $C_{1-3}$-alkyl- and $C_{1-3}$-alkyl-O—;

$R^4$ and $R^5$ are selected independently of each other from the group $R^{4a}/R^{5a}$ consisting of
H, halogen, NC—, HO—, $C_{1-6}$-alkyl-, $C_{1-6}$-alkyl-O—, $C_{3-8}$-cycloalkyl-, $C_{3-8}$-cycloalkyl-$C_{1-3}$-alkyl-, $C_{3-8}$-cycloalkyl-O—, heterocyclyl-O—, heterocyclyl, heteroaryl, $R^7$—$CH_2$—O— and $R^7$—$(CH_2)_2$—O—,
wherein the above mentioned $C_{1-6}$-alkyl-, $C_{1-6}$-alkyl-O—, $C_{3-8}$-cycloalkyl-, $C_{3-8}$-cycloalkyl-$C_{1-3}$-alkyl-, $C_{3-8}$-cycloalkyl-O—, heterocyclyl-O—, heterocyclyl, heteroaryl, $R^7$—$CH_2$—O— and $R^7$—$(CH_2)_2$—O— groups, may optionally be substituted with 1 to 5 substituents independently selected from the group consisting of halogen, $C_{1-2}$-alkyl- optionally substituted with 1 to 5 halogen atoms, and $C_{1-2}$-alkyl-O— optionally substituted with 1 to 5 halogen atoms;

$R^6$ is selected from the group $R^{6a}$ consisting of
H, NC—, $C_{1-6}$-alkyl-, $C_{3-8}$-cycloalkyl-, $C_{3-8}$-cycloalkyl-$C_{1-3}$-alkyl- and $C_{3-8}$-cycloalkyl-O—
wherein the above mentioned $C_{1-6}$-alkyl- groups may optionally be substituted with 1-3 halogen atoms;

$R^7$ is selected from the group $R^{7a}$ consisting of
H, carbocyclyl, heterocyclyl and heteroaryl,
wherein the above mentioned carbocyclyl, heterocyclyl and heteroaryl-groups may optionally be substituted with 1 to 4 substituents independently selected from the group consisting of HO—, $C_{1-4}$-alkyl- optionally substituted with 1 to 3 halogen atoms, $C_{1-4}$-alkyl-O— optionally substituted with 1 to 3 halogen atoms and halogen; and $R^8$ is selected from the group $R^{8a}$ consisting of
$C_{3-6}$-cycloalkyl, heterocyclyl, heterocyclyl-$C_{1-3}$-alkyl-, phenyl and pyridyl,
wherein the above mentioned $C_{3-6}$-cycloalkyl, heterocyclyl, heterocyclyl-$C_{1-3}$-alkyl-, phenyl and pyridyl groups may optionally be substituted with 1 to 5 substituents independently selected from the group consisting of HO—, fluorine and $C_{1-3}$-alkyl- optionally substituted with 1 to 7 halogen atoms;
or a tautomer or pharmaceutically acceptable salt thereof.

2. A compound according to claim 1, wherein
$R^3$ is selected from the group $R^{3a1}$ consisting of
$C_{3-6}$-cycloalkyl-,
wherein the above mentioned $C_{3-6}$-cycloalkyl-group may optionally be substituted with 1 to 9 substituents independently selected from the group consisting of halogen, NC—, HO—, $C_{1-3}$-alkyl- and $C_{1-3}$-alkyl-O—.

3. A compound according to claim 1, wherein
A is selected from the group $A^b$ consisting of

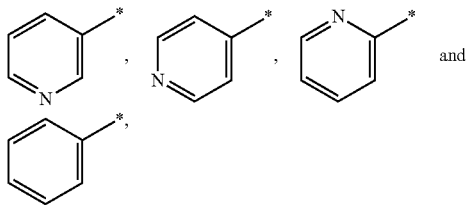

wherein the above mentioned phenyl- and pyridinyl-groups are substituted with $R^1$ and $R^2$.

4. A compound according to claim 1, wherein
A is selected from the group $A^e$ consisting of

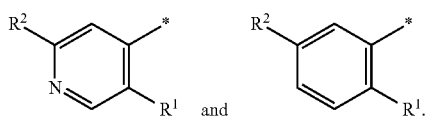

5. A compound according to claim 1, wherein
$R^1$ is selected from the group $R^{1b}$ consisting of
H, halogen, $C_{1-6}$-alkyl- and $C_{3-6}$-cycloalkyl
wherein the above mentioned $C_{1-6}$-alkyl- and $C_{3-6}$-cycloalkyl-groups may optionally be substituted with 1 to 5 substituents independently selected from the group consisting of halogen, HO— and $C_{1-3}$-alkyl- optionally substituted with 1 to 7 fluorine atoms.

6. A compound according to claim 1, wherein
$R^1$ is selected from the group $R^{1c}$ consisting of
H, $H_3C$—, $F_3C$—, $F_2HC$—, $FH_2C$—, fluorine, chlorine and bromine.

7. A compound according to claim 1, wherein
$R^2$ is selected from the group $R^{2b1}$ consisting of
HO—, $C_{1-4}$-alkyl-, $C_{1-4}$-alkyl-O—, $C_{3-6}$-cycloalkyk $C_{3-6}$-cycloalkyl-$C_{1-3}$-alkyl-, heterocyclyl, heterocyclyl-$C_{1-3}$-alkyl-, phenyl, heteroaryl, $R^8$—$(CH_2)_n$—O— with n is 0, 1, 2 or 3 and $R_8$—$(CH_2)_m$—(CH)($CH_3$)—$(CH_2)_o$—O— with m is 0 or 1 and o is 0 or 1
wherein the above mentioned $C_{1-4}$-alkyl- and $C_{1-4}$-alkyl-O— groups are substituted with 1 to 3 substituents independently selected from the group consisting of HO— and $C_{1-3}$-alkyl-O— optionally substituted with 1 to 7 fluorine atoms, and
wherein the above mentioned $C_{1-4}$-alkyl- and $C_{1-4}$-alkyl-O— groups may optionally be substituted with 1 to 3 substituents independently selected from the group consisting of halogen, and $C_{1-3}$-alkyl- optionally substituted with 1 to 7 fluorine atoms, and
wherein the above mentioned $C_{3-6}$-cycloalkyl-, $C_{3-6}$-cycloalkyl-$C_{1-3}$-alkyl-, heterocyclyl, heterocyclyl-$C_{1-3}$-alkyl-, $R^8$—$(CH_2)_n$—O— and and $R^8$—$(CH_2)_m$—(CH)($CH_3$)—$(CH_2)_o$—O— groups may optionally be substituted with 1 to 3 substituents independently selected from the group consisting of halogen, HO—, $C_{1-3}$-alkyl-O— optionally substituted with 1 to 7 fluorine atoms, and $C_{1-3}$-alkyl-optionally substituted with 1 to 7 fluorine atoms.

8. A compound according to claim 1, wherein
$R^2$ is selected from the group $R^{2d1}$ consisting of
HO—, $C_{1-4}$-alkyl-, $C_{1-4}$-alkyl-O—, $C_{3-6}$-cycloalkyk $C_{3-6}$-cycloalkyl-$C_{1-3}$-alkyl-, a saturated 5 or 6 membered monocyclic heterocycle containing one heteroatom selected from N or O, $R^8$—$(CH_2)_n$—O— with n is 0, 1 or 2, and $R^8$—$(CH_2)_m$—(CH)($CH_3$)—$(CH_2)_o$—O— m is 0 or 1 and o is 0 or 1
wherein the above mentioned $C_{1-4}$-alkyl- and $C_{1-4}$-alkyl-O-groups are substituted with 1 to 5 substituents independently selected from the group consisting of HO—, and $C_{1-3}$-alkyl-O— optionally substituted with 1 to 7 fluorine atoms, and
wherein the above mentioned $C_{1-4}$-alkyl- and $C_{1-4}$-alkyl-O-groups may optionally be substituted with 1 to 5 substituents independently selected from the group consisting of halogen, and $C_{1-3}$-alkyl-optionally substituted with 1 to 7 fluorine atoms, and
wherein the above mentioned $C_{3-6}$-cycloalkyl-, $C_{3-6}$-cycloalkyl-$C_{1-3}$-alkyl-, saturated 5 or 6 membered monocyclic heterocycle containing one heteroatom selected from N or O, $R^8$—$(CH_2)_n$—O— and and $R^8$—$(CH_2)_m$—(CH)($CH_3$)—$(CH_2)_o$—O— groups may optionally be substituted with 1 to 5 substituents independently selected from the group consisting of halogen, HO—, optionally substituted with 1 to 7 fluorine atoms, and $C_{1-3}$-alkyl-optionally substituted with 1 to 7 fluorine atoms.

9. A compound according to claim 1, wherein
$R^3$ is selected from the group $R^{3b}$ consisting of
H, $C_{1-3}$-alkyl-, cyclobutyl- and cyclopropyl-,
wherein the above mentioned $C_{1-3}$-alkyl-, cyclobutyl- and cyclopropyl-groups may optionally be substituted with 1 to 7 substituents independently selected from the group consisting of halogen, $C_{1-3}$-alkyl-O—, NC— and HO—.

10. A compound according to claim 1, wherein
$R^3$ is selected from the group $R^{3c}$ consisting of
H, $H_3C$— and cyclopropyl-,
wherein the above mentioned $H_3C$— and cyclopropyl-groups may optionally be substituted with 1 to 3 fluorine atoms.

11. A compound according to claim 1, wherein
$R^4$ and $R^5$ are selected independently of each other from the group $R^{4b}/R^{5b}$ consisting of
H, halogen, HO—, $H_3C$—, $F_3C$—, $H_3C$—O—, $F_2HC$—O—, $FH_2C$—O—, $F_3C$—O—, $C_{1-4}$-alkyl-O—, $R^7$—$CH_2$—O— and $R^7$—$(CH_2)_2$—O—,
wherein the above mentioned $C_{1-4}$-alkyl-O—, $R^7$—$CH_2$—O— and $R^7$—$(CH_2)_2$—O— groups, may optionally be substituted with 1 to 5 substituents independently selected from the group consisting of halogen, $C_{1-2}$-alkyl- optionally substituted with 1 to 5 halogen atoms, and $C_{1-2}$-alkyl-O— optionally substituted with 1 to 5 halogen atoms.

12. A compound according to claim 1, wherein
$R^4$ and $R^5$ are selected from the group $R^{4d}/R^{5d}$ consisting of H—.

13. A compound according to claim 1, wherein
$R^6$ is selected from the group $R^{6b}$ consisting of
H, $C_{1-4}$-alkyl- and cyclopropyl-,
wherein the above mentioned $C_{1-4}$-alkyl-group may optionally be substituted with 1-3 fluorine and/or chlorine atoms.

14. A compound according to claim 1, wherein
R$^6$ is selected from the group R$^{6c}$ consisting of
H and C$_{1-2}$-alkyl-,
wherein the above mentioned C$_{1-2}$-alkyl-group may optionally be substituted with 1-3 fluorine and/or chlorine atoms.

15. A compound according to claim 1, wherein
R$^6$ is selected from the group R$^{6e}$ consisting of
H$_3$C—, FH$_2$C—, F$_2$HC— and F$_3$C—.

16. A compound according to claim 1, wherein
R$^7$ is selected from the group R$^{7b}$ consisting of
H, phenyl, heteroaryl, cycloalkyl and heterocyclyl
wherein the above mentioned phenyl, heteroaryl, cycloalkyl and heterocyclyl-groups may optionally be substituted with 1 to 4 substituents independently selected from the group consisting of halogen, and C$_{1-3}$-alkyl-O— optionally substituted with 1 to 3 halogen atoms.

17. A compound according to claim 1, wherein
R$^7$ is selected from the group R$^{7c}$ consisting of
H and phenyl,
wherein the above mentioned phenyl group may optionally be substituted with 1 to 4 substituents independently selected from the group consisting of halogen and C$_{1-3}$-alkyl-O— optionally substituted with 1 to 3 halogen atoms.

18. A compound according to claim 1, wherein
R$^8$ is selected from the group R$^{8b}$ consisting of
C$_{3-6}$-cycloalkyk, heterocyclyl and heterocyclyl-C$_{1-3}$-alkyl-,
wherein the above mentioned C$_{3-6}$-cycloalkyl, heterocyclyl and heterocyclyl-C$_{1-3}$-alkyl-groups may optionally be substituted with 1 to 5 substituents independently selected from the group consisting of HO—, fluorine and C$_{1-3}$-alkyl- optionally substituted with 1 to 7 halogen atoms.

19. A compound according to claim 1, wherein
R$^8$ is selected from the group R$^{8c1}$ consisting of
C$_{3-6}$-cycloalkyl and a saturated 4 to 6 membered monocyclic heterocycle containing one or two heteroatoms selected from N or O,
wherein the above mentioned C$_{3-6}$-cycloalkyl and heterocyclyl-groups may optionally be substituted with 1 to 5 substituents independently selected from the group consisting of HO—, fluorine and C$_{1-3}$-alkyl- optionally substituted with 1 to 7 halogen atoms.

20. A compound according to claim 1, wherein A is

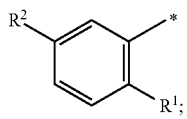

R$^1$ is selected from the group R$^{1c1}$ consisting of
H$_3$C—, fluorine and chlorine;
R$^2$ is selected from the group R$^{2f1}$ consisting of

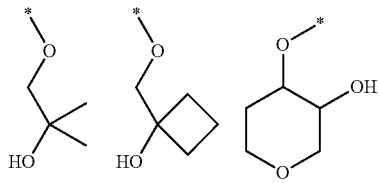

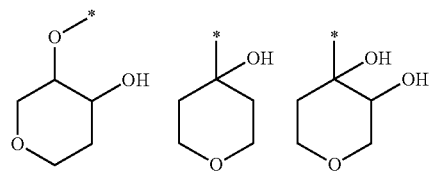

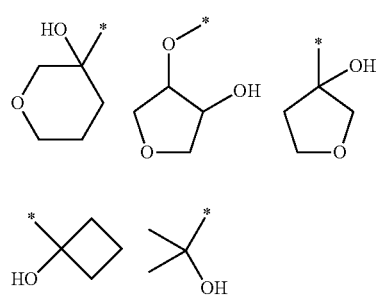

R$^3$ is selected from the group R$^{3c}$ consisting of
H, H$_3$C— and cyclopropyl—,
wherein the above mentioned H$_3$C— and cyclopropyl-groups may optionally be substituted with 1 to 3 fluorine atoms;
R$^4$ is H;
R$^5$ is H;
R$^6$ is H$_3$C—.

21. A compound according to claim 1, selected from the group consisting of:

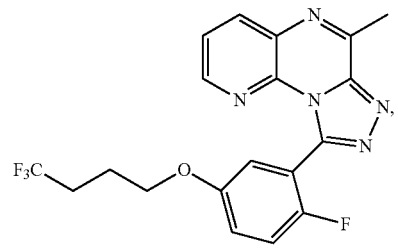

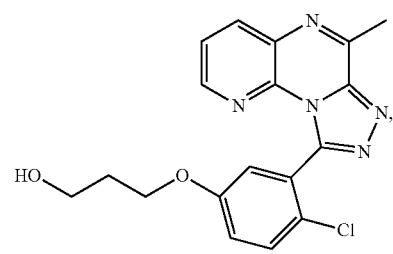

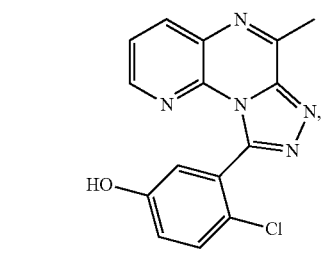

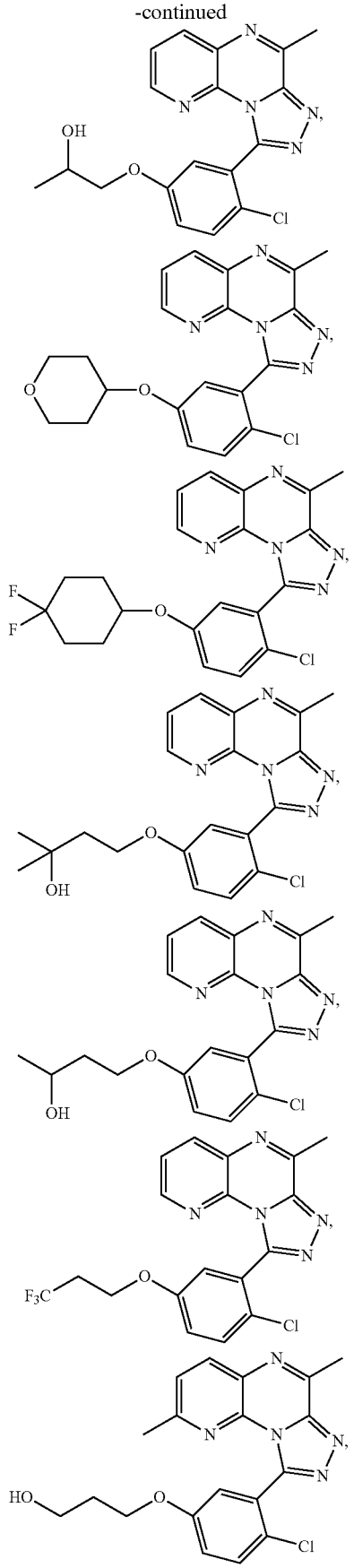
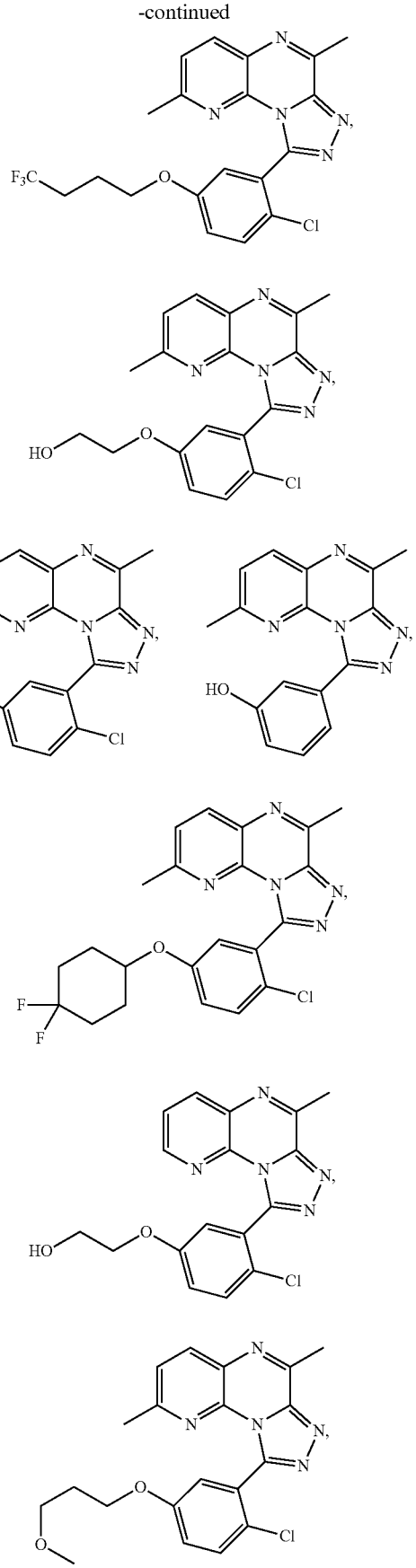

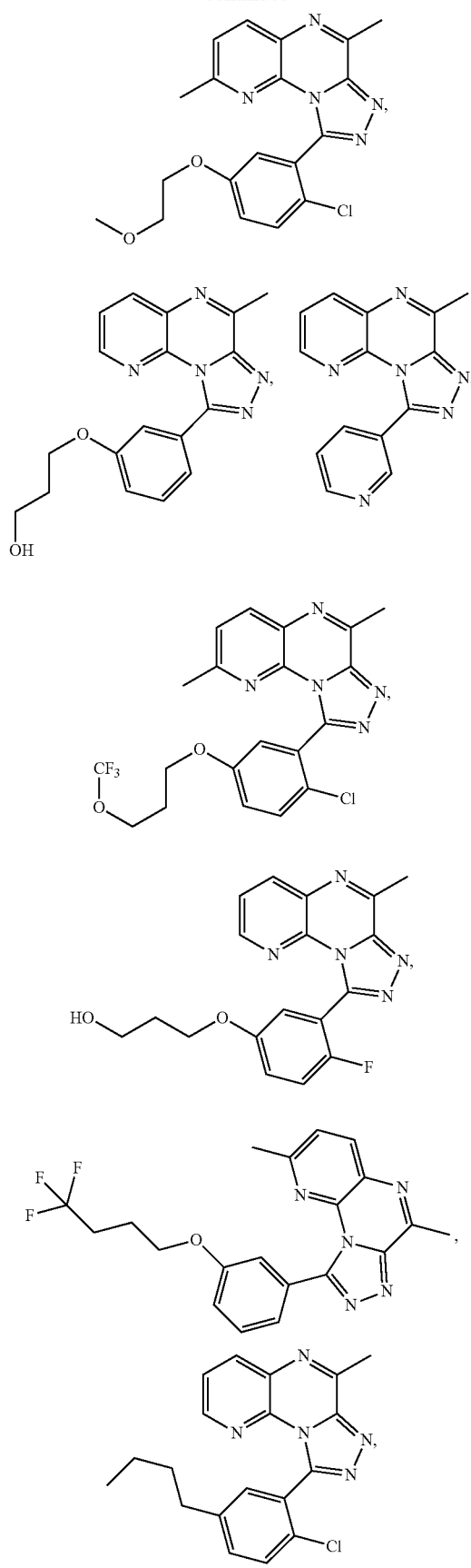
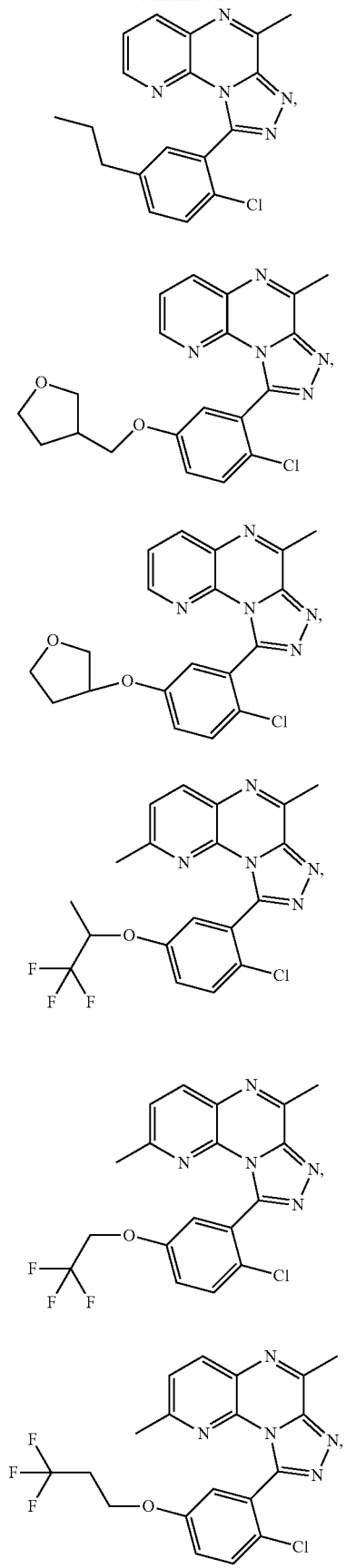

199
-continued
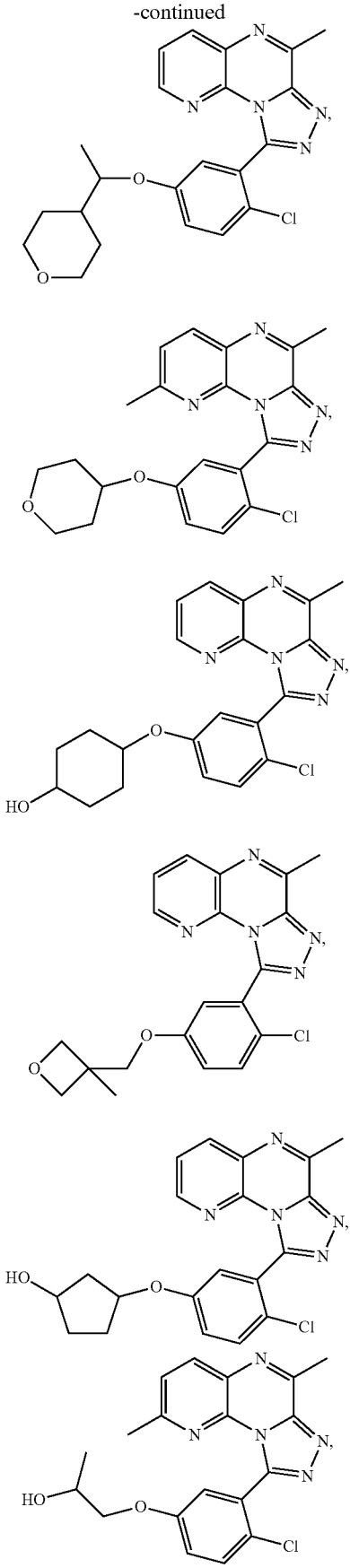
200
-continued
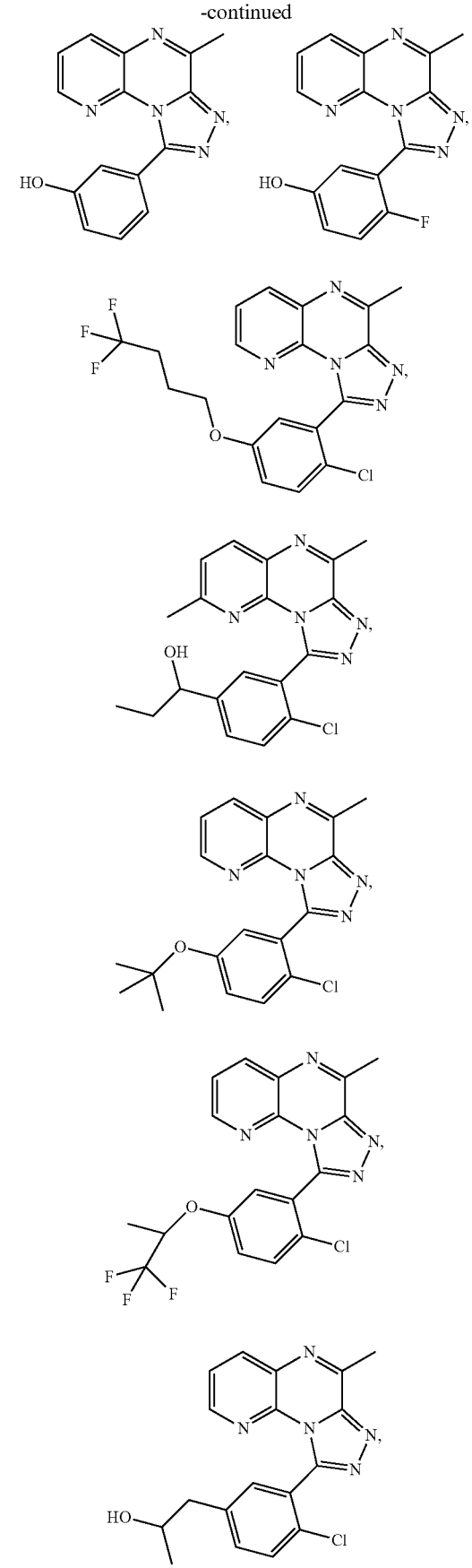

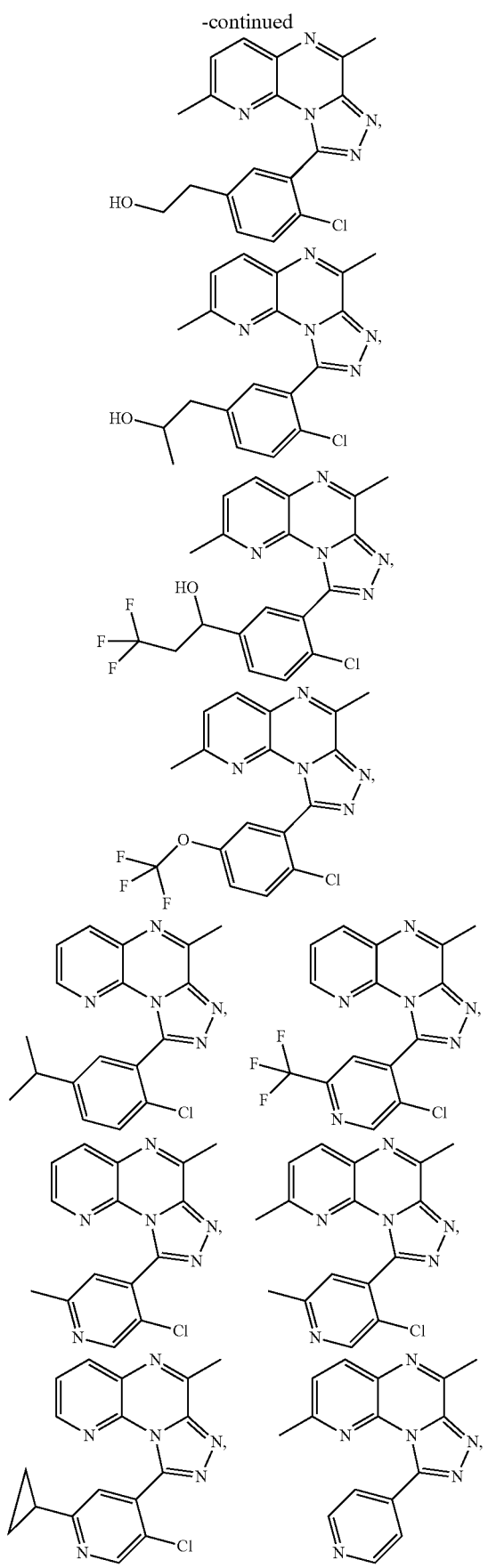
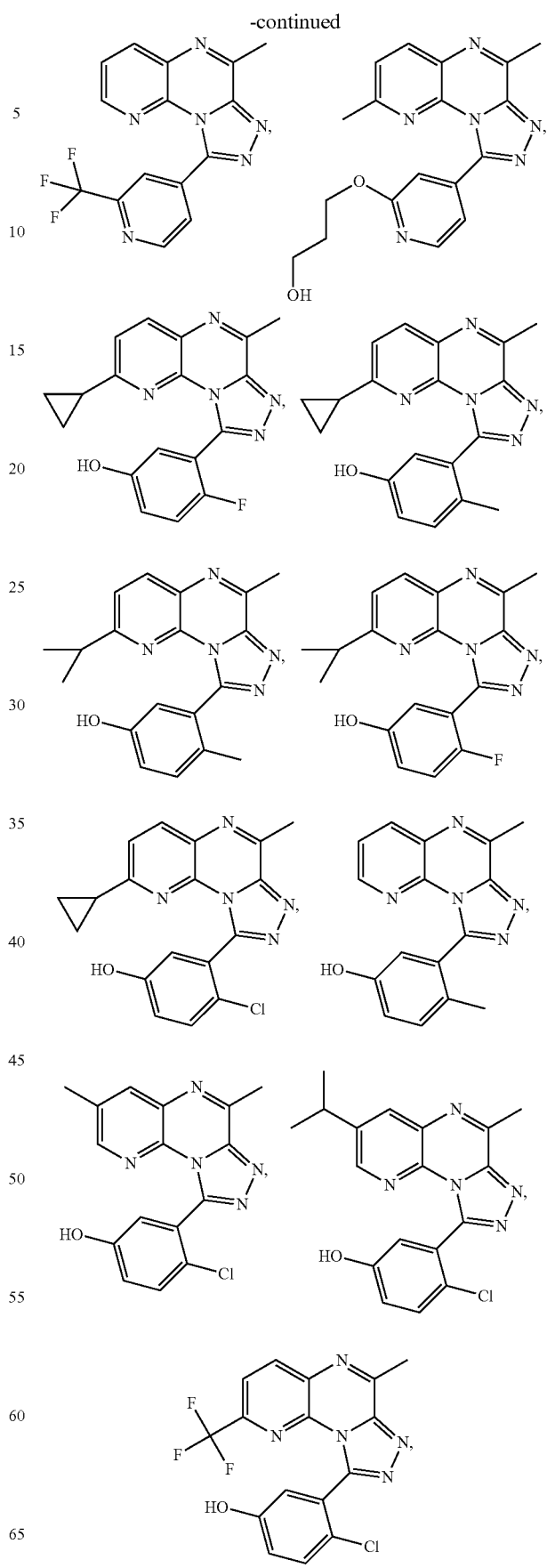

203
-continued
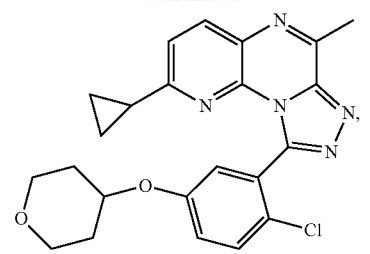
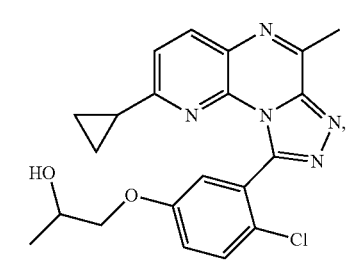
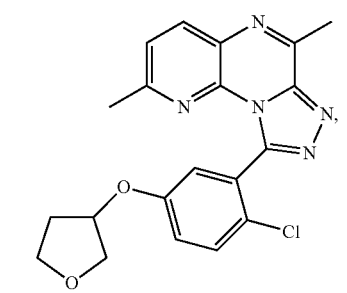
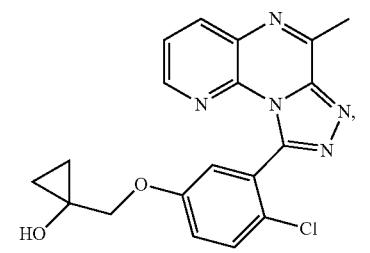
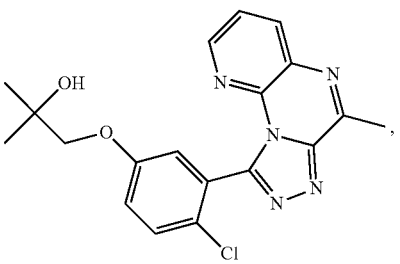
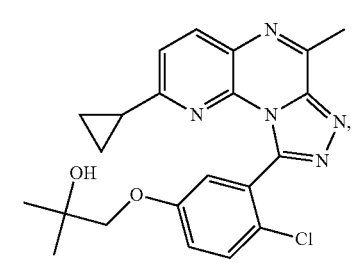
204
-continued
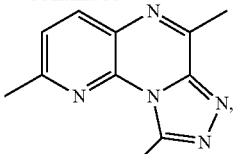
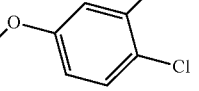
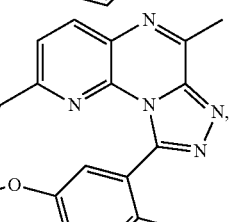
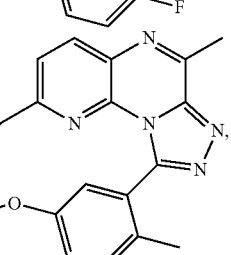
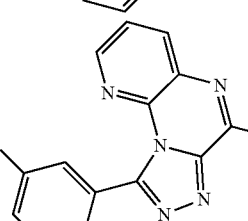
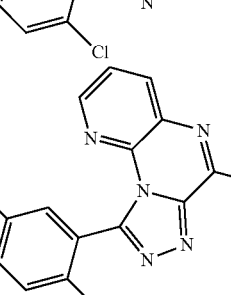
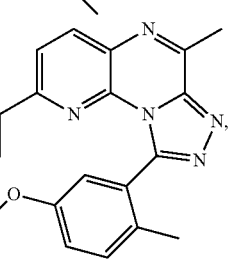
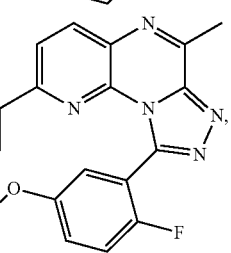

205
-continued
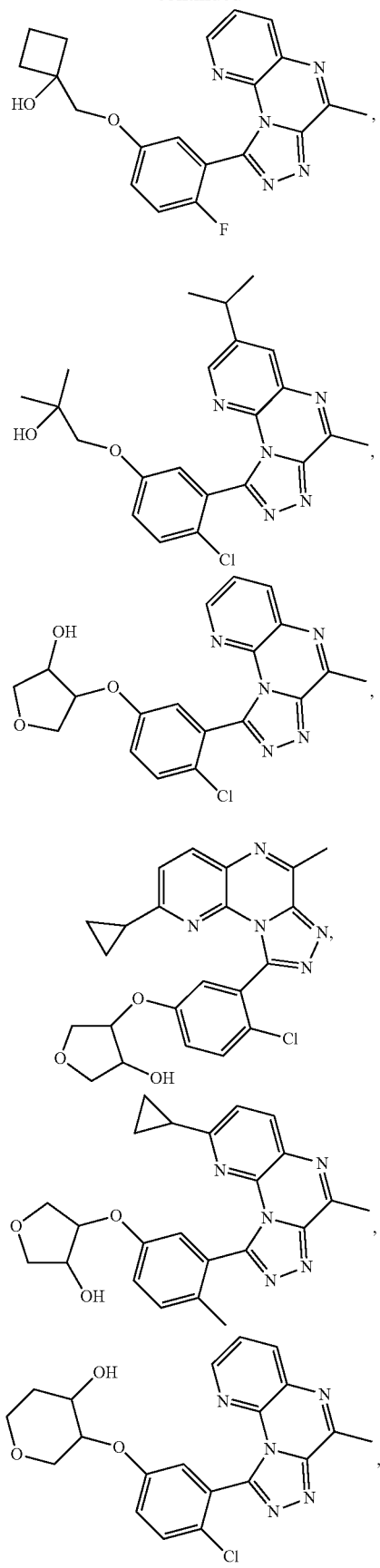
206
-continued
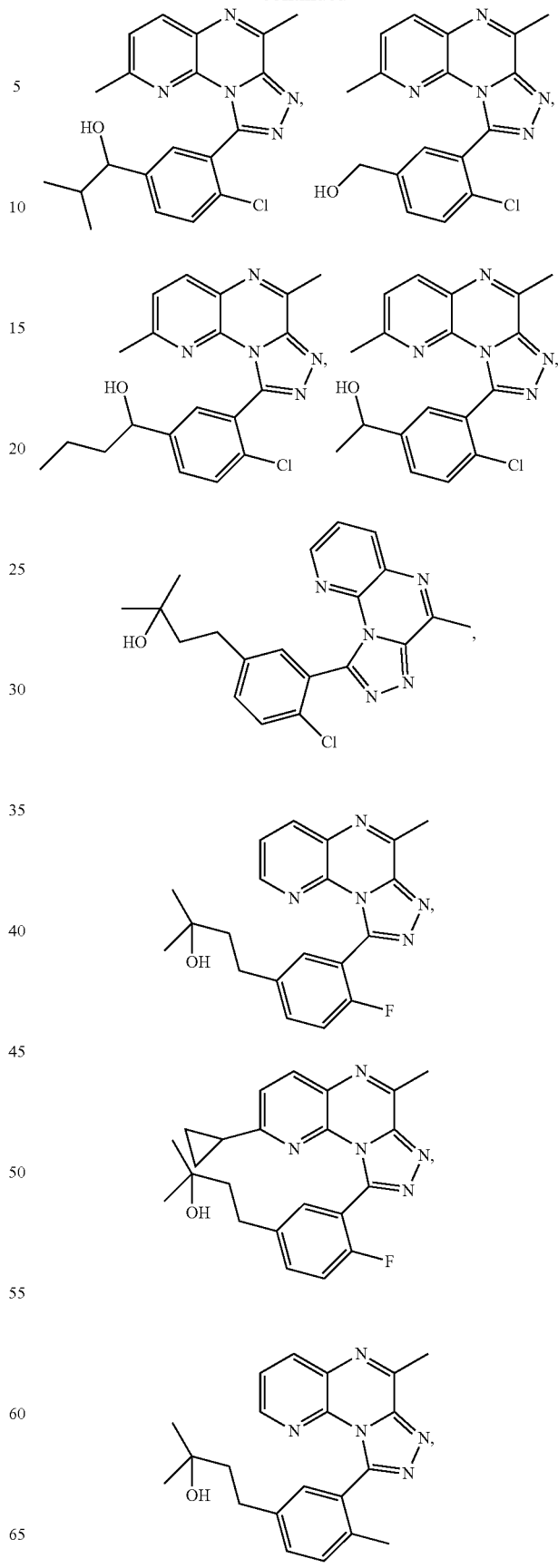

207
-continued
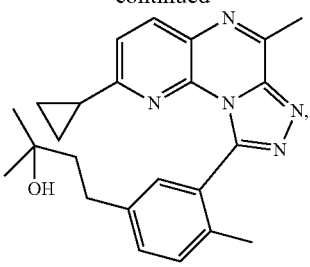
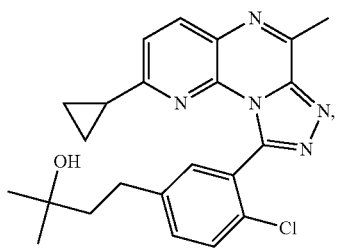
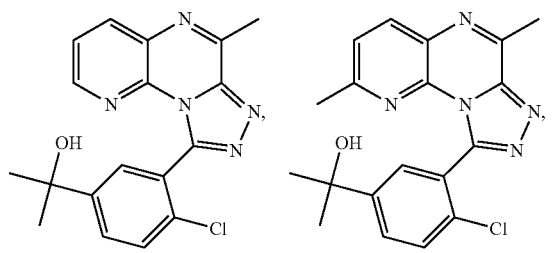
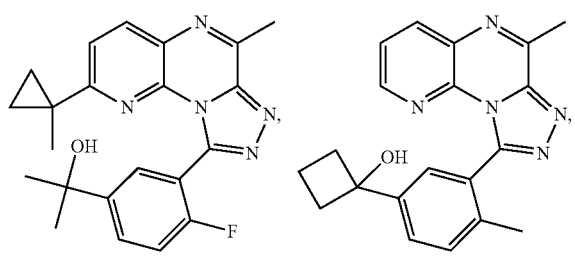
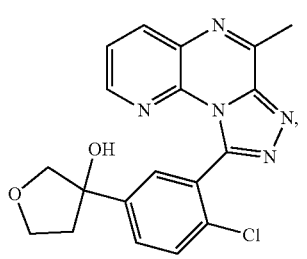
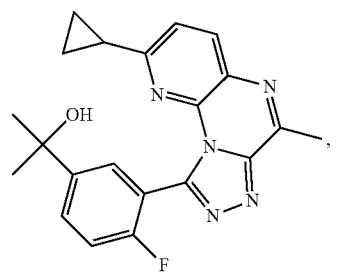
208
-continued
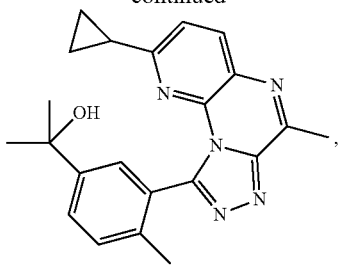
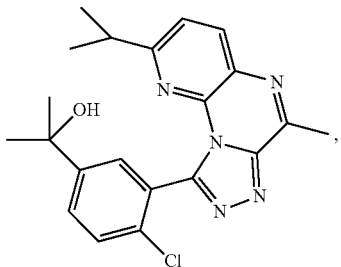
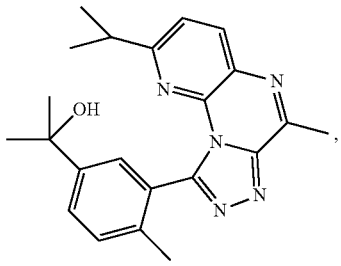
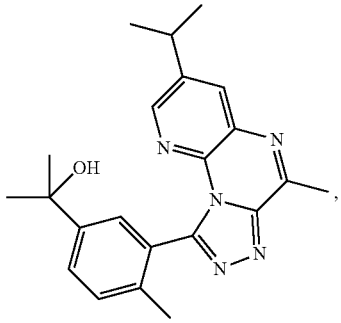
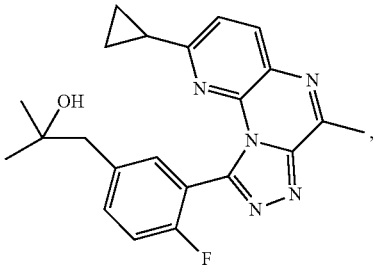
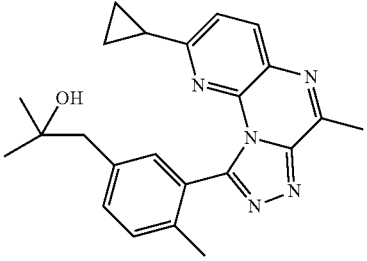

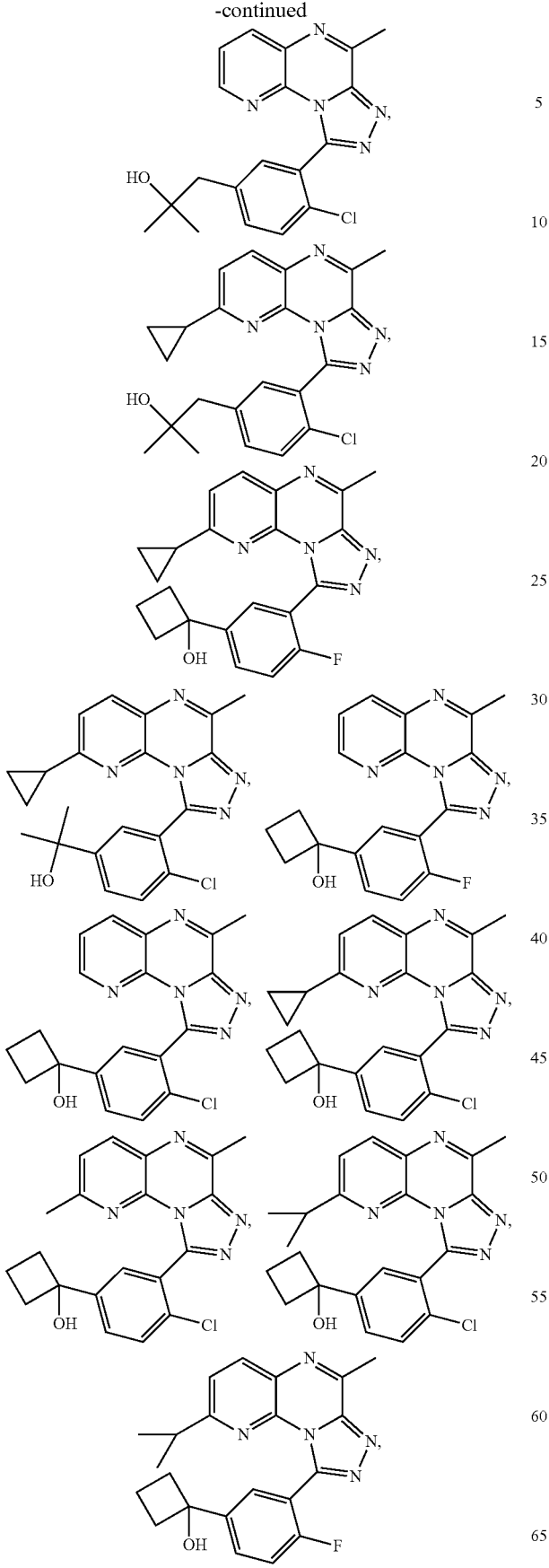
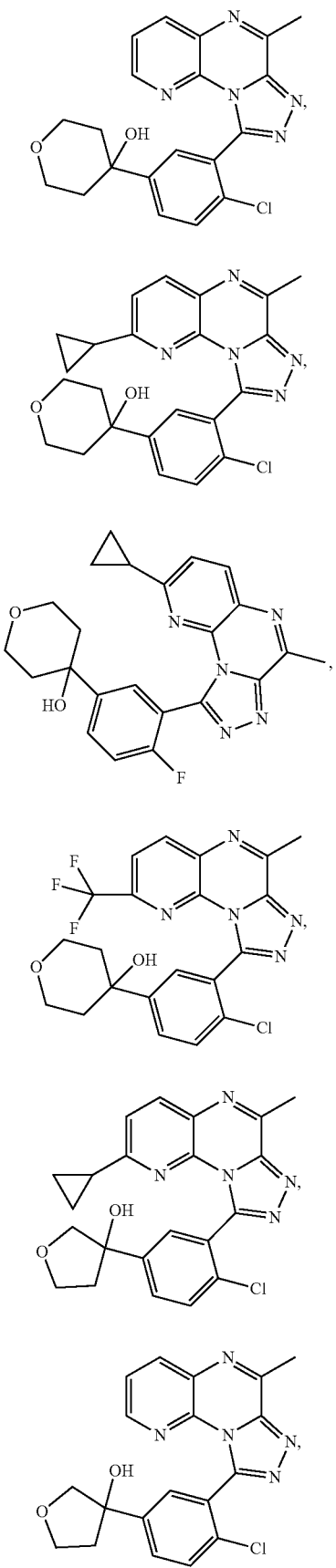

211
-continued
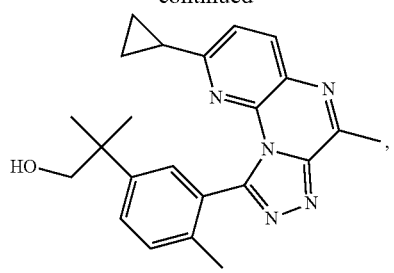
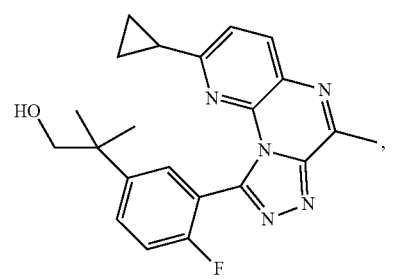
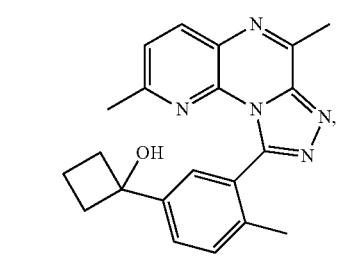
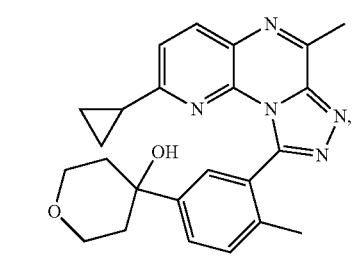
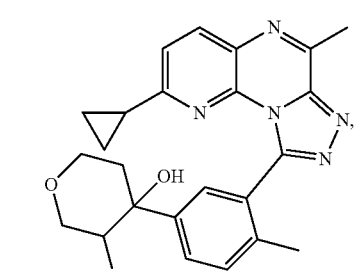
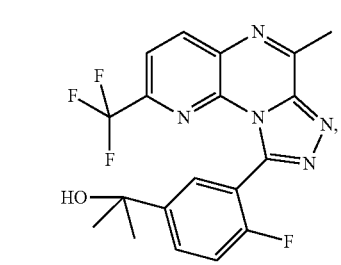
212
-continued
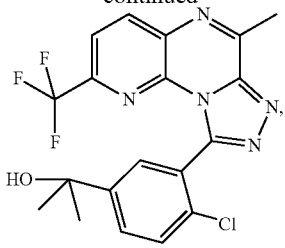
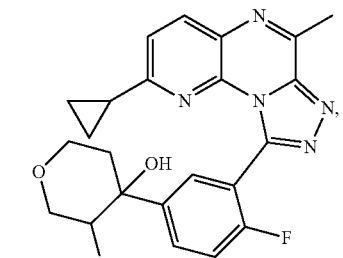
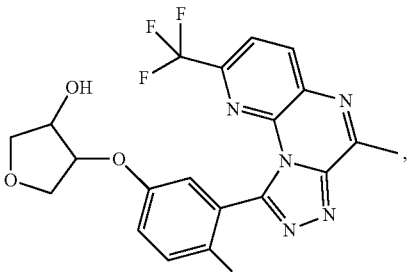
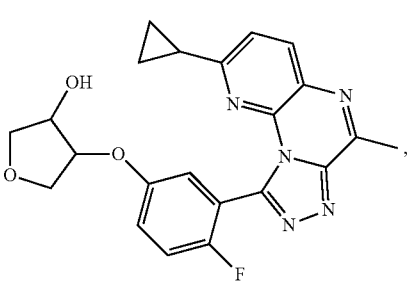
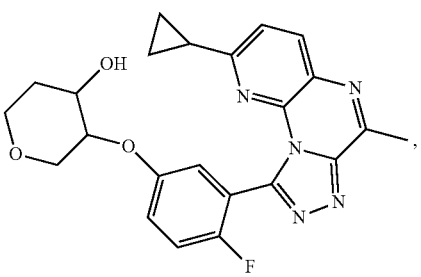
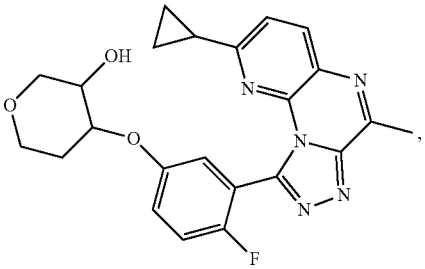

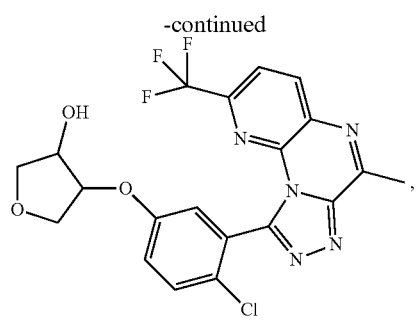

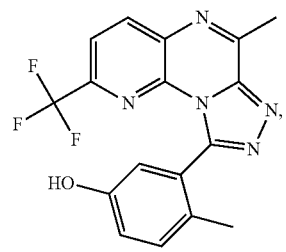

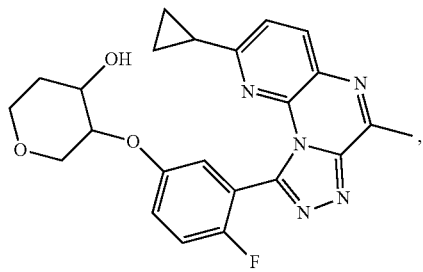

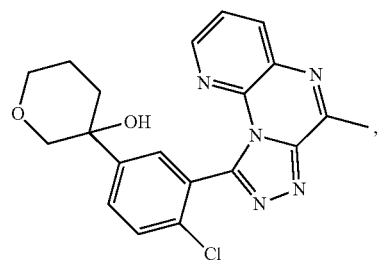

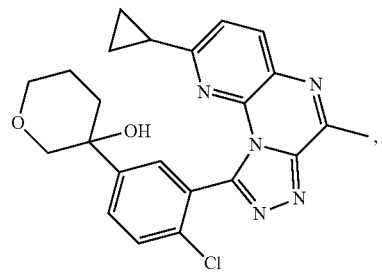

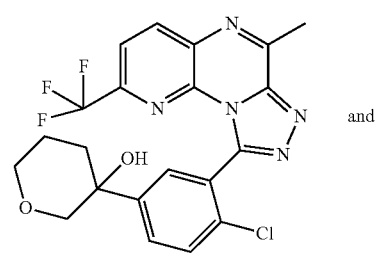 and

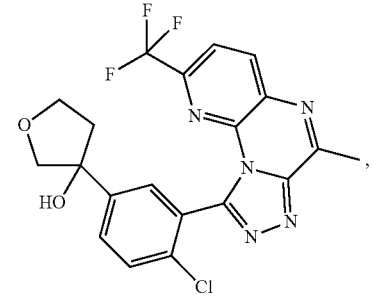 [SMILES: Cc1nc2ccc(C(F)(F)F)nc2n2c(-c3cc(C4(O)CCOC4)ccc3Cl)nnc12]

or a tautomer or pharmaceutically acceptable salt thereof.

22. The compound, according to claim 1, of the formula

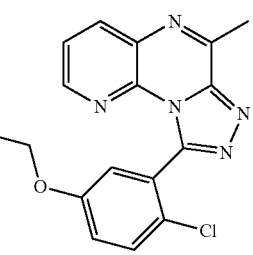

or a tautomer or pharmaceutcally acceptable salt thereof.

23. The compound, according to claim 1, of the formula

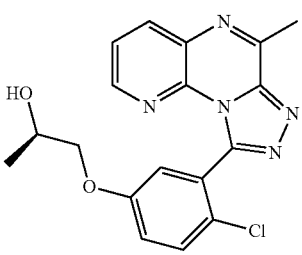 [SMILES: Cc1nc2cccnc2n2c(-c3cc(OC[C@@H](C)O)ccc3Cl)nnc12]

or a tautomer or pharmaceutically acceptable salt thereof.

24. The compound, according to claim 1, of the formula

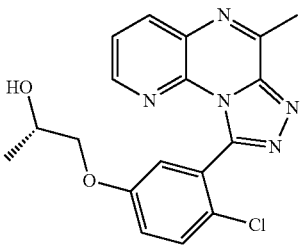 [SMILES: Cc1nc2cccnc2n2c(-c3cc(OC[C@H](C)O)ccc3Cl)nnc12]

or a tautomer or pharmaceutically acceptable salt thereof.

25. The compound, according to claim 1, of the formula

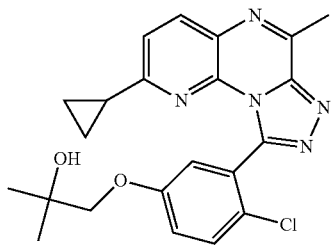

or a tautomer or pharmaceutically acceptable salt thereof.

26. The compound, according to claim 1, of the formula

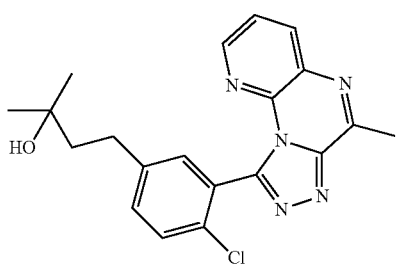 [SMILES: Cc1nc2cccnc2n2c(-c3cc(CCC(C)(C)O)ccc3Cl)nnc12]

or a tautomer or pharmaceutically acceptable salt thereof.

27. The compound, according to claim 1, of the formula

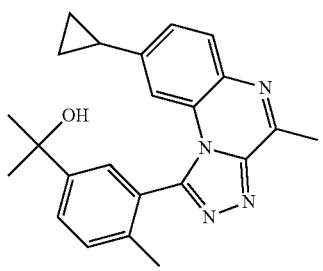 [SMILES: Cc1ccc(C(C)(C)O)cc1-c1nnc2c(C)nc3ccc(C4CC4)cc3n12]

or a tautomer or pharmaceutically acceptable salt thereof.

28. The compound, according to claim 1, of the formula

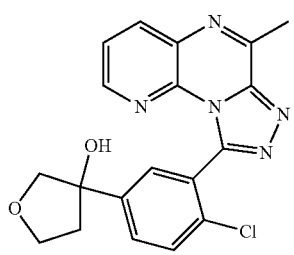 [SMILES: Cc1nc2cccnc2n2c(-c3cc(C4(O)CCOC4)ccc3Cl)nnc12]

or a tautomer or pharmaceutically acceptable salt thereof.

29. The compound, according to claim 1, of the formula

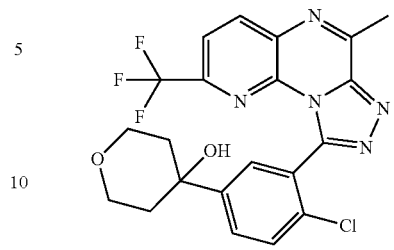

or a tautomer or pharmaceutically acceptable salt thereof.

30. The compound, according to claim 1, of the formula

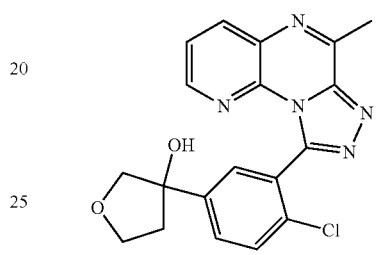

or a tautomer or pharmaceutically acceptable salt thereof.

31. The enantiomomer of the compound according to claim 30, of the formula

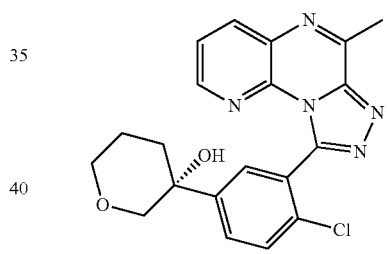

or a tautomer or pharmaceutically acceptable salt thereof.

32. The enantiomomer of the compound according to claim 30, of the formula

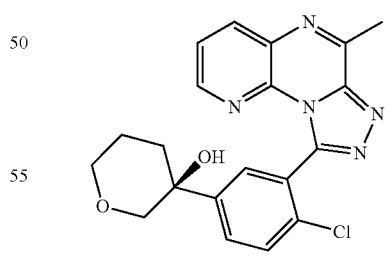

or a tautomer or pharmaceutically acceptable salt thereof.

33. A pharmaceutical composition containing a compound according to claim 1 or a pharmaceutically acceptable salt thereof together with a pharmaceutically acceptable carrier.

34. A method for inhibiting phosphodiesterase 2 activity and/or phosphodiesterase 10 activity in a host, which method comprises administering to said host an inhibitory amount of a compound of formula I

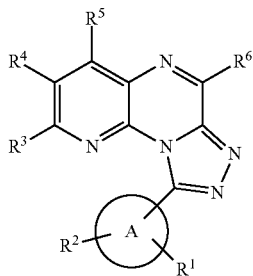

wherein
A is selected from the group $A^a$ consisting of

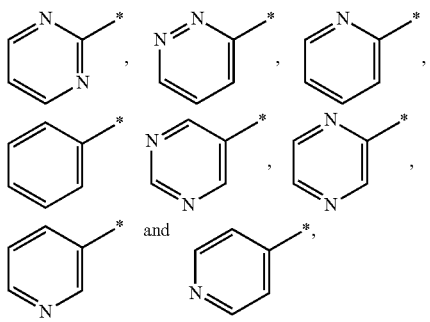

wherein the above mentioned phenyl-, pyridinyl-, pyrimidinyl-, pyridazinyl- and pyrazinyl- groups are substituted with $R^1$ and $R^2$;

$R^1$ is selected from the group $R^{1a}$ consisting of
H, halogen, NC—, $C_{1-6}$-alkyl-, $C_{1-6}$-alkyl-O—, $C_{3-6}$-cycloalkyl and $R^8$—$(CH_2)_n$—O— wherein n is 0, 1, 2, 3 or 4,
wherein the above mentioned $C_{1-6}$-alkyl-, $C_{1-6}$-alkyl-O—, $C_{3-6}$-cycloalkyl and $R^8$—$(CH_2)_n$—O—groups may optionally be substituted with 1 to 5 substituents independently selected from the group consisting of halogen, HO— and $C_{1-3}$-alkyl- optionally substituted with 1 to 7 fluorine atoms;

$R^2$ is selected from the group $R^{2a1}$ consisting of
HO—, $C_{1-6}$-alkyl-, $C_{1-6}$-alkyl-O—, $C_{3-6}$-cycloalkyl, $C_{3-6}$-cycloalkyl-$C_{1-3}$-alkyl-, heterocyclyl, heterocyclyl-$C_{1-3}$-alkyl-, phenyl, heteroaryl, $R^8$—$(CH_2)_n$—O— wherein n is 0, 1, 2, 3 or 4, and $R^8$—$(CH_2)_m$—$(CH)(CH_3)$—$(CH_2)_o$—O— wherein m is 0, 1 or 2 and o is 0, 1 or 2
wherein the above mentioned $C_{1-6}$-alkyl- and $C_{1-6}$-alkyl-O— groups are substituted with 1 to 5 substituents independently selected from the group consisting of HO— and $C_{1-3}$-alkyl-O— optionally substituted with 1 to 7 fluorine atoms, and
wherein the above mentioned $C_{1-6}$-alkyk- and $C_{1-6}$-alkyl-O— groups may optionally be substituted with 1 to 5 substituents independently selected from the group consisting of halogen and $C_{1-3}$-alkyl- optionally substituted with 1 to 7 fluorine atoms,
and
wherein the above mentioned $C_{3-6}$-cycloalkyl, $C_{3-6}$-cycloalkyl-$C_{1-3}$-alkyl-, heterocyclyl, heterocyclyl-$C_{1-3}$-alkyl-, phenyl, heteroaryl, $R^8$—$(CH_2)_n$—O— and $R^8$—$(CH_2)_m$—$(CH)(CH_3)$—$(CH_2)_o$—O- groups may optionally be substituted with 1 to 5 substituents independently selected from the group consisting of halogen, HO—, $C_{1-3}$-alkyl-O— optionally substituted with 1 to 7 fluorine atoms, and $C_{1-3}$-alkyl- optionally substituted with 1 to 7 fluorine atoms;

$R^3$ is selected from the group $R^{3a}$ consisting of
H, halogen, NC—, $C_{1-4}$-alkyl- and $C_{3-6}$-cycloalkyl-,
wherein the above mentioned $C_{1-4}$-alkyl- and $C_{3-6}$-cycloalkyl-groups may optionally be substituted with 1 to 9 substituents independently selected from the group consisting of halogen, NC—, HO—, $C_{1-3}$-alkyl- and $C_{1-3}$-alkyl-O—;

$R^4$ and $R^5$ are selected independently of each other from the group $R^{4a}/R^{5a}$ consisting of
H, halogen, NC—, HO—, $C_{1-6}$-alkyl-, $C_{1-6}$-alkyl-O—, $C_{3-8}$-cycloalkyl-, $C_{3-8}$-cycloalkyl-$C_{1-3}$-alkyl-, $C_{3-8}$-cycloalkyl-O—, heterocyclyl-O—, heterocyclyl, heteroaryl, $R^7$—$CH_2$—O— and $R^7$—$(CH_2)_2$—O—,
wherein the above mentioned $C_{1-6}$-alkyl-, $C_{1-6}$-alkyl-O—, $C_{3-8}$-cycloalkyl-, $C_{3-8}$-cycloalkyl-$C_{1-3}$-alkyl-, $C_{3-8}$-cycloalkyl-O—, heterocyclyl-O—, heterocyclyl, heteroaryl, $R^7$—$CH_2$—O— and $R^7$—$(CH_2)_2$—O-groups, may optionally be substituted with 1 to 5 substituents independently selected from the group consisting of halogen, $C_{1-2}$-alkyl- optionally substituted with 1 to 5 halogen atoms, and $C_{1-2}$-alkyl-O— optionally substituted with 1 to 5 halogen atoms;

$R^6$ is selected from the group $R^{6a}$ consisting of
H, NC—, $C_{1-6}$-alkyl-, $C_{3-8}$-cycloalkyl-, $C_{3-8}$-cycloalkyl-$C_{1-3}$-alkyl- and $C_{3-8}$-cycloalkyl-O—
wherein the above mentioned $C_{1-6}$-alkyl- groups may optionally be substituted with 1-3 halogen atoms;

$R^7$ is selected from the group $R^{7a}$ consisting of
H, carbocyclyl, heterocyclyl and heteroaryl,
wherein the above mentioned carbocyclyl, heterocyl and heteroaryl- groups may optionally be substituted with 1 to 4 substituents independently selected from the group consisting of HO—, $C_{1-4}$-alkyl- optionally substituted with 1 to 3 halogen atoms, $C_{1-4}$-alkyl-O— optionally substituted with 1 to 3 halogen atoms and halogen; and $R^8$ is selected from the group $R^{8a}$ consisting of
$C_{3-6}$-cycloalkyl, heterocyclyl, heterocyclyl-$C_{1-3}$-alkyl-, phenyl and pyridyl, wherein the above mentioned $C_{3-6}$-cycloalkyl, heterocyclyl, heterocyclyl-$C_{1-3}$-alkyl-, phenyl and pyridyl groups may optionally be substituted with 1 to 5 substituents independently selected from the group consisting of HO—, fluorine and $C_{1-3}$-alkyl- optionally substituted with 1 to 7 halogen atoms;

or a tautomer or pharmaceutically acceptable salt thereof.

* * * * *